(12) United States Patent
Xian

(10) Patent No.: US 9,964,535 B2
(45) Date of Patent: May 8, 2018

(54) TREATMENT OF INFLAMMATORY DISEASES

(71) Applicant: The Jackson Laboratory, Bar Harbor, ME (US)

(72) Inventor: Wa Xian, Unionville, CT (US)

(73) Assignee: The Jackson Laboratory, Bar Harbor, ME (US)

( * ) Notice: Subject to any disclaimer, the term of this patent is extended or adjusted under 35 U.S.C. 154(b) by 27 days.

(21) Appl. No.: 14/853,192

(22) Filed: Sep. 14, 2015

(65) Prior Publication Data

US 2016/0061817 A1    Mar. 3, 2016

Related U.S. Application Data

(63) Continuation of application No. PCT/US2014/025776, filed on Mar. 13, 2014.

(60) Provisional application No. 61/793,110, filed on Mar. 15, 2013, provisional application No. 61/788,602, filed on Mar. 15, 2013.

(51) Int. Cl.
| | |
|---|---|
| *G01N 33/50* | (2006.01) |
| *C12Q 1/68* | (2018.01) |
| *A61K 38/17* | (2006.01) |
| *C07K 16/18* | (2006.01) |
| *C12N 15/113* | (2010.01) |

(52) U.S. Cl.
CPC ......... *G01N 33/5023* (2013.01); *A61K 38/17* (2013.01); *C07K 16/18* (2013.01); *C12N 15/113* (2013.01); *C12Q 1/6883* (2013.01); *C12N 2320/30* (2013.01); *C12Q 2600/158* (2013.01)

(58) Field of Classification Search
CPC .................................................. G01N 33/5023
See application file for complete search history.

(56) References Cited

U.S. PATENT DOCUMENTS

| | | | |
|---|---|---|---|
| 2005/0208496 A1 | 9/2005 | Ohtani et al. | |
| 2009/0269769 A1* | 10/2009 | Panja | G01N 33/5023 435/6.14 |
| 2011/0245217 A1* | 10/2011 | Freishtat | A61K 31/4025 514/180 |
| 2014/0030809 A1* | 1/2014 | Hijikata | C12N 9/12 435/455 |

FOREIGN PATENT DOCUMENTS

WO    WO-2012/123712 A1    9/2012

OTHER PUBLICATIONS

Atherton et al.,. "IL-13-induced changes in the goblet cell density of human bronchial epithelial cell cultures: MAP kinase and phosphatidylinositol 3-kinase regulation," *Am. J. Physiol. Lung Cell Mol. Physiol.*, 285:L730-L739 (2003).

* cited by examiner

*Primary Examiner* — Daniel C Gamett
(74) *Attorney, Agent, or Firm* — McCarter & English, LLP; Yu Lu

(57) ABSTRACT

The invention described herein relates to methods of screening for pro-inflammatory genes and anti-inflammatory genes which may be useful for treating an inflammatory disease, disorder, or otherwise abnormal condition, such as an inflammatory lung disease. The identified pro-inflammatory genes and anti-inflammatory genes may be used to produce pharmaceutical compositions for use in treating the inflammatory disease, disorder, or otherwise abnormal condition.

21 Claims, 19 Drawing Sheets

FIGURE 17
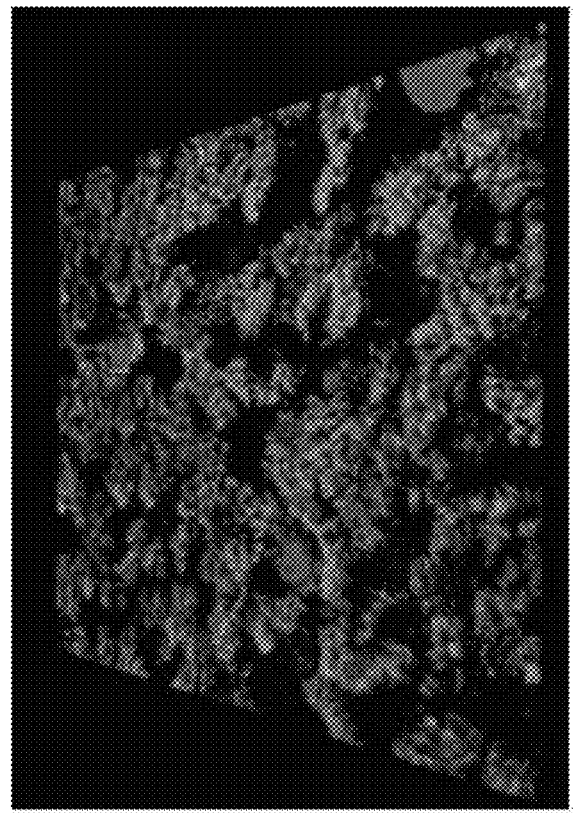
IL-13 + AMTN
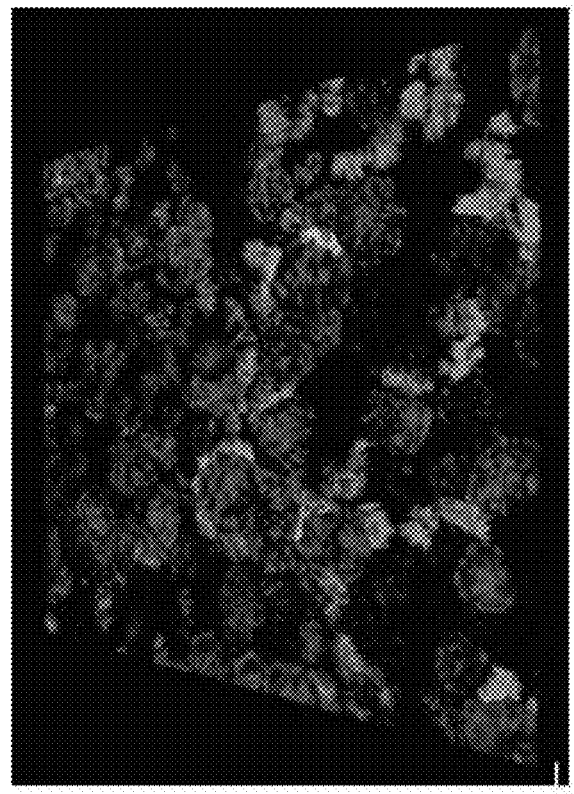
IL-13 treated

TREATMENT OF INFLAMMATORY DISEASES

REFERENCE TO RELATED APPLICATION

This application is a continuation of International Application No. PCT/US2014/025776, filed on Mar. 13, 2014, which claims the benefit of the filing date, under 35 U.S.C. § 119(e), of U.S. Provisional Application Nos. 61/793,110 and 61/788,602, both filed on Mar. 15, 2013, the entire contents of each which are incorporated herein by reference.

BACKGROUND OF THE INVENTION

Humans breath more than one cubic meter of air every hour, and the large quantities of particles, antigens, infectious agents and toxic gases and fumes that are present in inhaled air are usually dealt with by the lung. The interaction of these particles with the immune system and other lung defense mechanisms results in the generation of a controlled inflammatory response which is usually protective and beneficial. In general, this process regulates itself in order to preserve the integrity of the airway and alveolar epithelial surfaces where gas exchange occurs.

In some cases, however, the inflammatory response cannot be regulated and the potential for tissue injury is increased. Depending on the type of environmental exposure, genetic predisposition, and a variety of ill-defined factors, abnormally large numbers of inflammatory cells can be recruited at different sites of the respiratory system, resulting in illness or disease.

The inflammatory response to inhaled or intrinsic stimuli is characterized by a non-specific increase in the vascular permeability, the release of inflammatory and chemotactic mediators including histamine, eicosanoids, prostaglandins, cytokines and chemokines. These mediators modulate the expression and engagement of leukocyte-endothelium cell adhesion molecules allowing the recruitment of inflammatory cells present in blood.

A more specific inflammatory reaction involves the recognition and the mounting of an exacerbated, specific immune response to inhaled antigens. This reaction is involved in the development of asthma, Hypersensitivity pneumonitis (HP) and possibly sarcoidosis. Dysregulation in the repair mechanisms following lung injury may contribute to fibrosis and loss of function in asthma, pulmonary fibrosis, chronic obstructive pulmonary disease (COPD), and chronic HP.

Despite advances in the treatment of inflammatory illnesses, including pulmonary inflammatory diseases, treatment using available drugs or agents frequently results in undesirable side effects. For example, the inflammation of COPD is apparently resistant to corticosteroids, and consequently the need for the development of new anti-inflammatory drugs to treat this condition has been recognized. Similarly, while corticosteroids and other immunosuppressive medications have been routinely employed to treat pulmonary fibrosis, they have demonstrated only marginal efficacy. There is thus a need for new and reliable methods of treating inflammatory diseases, including pulmonary inflammatory diseases.

SUMMARY OF THE INVENTION

One aspect of the invention provides a method of identifying a target gene which may be useful for treating an inflammatory disease, disorder, or otherwise abnormal condition, the method comprising: a) providing a population of test cells, wherein: 1) the test cells are a clonal expansion of a single epithelial stem cell capable of propagating for at least about 20 (30, 40, 50, 60, 70, 100, 150, 200, 250, 300, 350, 400 or more) doublings while maintaining a multipotent phenotype; or, 2) the test cells are differentiated from the clonal expansion of the single epithelial stem cell; b) contacting the test cells with a pro-inflammatory cytokine associated with the inflammatory disease; c) identifying one or more genes the expression level of which has been modulated upon contacting the pro-inflammatory cytokine, as compared to that of control test cells not contacted by the pro-inflammatory cytokine, wherein the one or more genes identified in step c) are target gene(s) which may be useful for treating the inflammatory disease.

In certain embodiments, the pro-inflammatory cytokine is a T-helper 2 cytokine (such as IL-4, IL-5, IL-6, IL-10, IL-13, TNFα, IL-8, IL-10, IL-11, IL-17 (IL-17A, IL-17B, IL-17C, IL-17D, IL-17E, IL-17F), IL-1 family (IL-1α, IL-1β, IL-18, IL-33, IL-36α, IL-36β, or IL-36γ). For example, the pro-inflammatory cytokine may be IL-13 or TNFα.

In certain embodiments, the single epithelial stem cell is isolated from a subject predisposed to the inflammatory disease, or has the inflammatory disease (e.g., from an asthma or COPD patient).

In certain embodiments, the single epithelial stem cell is isolated from upper airway of the respiratory system, small intestine, or colon.

In certain embodiments, the test cells are upper airway epithelial cells differentiated in air-liquid interface (ALI) cultures.

In certain embodiments, the test cells are differentiated in ALI cultures while in contact with a fibroblast feeder layer (such as a 3T3-J2 feeder layer).

In certain embodiments, in step c), gene expression level is determined by quantitating mRNA expression. For example, gene expression level can be determined by microarray or real-time PCR or RNA-Seq.

In certain embodiments, step c) comprises identifying one or more genes the expression level of which is decreased upon contacting the pro-inflammatory cytokine.

In certain embodiments, the method further comprises: d) determining the effect of contacting a second population of test cells with both the pro-inflammatory cytokine and gene expression products of the one or more genes, wherein the one or more genes are identified as anti-inflammatory if at least one inflammatory phenotype induced by the pro-inflammatory cytokine is alleviated.

In certain embodiments, the test cells are a clonal expansion of a single upper airway epithelial stem cell, or are upper airway epithelial cells differentiated therefrom, and wherein the at least one inflammatory phenotype comprises goblet cell hyperplasia, goblet cell hypertrophy, and/or ciliated cell deciliation.

In certain embodiments, in step d), the second population of test cells are contacted by the pro-inflammatory cytokine and the gene expression products of the one or more genes substantially simultaneously.

In certain embodiments, in step d), the second population of test cells are first contacted by the pro-inflammatory cytokine to produce at least one inflammatory phenotype, before being contacted by the gene expression products of the one or more genes.

In certain embodiments, step c) comprises identifying one or more genes the expression level of which is increased upon contacting the pro-inflammatory cytokine.

In certain embodiments, the method further comprises: d) contacting a second population of test cells with the pro-inflammatory cytokine, and determining the effect thereon of inhibiting a function of the one or more genes, wherein the one or more genes are identified as pro-inflammatory if at least one inflammatory phenotype induced by the pro-inflammatory cytokine is alleviated.

In certain embodiments, the method further comprises: d) determining the effect of stimulating a function of the one or more genes in a second population of test cells, either in the presence or absence of the pro-inflammatory cytokine, wherein the one or more genes are identified as pro-inflammatory if at least one inflammatory phenotype is induced or enhanced in the test cells.

In certain embodiments, the test cells are a clonal expansion of a single upper airway epithelial stem cell, or are upper airway epithelial cells differentiated therefrom, and wherein the at least one inflammatory phenotype comprises goblet cell hyperplasia, goblet cell hypertrophy, and/or ciliated cell deciliation.

In certain embodiments, the second population of test cells are a second population of epithelial cells differentiated from the clonal expansion of the single epithelial stem cell.

In certain embodiments, the expression level of the target gene is increased or decreased by at least 2-fold, 3-fold, 5-fold, 10-fold, 20-fold, 50-fold, 100-fold or more compared to that of the control test cells.

Another aspect of the invention provides a method of identifying a target gene which may be useful for treating an inflammatory disease, disorder, or otherwise abnormal condition, the method comprising: a) carrying out the screening methods of the invention in more than one subject, each having the inflammatory disease, in order to identify for each subject a collection of pro-inflammatory genes or anti-inflammatory genes which may be useful for treating the inflammatory disease; b) identifying one or more genes commonly identified in two or more subjects; thereby identifying the target gene which may be useful for treating the inflammatory disease.

Another aspect of the invention provides a method of identifying a compound that is potentially useful for treating an inflammatory disease, disorder, or otherwise abnormal condition in a subject, the method comprising: a) providing a population of test cells, wherein: 1) the test cells are a clonal expansion of a single epithelial stem cell isolated from the subject, wherein the single epithelial stem cell is capable of propagating for at least about 20 (30, 40, 50, 60, 70, 100, 150, 200, 250, 300, 350, 400 or more) doublings while maintaining a multipotent phenotype; or, 2) the test cells are differentiated from the clonal expansion of the single epithelial stem cell; b) contacting the test cells with a pro-inflammatory cytokine associated with the inflammatory disease; c) contacting the test cells with a candidate compound or a control; and, d) identifying the candidate compound that antagonizes a function of the pro-inflammatory cytokine; thereby identifying the compound that is potentially useful for treating the inflammatory disease or condition in the subject.

In certain embodiments, the single epithelial stem cell is isolated from a tissue or organ affected by the inflammatory disease or condition, or from a tissue or organ in close proximity to the tissue or organ affected by the inflammatory disease or condition.

In certain embodiments, the subject has asthma or COPD, or is predisposed to have asthma or COPD.

In certain embodiments, the candidate compound is a small molecule with a molecular weight of less than about 500 Da or 1000 Da, a peptide, a protein, a polynucleotide (antisense, siRNA, miRNA, shRNA, ribozyme, or polynucleotide encoding the same), a lipid, a sterol, or a polysaccharide.

In certain embodiments, the candidate compound is a drug known to be effective in treating the inflammatory disease or condition.

In certain embodiments, step b) is carried out before step c), and wherein the test cells exhibit a phenotype in response to being contacted by the pro-inflammatory cytokine prior to step c).

In certain embodiments, step b) is carried out substantially simultaneously with step c).

In certain embodiments, step b) is carried out after step c).

In certain embodiments, in step d), the candidate compound antagonizes the function of the pro-inflammatory cytokine by alleviating a phenotype of the test cells in response to being contacted by the pro-inflammatory cytokine.

In certain embodiments, the phenotype is increased expression of a pro-inflammatory gene (such as one listed in Tables 3 and 4), or decreased expression of an anti-inflammatory gene (such as one listed in Tables 1 and 2).

Another aspect of the invention provides a pharmaceutical composition for treating an inflammatory disease, disorder, or otherwise abnormal condition (e.g., an inflammatory lung disease), comprising: a) a protein or a polypeptide or a functional portion thereof encoded by an anti-inflammatory gene selected from those listed in Tables 1 and 2, such as ABI3BP, AMTN, APOD, BMP8A, C3, CP, GLIPR1, FN1, IGFBP3, IGFBP6, LGALS1, LTBP1, MSMB, OLFM4, PLUNC, PPBP, SERPINA3, and TNFSF15, or b) an antagonist of a pro-inflammatory gene selected from: those listed in Tables 3 and 4, such as AGR2, ANG, C20orf114, CA2, CCL26, CD200R1, CST1, CST2, DEFB118, DPP4, EPGN, FETUB, GGH, ITLN1, KITLG, PLA2G7, PDCD1LG2, POSTN, PTHLH, SAA4, SERPINB2, SMPDL3B, SPINK5, ST6GAL1, STATH, SULF1, TCN1, TFF1, TIMP1, TMPRSS2, TNFSF10, and, one or more pharmaceutically acceptable excipients, stabilizers or preservatives.

In certain embodiments, the antagonist comprises an RNAi agent (siRNA, miRNA, shRNA), an antisense sequence, a ribozyme, or a polynucleotide encoding the RNAi agent, the antisense sequence, or the ribozyme.

In certain embodiments, the antagonist comprises an antibody specific for a protein or polypeptide encoded by the pro-inflammatory gene.

Another aspect of the invention provides a pharmaceutical composition for treating an inflammatory disease, disorder, or otherwise abnormal condition (e.g., inflammatory lung disease), comprising an agent which induces the expression of the anti-inflammatory gene of the invention, or which mimics the activity of the gene product of the anti-inflammatory gene of the invention, further comprising one or more pharmaceutically acceptable excipients, stabilizers or preservatives.

Another aspect of the invention provides a method of treating a subject having an inflammatory disease, disorder, or otherwise abnormal condition (e.g., an inflammatory lung disease), the method comprising: a) inhibiting in the subject the function of one or more genes identified as pro-inflammatory according to the screening methods of the invention; or b) stimulating in the subject the function of one or more genes identified as anti-inflammatory according to the screening methods of the invention.

In certain embodiments, the function of the one or more genes identified as pro-inflammatory is inhibited by antisense, RNAi (siRNA, miRNA, shRNA etc.), antibody, or dominant negative antagonist thereof.

In certain embodiments, the function of the one or more genes identified as anti-inflammatory is stimulated by administering a gene product of (e.g., a protein or polypeptide or a functional portion thereof encoded by) the one or more genes identified as anti-inflammatory.

In certain embodiments, the protein or polypeptide comprises any one or more of those encoded by the anti-inflammatory genes listed in Tables 1 and 2, such as ABI3BP, AMTN, APOD, BMP8A, C3, CP, GLIPR1, FN1, IGFBP3, IGFBP6, LGALS1, LTBP1, MSMB, OLFM4, PLUNC, PPBP, SERPINA3, and TNFSF15.

In certain embodiments, the function of the one or more genes identified as anti-inflammatory is stimulated by exogenously expressing the one or more genes identified as anti-inflammatory.

In certain embodiments, the inflammatory disease is a disorder associated with inflammation or otherwise has an inflammation component, such as, but are not limited to: acne vulgaris, asthma, COPD, autoimmune diseases, celiac disease, chronic (plaque) prostatitis, glomerulonephritis, hypersensitivities, inflammatory bowel diseases (IBD, Crohn's disease, ulcerative colitis), pelvic inflammatory disease, reperfusion injury, rheumatoid arthritis, sarcoidosis, transplant rejection, vasculitis, interstitial cystitis, atherosclerosis, allergies (type 1, 2, and 3 hypersensitivity, hay fever), inflammatory myopathies, as systemic sclerosis, and include dermatomyositis, polymyositis, inclusion body myositis, Chediak-Higashi syndrome, chronic granulomatous disease, Vitamin A deficiency, cancer (solid tumor, gallbladder carcinoma), periodontitis, granulomatous inflammation (tuberculosis, leprosy, sarcoidosis, and syphilis), fibrinous inflammation, purulent inflammation, serous inflammation, ulcerative inflammation, and ischaemic heart disease, type I diabetes, and diabetic nephropathy.

In certain embodiments, the inflammatory disease is an inflammatory lung disease is selected from: asthma (e.g., acute inflammatory asthma, allergic asthma, iatrogenic asthma), COPD, pulmonary hypertension, neonatal pulmonary hypertension, neonatal bronchopulmonary dysplasia, chronic obstructive pulmonary disease, acute bronchitis, chronic bronchitis, emphysema, bronchiolitis, bronchiectasis, radiation pneumonitis, hypersensitivity, pneumonitis, acute smoke inhalation, thermal lung injury, cystic fibrosis, alveolar proteinosis, alpha-I-protease deficiency, pulmonary inflammatory disorders, pneumonia, acute respiratory distress syndrome, acute lung injury, idiopathic respiratory distress syndrome, or idiopathic pulmonary fibrosis.

In certain embodiments, the inflammatory disease is an autoimmune disease or disorder that is associated with inflammation or has an inflammation component, e.g., corresponding to one or more types of hypersensitivity. Exemplary autoimmune diseases or disorders that correspond to one or more types of hypersensitivity include: atopic allergy, atopic dermatitis, autoimmune hemolytic anemia, autoimmune hepatitis, autoimmune polyendocrine syndrome, autoimmune urticaria, celiac disease, cold agglutinin disease, contact dermatitis, Crohn's disease, diabetes mellitus type 1, discoid lupus erythematosus, erythroblastosis fetalis, Goodpasture's syndrome, Graves' disease, Guillain-Barre syndrome (GBS), Hashimoto's encephalopathy, Hashimoto's thyroiditis, idiopathic thrombocytopenic purpura, autoimmune thrombocytopenic purpura, IgA nephropathy, lupus erythematosus, Ménière's disease, multiple sclerosis, myasthenia gravis, narcolepsy, neuromyelitis optica, Devic's disease, neuromyotonia, ocular cicatricial pemphigoid, opsoclonus myoclonus syndrome, PANDAS (pediatric autoimmune neuropsychiatric disorders associated with *streptococcus*), paraneoplastic cerebellar degeneration, pemphigus vulgaris, pernicious anaemia, psoriasis, psoriatic arthritis, rheumatoid arthritis, rheumatic fever, sarcoidosis, scleroderma, subacute bacterial endocarditis (SBE), systemic lupus erythematosis, Lupus erythematosis, temporal arteritis (also known as "giant cell arteritis"), thrombocytopenia, ulcerative colitis, undifferentiated connective tissue disease, urticarial vasculitis, and vasculitis.

In certain embodiments, the inflammatory disease comprises an inflammatory condition in liver selected from: cirrhosis, liver cancer, and acute or chronic hepatitis caused by viral infection (e.g., by HAV, HBV, HCV, HDV, HEV, HFV, and HGV), alcoholic hepatitis, drug or chemical intoxication (such as carbon-tetrachloride, amethopterin, tetracycline, acetaminophen, fenoprofen, etc.), mononucleosis, amebic dysentery, and other systematic infections by EBV, CMV, or bacteria.

In certain embodiments, the inflammatory disease comprises an inflammatory condition in kidney selected from: acute or chronic nephritis, interstitial nephritis, lupus nephritis, IgA nephropathy (Berger's disease), glomerulonephritis, membranoproliferative glomerulonephritis (MPGN), autoimmune disorders related to CKD and inflammation, Goodpasture's syndrome, Wegener's granulomatosis, pyelonephritis, athletic nephritis, kidney stones, or gout.

In certain embodiments, the inflammatory disease is an inflammatory condition in the bowel disease (IBD) selected from Crohn's disease, ulcerative colitis, collagenous colitis, lymphocytic colitis, ischaemic colitis, diversion colitis, Behçet's disease, or indeterminate colitis.

In certain embodiments, the inflammatory disease comprises an inflammatory condition in pancreas selected from: pancreatitis caused by alcohol, gallstone, medication (e.g., use of corticosteroids such as prednisolone, HIV drugs such as didanosine and pentamidine, diuretics, the anticonvulsant valproic acid, the chemotherapeutic agents L-asparaginase and azathioprine, estrogen by way of increased blood triglycerides, cholesterol-lowering statins, and the antihyperglycemic agents like metformin, vildagliptin, sitagliptin, and diabetes drug gliptins), trauma, mumps, autoimmune disease, scorpion stings, high blood calcium, high blood triglycerides, hypothermia, endoscopic retrograde cholangiopancreatography (ERCP), Pancreas divisum, pregnancy, diabetes mellitus type 2, pancreatic cancer, pancreatic duct stones, vasculitis (inflammation of the small blood vessels in the pancreas), coxsackievirus infection, and *porphyria*—particularly acute intermittent *porphyria* and erythropoietic protoporphyria, viral infection (by coxsackie virus, cytomegalovirus, Hepatitis B, herpes simplex virus, mumps, varicella-zoster virus), bacterial infection (*Legionella, Leptospira, Mycoplasma, Salmonella*), fungal infection (*Aspergillus*), or parasitic infection (*Ascaris, Cryptosporidium, Toxoplasma*).

In certain embodiments, the method comprises administering any of the pharmaceutical composition of the invention.

Another aspect of the invention provides a method of identifying a subject suitable for therapeutic intervention, wherein the subject has an inflammatory disease, or is predisposed to develop the inflammatory disease, the method comprising: a) using the screening methods of the invention, identifying one or more pro-inflammatory genes or one or more anti-inflammatory genes, b) isolating from a candidate subject a single epithelial stem cell capable of propagating at least about 20 (30, 40, 50, 60, 70, 100, 150, 200, 250, 300, 350, 400 or more) doublings while maintaining a multipotent phenotype; c) determining the expression level of the pro-inflammatory genes or the anti-inflammatory genes in the clonal expansion, or in cells differentiated from the clonal expansion, d) identifying subjects having increased expression of the pro-inflammatory genes or having decreased expression of the anti-inflammatory genes, as being suitable for therapeutic intervention.

In certain embodiments, the method further comprises treating subjects identified in step d) according to the treatment method of the invention.

Another aspect of the invention provides a method of treating cancer, comprising inhibiting in a subject in need of treatment a function of one or more genes identified as pro-inflammatory according to the screening methods of the invention.

In certain embodiments, the method comprises administering to the subject a pharmaceutical composition comprising an antagonist to the function of the one or more genes identified as pro-inflammatory, wherein the antagonist is an antisense polynucleotide, an RNAi reagent (siRNA, miRNA, shRNA etc.), an antibody, or a dominant negative antagonist thereof.

Another aspect of the invention provides a method of screening for a compound that may be useful for treating an inflammatory disease, disorder, or otherwise abnormal condition in a subject, the method comprising: (1) providing a first population of test cells, wherein: a) the first population of test cells are a clonal expansion of a first single epithelial stem cell isolated from a diseased tissue of the subject, wherein the first single epithelial stem cell is capable of propagating for at least about 20 (30, 40, 50, 60, 70, 100, 150, 200, 250, 300, 350, 400 or more) doublings while maintaining a multipotent phenotype; or, b) the first population of test cells are differentiated from the clonal expansion of the first single epithelial stem cell; (2) providing a second population of test cells, wherein: a) the second population of test cells are a clonal expansion of a second single epithelial stem cell isolated from a matching normal tissue of the subject, wherein the second single epithelial stem cell is capable of propagating for at least about 20 (30, 40, 50, 60, 70, 100, 150, 200, 250, 300, 350, 400 or more) doublings while maintaining a multipotent phenotype; or, b) the second population of test cells are differentiated from the clonal expansion of the second single epithelial stem cell; (3) contacting the first and the second populations of test cells with a candidate therapeutic agent; and, (4) determining and comparing the effects of the candidate therapeutic agent on the first and second population of test cells; wherein the candidate therapeutic agent is identified as the compound that may be useful for treating the inflammatory disease, disorder, or otherwise abnormal condition, if the candidate therapeutic agent alleviates at least one symptom of the first population of test cells, and does not produce an undesirable effect on the second population of test cells.

It is contemplated that any embodiments described herein, including embodiments described in the examples and figures, and embodiments described under different aspects of the invention, can be combined with any one or more other embodiments where applicable.

BRIEF DESCRIPTION OF THE DRAWINGS

FIG. 1). With IL-13 treatment, the ciliated cell differentiation was blocked and the goblet cells appear to be hypertrophic (cf. FIG. 1).

FIG. 17 is a set of representative 3D images showing the rescue of the IL-13 phenotype by AMTN.

DETAILED DESCRIPTION OF THE INVENTION

1. Overview

Figure 1:
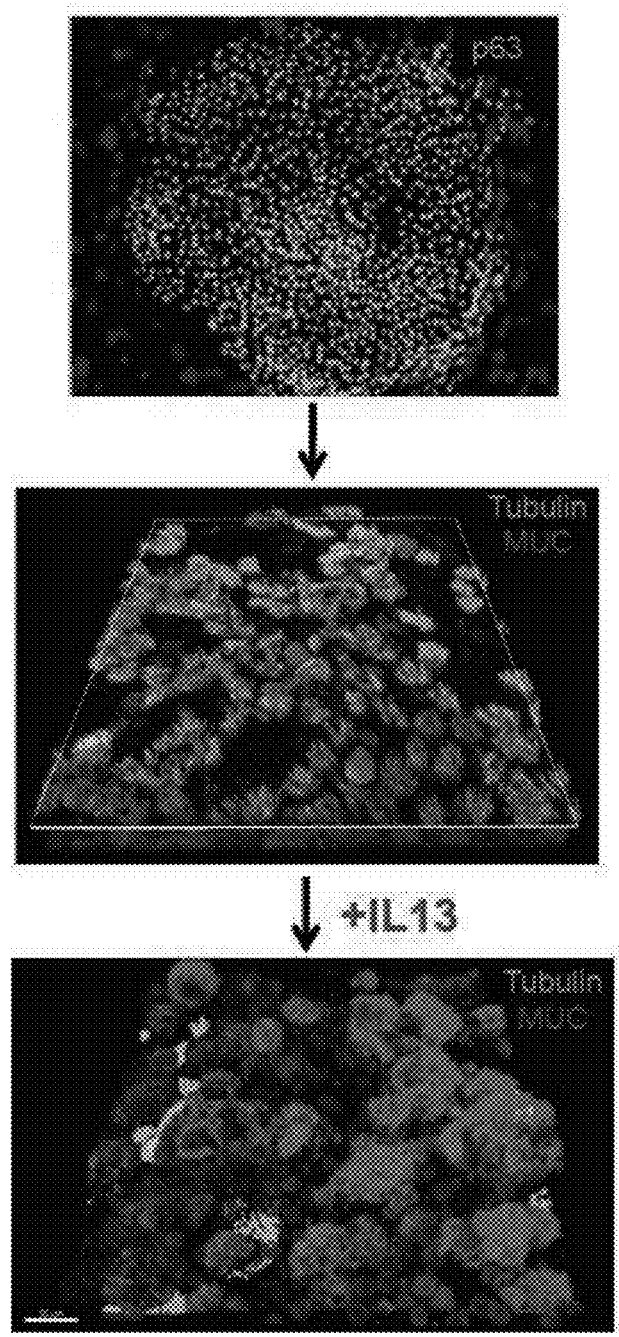
FIG. 1 shows a representative model of upper airway epithelia derived from isolated human upper airway stem cells, which model is suitable for screening for pro- and anti-inflammatory genes in response to treatment by pro-inflammatory cytokine (such as IL-13). Cloned human upper airway stem cells were expanded to establish pedigree cell lines that can be propagated in vitro indefinitely. These stem cells uniformly express the stratified epithelial stem cell marker p63 (top panel, bright dots in each cell). The stem cells were differentiated in air-liquid interface (ALI) cultures to yield an excellent model for the upper airway epithelia, as demonstrated by tubulin expression in differentiated ciliated cells (middle panel, bright staining in largely continuous cells having "spike" like structures) and mucin 5AC expression in differentiated goblet cells (middle panel, staining in the few relatively round cells surrounded by the spiked ciliated cells). Treatment of these differentiated structures with IL-13, a T-helper 2 cytokine and known driver of asthma, results in an asthma-like remodeling over 3-10 days consisting of goblet cell hypertrophy and deciliation (lower panel, see greatly expanded round cells, and almost diminished spiked cells).
Figure 2:
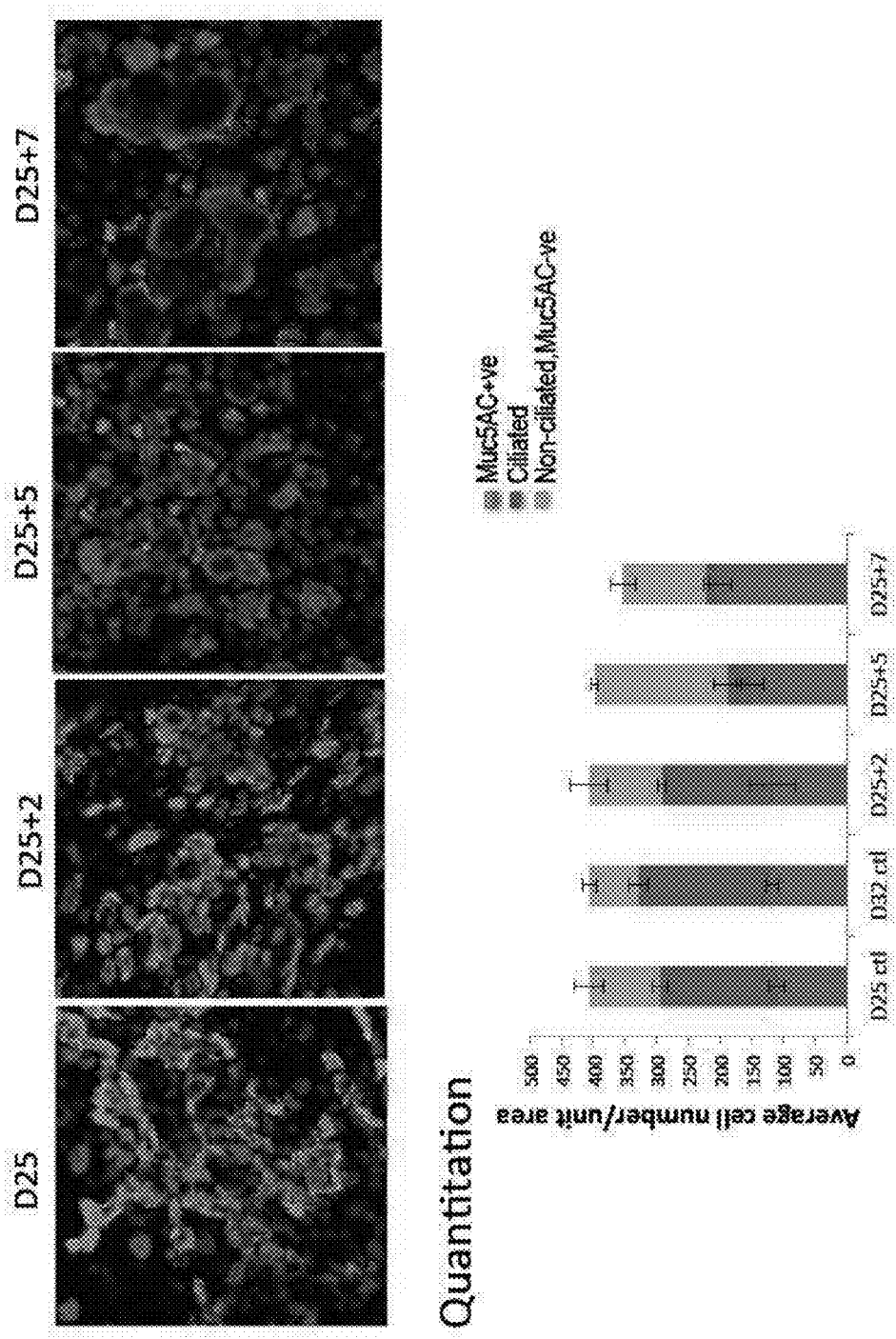
FIG. 2 top panels show the kinetic process of IL-13 induced goblet cell hyperplasia (increase in number) and hypertrophy (increase in size) in vitro. The confocal immunofluorescent (IF) images of various time points following IL-13 treatment. D25: Day 25 after initiation of ALI differentiation, with no IL-13 treatment. D25+2, D25+5, and D25+7: 2, 5, and 7 days after IL-13 treatment, respectively, after 25 days of ALI differentiation in the absence of IL-13 treatment. The lower panel shows quantitation of ciliated cells and goblet cells, and reveals dramatically increased number of goblet cells and decreased number of cells with motile cilia following IL-13 treatment. D25 ctl and D32 ctl are controls without IL-13 treatment at days 25 and 32, respectively.
Figure 3:
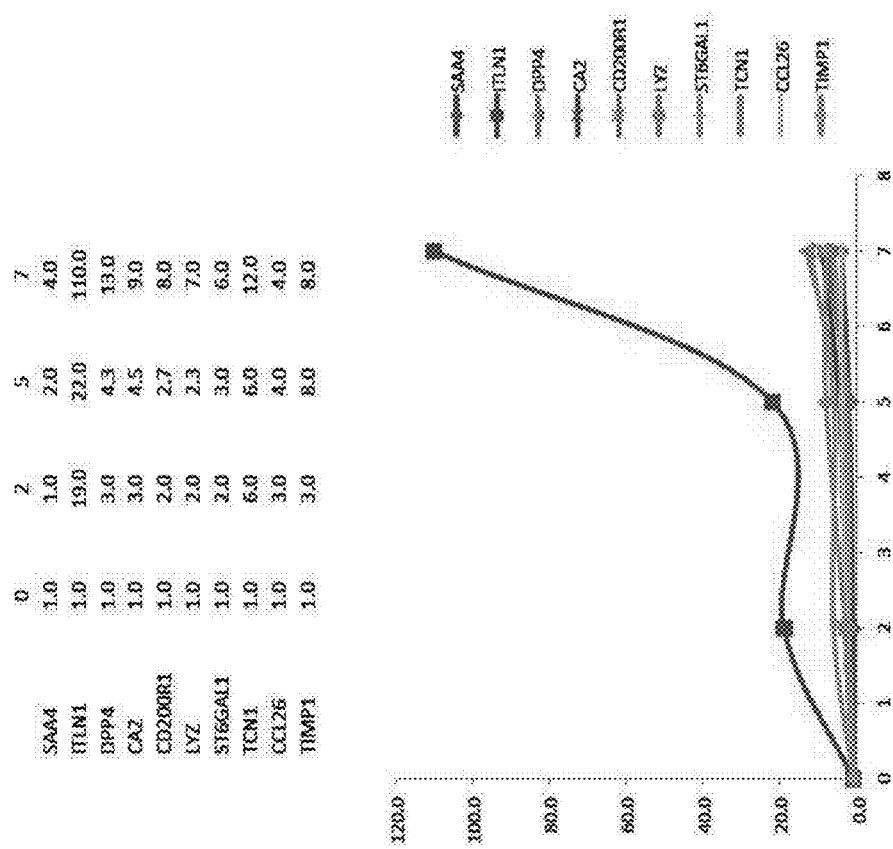
FIG. 3 shows RNA expression level of representative genes at various time points after IL-13 treatment. The day 25 air-liquid interface cultures were treated with IL-13 for 2 days, 5 days and 7 days. The samples collected include: day 25 untreated control, day 27 untreated control, day 30 untreated control, and day 32 untreated control; day 25+2 days treatment of IL-13, day 25+5 days treatment of IL-13, and day 25+7 days treatment of IL-13. The data shown were calculated by dividing the microarray signal intensity of treated samples with that of untreated samples at the same time point (e.g., day 25+2 days IL-13 treated vs. day 27 untreated). Certain genes such as ITLN1 show continuously upregulated expression pattern, which may be indicative of genes playing a role in pro-inflammatory response.
Figure 4:
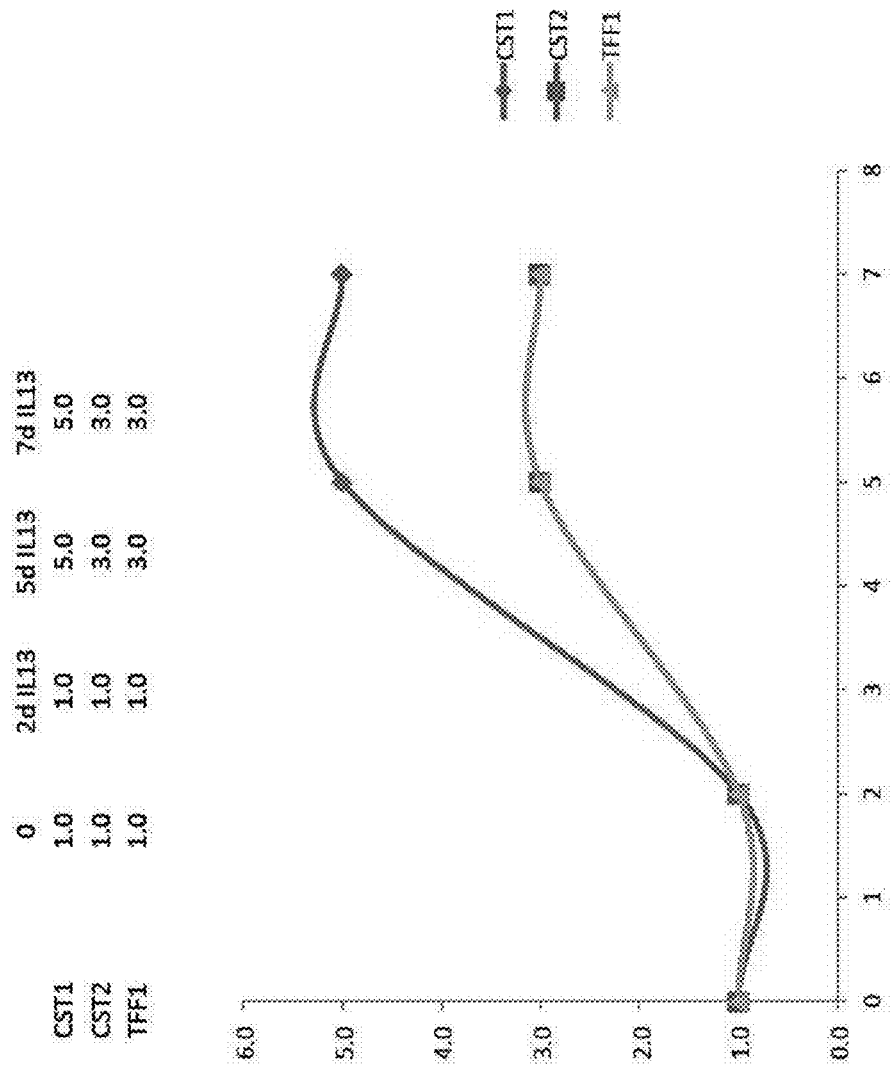
FIG. 4 shows expression profiles of several potential pro-inflammatory genes in response to IL-13 treatment. The genes that are upregulated first and then reach a plateau after about 5 days of treatment.
Figure 5:
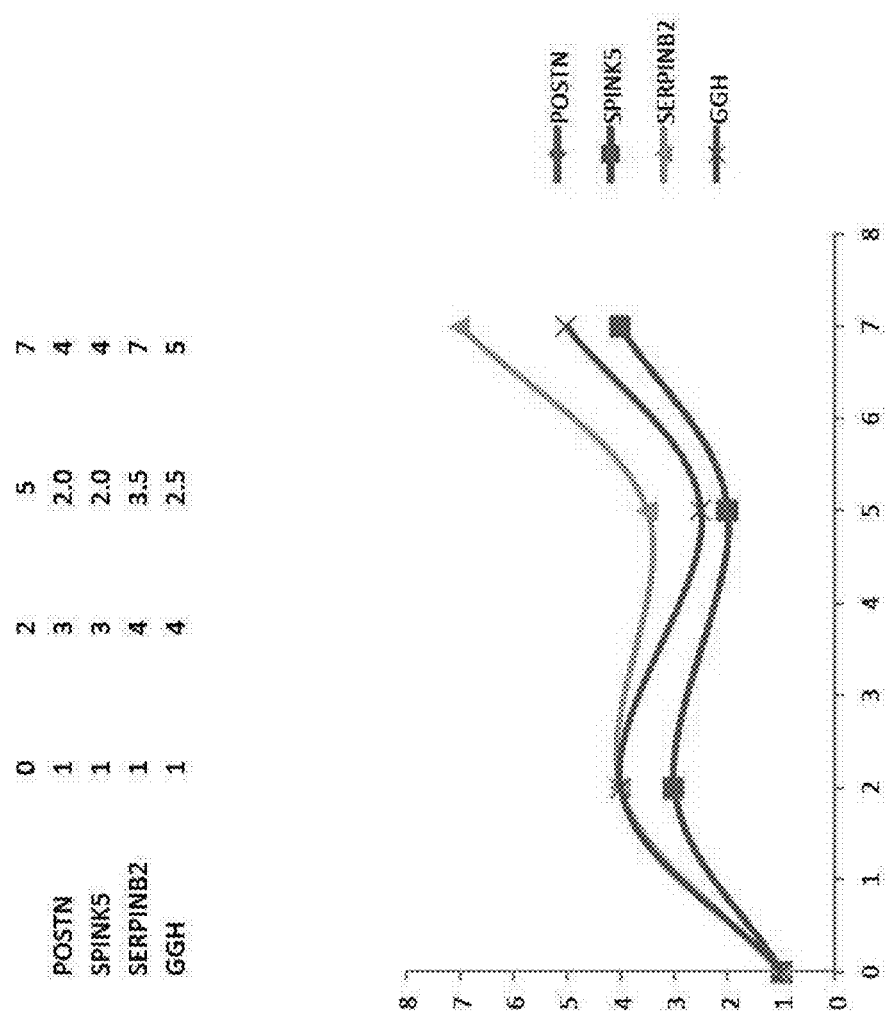
FIG. 5 shows expression profiles of several potential pro-inflammatory genes in response to IL-13 treatment. The genes have an undulating expression pattern.
Figure 6:
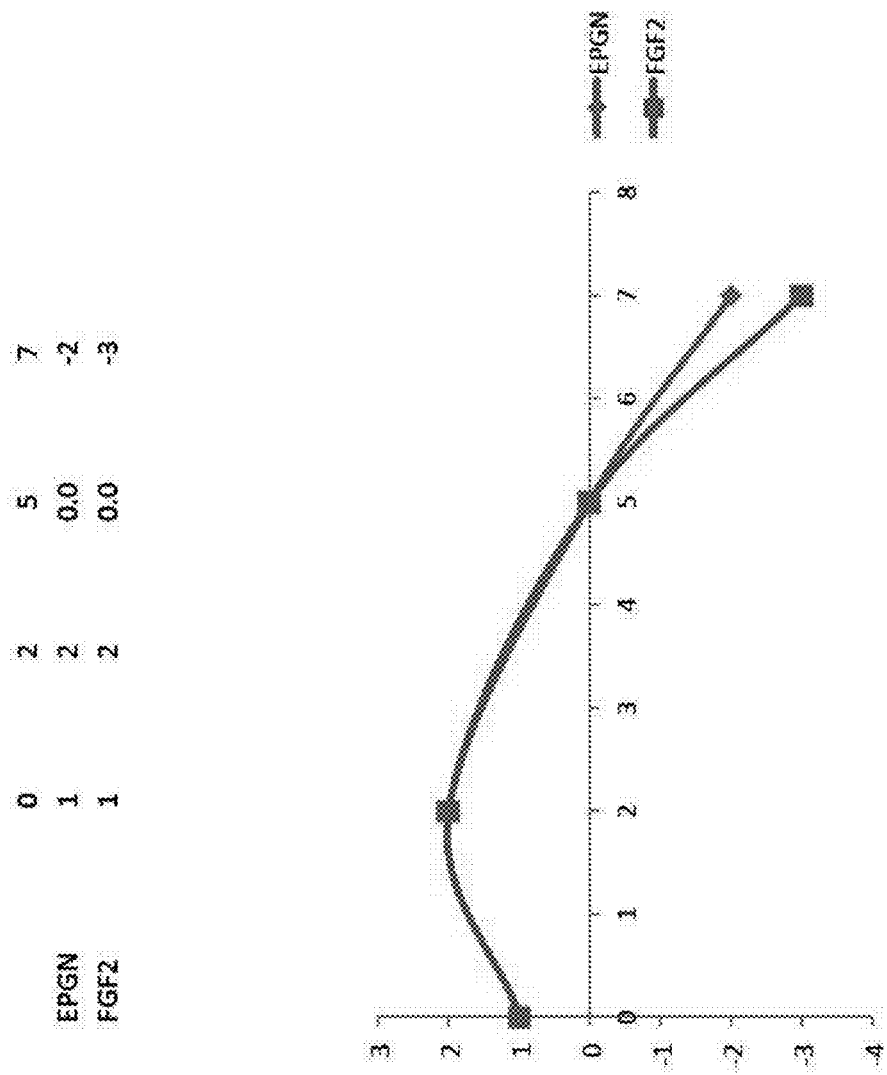
FIG. 6 shows expression profiles of several potential pro-inflammatory genes in response to IL-13 treatment. The genes are quickly upregulated following IL-13 treatment, but eventually are downregulated.
Figure 7:
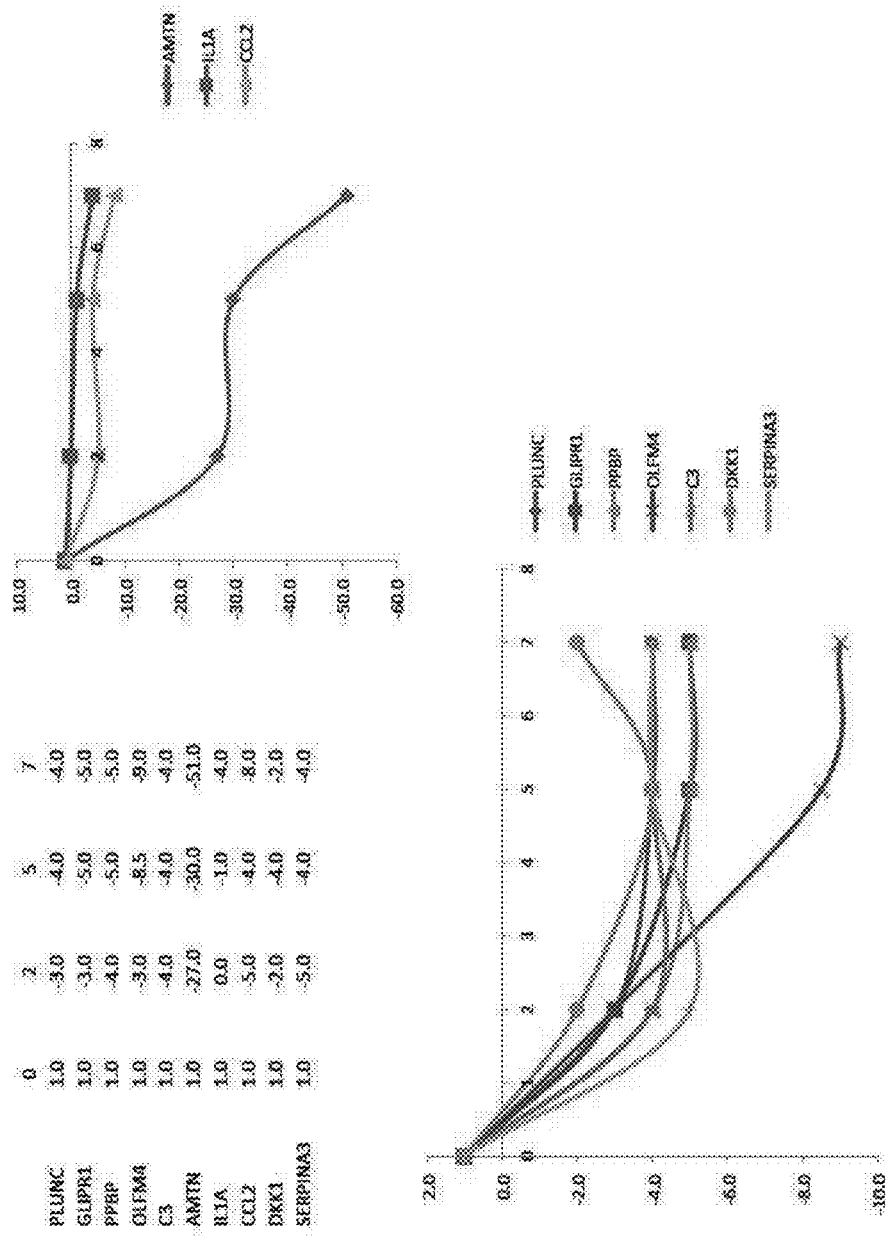
FIG. 7 shows expression profiles of several potential anti-inflammatory genes in response to IL-13 treatment. The genes are significantly downregulated following IL-13 treatment. See AMTN, PLUNC and SERPINA3. These genes potentially play a role of being anti-inflammatory.
Figure 8:
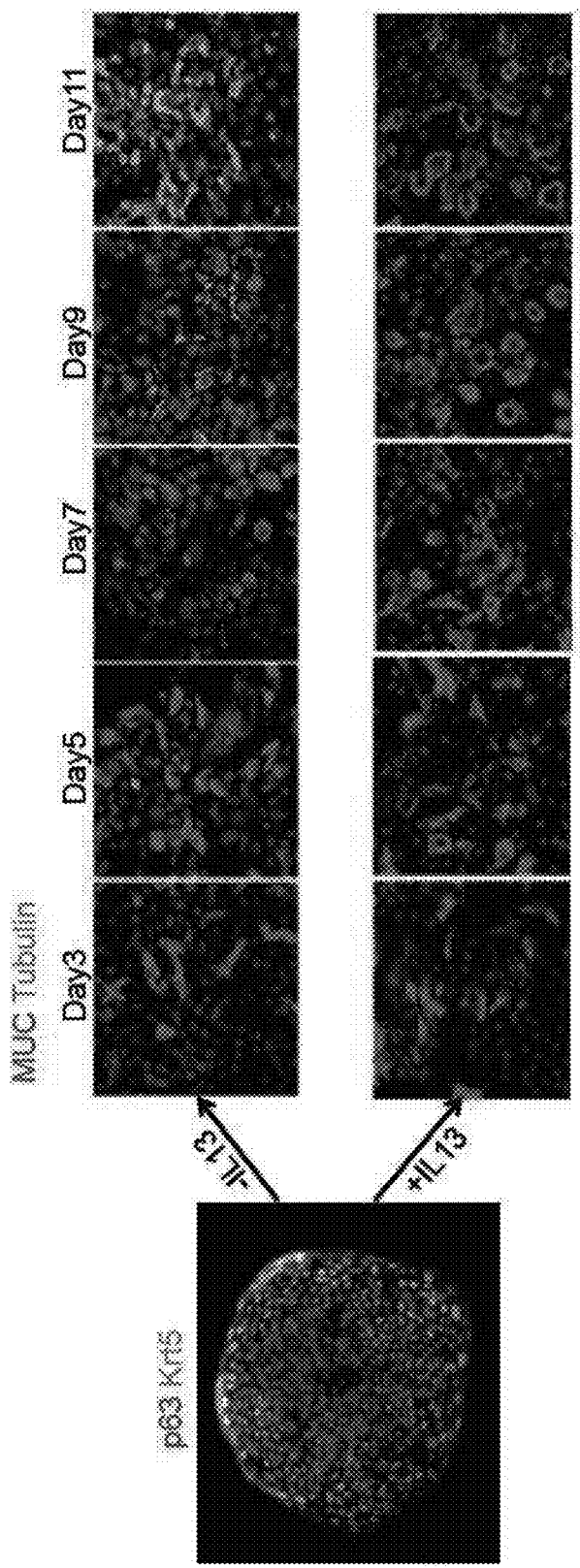
FIG. 8 shows that treatment of the differentiating upper airway stem cells in the air-liquid interface by the pro-inflammatory cytokine IL-13 blocks ciliated cell differentiation and leads to goblet cell hypertrophy. Cloned upper airway stem cells were seeded and grown to a monolayer on filters in an ALI apparatus and then exposed to air on day 0 with and without IL-13. Samples at different time points following the treatment were collected for both imaging and RNA extraction. Matching untreated samples at the same time points were used as controls. Without IL-13 in the medium, the upper airway stem cells properly differentiate into goblet cells and ciliated cells. See patterns of tubulin and MUC marker expression pattern (cf.
Figure 9:
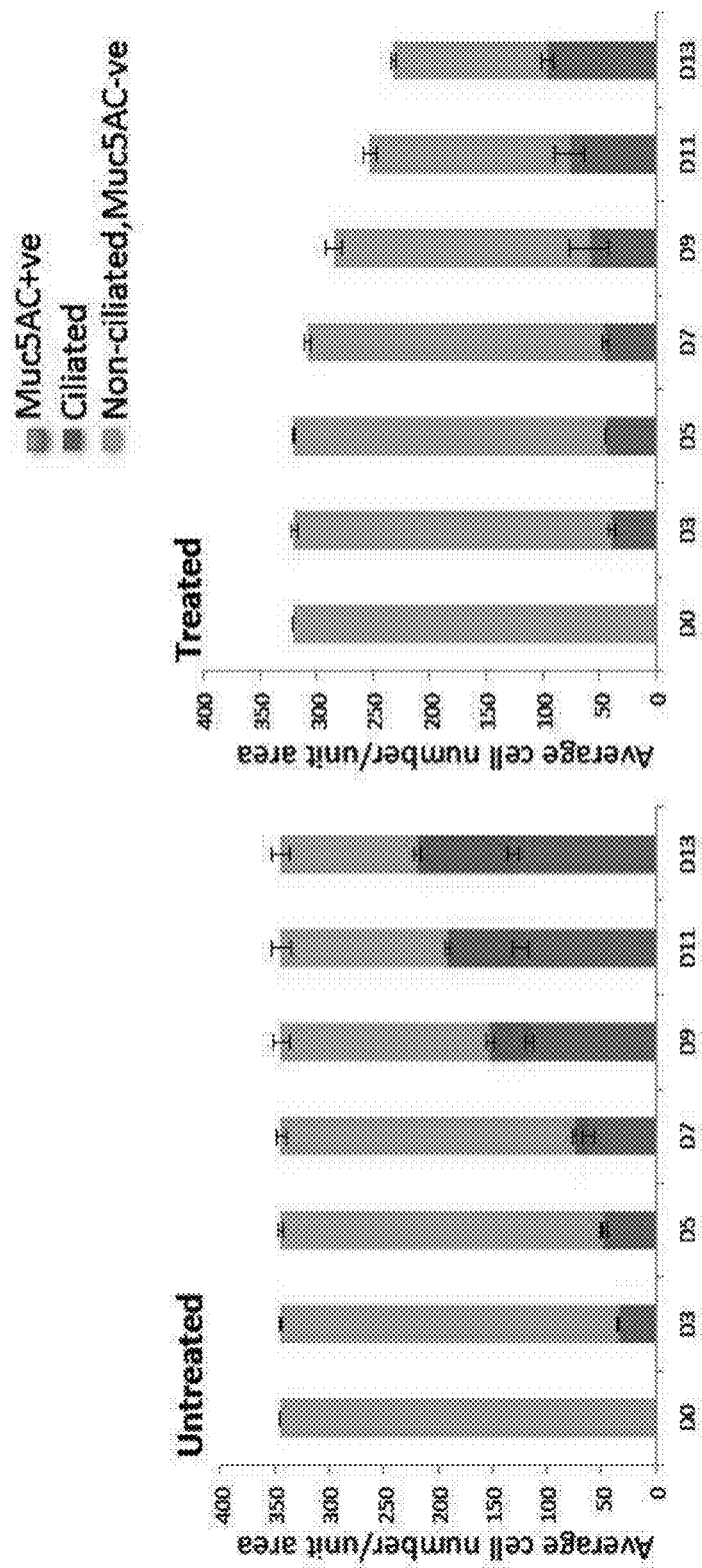
FIG. 9 shows quantification of the IL-13 induced inhibition of ciliogenesis (missing ciliated cells). Although the number of goblet cells is not significantly reduced following IL-13 treatment, immunofluorescence with anti-mucin antibodies shows the overproduction of mucin in IL-13 treated samples.
Figure 10:
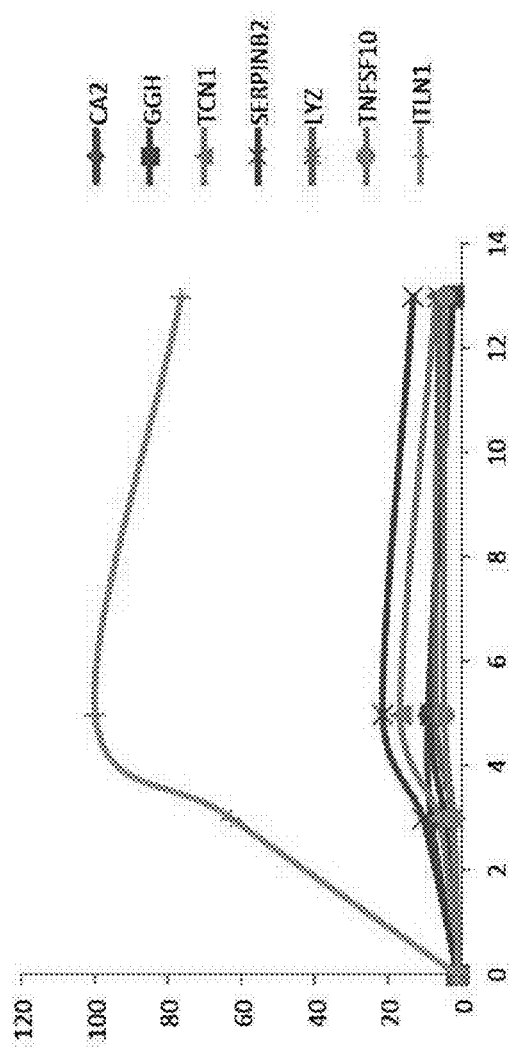
FIG. 10 shows the result of transcriptome analysis for certain IL-13 treated samples. The genes are upregulated initially and then plateau or become downregulated.
Figure 11:
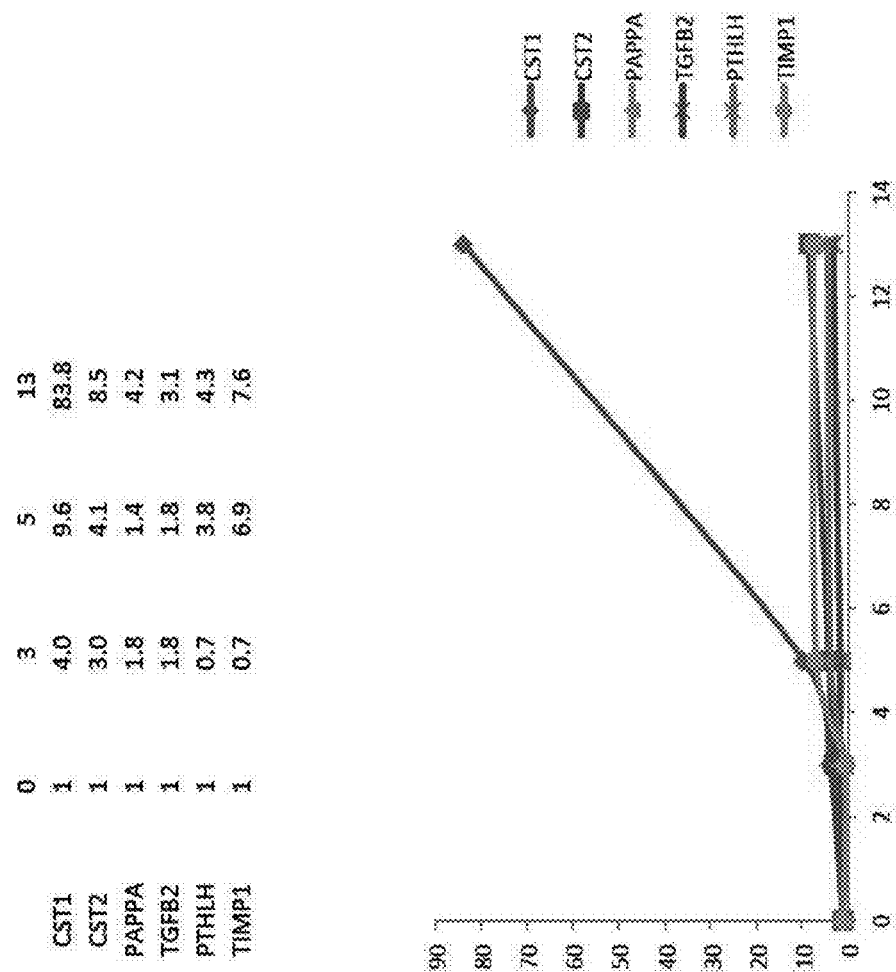
FIG. 11 shows the result of transcriptome analysis for certain IL-13 treated samples.
Figure 12:
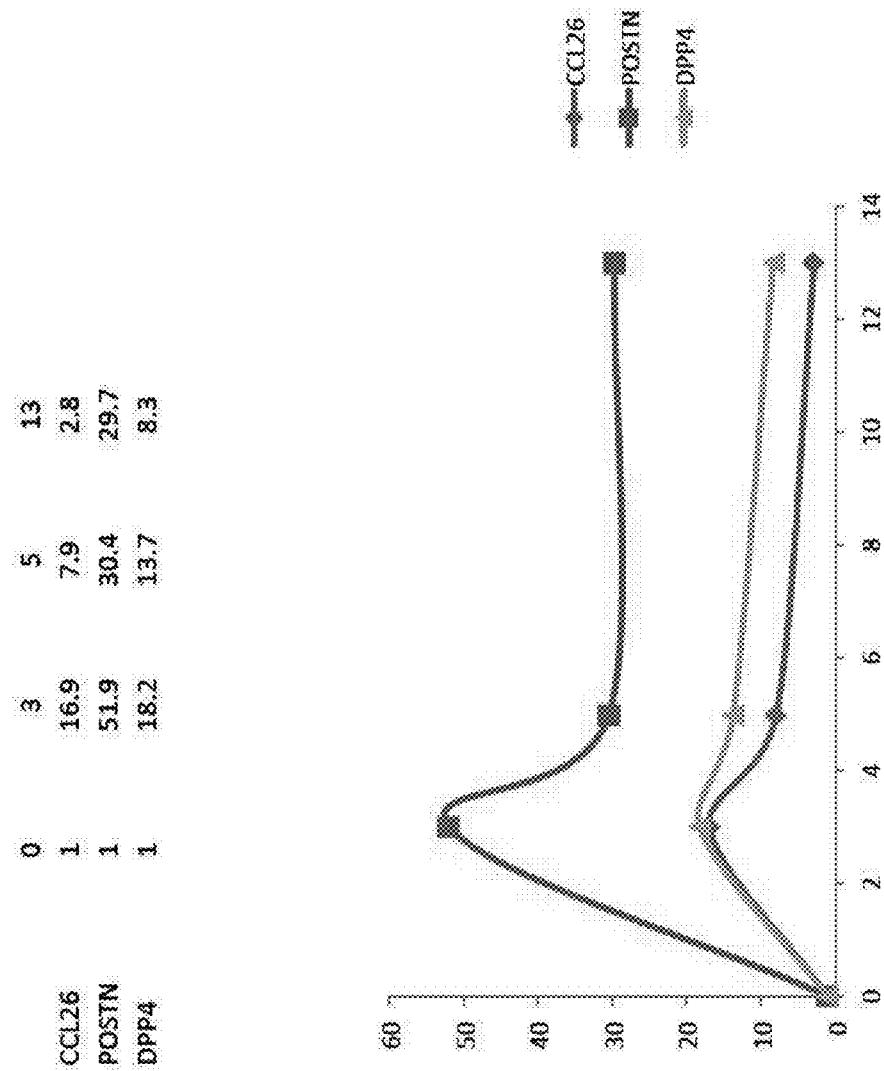
FIG. 12 shows the result of transcriptome analysis for certain IL-13 treated samples. The genes are upregulated at day 3 following IL-13 treatment, and then appear downregulated at day 5.
Figure 13:
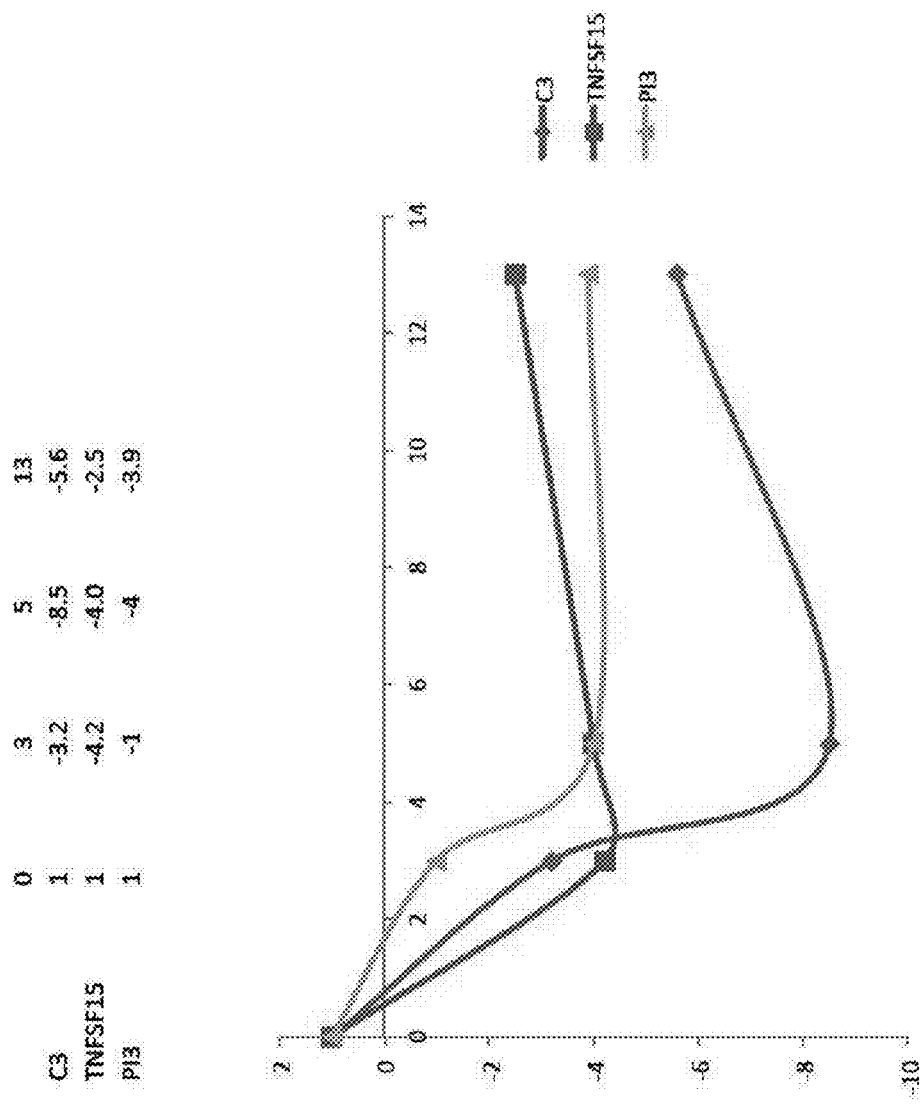
FIG. 13 shows the result of transcriptome analysis for certain IL-13 treated samples. The genes are downregulated following IL-13 treatment, and may function normally to suppress inflammation.
Figure 14:
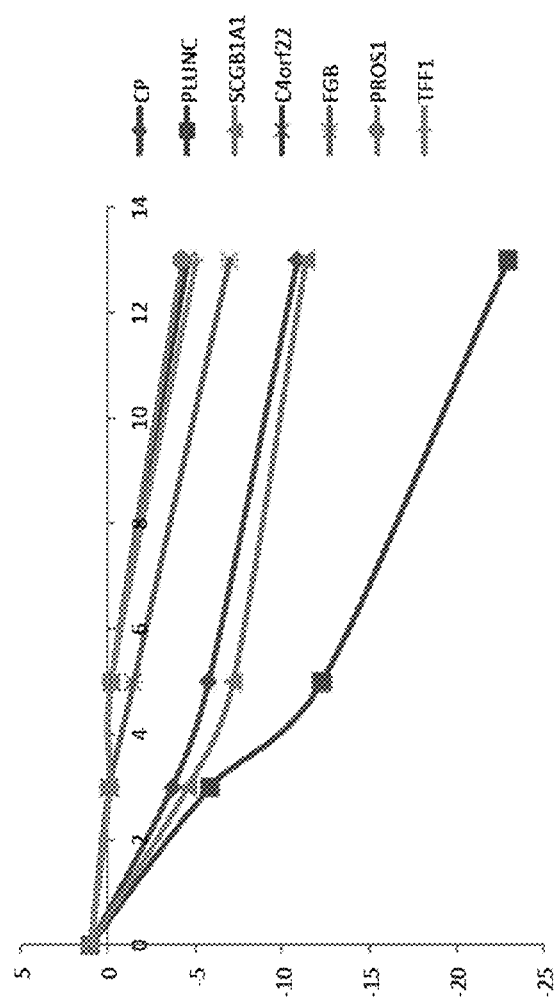
FIG. 14 shows the result of transcriptome analysis for certain IL-13 treated samples. The genes are downregulated following IL-13 treatment, and may function to suppress inflammation.

The invention described herein relates to methods of screening for pro-inflammatory genes and anti-inflammatory genes which may be useful for treating an inflammatory disease, disorder, or otherwise abnormal condition, such as an inflammatory lung disease. The identified pro-inflammatory genes and anti-inflammatory genes may be used to produce pharmaceutical compositions for use in treating the inflammatory disease, disorder, or otherwise abnormal condition.

Thus in one aspect, the invention provides a method of identifying a target gene which may be useful for treating an inflammatory disease, disorder, or otherwise abnormal condition (or simply "an inflammatory disease"), the method comprising: a) providing a population of test cells, wherein: 1) the test cells are a clonal expansion of a single epithelial stem cell capable of propagating for at least about 20 (30, 40, 50, 60, 70, 100, 150, 200, 250, 300, 350, 400 or more) doublings while maintaining a multipotent phenotype; or, 2) the test cells are differentiated from the clonal expansion of the single epithelial stem cell; b) contacting the test cells with a pro-inflammatory cytokine associated with the inflammatory disease; c) identifying one or more genes the expression level of which has been modulated upon contacting the pro-inflammatory cytokine, as compared to that of control test cells not contacted by the pro-inflammatory cytokine, wherein the one or more genes identified in step c) are target gene(s) which may be useful for treating the inflammatory disease, disorder, or otherwise abnormal condition.

As used herein, "inflammatory disease, disorder, or otherwise abnormal condition," may include disorders associated with inflammation or have an inflammation component, such as, but are not limited to: acne vulgaris, asthma, COPD, autoimmune diseases, celiac disease, chronic (plaque) prostatitis, glomerulonephritis, hypersensitivities, inflammatory bowel diseases (IBD, Crohn's disease, ulcerative colitis), pelvic inflammatory disease, reperfusion injury, rheumatoid arthritis, sarcoidosis, transplant rejection, vasculitis, interstitial cystitis, atherosclerosis, allergies (type 1, 2, and 3 hypersensitivity, hay fever), inflammatory myopathies, as systemic sclerosis, and include dermatomyositis, polymyositis, inclusion body myositis, Chediak-Higashi syndrome, chronic granulomatous disease, Vitamin A deficiency, cancer (solid tumor, gallbladder carcinoma), periodontitis, granulomatous inflammation (tuberculosis, leprosy, sarcoidosis, and syphilis), fibrinous inflammation, purulent inflammation, serous inflammation, ulcerative inflammation, and ischaemic heart disease, type I diabetes, and diabetic nephropathy.

In certain embodiments, the inflammatory disease, disorder, or otherwise abnormal condition includes many autoimmune diseases or disorders that are associated with inflammation or have an inflammation component, e.g., corresponding to one or more types of hypersensitivity. Exemplary autoimmune diseases or disorders that correspond to one or more types of hypersensitivity include: atopic allergy, atopic dermatitis, autoimmune hemolytic anemia, autoimmune hepatitis, autoimmune polyendocrine syndrome, autoimmune urticaria, celiac disease, cold agglutinin disease, contact dermatitis, Crohn's disease, diabetes mellitus type 1, discoid lupus erythematosus, Erythroblastosis fetalis, Goodpasture's syndrome, Graves' disease, Guillain-Barré syndrome (GBS), Hashimoto's encephalopathy, Hashimoto's thyroiditis, idiopathic thrombocytopenic purpura, autoimmune thrombocytopenic purpura, IgA nephropathy, lupus erythematosus, Ménière's disease, multiple sclerosis, myasthenia gravis, narcolepsy, neuromyelitis optica, Devic's disease, neuromyotonia, ocular cicatricial pemphigoid, opsoclonus myoclonus syndrome, PANDAS (pediatric autoimmune neuropsychiatric disorders associated with *streptococcus*), paraneoplastic cerebellar degeneration, pemphigus vulgaris, pernicious anaemia, psoriasis, psoriatic arthritis, rheumatoid arthritis, rheumatic fever, sarcoidosis, scleroderma, subacute bacterial endocarditis (SBE), systemic lupus erythematosis, Lupus erythematosis, temporal arteritis (also known as "giant cell arteritis"), thrombocytopenia, ulcerative colitis, undifferentiated connective tissue disease, urticarial vasculitis, and vasculitis.

Inflammatory disease, disorder, or otherwise abnormal condition in liver may include cirrhosis, liver cancer, and acute or chronic hepatitis caused by viral infection (e.g., by HAV, HBV, HCV, HDV, HEV, HFV, and HGV), alcoholic hepatitis, drug or chemical intoxication (such as carbontetrachloride, amethopterin, tetracycline, acetaminophen, fenoprofen, etc.), mononucleosis, amebic dysentery, and other systematic infections by EBV, CMV, or bacteria.

Inflammatory disease, disorder, or otherwise abnormal condition in kidney may be associated with acute or chronic nephritis, interstitial nephritis, lupus nephritis, IgA nephropathy (Berger's disease), glomerulonephritis, membranoproliferative glomerulonephritis (MPGN), autoimmune disorders related to CKD and inflammation, Goodpasture's syndrome, Wegener's granulomatosis, pyelonephritis, athletic nephritis, kidney stones, and gout.

Inflammatory bowel disease (IBD) is a group of inflammatory conditions of the colon and small intestine. The major types of IBD are Crohn's disease and ulcerative colitis. Other forms of IBD, which are not always classified as typical IBD, include collagenous colitis, lymphocytic colitis, ischaemic colitis, diversion colitis, Behçet's disease, and indeterminate colitis.

Inflammatory disease, disorder, or otherwise abnormal condition in pancreas includes various forms of pancreatitis with a variety of causes and symptoms, including pancreatitis caused by gallstone, medication (e.g., use of corticosteroids such as prednisolone, HIV drugs such as didanosine and pentamidine, diuretics, the anticonvulsant valproic acid, the chemotherapeutic agents L-asparaginase and azathioprine, estrogen by way of increased blood triglycerides, cholesterol-lowering statins, and the antihyperglycemic agents like metformin, vildagliptin, sitagliptin, and diabetes drug gliptins), trauma, mumps, autoimmune disease, scorpion stings, high blood calcium, high blood triglycerides, hypothermia, endoscopic retrograde cholangiopancreatography (ERCP), Pancreas divisum, pregnancy, diabetes mellitus type 2, pancreatic cancer, pancreatic duct stones, vasculitis (inflammation of the small blood vessels in the pancreas), coxsackievirus infection, and *porphyria*—particularly acute intermittent *porphyria* and erythropoietic protoporphyria, viral infection (by coxsackie virus, cytomegalovirus, Hepatitis B, herpes simplex virus, mumps, varicella-zoster virus), bacterial infection (*Legionella, Leptospira, Mycoplasma, Salmonella*), fungal infection (*Aspergillus*), or parasitic infection (*Ascaris, Cryptosporidium, Toxoplasma*).

A salient feature of the screening methods of the invention is that the test cells used for the methods are either (1) adult stem cells that are a clonal expansion of a single epithelial stem cell capable of propagating for at least about 20 (30, 40, 50, 60, 70, 100, 150, 200, 250, 300, 350, 400 or more) doublings while maintaining a multipotent phenotype; or (2) cells differentiated from the clonal expansion of the single epithelial stem cell.

As used herein, a "multipotent phenotype" includes one or more or all of the following characteristics selected from: having an immature morphology characterized by small round cell shape and/or high nuclear/cytoplasm ratio; lacking the expression (RNA or protein expression) of one or more marker genes specific for a differentiated cell type that, for example, normally resides in the tissue or organ from which the stem cell is isolated; capable of differentiating into one or more differentiated cell types that normally resides in the tissue or organ from which the stem cell is isolated. Such differentiated cell types may be characterized or identified by the expression (RNA or protein expression) of one or more marker genes specific for the differentiated cell type, or a cellular morphology or multi-cellular structure characteristic of or resembling the tissue or organ from which the stem cell is isolated.

Methods of isolating adult stem cells have been described in detail in a co-pending, co-owned application filed on the same day (Mar. 15, 2013), entitled "Isolation of Non-Embryonic Stem Cells and Uses Thereof," as U.S. Provisional Application No. 61/792,027 (incorporated herein by reference). An exemplary adult stem cell isolation method is described in Section 2 below (Isolation of Adult Stem Cells).

Adult stem cells can be isolated from any animal tissue or organ containing such stem cells, including tissues from human, non-human mammal, non-human primate, rodent (including but not limited to mouse, rat, hamster, guinea pig, rabbit), livestock animals (including but not limited to pig, cattle, sheep, goat, horse, camel), companion animals, bird, reptile, fish, or other vertebrates, etc.

The tissue or organ may be obtained from or originates in any parts of the animal, including but not limited to lung, stomach, small intestine, colon, intestinal metaplasia, fallopian tube, kidney, pancreas, bladder, esophagus, or liver, or a portion/section thereof.

In certain embodiments, the adult tissue or organ is obtained from a tissue comprising epithelial tissue. In certain embodiments, the adult tissue is obtained from gastrointestinal (GI) tract.

In certain embodiments, the single epithelial stem cell is isolated from upper airway of the respiratory system, small intestine, or colon.

In certain embodiments, the adult tissue or organ is obtained from a portion of a tissue or organ. For example, the adult tissue or organ may be isolated from the duodenum portion of the small intestine, or the jejunum portion of the small intestine, or the ileum portion of the small intestine. The adult tissue or organ may also be isolated from the cecum portion of the large intestine, or the colon portion of the large intestine, or the rectum portion of the large intestine. The adult tissue or organ may be isolated from the greater curvature, the lesser curvature, the angular incisure, the cardia, the body, the fundus, the pylorus, the pyloric antrum, or the pyloric canal of the stomach. The adult tissue or organ may further be isolated from the upper airway, or the distal airway of the lung.

In certain embodiments, the adult tissue or organ is isolated from a healthy or normal individual.

In certain embodiments, the adult tissue or organ is isolated from an individual affected by an inflammatory disease, disorder, or otherwise abnormal condition, e.g., asthma or COPD.

In certain embodiments, the adult tissue or organ is isolated from an individual having an inflammatory disease, disorder, or otherwise abnormal condition, although the adult tissue or organ itself may not have been inflicted with the disease, disorder, or abnormal condition. In certain embodiments, the adult tissue or organ may be nearby or distant from the disease, disorder, or abnormal tissue.

In certain embodiments, the adult tissue or organ is isolated from an individual pre-disposed to develop a disease, disorder, or otherwise abnormal condition, or in high risk of developing the disease, disorder, or otherwise abnormal condition, based on, for example, genetic composition, family history, life style choice (e.g., smoking, diet, exercise habit) of the individual, although the individual has not yet developed the disease, disorder, or otherwise abnormal condition, or displayed a detectable symptom of the disease, disorder, or otherwise abnormal condition.

The adult stem cells so isolated are capable of self-renewal, as partly evidenced by the fact that they can propagate in vitro essentially indefinitely, such as being capable of propagating for at least about 20 (30, 40, 50, 60, 70, 100, 150, 200, 250, 300, 350, 400 or more) doublings while maintaining a multipotent phenotype.

The adult stem cells so isolated are also pluripotent, as partly evidenced by the fact that they are capable of differentiating into multiple differentiated cells normally found within the tissue or organ from which such stem cells are isolated.

For example, in certain embodiments, the test cells are upper airway epithelial cells differentiated in air-liquid interface (ALI) cultures. The test cells so differentiated may comprise goblet cells and ciliated cells, each expressing unique markers that can be distinguished via immunofluorescent staining (IF).

In certain embodiments, in the ALI culture, stem cells (such as the upper airway stem cells) are differentiated in contact with a fibroblast feeder layer, such as the 3T3-J2 feeder layer. It appears that such tissue specific epithelial stem cells differentiated in the air-liquid interface while in contact with the feeder layer have greatly enhanced in vitro differentiation.

The adult stem cells so isolated are relatively homogeneous, and are further capable of being genetically manipulated by any of the art recognized molecular biology techniques, such as transfection and infection for modulating the expression of an endogenous gene, or promoting the expression of an exogenous gene. This is partly due to the fact that the isolated adult stem cells can propagate as a substantially pure clone, in which all cells within a clonal expansion originates from a single isolated stem cell, and at least about 40%, 50%, 60%, 70%, 80%, 90% or more cells within the clonal expansion maintains the self-renewal and multipotent phenotype of the original single stem cell, and can be passaged indefinitely in vitro.

These pure clones could be derived from multiple patients with a particular disease (such as asthma or COPD), and subjected to genomic analysis to stratify them with regards to mutations or gene alleles that would identify disease subsets of particular value in screening and ascertaining utility of a given anti-disease (e.g., anti-asthma) drug.

Regardless of the identity of the test cell, in certain embodiments, one step of the screening methods of the invention comprises contacting the test cells with a pro-inflammatory cytokine associated with the inflammatory disease.

As used herein, "associated with the inflammatory disease" refers to the situation that the pro-inflammatory cytokine is known to cause the inflammatory disease, disorder, or otherwise abnormal condition, exacerbates at least one symptom of the inflammatory disease, disorder, or otherwise abnormal condition, or is known to be overexpressed in the inflammatory disease, disorder, or otherwise abnormal condition.

The screening methods of the invention is applicable for any pro-inflammatory cytokine, including pro-inflammatory cytokine that is a T-helper 2 cytokine (such as IL-4, IL-5, IL-6, IL-10, IL-13), or TNFα, IL-8, IL-10, IL-11, IL-17 (IL-17A, IL-17B, IL-17C, IL-17D, IL-17E, IL-17F), IL-1 family (IL-1α, IL-1β, IL-18, IL-33, IL-36α, IL-36β, IL-36γ).

In certain embodiments, the pro-inflammatory cytokine is IL-13. In certain embodiments, the pro-inflammatory cytokine is TNFα.

In certain embodiments, one step of the method comprises identifying one or more genes the expression level of which has been modulated (e.g., increased or decreased) upon contacting the pro-inflammatory cytokine, as compared to that of control test cells not contacted by the pro-inflammatory cytokine, wherein the one or more genes identified in step c) are target gene(s) which may be useful for treating the inflammatory disease.

Numerous art-recognized methods can be used to detect and/or quantitate level of gene expression, such as by Northern blot, Southern blot, immunofluorescent staining, immunohistochemistry (IHC), etc.

In certain embodiments, gene expression level is determined by quantitating mRNA expression, such as by microarray or real-time PCR or RNA-Seq.

A DNA microarray (also commonly known as DNA chip or biochip) is a collection of microscopic DNA spots attached to a solid surface, and can be used to measure the expression levels of large numbers of genes simultaneously or to genotype multiple regions of a genome. Each DNA spot contains picomoles ($10^{-12}$ moles) of a specific DNA sequence or probes that hybridizes to a target cDNA or cRNA (also called anti-sense RNA) sample under high-stringency conditions. Probe-target hybridization is usually detected and quantified by detection of fluorophore-, silver-, or chemiluminescence-labeled targets to determine relative abundance of nucleic acid sequences in the target.

Microarray and real time PCR apparatus suitable for the screening methods of the invention are commercially available, including the ones used in the examples hereinbelow.

A real-time PCR instrument is a machine that amplifies and detects DNA by combining the functions of a thermal cycler with a fluorometer, thus enabling the process of real-time PCR. The first real-time PCR machine was described in 1992 (Higuchi et al., "Simultaneous amplification and detection of specific DNA sequences," *Biotechnology* (NY) 10(4):413-417, 1992), and commercial models became available in 1996. To date, numerous different real time PCR models are offered by many different manufacturers and are readily available.

RNA-seq is described, for example, in Ryan et al. 2008, *Biotechniques* 45:81-94; Wang et al., 2009, *Nature Rev. Genet.* 10:57-63; Maher et al. 2009, *Nature* 458:97-101; which are incorporated by reference herein in their entireties.

In certain embodiments, the expression level of the target gene is increased or decreased by at least 2-fold, 3-fold, 5-fold, 10-fold, 20-fold, 50-fold, 100-fold or more compared to that of the control test cells.

In certain embodiments, step c) of the screening methods of the invention comprises identifying one or more genes the expression level of which is decreased upon contacting the pro-inflammatory cytokine. Such genes are potential anti-inflammatory genes, and may be useful as encoding protein-based therapeutic agent for treating inflammatory disease, disorder, or otherwise abnormal conditions.

In certain embodiments, the method further comprises: d) determining the effect of contacting a second population of test cells with both the pro-inflammatory cytokine and gene expression products of the one or more genes, wherein the one or more genes are identified as anti-inflammatory if at least one inflammatory phenotype induced by the pro-inflammatory cytokine is alleviated.

According to this embodiment of the invention, the role of the potential anti-inflammatory genes is further verified or validated by determining whether the presence of a gene product of the anti-inflammatory gene antagonizes the function of the pro-inflammatory cytokine, by alleviating at least one inflammatory phenotype induced by the pro-inflammatory cytokine.

For example, in certain embodiments, the test cells are a clonal expansion of a single upper airway epithelial stem cell, or are upper airway epithelial cells differentiated therefrom, and wherein the at least one inflammatory phenotype comprises goblet cell hyperplasia, goblet cell hypertrophy, and/or ciliated cell deciliation (e.g., the step determines whether at least one inflammatory phenotype, such as goblet cell hyperplasia, goblet cell hypertrophy, and/or ciliated cell deciliation, is alleviated due to the presence of the anti-inflammatory gene product.

In certain embodiments, in step d), the second population of test cells may be contacted by the pro-inflammatory cytokine and the gene expression products of the one or more genes substantially simultaneously. According to this embodiment, an anti-inflammatory gene identified by the screening methods of the invention may be able to prevent or inhibit the development of an adverse inflammatory phenotype resulting from contacting the test cells with the pro-inflammatory cytokine.

In certain embodiments, in step d), the second population of test cells are first contacted by the pro-inflammatory cytokine to produce at least one inflammatory phenotype, before being contacted by the gene expression products of the one or more genes. According to this embodiment, an anti-inflammatory gene identified by the screening methods of the invention may be able to reverse an already developed adverse inflammatory phenotype resulting from contacting the test cells with the pro-inflammatory cytokine.

In certain embodiments, step c) of the screening methods of the invention comprises identifying one or more genes the expression level of which is increased upon contacting the pro-inflammatory cytokine. Such genes are potential pro-inflammatory genes, and may be useful as therapeutic target Inhibiting the function of such therapeutic target or pro-inflammatory genes may be achieved by, for example, various RNA based antagonistic methods such as antisense, RNAi, or ribozyme.

For example, in one embodiment, the screening methods of the invention may further comprise: d) contacting a second population of test cells with the pro-inflammatory cytokine, and determining the effect thereon of inhibiting a function of the one or more genes, wherein the one or more genes are identified as pro-inflammatory if at least one inflammatory phenotype induced by the pro-inflammatory cytokine is alleviated.

While not wishing to be bound by any particular theory, the identified pro-inflammatory gene may function downstream of the pro-inflammatory cytokine, but upstream of a number of other inflammatory events that can be blocked if the activity of the identified pro-inflammatory gene is inhibited. Thus this embodiment of the invention may further validate or verify the role of the identified pro-inflammatory genes in the inflammatory disease, disorder, or otherwise abnormal condition.

In another related embodiment, the screening methods of the invention may further comprise: d) determining the effect of stimulating a function of the one or more genes in a second population of test cells, either in the presence or absence of the pro-inflammatory cytokine, wherein the one or more genes are identified as pro-inflammatory if at least one inflammatory phenotype is induced or enhanced in the test cells.

While not wishing to be bound by any particular theory, the identified pro-inflammatory gene may function upstream of a number of other inflammatory events, which can be stimulated by activation of the pro-inflammatory gene, either in the presence or absence of the pro-inflammatory cytokine. Thus this embodiment of the invention may also validate or verify the role of the identified pro-inflammatory genes in the inflammatory disease, disorder, or otherwise abnormal condition.

For example, the test cells may be a clonal expansion of a single upper airway epithelial stem cell, or are upper airway epithelial cells differentiated therefrom, and wherein the at least one inflammatory phenotype comprises goblet cell hyperplasia, goblet cell hypertrophy, and/or ciliated cell deciliation.

Another aspect of the invention provides a method of identifying a target gene which may be useful for treating an inflammatory disease, disorder, or otherwise abnormal condition, the method comprising: a) carrying out any one of the screening methods of the invention in more than one subject, each having the inflammatory disease, in order to identify for each subject a collection of pro-inflammatory genes or anti-inflammatory genes which may be useful for treating the inflammatory disease; b) identifying one or more genes commonly identified in two or more subjects; thereby identifying the target gene which may be useful for treating the inflammatory disease.

According to this aspect of the invention, although two or more individuals may have apparently the same inflammatory disease, disorder, or otherwise abnormal condition, the pro-inflammatory genes and anti-inflammatory genes identified by the screening methods of the invention may be different from individual to individual. While not wishing to be bound by any particular theory, it is possible that the identified pro-inflammatory genes and anti-inflammatory genes could be partly affected by the genetic composition, gender, age, race, ethnic background, disease severity or stage, or other complications of each individual. Therefore, by identifying the common pro-inflammatory genes and anti-inflammatory genes, it is more likely that the therapeutic compositions derived therefrom may be generally applicable for the general patient population apparently having the same inflammatory disease, disorder, or otherwise abnormal condition.

In certain embodiments, the method comprises selecting individuals that are matched in one or more of: genetic composition, gender, age, race, ethnic background, disease severity or stage, or other complications.

On the other hand, however, by identifying pro-inflammatory genes and anti-inflammatory genes unique to each individual patient, it is more likely that the therapeutic compositions derived therefrom is tailored to the unique disease in a specific patient, and may be better suited to be personalized medicine for the individual involved.

The other embodiments for this aspect of the invention are identical or similar to the embodiments described in the other aspects (such as the screening methods of the invention), and will not be repeated here.

Another aspect of the invention provides a method of identifying a compound that is potentially useful for treating an inflammatory disease, disorder, or otherwise abnormal condition in a subject, the method comprising: a) providing a population of test cells, wherein: 1) the test cells are a clonal expansion of a single epithelial stem cell isolated from the subject, wherein the single epithelial stem cell is capable of propagating for at least about 20 (30, 40, 50, 60, 70, 100, 150, 200, 250, 300, 350, or 400 or more) doublings while maintaining a multipotent phenotype; or, 2) the test cells are differentiated from the clonal expansion of the single epithelial stem cell; b) contacting the test cells with a pro-inflammatory cytokine associated with the inflammatory disease; c) contacting the test cells with a candidate compound or a control; and, d) identifying the candidate compound that antagonizes a function of the pro-inflammatory cytokine; thereby identifying the compound that is potentially useful for treating the inflammatory disease or condition in the subject.

According to this aspect of the invention, compounds as potential drugs for treating the inflammatory disease, disorder, or otherwise abnormal condition can be identified for each individual patient in need of treatment, resulting in personalized medicine tailored to treat a specific disease in a specific patient.

In a related embodiment, genomic sequencing of cloned stem cells from individual patients may reveal driving mutations that cause the diseases within each patient, thus providing target genes for personalized remedial treatment. Certain patients with specific genetic mutations might be particularly susceptible to one drug. For instance, different mutations that drive asthma (e.g., mutations that cause loss-of-function of any one of the identified anti-inflammatory genes) may be identified in individual patients, thus allowing specific treatment of specific patients based on their specific genotypes, e.g., delivering a protein or polynucleotide based therapeutic agent that specifically compensates or corrects the genetic defect in that patient.

In certain embodiments, the single epithelial stem cell is isolated from a tissue or organ affected by the inflammatory disease or condition, or from a tissue or organ in close proximity to the tissue or organ affected by the inflammatory disease or condition.

In certain embodiments, the subject has asthma or COPD, or is predisposed to have asthma or COPD.

Any candidate compounds may be used in the drug screening method of the invention. Representative compounds may include, without limitation, a small molecule with a molecular weight of less than about 500 Da or 1000 Da, a peptide, a protein, a polynucleotide (antisense, siRNA, miRNA, shRNA, ribozyme, or polynucleotide encoding the same), a lipid, a sterol, or a polysaccharide.

In certain embodiments, the candidate compound is a drug known to be effective in treating the inflammatory disease or condition. This, for example, allows the identification of the best therapeutic agent for an individual, from amongst a collection of therapeutic agents known to be effective to treat the inflammatory disease, disorder, or otherwise abnormal condition in the general population.

In certain embodiments, step b) is carried out before step c), and wherein the test cells exhibit a phenotype in response to being contacted by the pro-inflammatory cytokine prior to step c). Compound identified according to this embodiment may be able to reverse or rescue an adverse phenotype caused by the pro-inflammatory cytokine.

In certain embodiments, step b) is carried out substantially simultaneously with step c). In certain embodiments, step b) is carried out after step c). Compound identified according to this embodiment may be able to prevent or delay the development of an adverse phenotype caused by the pro-inflammatory cytokine.

In certain embodiments, in step d), the candidate compound antagonizes the function of the pro-inflammatory cytokine by alleviating a phenotype of the test cells in response to being contacted by the pro-inflammatory cytokine.

In certain embodiments, the phenotype may be increased expression of a pro-inflammatory gene (such as any one listed in Tables 3 and 4), or decreased expression of an anti-inflammatory gene (such as any one listed in Tables 1 and 2).

The other embodiments for this aspect of the invention are identical or similar to the embodiments described in the other aspects (such as the screening methods of the invention), and will not be repeated here.

Another aspect of the invention provides a pharmaceutical composition for treating an inflammatory disease (e.g., inflammatory lung disease), comprising: a) a protein or a polypeptide or a functional portion thereof encoded by an anti-inflammatory gene selected from ABI3BP, AMTN, APOD, BMP8A, C3, CP, GLIPR1, FN1, IGFBP3, IGFBP6, LGALS1, LTBP1, MSMB, OLFM4, PLUNC, PPBP, SERPINA3, and TNFSF15, or b) an antagonist of a pro-inflammatory gene selected from: AGR2, ANG, C20orf114, CA2, CCL26, CD200R1, CST1, CST2, DEFB118, DPP4, EPGN, FETUB, GGH, ITLN1, KITLG, PLA2G7, PDCD1LG2, POSTN, PTHLH, SAA4, SERPINB2, SMPDL3B, SPINK5, ST6GAL1, STATH, SULF1, TCN1, TFF1, TIMP1, TMPRSS2, TNFSF10, CCL2, and IL-1A, and, one or more pharmaceutically acceptable excipients, stabilizers or preservatives.

In certain embodiments, the antagonist comprises an RNAi agent (siRNA, miRNA, shRNA), an antisense sequence, a ribozyme, or a polynucleotide encoding the RNAi agent, the antisense sequence, or the ribozyme.

In certain embodiments, the antagonist comprises an antibody specific for a protein or polypeptide encoded by the pro-inflammatory gene.

The other embodiments for this aspect of the invention are identical or similar to the embodiments described in the other aspects (such as the screening methods of the invention), and will not be repeated here.

Another aspect of the invention provides a pharmaceutical composition for treating an inflammatory disease (e.g., inflammatory lung disease), comprising an agent which induces the expression of any of the anti-inflammatory genes of the invention, or which mimics the activity of the gene product of any of the anti-inflammatory gene of the invention, further comprising one or more pharmaceutically acceptable excipients, stabilizers or preservatives.

The other embodiments for this aspect of the invention are identical or similar to the embodiments described in the other aspects (such as the screening methods of the invention), and will not be repeated here.

Another aspect of the invention provides a method of treating a subject having an inflammatory disease, disorder, or otherwise abnormal condition (e.g., inflammatory lung disease, such as asthma or COPD), the method comprising: a) inhibiting in the subject the function of one or more genes identified as pro-inflammatory according to the screening methods of the invention; or b) stimulating in the subject the function of one or more genes identified as anti-inflammatory according to the screening methods of the invention.

For example, the function of the one or more genes identified as pro-inflammatory can be inhibited by antisense, RNAi (siRNA, miRNA, shRNA etc.), antibody, or dominant negative antagonist thereof.

In certain embodiments, the function of the one or more genes identified as anti-inflammatory can be stimulated by administering a gene product of (e.g., a protein or polypeptide or a functional portion thereof encoded by) the one or more genes identified as anti-inflammatory. For example, the protein or polypeptide may comprise: ABI3BP, AMTN, APOD, BMP8A, C3, CP, GLIPR1, FN1, IGFBP3, IGFBP6, LGALS1, LTBP1, MSMB, OLFM4, PLUNC, PPBP, SERPINA3, and TNFSF15.

In certain embodiments, the function of the one or more genes identified as anti-inflammatory can be stimulated by exogenously expressing the one or more genes identified as anti-inflammatory.

In certain embodiments, the inflammatory disease, disorder, or otherwise abnormal condition is an inflammatory lung disease selected from: asthma (e.g., acute inflammatory asthma, allergic asthma, iatrogenic asthma), COPD, pulmonary hypertension, neonatal pulmonary hypertension, neonatal bronchopulmonary dysplasia, chronic obstructive pulmonary disease, acute bronchitis, chronic bronchitis, emphysema, bronchiolitis, bronchiectasis, radiation pneumonitis, hypersensitivity, pneumonitis, acute smoke inhalation, thermal lung injury, cystic fibrosis, alveolar proteinosis, alpha-I-protease deficiency, pulmonary inflammatory disorders, pneumonia, acute respiratory distress syndrome, acute lung injury, idiopathic respiratory distress syndrome, or idiopathic pulmonary fibrosis.

In certain embodiments, the inflammatory disease, disorder, or otherwise abnormal condition may include disorders associated with inflammation or have an inflammation component, such as, but are not limited to: acne vulgaris, asthma, COPD, autoimmune diseases, celiac disease, chronic (plaque) prostatitis, glomerulonephritis, hypersensitivities, inflammatory bowel diseases (IBD, Crohn's disease, ulcerative colitis), pelvic inflammatory disease, reperfusion injury, rheumatoid arthritis, sarcoidosis, transplant rejection, vasculitis, interstitial cystitis, atherosclerosis, allergies (type 1, 2, and 3 hypersensitivity, hay fever), inflammatory myopathies, as systemic sclerosis, and include dermatomyositis, polymyositis, inclusion body myositis, Chediak-Higashi syndrome, chronic granulomatous disease, Vitamin A deficiency, cancer (solid tumor, gallbladder carcinoma), periodontitis, Granulomatous inflammation (tuberculosis, leprosy, sarcoidosis, and syphilis), fibrinous inflammation, purulent inflammation, serous inflammation, ulcerative inflammation, and ischaemic heart disease, type I diabetes, and diabetic nephropathy.

In certain embodiments, the inflammatory disease, disorder, or otherwise abnormal condition includes many autoimmune diseases or disorders that are associated with inflammation or have an inflammation component, e.g., corresponding to one or more types of hypersensitivity. Exemplary autoimmune diseases or disorders that correspond to one or more types of hypersensitivity include: atopic allergy, atopic dermatitis, autoimmune hemolytic anemia, autoimmune hepatitis, autoimmune polyendocrine syndrome, autoimmune urticaria, celiac disease, cold agglutinin disease, contact dermatitis, Crohn's disease, diabetes mellitus type 1, discoid lupus erythematosus, Erythroblastosis fetalis, Goodpasture's syndrome, Graves' disease, Guillain-Barré syndrome (GBS), Hashimoto's encephalopathy, Hashimoto's thyroiditis, idiopathic thrombocytopenic purpura, autoimmune thrombocytopenic purpura, IgA nephropathy, lupus erythematosus, Ménière's disease, multiple sclerosis, myasthenia gravis, narcolepsy, neuromyelitis optica, Devic's disease, neuromyotonia, ocular cicatricial pemphigoid, opsoclonus myoclonus syndrome, PANDAS (pediatric autoimmune neuropsychiatric disorders associated with *streptococcus*), paraneoplastic cerebellar degeneration, pemphigus vulgaris, pernicious anaemia, psoriasis, psoriatic arthritis, rheumatoid arthritis, rheumatic fever, sarcoidosis, scleroderma, subacute bacterial endocarditis (SBE), systemic lupus erythematosis, Lupus erythematosis, temporal arteritis (also known as "giant cell arteritis"), thrombocytopenia, ulcerative colitis, undifferentiated connective tissue disease, urticarial vasculitis, and vasculitis.

In certain embodiments, the method comprises administering a pharmaceutical composition of the invention.

The other embodiments for this aspect of the invention are identical or similar to the embodiments described in the other aspects (such as the screening methods of the invention), and will not be repeated here.

Another aspect of the invention provides a method of identifying a subject suitable for therapeutic intervention, wherein the subject has an inflammatory disease, disorder, or otherwise abnormal condition, or is predisposed to develop the inflammatory disease, disorder, or otherwise abnormal condition, the method comprising: a) using the screening methods of the invention to identify one or more pro-inflammatory genes or one or more anti-inflammatory genes, b) isolating from a candidate subject a single epithelial stem cell capable of propagating at least about 20 (30, 40, 50, 60, 70, 100, 150, 200, 250, 300, 350, 400 or more) doublings while maintaining a multipotent phenotype; c) determining the expression level of the pro-inflammatory genes or the anti-inflammatory genes in the clonal expansion, or in cells differentiated from the clonal expansion, d) identifying subjects having increased expression of the pro-inflammatory genes or having decreased expression of the anti-inflammatory genes compared to normal control, as being suitable for therapeutic intervention.

According to this aspect of the invention, normal expression level of the pro-inflammatory genes and anti-inflammatory genes identified using any of the screening methods of the invention may serve as diagnostic markers. Individuals either having higher than normal pro-inflammatory gene expression or lower than normal anti-inflammatory gene expression may be considered at risk or predisposed to develop the inflammatory disease, disorder, or otherwise abnormal condition, and may be subject to preventive or therapeutic intervention for the inflammatory disease, disorder, or otherwise abnormal condition.

In certain embodiments, the method may further comprise treating subjects identified in step d) according to the subject method of treatment.

The other embodiments for this aspect of the invention are identical or similar to the embodiments described in the other aspects (such as the screening methods of the invention), and will not be repeated here.

Another aspect of the invention provides a method of treating cancer, comprising inhibiting in a subject in need of treatment a function of one or more genes identified as pro-inflammatory according to the screening methods of the invention.

Central to the development of cancer are genetic changes that confer the cancer cells with abilities such as self-sufficient growth and resistance to anti-growth and pro-death signals. However, activated oncogenes or dysfunctional tumor suppressors maybe alone insufficient for tumorigenesis. Tumor promotion and progression are frequently dependent on ancillary processes provided by cells of the tumor environment but that are not necessarily cancerous themselves. For example, inflammation has long been associated with the development of cancer, and plays a role in many physiologic processes, such as the maintenance of tissue homeostasis and repair, that may provide connection between inflammatory and cancer.

Thus, the pro-inflammatory genes identified using the screening methods of the invention may play a key role in inflammation associated with cancer, and, in the case of secreted proteins, may be secreted by cancer cells to facilitate cancer development and progression. Therefore, inhibiting the function of these pro-inflammatory genes may directly or indirectly inhibit cancer growth or progression.

In certain embodiments, the method comprises administering to the subject a pharmaceutical composition comprising an antagonist to the function of the one or more genes identified as pro-inflammatory, wherein the antagonist is an antisense polynucleotide, an RNAi reagent (siRNA, miRNA, shRNA etc.), an antibody, or a dominant negative antagonist thereof.

The other embodiments for this aspect of the invention are identical or similar to the embodiments described in the other aspects (such as the screening methods of the invention), and will not be repeated here.

Another aspect of the invention provides a method of screening for a compound that may be useful for treating an inflammatory disease, disorder, or otherwise abnormal condition in a subject, the method comprising: (1) providing a first population of test cells, wherein: a) the first population of test cells are a clonal expansion of a first single epithelial stem cell isolated from a diseased tissue of the subject, wherein the first single epithelial stem cell is capable of propagating for at least about 20 (30, 40, 50, 60, 70, 100, 150, 200, 250, 300, 350, 400 or more) doublings while maintaining a multipotent phenotype; or, b) the first population of test cells are differentiated from the clonal expansion of the first single epithelial stem cell; (2) providing a second population of test cells, wherein: a) the second population of test cells are a clonal expansion of a second single epithelial stem cell isolated from a matching normal tissue of the subject, wherein the second single epithelial stem cell is capable of propagating for at least about 20 (30, 40, 50, 60, 70, 100, 150, 200, 250, 300, 350, 400 or more) doublings while maintaining a multipotent phenotype; or, b) the second population of test cells are differentiated from the clonal expansion of the second single epithelial stem cell; (3) contacting the first and the second populations of test cells with a candidate therapeutic agent; and, (4) determining and comparing the effects of the candidate therapeutic agent on the first and second population of test cells; wherein the candidate therapeutic agent is identified as the compound that may be useful for treating the inflammatory disease, disorder, or otherwise abnormal condition, if the candidate therapeutic agent alleviates at least one symptom of the first population of test cells, and does not produce an undesirable effect on the second population of test cells.

According to this embodiment of the invention, adult stem cells may be isolated from the diseased and (relatively) normal tissues from the same individual inflicted with an inflammatory disease, disorder, or otherwise abnormal condition. Screening of candidate drug compounds can then be conducted on pedigree cell lines established based on both stem cell lines, in order to identify lead drug compounds that simultaneously alleviates a symptom of the diseased tissue and not causing an undesirable side effect in the relatively normal tissue. Such screens can be used, for example, drug efficacy vs. toxicity, thus identifying a drug that has the highest therapeutic index.

The other embodiments for this aspect of the invention are identical or similar to the embodiments described in the other aspects (such as the screening methods of the invention), and will not be repeated here.

2. Isolation of Adult Stem Cells

Adult stem cells can be isolated according to the methods described herein, or using any of the similar methods described in a co-pending, co-owned application filed on the same day (Mar. 15, 2013), entitled "Isolation of Non-Embryonic Stem Cells and Uses Thereof," as U.S. Provisional Application No. 61/792,027 (incorporated herein by reference).

In certain embodiments, a method for isolating an adult stem cell from an adult tissue, which adult stem cell may be used for the methods of the invention may comprise the following steps: (1) culturing dissociated (cuboidal or columnar) epithelial cells from an adult tissue, in contact with a first population of lethally irradiated feeder cells and a basement membrane matrix, to form epithelial cell clones, in a medium comprising: (a) a Notch agonist; (b) a ROCK (Rho Kinase) inhibitor; (c) a Bone Morphogenetic Protein (BMP) antagonist; (d) a Wnt agonist; (e) a mitogenic growth factor; and, (f) insulin or IGF; the medium optionally further comprising at least one of: (g) a TGFβ signaling pathway inhibitor (e.g., a TGFβ inhibitor or a TGFβ receptor inhibitor); and, (h) nicotinamide or an analog, precursor, or mimic thereof; (2) isolating single cells from the epithelial cell clones, and, (3) culturing isolated single cells from step (2) individually to form single cell clones, in contact with a second population of lethally irradiated feeder cells and a second basement membrane matrix in the medium; wherein each of the single cell clones represents a clonal expansion of the non-embryonic stem cell, thereby isolating the non-embryonic stem cell.

The adult tissue may be obtained from or originates in lung, stomach, small intestine, colon, intestinal metaplasia, fallopian tube, kidney, pancreas, bladder, esophagus, liver, or a portion/section thereof.

The adult tissue may be a disease tissue, a disorder tissue, an abnormal condition tissue, or a tissue from a patient having the disease, disorder, or abnormal condition. For example, the disease, disorder, or abnormal condition may be an autoimmune disease (e.g., those with an inflammation component), and/or an inflammatory disorder or disorder associated with inflammation.

The adult stem cell may be isolated from a human, or any other non-human mammal, non-human primate, rodent, pets, livestock animals, companion animals, amphibians, fish, reptiles, or other domesticated animals.

A suitable feeder cell is the mouse 3T3-J2 cell clone, which is well known in the art (see, for example, Todaro and Green, "Quantitative studies of the growth of mouse embryo cells in culture and their development into established lines," *J. Cell Biol.* 17:299-313, 1963), and is readily available to the public. For example, Waisman Biomanufacturing (Madison, Wis.) sells irradiated 3T3-J2 feeder cells produced and tested according to cGMP guidelines. These cells were originally obtained from Dr. Howard Green's laboratory under a material transfer agreement, and according to the vender, are of the quality sufficient to support, for example, skin gene therapy and wound healing clinical trials. Also according to the vender, each vial of the 3T3 cells contains a minimum of 3×10$^6$ cells that have been manufactured in fully compliant cleanrooms, and are certified *mycoplasma* free and low endotoxin. In addition, the cell bank has been fully tested for adventitious agents, including murine viruses. These cells have been screened for keratinocyte culture support and do not contain mitomycin C.

A suitable the basement membrane matrix is a laminin-containing basement membrane matrix (e.g., MATRIGEL™ basement membrane matrix (BD Biosciences)), preferably growth factor-reduced.

In certain embodiments, the medium further comprises 10% FBS that is not heat inactivated.

In certain embodiments, the Notch agonist comprises Jagged-1.

In certain embodiments, the ROCK inhibitor comprises Rho Kinase Inhibitor VI (Y-27632, (R)-(+)-trans-N-(4-Pyridyl)-4-(1-aminoethyl)-cyclohexanecarboxamide)), Fasudil or HA1071 (5-(1,4-diazepan-1-ylsulfonyl)isoquinoline), or H1152 ((S)-(+)-2-methyl-1-[(4-methyl-5-isoquinolinyl)sulfonyl]-hexahydro-1H-1,4-diazepine dihydrochloride).

In certain embodiments, the BMP antagonist comprises Noggin, DAN, a DAN-like proteins comprising a DAN cysteine-knot domain (e.g., Cerberus and Gremlin), Chordin, a chordin-like protein comprising a chordin domain, Follistatin, a follistatin-related protein comprising a follistatin domain, sclerostin/SOST, decorin, or α-2 macroglobulin.

In certain embodiments, the Wnt agonist comprises R-spondin 1, R-spondin 2, R-spondin 3, R-spondin 4, an R-spondin mimic, a Wnt family protein (e.g., Wnt-3a, Wnt 5, Wnt-6a), Norrin, or a GSK-inhibitor (e.g., CHIR99021).

In certain embodiments, the mitogenic growth factor comprises EGF (and/or Keratinocyte Growth Factor, TGFα, BDNF, HGF, bFGF (e.g., FGF7 or FGF10)).

In certain embodiments, the TGFβ receptor inhibitor comprises SB431542 (4-(4-(benzo[d][1,3]dioxol-5-yl)-5-(pyridin-2-yl)-1H-imidazol-2-yl)benzamide), A83-01, SB-505124, SB-525334, LY 364947, SD-208, or SJN 2511.

In certain embodiments, the TGFβ (signaling) inhibitor binds to and reduces the activity of one or more serine/threonine protein kinases selected from the group consisting of ALK5, ALK4, TGF-beta receptor kinase 1 and ALK7.

In certain embodiments, the TGFβ (signaling) inhibitor is added at a concentration of between 1 nM and 100 μM, between 10 nM and 100 μM, between 100 nM and 10 μM, or approximately 1 μM.

In certain embodiments, a modified growth medium (or simply modified medium) suitable for isolating adult stem cell comprises: 5 μg/mL insulin; 2 nM of (3,3',5-Triiodo-L-Thyronine); 400 ng/mL hydrocortisone; 24.3 μg/mL adenine; 10 ng/mL EGF; 10% fetal bovine serum (without heat inactivation); 1 μM Jagged-1; 100 ng/mL noggin; 125 ng/mL R-spondin 1; 2.5 μM Y-27632; and 1.35 mM L-glutamine in DMEM:F12 3:1 medium, optionally further comprising 0.1 nM cholera enterotoxin.

In certain embodiments, the medium further comprises about 2 μM SB431542.

In certain embodiments, the medium further comprises about 10 mM nicotinamide.

In certain embodiments, the medium further comprises about 2 μM SB431542 and 10 mM nicotinamide.

Methods of using the modified medium to isolate adult stem cells are described in detail in the co-pending co-owned application filed on the same day (Mar. 15, 2013), entitled "Isolation of Non-Embryonic Stem Cells and Uses Thereof," as U.S. Provisional Application No. 61/792,027 (incorporated herein by reference). An illustrative example is also provided herein.

In brief, a human adult tissue (e.g., intestinal biopsy) is enzymatically digested and seeded on the lethally irradiated 3T3-J2 feeder (originally obtained from Prof. Howard Green's laboratory at the Harvard Medical School, Boston, Mass., USA) in the presence of a modified growth medium. The stem cells selectively grow under these conditions and can be passaged indefinitely in vitro.

The day prior to receiving the human tissues, irradiated 3T3-J2 cells are seeded on Matrigel coated plates (BD Matrigel™, Basement Membrane Matrix, Growth Factor Reduced (GFR), cat. no. 354230). For this, the Matrigel is thawed on ice and diluted in cold 3T3-J2 medium at the concentration of 10%. The 3T3-J2 growth medium contains DMEM (Invitrogen cat. no. 11960; high glucose (4.5 g/L), no L-glutamine, no sodium pyruvate), 10% bovine calf serum (not heat inactivated), 1% penicillin-streptomycin and 1% L-glutamine. The tissue culture plates are pre-cooled at −20° C. for 15 min, then diluted Matrigel is added on the cold plates, and the plates are swirled to evenly distribute the diluted Matrigel, then superfluous Matrigel is removed. Subsequently the plates are incubated for 15 min in a 37° C. incubator to allow the Matrigel layer to solidify.

Frozen irradiated 3T3-J2 cells are thawed and plated on the top of the Matrigel in the presence of 3T3-J2 growth medium. The morning after, the 3T3-J2 medium is replaced by basic growth medium (insulin or an insulin-like growth factor; T3 (3,3',5-Triiodo-L-Thyronine); hydrocortisone; adenine; EGF; and 10% fetal bovine serum (without heat inactivation), in DMEM:F12 3:1 medium supplemented with L-glutamine) before being used as feeder layer for human cells. 1 L of basic growth medium contains 675 ml DMEM (Invitrogen cat. no. 11960; high glucose (4.5 g/L), no L-glutamine, no sodium pyruvate), 225 ml F12 (F-12 nutrient mixture (HAM), Invitrogen cat. no. 11765; containing L-glutamine), 100 ml FBS (Hyclone cat. no. SV30014.03; not heat inactivated), 6.75 ml of 200 mM L-glutamine (GIBCO cat. no. 25030), 10 ml adenine (Calbiochem cat. no. 1152; for the stock solution 243 mg of adenine were added to 100 ml of 0.05 M HCl and stirred for about one hour at RT until the solution was dissolved before filter sterilization. The solution can be stored at −20° C. until use), 1 ml of a 5 mg/ml stock solution of insulin (Sigma cat. no. 1-5500), 1 ml of $2\times10^{-6}$ M T3 (3,3',5-Triiodo-L-Thyronine) solution (Sigma cat. no. T-2752; for the stock solution 13.6 mg T3 were dissolved in 15 ml of 0.02N NaOH, and adjusted to 100 ml with phosphate buffered saline (PBS), resulting in a concentrated stock of $2\times10^{-4}$ M, that can be stored at −20° C. 0.1 ml of the concentrated stock are diluted to 10 ml with PBS to create a working stock of $2\times10^{-6}$ M), 2 ml of 200 μg/ml hydrocortisone (Sigma cat. no. H-0888), 1 ml of 10 μg/ml EGF (Upstate Biotechnology cat. no. 01-107), and 10 ml Penicillin-Streptomycin containing 10,000 units of penicillin and 10,000 μg of streptomycin per ml (GIBCO cat. no. 15140).

Human (intestinal, liver, or other) tissue biopsies (transferred from hospital in cold wash buffer on ice) are washed vigorously using 30 ml cold wash buffer (F12: DMEM 1:1; 1.0% penicillin-streptomycin; 0.1% fungizone and 2.5 ml of 100 μg/ml gentamycin) for three times and followed washing once with cold PBS. The biopsy is minced and soaked in digestion medium (BD Cell Recovery Solution cat. no. 354253) and incubated at 4° C. for 8-12 h with gentle shaking. Alternatively, the tissue can be digested using 2 mg/mL collagenase type IV (Gibco, cat. no. 17104-109) and incubated at 37° C. for 1-2 h while gently shaking. The digested tissues are pelleted and washed five times with 30 mL cold wash buffer each. After the final wash, the samples are spun down and resuspended in modified growth medium and seeded on the feeder. The modified growth medium for human adult intestine epithelial stem cells consisted of basic growth medium and the following factors: rock inhibitor (R)-(+)-trans-N-(4-Pyridyl)-4-(1-aminoethyl)-cyclohexanecarboxamide (Y-27632, Rho Kinase Inhibitor VI, Calbiochem, cat. no. 688000) at a working concentration of 2.5 μM; recombinant R-spondin 1 protein (R&D, cat. no. 4645-RS) at a working concentration of 125 ng/ml; recombinant noggin protein (Peprotech, cat. no. 120-10c) at a working concentration of 100 ng/ml; Jagged-1 peptide (188-204) (AnaSpec Inc. cat. no. 61298) at a working concentration of 1 μM; SB431542: 4-(4-(benzo[d][1,3]dioxol-5-yl)-5-(pyridin-2-yl)-1H-imidazol-2-yl)benzamide (Cayman Chemical Company, cat. no. 13031) at a working concentration of 2 μM; nicotinamide (Sigma, cat. no. N0636-100G) at a working concentration of 10 mM. The modified growth medium for human fetal intestine epithelial stem cells consisted of basic growth medium and the following factors: rock inhibitor (R)-(+)-trans-N-(4-Pyridyl)-4-(1-aminoethyl)-cyclohexanecarboxamide (Y-27632, Rho Kinase Inhibitor VI, Calbiochem, cat. no. 688000) at a working concentration of 2.5 μM; recombinant R-spondin 1 protein (R&D, cat. no. 4645-RS) at a working concentration of 125 ng/ml; recombinant noggin protein (Peprotech, cat. no. 120-10c) at a working concentration of 100 ng/ml; Jagged-1 peptide (188-204) (AnaSpec Inc. cat. no. 61298) at a working concentration of 1 μM; nicotinamide (Sigma, cat. no. N0636-100G) at a working concentration of 10 mM. After three to four days the first epithelial cell colonies are detectable. Then cells are trypsinized with warm 0.25% trypsin (Invitrogen, cat. no 25200056) for 10 min, neutralized, resuspended in the modified growth medium, passed through 40 micron cell strainer and seeded as single cells onto a new plate containing a 3T3-J2 feeder layer. The medium is changed every two days. 3 days later, individual clones of adult human epithelial stem cells are observed.

A single colony is then picked using a cloning ring and expanded to develop a pedigree cell line, i.e. a cell line that has been derived from a single cell.

Alternatively, single cells from the dissociated single cell suspension derived from these colonies can be selected using a glass pipette under a microscope and individually transferred to 96 well plates previously coated with 10% Matrigel and seeded with the feeder cells. Once the single cell forms colony in the 96 well plates, the colony can be expanded to develop a pedigree cell line.

More than 70% of the epithelial stem cells in culture are expected to maintain the clonogenic ability. Furthermore, these epithelial stem cells are expected to maintain their ability for self-renewal (e.g., self-propagating virtually indefinitely in vitro), for multipotent differentiation to form differentiated cells or structures.

Detailed descriptions for isolated stem cell differentiation into their respective progeny differentiated cells are known in the art. See, e.g., WO 2010/090513, WO 2012/014076, WO 2012/168930, and WO 2012/044992, all incorporated herein by reference.

For example, the isolated stem cell may be upper airway stem cells capable of differentiating into goblet cells and ciliated cells in an air-liquid interface (ALI) model, which is briefly described below. This model can be used in the screening methods of the invention to identify pro-inflammatory genes and anti-inflammatory genes whose expression level is modulated in response to treatment by a pro-inflammatory cytokine (e.g., IL-13).

Briefly, isolated small intestine stem cells can be differentiated on air-liquid interface (ALI) with collagen and 3T3-J2 insert. About $1\times10^5$ 3 T3-J2 cells are first plated on each well of a Transwell-COL plate (Collagen coated transwell, 24 well plate, Cat. 3495, Corning Inc.). About 700 μL of 3T3 growth Medium is added to the outside chamber of each well, and about 200 μL of 3T3 growth medium (DMEM Invitrogen cat. no. 11960, high glucose (4.5 g/L), no L-glutamine, no sodium pyruvate; 10% bovine calf serum, not heat inactivated; 1% penicillin-streptomycin and 1% L-glutamine) is added to the inside chamber of each well.

The day after, 3T3 cells are washed once with the CFAD medium (Allen-Hoffmann and Rheinwald, *Proc. Natl. Acad. Sci. USA* 81:7802-7806, 1984; Simon and Green, *Cell* 40:677-683, 1985; Barrandon and Green, *Proc. Natl. Acad. Sci. USA* 84:2302-2306, 1987; Kumar et al., *Cell* 147:525-538, 2011). or a base medium (supra), then upper airway stem cell clones are transferred onto the transwell. Each outside chamber of the transwell plate is filled by about 700 μL of stem cell growth medium (e.g., a modified growth medium described above, or CFAD+1 μM Jagged-1+100 ng/mL Noggin+125 ng/mL R-Spondin-1+2.5 μM Rock inhibitor), and each inside chamber of the transwell is filled by 200 μL of stem cell growth medium.

The stem cell growth medium is changed about every 1-2 days, both inside and outside of each transwell insert. After confluence was reached, the medium is change to differentiation medium (stem cell growth medium plus 2 μM GSK3 inhibitor), with about 700 μL of differentiation medium in the outside chamber of each transwell, but with no medium in the inside chambers. The differentiated structure is expected to form in about one month (e.g., 25 days). The differentiated structure can then be used in the screening methods of the invention.

3. Anti-Inflammatory Genes

Using the screening methods of the invention, certain genes have been identified as potential anti-inflammatory genes in that their expression level (e.g., expression as measured by mRNA expression) is dramatically decreased after contacting the test cells by a proinflammatory cytokine (e.g., IL-13), as compared to untreated control (see fold reduction in Tables 1 and 2 below). Furthermore, the invention has provided evidence that overexpressing or restoring the expression of the subject anti-inflammatory genes can antagonize the function of the pro-inflammatory cytokine, such that at least one adverse phenotype induced by the pro-inflammatory cytokine is inhibited or reversed.

Certain genes identified by the various screening assays of the invention as being anti-inflammatory are listed in the two tables below (Tables 1 and 2), with the genes in bold representing those common to both assays (stem cell-based assay vs. differentiated structures-based assay). Other genes of particular interest as being anti-inflammatory are italicized. The expression fold reduction after IL-13 treatment, either over 3, 5, and 13 days for isolated upper airway stem cells, or over 2, 5, and 7 days for differentiated cells in air-liquid interface (ALI), as compared to time-matched untreated control cells, are listed in the $1^{st}$ to the $3^{rd}$ column after each gene name.

In general, these anti-inflammatory genes may encode protein factors (e.g., secreted protein factors) that may be formulated as pharmaceutical compositions for treating inflammatory diseases, disorders, or abnormal conditions. Either the wildtype protein, its functional fragments (based on the anti-inflammatory functional assay of the invention), homologs sharing significant sequence identity, and fusion proteins thereof (e.g., His tagged version or other tagged version that may facilitate recombinant production), with or without beneficial post-translation modification (such as PEGylation, glycosylation, addition of lipid moieties etc.), may be used in the pharmaceutical composition of the invention for treating inflammatory diseases, disorders, or abnormal conditions.

The human sequences of these genes are described individually below for the representative anti-inflammatory genes of the invention. These sequences can be used as query sequences to identify additional homologs from other species using, for example, standard sequence comparison software in public or proprietary sequence databases, including BLASTp or BLASTn searches in NCBI sequences databases (such as the non-redundant sequence database, or sequence databases for specific model organisms including mouse, rat, bovine, zebrafish, gorilla, Drosophila, etc.).

In general, these homologs or fragments thereof sharing at least about 40%, 50%, 60%, 70%, 80%, 85%, 90%, 95%, 97%, 99% protein sequence identity may replace the human protein for use as a pharmaceutical composition of the invention. Preferably, the homologs or fragments thereof preserves at least about 50%, 60%, 70%, 80%, 90%, 90%, 95% of the biological activity of the human protein in the anti-inflammatory assay of the invention, e.g., assay to determine the extent of a test protein to antagonize the effect of a pro-inflammatory cytokine (e.g., IL-13) in the ALI differentiated upper airway stem cells of the invention.

The percentage values for the biological activity can be calculated based on comparison between the test homolog polypeptide with the human protein. For example, if a unit amount of test polypeptide (e.g., 1 mole) achieves substantially the same degree of anti-inflammatory effect (e.g., based on RNA expression level of a marker gene or immunofluorescent data) as compared to the human protein at a reduced unit amount (e.g., 0.7 μmol), then the test polypeptide is about 70% as effective as the human protein.

TABLE 1

Representative Anti-Inflammatory Genes and Expression Fold Reduction - Differentiated Cells
Genes Downregulated in Differentiated Cells

|  | Day 2* | Day 5* | Day 7* |
|---|---|---|---|
| AMTN | −27.0 | −30.0 | −51.0 |
| *OLFM4* | −3.0 | −9.0 | −9.0 |
| GLIPR1 | −3.0 | −5.0 | −5.0 |
| *PPBP* | −4.0 | −5.0 | −5.0 |
| FN1 | −2.0 | −1.1 | −4.0 |
| SERPINA3 | −5.0 | −4.0 | −4.0 |
| C3 | −4.0 | −4.0 | −4.0 |
| PLUNC | −3.0 | −4.0 | −4.0 |
| LGALS1 | −3.0 | −3.0 | −3.0 |
| SPARC | −3.0 | −1.7 | −3.0 |
| HEG1 | −1.0 | −1.5 | −3.0 |
| TNFSF15 | −1.0 | −3.0 | −3.0 |
| INHBA | −4.0 | −1.5 | −3.0 |
| MXRA5 | −3.0 | −2.0 | −3.0 |
| CYR61 | −2.0 | −1.3 | −2.0 |
| SERPINE1 | −1.0 | −1.0 | −2.0 |
| CTHRC1 | −1.0 | −2.0 | −2.0 |
| VCAN | −3.0 | −1.5 | −2.0 |
| IGFL3 | −1.0 | −2.0 | −2.0 |
| THBS1 | −3.0 | −2.0 | −2.0 |
| LAMC2 | −2.0 | −1.3 | −2.0 |
| TNC | −3.0 | −1.3 | −2.0 |
| CTGF | −1.4 | −1.4 | −2.0 |
| CCDC3 | −2.0 | −2.0 | −2.0 |
| CXCL5 | −2.0 | −2.0 | −2.0 |
| LTB1 | −2.0 | −2.0 | −2.0 |
| DKK1 | −2.0 | −4.0 | −2.0 |
| KAL1 | −2.0 | −1.0 | −2.0 |
| ADAM12 | −3.0 | −1.3 | −1.8 |
| SDF2 | −2.0 | −1.6 | −1.0 |
| MSMB | −2.0 | −3.0 | −1.0 |
| IGFBP3 | −2.0 | −2.0 | −1.0 |
| PSAP | −2.0 | −1.0 | −1.0 |
| EFEMP1 | −2.0 | −2.5 | −1.0 |
| NPNT | −2.0 | −1.0 | −1.0 |
| C20orf70 | −2.0 | −1.5 | −1.0 |
| PI3 | −3.0 | −1.0 | −1.0 |
| CLCA2 | −2.0 | −1.0 | 2.0 |

*Days 2, 5, and 7: IL-13 was added on Day 0 to cells differentiated in ALI culture for 25 days, and expression fold reduction for each listed gene was measured at Days 2, 5, and 7.

TABLE 2

Representative Anti-Inflammatory Genes and Expression Fold Reduction - Stem Cells
Gene Downregulated in Stem Cells

|  | Day 3^ | Day 5^ | Day 13^ |
|---|---|---|---|
| PLUNC | −5.9 | −12.3 | −23.0 |
| AMTN | −5.3 | −1 | −1.0 |
| TNFSF15 | −4.2 | −4.0 | −2.5 |
| MSMB | −3.9 | −1.8 | −1.0 |
| *APOD* | −3.8 | −2.9 | −5.1 |
| *CP* | −3.7 | −5.8 | −10.9 |
| *BMP8A* | −3.4 | −1 | −1.0 |
| FN1 | −3.3 | −1.7 | 4.1 |
| C3 | −3.2 | −8.5 | −5.6 |
| IGFBP3 | −3.1 | −3.8 | −3.9 |
| LGALS1 | −3.1 | −1 | −1.0 |
| *IGFBP6* | −2.8 | −1.9 | −1.5 |
| SERPINA3 | −2.6 | 1 | 2.7 |
| *ABI3BP* | −2.5 | −1.9 | −2.4 |
| CLU | −2.3 | −1.6 | −2.0 |
| *LTBP1* | −2.3 | −2 | −1.0 |
| GLIPR1 | −2.3 | −1.8 | 2.7 |
| CCDC80 | −2.1 | −3.6 | −4.8 |
| SERPINE2 | −2.1 | −1.9 | −1.0 |
| TF | −2.1 | −2 | −1.0 |
| FAM3D | −2.0 | −2.6 | −2.7 |
| FGFBP1 | −1.9 | −1.0 | −2.2 |

TABLE 2-continued

Representative Anti-Inflammatory Genes
and Expression Fold Reduction - Stem Cells
Gene Downregulated in Stem Cells

| | Day 3^ | Day 5^ | Day 13^ |
|---|---|---|---|
| COLEC10 | −1.9 | 2.1 | 1.0 |
| IL18 | −1.8 | −2.5 | −1.9 |
| VCAN | −1.7 | −1.4 | −2.6 |
| CXCL5 | −1.7 | −2.6 | −1.0 |
| PTGFR | −1.6 | −1.6 | −2.7 |
| IFNE | −1.5 | −2.7 | −2.0 |
| CXADR | −1.5 | −4.8 | 4.3 |
| EREG | −1.4 | −1.9 | −2.3 |
| EXTL2 | −1.2 | −2.7 | −1.0 |
| IFNK | −1.2 | −2.5 | −1.0 |
| KLK9 | −1.2 | −2 | −1.0 |
| NPPC | −1.2 | −2.3 | −1.0 |
| NTF4 | −1.2 | −2 | −1.0 |
| RNASE3 | −1.2 | −2.3 | −1.0 |
| PI3 | −1 | −4 | −3.9 |
| C2orf40 | −1.0 | −1.2 | −3.4 |
| C4orf22 | −1.0 | −1.2 | −4.6 |
| FGA | −1.0 | −1.2 | −2.6 |
| FGB | −1.0 | −1.5 | −7.0 |

^Days 3, 5, and 13: IL-13 was added on Day 0 to upper airway stem cells in ALI culture, and expression fold reduction for each listed gene was measured at Days 3, 5, and 13.

In certain embodiments, the invention provides pharmaceutical compositions that can be used to treat inflammatory diseases, comprising one or more of the anti-inflammatory genes or gene products selected from the group consisting of: any one or more of the anti-inflammatory genes listed in Tables 1 and 2, such as ABI3BP, AMTN, APOD, BMP8A, C3, CP, FN1, GLIPR1, IGFBP3, IGFBP6, LGALS1, LTBP1, MSMB, OLFM4, PLUNC, PPBP, SERPINA3, and TNFSF15.

Representative anti-inflammatory genes are further described below.

AMTN (Amelotin) (GenBank: AB593161.1; NCBI Ref. Seq. NM_212557.2)

The mineralized portions of teeth, the dentin and enamel, are formed by mesenchyme-derived odontoblasts and epithelium-derived ameloblasts, respectively. As ameloblasts differentiate, they deposit specific proteins necessary for enamel formation, including amelogenin (AMELX), enamelin (ENAM), and ameloblastin (AMBN), in the organic enamel matrix. Amelotin is specifically expressed in maturation-stage ameloblasts.

Iwasaki et al. (*J. Dent. Res.* 84:1127-1132, 2005) first identified AMTN as an ameloblast-specific gene by differential display PCR of various microdissected cell types of the dental organ from 10-day-old mouse incisors. Human AMTN encodes a predicted 209-amino acid protein that is 60% identical to the 213-amino acid mouse protein. The mouse and human proteins both contain N-terminal signal sequences and are rich in proline, leucine, and threonine. Northern blot analysis of postnatal and adult mouse tissues showed that AMTN was expressed exclusively in teeth. In situ hybridization analysis revealed that AMTN was expressed only in maturation-stage ameloblasts during mouse tooth development. AMTN protein was efficiently secreted from transfected cells in culture.

Moffatt et al. (*Biochem. J.* 399:37-46, 2006) cloned rat and pig AMTN, and determined that AMTN is conserved in mammals Immunofluorescence analysis of mouse and rat mandible localized AMTN protein in the basal lamina of maturation-stage ameloblasts of incisors and unerupted molars. AMTN was also detected in the internal basal lamina of junctional epithelium in molars.

The human AMTN protein and cDNA sequences are listed below.

```
NCBI Reference Sequence: NP_997722.1:
                                              (SEQ ID NO: 1)
MRSTILLFCLLGSTRSLPQLKPALGLPPTKLAPDQGTLPNQQQSNQVFPSLSLIPLTQMLTLGPDLHL

LNPAAGMTPGTQTHPLTLGGLNVQQQLHPHVLPIFVTQLGAQGTILSSEELPQIFTSLIIHSLFPGGILP

TSQAGANPDVQDGSLPAGGAGVNPATQGTPAGRLPTPSGTDDDFAVTTPAGIQRSTHAIEEATTES

ANGIQ

NCBI Reference Sequence: NM_212557.2:
                                              (SEQ ID NO: 2)
     aattttttcac cagagtaaac ttgagaaacc aactggacct tgagtattgt acattttgcc    61
tcgtggaccc aaaggtagca atctgaaaca tgaggagtac gattctactg ttttgtcttc   121
taggatcaac tcggtcatta ccacagctca aacctgcttt gggactccct cccacaaaac   181
tggctccgga tcagggaaca ctaccaaacc aacagcagtc aaatcaggtc tttccttctt   241
taagtctgat accattaaca cagatgctca cactggggcc agatctgcat ctgttaaatc   301
ctgctgcagg aatgacacct ggtacccaga cccacccatt gaccctggga gggttgaatg   361
tacaacagca actgcaccca catgtgttac caattttttgt cacacaactt ggagcccagg   421
gcactatcct aagctcagag gaattgccac aaatcttcac gagcctcatc atccattcct   481
tgttcccggg aggcatcctg cccaccagtc aggcagggc taatccagat gtccaggatg   541
gaagccttcc agcaggagga gcaggtgtaa atcctgccac ccagggaacc ccagcaggcc   601
gcctcccaac tcccagtggc acagatgacg actttgcagt gaccacccct gcaggcatcc   661
aaaggagcac acatgccatc gaggaagcca ccacagaatc agcaaatgga attcagtaag   721
ctgtttcaaa ttttttcaac taagctgcct cgaatttggt gatacatgtg aatctttatc   781
```

-continued

```
attgattata ttatggaata gattgagaca cattggatag tcttagaaga aattaattct    841
taatttacct gaaaatattc ttgaaatttc agaaaatatg ttctatgtag agaatcccaa    901
cttttaaaaa caataattca atggataaat ctgtctttga aatataacat tatgctgcct    961
ggatgatatg catattaaaa catatttgga aaactggaaa aaaaaaaaaa aaaaaaaaaa   1021
aaaaaaaaaa aaaaaaaaaa aaaaaaaaaa aaaaaaaaa aaaaaaaaaa aa
```

At least about 15 related sequences have been identified and linked to the NCBI RefSeq entry for the human sequence.

Various AMTN expression vectors are commercially available, some of which are linked to the above NCBI Ref. Seq. entry. For example, human amelotin (AMTN) as transfection-ready DNA (pCMV6-XL5, SKU SC308653); Myc-DDK-tagged ORF clone of Homo sapiens amelotin (AMTN) as transfection-ready DNA (pCMV6-Entry, SKU RC221473) and two other constructs are available from OriGene Technologies, Inc. (Rockville, Md.).

AMTN (Human) Recombinant Protein (P01) (Cat. No. H00401138-P01) is available from Abnova (Taiwan, ROC). Such protein products may be suitable for formulating pharmaceutical composition comprising the AMTN protein.

Other commercially available resources linked to the human NCBI RefSeq entry include: siRNA and shRNA sequences from Santa Cruz Biotechnology (Santa Cruz, Calif.) or OriGen (Rockville, Md.), monoclonal antibody from Abnova (Taiwan, ROC), qPCR primers from GeneCopoeia, Inc. (Rockville, Md.), and other primer/probes for verifying expression level of constructs from Life Technologies Corporation (Grand Island, N.Y.).

ABI3BP (Human ABI Family, Member 3 (NESH) Binding Protein, also Known as TARSH or NESHBP) (NCBI Reference Sequence: NM_015429.3 and NP_056244.2)

Using the yeast 2-hybrid system to identify potential partners of the Nesh protein, which contains an SH3 domain and proline-rich sequences similar to those of E3B1, Matsuda et al. (J. Hum. Genet. 46: 483-486, 2001) isolated a novel full-length cDNA designated TARSH. TARSH encodes a 486-amino acid protein containing an SH3 binding motif, a nuclear targeting sequence, and no catalytic domain.

The human ABI3BP protein and cDNA sequences are listed below.

```
NCBI Reference Sequence: NP_056244.2:
                                                                (SEQ ID NO: 3)
   1 mrggkcnmls slgclllcgs itlalgnaqk lpkgkrpnlk vhinttsdsi llkflrpspn 61 vkleglllgy gsnvspnqyf plpaegkfte aivdaepkyl ivvrpappps qkkscsgktr 121 srkplqlvvg tltpssvfls wgflinphhd wtlpshcpnd rfytiryrek dkekkwifqi 181 cpatetiven lkpntvyefg vkdnveggiw skifnhktvv gskkvngkiq stydqdhtvp 241 ayvprklipi tiikqviqnv thkdsakspe kaplggvilv hliipglnet tvklpaslmf 301 eisdalktql aknetlalpa esktpeveki sarpttvtpe tvprstkptt ssaldvsett 361 lassekpwiv ptakisedsk vlqpqtatyd vfsspttsde peisdsytat sdrildsipp 421 ktsrtleqpr atlapsetpf vpqkleifts pemqpttpap qqttsipstp krrprpkppr 481 tkperttsag titpkisksp eptwttpapg ktqfislkpk iplspevtht kpapkqtpra 541 ppkpktsprp ripqtqpvpk vpqrvtakpk tspspevsyt tpapkdvllp hkpypevsqs 601 epapletrgi pfipmispsp sqeelqttle etdqstqepf ttkiprttel akttqaphrf 661 yttvrprtsd kphirpgvkq aprpsgadrn vsvdsthptk kpgtrrpplp prpthprrkp 721 lppnnvtgkp gsagiissgp ittpplrstp rptgtpleri etdikqptvp asgeelenit 781 dfsssptret dplgkprfkg phvryiqkpd nspcsitdsv krfpkeeate gnatsppqnp 841 ptnltvvtve gcpsfvildw ekplndtvte yevisrengs fsgknksiqm tnqtfstven 901 lkpntsyefq vkpknplgeg pvsntvafst esadprvsep vsagrdaiwt erpfnsdsys 961 eckgkqyvkr twykkfvgvq lcnslrykiy lsdsltgkfy nigdqrghge dhcqfvdsfl 1021 dgrtgqqlts dqlpikegyf ravrqepvqf geigghtqin yvqwyecgtt ipgkw NCBI Reference Sequence: NM_015429.3:
                                                                (SEQ ID NO: 4)
   1 gtgcagccgc ccgcctctgt cactgggaga cagtccactt aaatgcagct ccagggttgc 61 gaggcaccca ccagcatcat tccccatgcg aggtggcaaa tgcaacatgc tctccagttt
```

-continued

```
 121 ggggtgtcta cttctctgtg gaagtattac actagccctg ggaaatgcac agaaattgcc
 181 aaaaggtaaa aggccaaacc tcaaagtcca catcaatacc acaagtgact ccatcctctt
 241 gaagttcttg cgtccaagtc caaatgtaaa gcttgaaggt cttctcctgg gatatggcag
 301 caatgtatca ccaaaccagt acttccctct tcccgctgaa gggaaattca cagaagctat
 361 agttgatgca gagccgaaat atctgatagt tgtgcgacct gctccacctc caagtcaaaa
 421 gaagtcatgt tcaggtaaaa ctcgttctcg caaacctctg cagctggtgg ttggcactct
 481 gacaccgagc tcggtcttcc tgtcctgggg tttcctcatc aacccacacc atgactggac
 541 attgccaagt cactgtccca atgacagatt ttatacaatt cgctatcgag aaaaggataa
 601 agaaaagaag tggatttttc aaatctgtcc agccactgaa acaattgtgg aaaacctaaa
 661 gcccaacaca gtttatgaat ttggagtgaa agacaatgtg gaaggtggaa tttggagtaa
 721 gattttcaat cacaagactg ttgttggaag taaaaaagta aatgggaaaa tccaaagtac
 781 ctatgaccaa gaccacacag tgccagcata tgtcccaagg aaactaatcc caataacaat
 841 catcaagcaa gtgattcaga atgttactca caaggattca gctaaatccc cagaaaaagc
 901 tccactggga ggagtgatac tagtccacct tattattcca ggtcttaatg aaactactgt
 961 aaaacttcct gcatccctaa tgtttgagat ttcagatgca ctcaagacac aattagctaa
1021 gaatgaaacc ttggcattac ctgccgaatc taaaacacca gaggttgaaa aaatctcagc
1081 acgacccaca acagtgactc ctgaaacagt tccaagaagc actaaaccca ctacgtctag
1141 tgcattagat gtttcagaaa caacactggc ttcaagtgaa aagccatgga ttgtgcctac
1201 agctaaaata tctgaagatt ccaaagttct gcagcctcaa actgcaactt atgatgtttt
1261 ctcaagccct acaacatcag atgagcctga gatatcagat tcctacacag caacaagtga
1321 tcgtattctg gattctatcc cacctaaaac ttctagaact cttgaacagc aagggcaac
1381 actggctcca agtgaaacac catttgttcc tcaaaaactg gaaatcttta ccagtccaga
1441 aatgcagcct acgacacctg ctccccagca aactacatct atcccttcta cacctaaacg
1501 acgcccccgg cccaaaccgc caagaaccaa acctgaaaga accacaagtg ccggaacaat
1561 tacacctaaa atttctaaaa gccctgaacc tacatggaca acaccggctc ccggtaaaac
1621 acaatttatt tctctgaaac ctaaaatccc tctcagccca gaagtgacac acaccaaacc
1681 tgctcccaag cagacaccac gtgctcctcc taagccaaaa acatcaccac gcccaagaat
1741 cccacaaaca caaccagttc ctaaggtgcc ccagcgtgtt actgcaaaac caaaaacgtc
1801 accaagtcca gaagtgtcat acaccacacc tgctccaaaa gatgtgctcc ttcctcataa
1861 accatacccct gaggtctctc agagcgaacc tgctcctcta gagacacgag gcatcccttt
1921 tatacccatg atttccccaa gtcctagtca agaggaacta cagaccactc tggaagaaac
1981 agaccaatcc acccaagaac ctttcacaac taagattcca cgaacaactg aactagcaaa
2041 gacaactcag gcgccacaca gattttatac tactgtgagg cccagaacat ctgacaagcc
2101 acacatcaga cctggggtca agcaagcacc caggccatca ggtgctgata gaaatgtatc
2161 agtggactct acccaccccca ctaaaaagcc agggactcgc cgcccaccct tgccacccag
2221 acctacacac ccacgaagaa aacctttacc accaaataat gtcactggaa agccaggaag
2281 tgcaggaatc atttcatcag gcccaataac tacaccaccc ctgaggtcaa cacccaggcc
2341 tactggaact cccttggaga gaatagagac agatataaag caaccaacag ttcctgcctc
2401 tggagaagaa ctggaaaata taactgactt tagctcaagc ccaacaagag aaactgatcc
2461 tcttgggaag ccaagattca aaggacctca tgtgcgatac atccaaaagc ctgacaacag
2521 tccctgctcc attactgact ctgtcaaacg gttccccaaa gaggaggcca cagaggggaa
```

```
2581 tgccaccagc ccaccacaga acccacccac caacctcact gtggtcaccg tggaagggtg 2641 cccctcattt gtcatcttgg actgggaaaa gccactaaat gacactgtca ctgaatatga 2701 agttatatcc agagaaaatg ggtcattcag tgggaagaac aagtccattc aaatgacaaa 2761 tcagacattt tccacagtag aaaatctgaa accaaacacg agttatgaat tccaggtgaa 2821 acccaaaaac ccgcttggtg aaggcccggt cagcaacaca gtggcattca gtactgaatc 2881 agcggaccca agagtgagtg agccagtttc tgcaggaaga gatgccatct ggactgaaag 2941 acccttta at tcagactctt actcagagtg taagggcaaa caatatgtca aaaggacatg 3001 gtataaaaaa tttgtaggag tgcagctgtg caactctctc agatacaaga tttacttgag 3061 cgactccctc acaggaaaat tttataacat aggtgatcag aggggccatg gagaagatca 3121 ctgccagttt gtggattcat ttttagatgg acgcactggg cagcaactca cttctgacca 3181 gttaccaatc aaagaaggtt atttcagagc agttcgccag gaacctgtcc aatttggaga 3241 aataggtggt cacacccaaa tcaattatgt tcagtggtat gaatgtggga ctacaattcc 3301 tggaaaatgg tagatgctgc acaaagttac cttctgtttc atcattgcaa acaaaaatca 3361 ttgaaaatac tatgccgcat tcatttaaag ctattttgtt tactatgtat aaaagtctac 3421 aatctaatta atagcaatac tagatgttta ttattagaaa agattgctga gagtatttat 3481 caggttttac aaagtcattt taagaaagca agatactgat gttaacagaa taacattttt 3541 ggggaagctg gctccctatt catggtattt taagagatca tttgtatatt atttatcaca 3601 ctgttgtaat gatgttttga gatacttta taacaaaatt aacatcaaaa aggtatatac 3661 ttttttaaaaa aaatttactt ttattgatgt gtactcttcc tattgatgag ttaattccat 3721 aaatctctac ttagtttaac ttattggatc aaattatctt cagcatgtat atctggggaa 3781 aaaaggtccg aattttcaca tttatattta aacttcaatt ttttatattt aaacttcaat 3841 tttttagcaa cagctgaata gctttgcgga ggagtttaat agttacacat tcatgctaat 3901 atacatttcc tttaaacatc cacaaattct taaaaagatt gaatcagtaa atttcatttc 3961 agctaaaaat ggagtctaat atattgtttc aaaagataca ttttttaccca ccataaatgt 4021 tacaatatct gaatatgctt tgtcaaacta tcccttatg caatcgtctt catattgttt 4081 ttatgattct aatcaagctg tatgtagaga ctgaatgtga agtcaagtct gagcacaaaa 4141 agataatgca cgatgagatt gcctaccatt ttataggata tttactatgt atttatacgt 4201 taagacctct atgaatgaat gtatcagaga atgtctttgt aactgtttaa ttcaatctgt 4261 aataaaaatc taactaacta actcatttat ttctattaaa aaggtattgt cctttaggcg 4321 gggaatggga atccttgctg cactgttgca gtcattctga aaggacctt ccctgtactt 4381 acctttcaac atgcttcaat cttatcaacg ctacatttg tattttcaa acaagtataa 4441 attctgcaat aaagagatgt agtttttttt taaaaaaaaa aaaaaaa
```

At least about 33 related sequences have been identified and linked to the NCBI RefSeq entry for the human sequence.

Various ABI3BP expression vectors are commercially available, some of which are linked to the above NCBI Ref. Seq. entry. For example, *Homo sapiens* ABI family, member 3 (NESH) binding protein (ABI3BP) as transfection-ready DNA (pCMV6-XL4, SKU SC127786); and other constructs are available from OriGene Technologies, Inc. (Rockville, Md.).

ABI3BP (Human) Recombinant Protein (Q01) (Cat. No. H00025890-Q01) is available from Abnova (Taiwan, ROC). Such protein products may be suitable for formulating pharmaceutical composition comprising the ABI3BP protein.

Other commercially available resources linked to the human NCBI RefSeq entry include: siRNA and shRNA sequences from Santa Cruz Biotechnology (Santa Cruz, Calif.) or OriGen (Rockville, Md.), monoclonal antibody from Abnova (Taiwan, ROC), and other primer/probes for verifying expression level of constructs from Life Technologies Corp. (Grand Island, N.Y.).

APOD (Human Apolipoprotein D) (NCBI Reference Sequence: NM_001647.3 and NP_001638.1)

Apolipoprotein D (ApoD) is a member of the alpha(2mu)-microglobulin superfamily of carrier proteins also known as liROCalins (e.g., liROCalin-1). It is a protein component of high-density lipoprotein in human plasma, comprising about 5% of total high-density lipoprotein (Fielding and Fielding, *Proc. Nat. Acad. Sci.* 77: 3327-3330, 1980). It is a glycoprotein of estimated molecular weight 33,000 Da. ApoD is closely associated with the enzyme lecithin:cholesterol acyltransferase (LCAT) (see Drayna et al., *J. Biol. Chem.* 261: 16535-16539, 1986). The 169-amino acid ApoD protein share little similarity to other lipoprotein sequences but had a high degree of homology to plasma retinol-binding protein, a member of the alpha(2mu)-globulin superfamily. ApoD mRNA has been detected in many tissues.

Zeng et al. (*Proc. Nat. Acad. Sci.* 93: 6626-6630, 1996) identified apoD as aROCrine secretion odor-binding protein-2 (ASOB2), 1 of 2 glycoproteins that bind E-3-methyl-2-hexenoic acid (E-3M2H), the most abundant axillary odor component in human males. The pattern of glycosylation for axillary apoD differs from that reported for plasma apoD, suggesting that there may be different sites of expression for the 2 glycoproteins. In situ hybridization of an oligonucleotide probe against apoD mRNA with axillary tissue demonstrated that the message for synthesis of this protein is specific to the aROCrine glands.

The human APOD protein and cDNA sequences are listed below.

```
NCBI Reference Sequence: NP_001638.1:
                                                    (SEQ ID NO: 5)
    1 mvmlllllsa laglfgaaeg qafhlgkcpn ppvqenfdvn kylgrwyeie kipttfengr 61 ciqanyslme ngkikvlnqe lradgtvnqi egeatpvnlt epaklevkfs wfmpsapywi 121 latdyenyal vysctciiql fhvdfawila rnpnlppetv dslkniltsn nidvkkmtvt 181 dqvncpkls NCBI Reference Sequence: NM_001647.3:
                                                    (SEQ ID NO: 6)
    1 tctctctcgc acacataccc acacacacac acacacacac acacgcgcgc gcgaaaacaa 61 tatctcatttt cttcttcagg gagcagctgt gaaggaaatc gggggaggag gatggacaca 121 acatcccatc tttgtgtttc gatacagact aagcttttag gccaaccctc ctgactggat 181 gggggcggcg ggcgtggcat gcatgaaaag taaacatcag agacctgaag aagcttataa 241 aatagcttgg gagaggccag tcaccaagac aggcatctca aatcggctga ttctgcatct 301 ggaaactgcc ttcatcttga agaaaagct ccaggtccct tctccagcca cccagcccca 361 agatggtgat gctgctgctg ctgctttccg cactggctgg cctcttcggt gcggcagagg 421 gacaagcatt tcatcttggg aagtgcccca atcctccggt gcaggagaat tttgacgtga 481 ataagtatct cggaagatgg tacgaaattg agaagatccc aacaaccttt gagaatggac 541 gctgcatcca ggccaactac tcactaatgg aaaacggaaa gatcaaagtg ttaaaccagg 601 agttgagagc tgatggaact gtgaatcaaa tcgaaggtga agccacccca gttaacctca 661 cagagcctgc caagctggaa gttaagttt cctggtttat gccatcggca ccgtactgga 721 tcctggccac cgactatgag aactatgccc tcgtgtattc ctgtacctgc atcatccaac 781 tttttcacgt ggattttgct tggatcttgg caagaaaccc taatctccct ccagaaacag 841 tggactctct aaaaaatatc ctgacttcta ataacattga tgtcaagaaa atgacggtca 901 cagaccaggt gaactgcccc aagctctcgt aaccaggttc tacagggagg ctgcacccac 961 tccatgttac ttctgcttcg ctttcccta cccccccccc ataaagacaa accaatcaac 1021 cacgacaaag gaagttgacc tgaacatgta accatgccct accctgttac cttgctagct 1081 gcaaaataaa cttgttgctg acctgctgtg ctcgcagtag attccaagtt aaaaaaaaaa 1141 aaaaaaaa
```

At least about 27 related sequences have been identified and linked to the NCBI RefSeq entry for the human sequence.

Various APOD expression vectors are commercially available, some of which are linked to the above NCBI Ref. Seq. entry. For example, *Homo sapiens* apolipoprotein D (APOD) as transfection-ready DNA (pCMV6-XL5, SKU SC127272); and other constructs are available from OriGene Technologies, Inc. (Rockville, Md.).

APOD (Human) Recombinant Protein (Cat. No. P4052) is available from Abnova (Taiwan, ROC). Such protein products may be suitable for formulating pharmaceutical composition comprising the APOD protein.

Other commercially available resources linked to the human NCBI RefSeq entry include: siRNA and shRNA sequences from Santa Cruz Biotechnology (Santa Cruz, Calif.) or OriGen (Rockville, Md.), monoclonal antibody from BioLogo (Kronshagen, Germany), and other primer/probes for verifying expression level of constructs from Life Technologies Corp. (Grand Island, N.Y.).

BMP8A (Human Bone Morphogenetic Protein 8a) (NCBI Reference Sequence: NM_181809.3 and NP_861525.2)

Bone morphogenetic protein 8A (BMP8A) is a polypeptide member of the TGFβ superfamily of proteins. Like the other bone morphogenetic proteins (BMPs), it is involved in the development of bone and cartilage, and may also be involved in epithelial osteogenesis. It further plays a role in bone homeostasis. BMP8a is a disulfide-linked homodimer.

The human BMP8a protein and cDNA sequences are listed below.

```
NCBI Reference Sequence: NP_861525.2:
                                                             (SEQ ID NO: 7)
     1 maarpgplwl lgltlcalgg ggpglrpppg cpqrrlgare rrdvqreila vlglpgrprp 61 rappaasrlp asaplfmldl yhamagddde dgapaeqrlg radlvmsfvn mverdralgh 121 qephwkefrf dltqipagea vtaaefriyk vpsihllnrt lhvsmfqvvq eqsnresdlf 181 fldlqtlrag degwlvldvt aasdcwllkr hkdlglrlyv etedghsvdp glagllgqra 241 prsqqpfvvt ffraspspir tpravrplrr rqpkksnelp qanrlpgifd dvrgshgrqv 301 crrhelyvsf qdlgwldwvi apqgysayyc egecsfplds cmnatnhail qslvhlmkpn 361 avpkaccapt klsatsvlyy dssnnvilrk hrnmvvkacg ch NCBI Reference Sequence: NM_181809.3:
                                                             (SEQ ID NO: 8)
     1 ggtcgctgcc ggagctcgcc ggtcgcccct gcgctgcgcg gaccgcagcc acagccggac 61 tggtgggaac ggcggcgaca gacggattgg ctgacagtcc cagccctcag aacagcccg 121 gcctcgaagc gttggcgtct gcgtccgcgt cagcgtccgc ttgtcccgga gccggggcag 181 gtgcgcgcgg ggggcgctcc agggaccgcg ctgaggccgc agacgccgcc cgccgagccc 241 cgccccctgc tcgccgaact cagctccccg ttcgccgtcg gggcgtcccc gggcccaggg 301 gcggcggcgg agctgatgtg cgcccgctga gcgccccccgg cccgccatgg ccgcgcgccc 361 cggaccgctc tggcttctgg gcctgacgtt gtgcgcgctg ggcgggggcg gccccggcct 421 gcgacccccg cccggctgtc cccagcgacg tctgggcgcg cgcgagcgcc gggacgtgca 481 gcgcgagatc ctggcggtgc tcgggctacc cgggcggccc cggccccgcg cgccacccgc 541 cgcctcccgg ctgccgcgt ccgcgccgct cttcatgctg gacctgtacc acgccatggc 601 tggcgacgac gacgaggacg gcgcgcccgc ggagcagcgc ctgggccgcg ccgacctggt 661 catgagcttc gtcaacatgg tggagcgaga ccgtgccctg ggccaccagg agcccattg 721 gaaggagttc cgctttgacc tgacccagat cccggctggg gaggcggtca cagctgcgga 781 gttccggatt tacaaggtgc ccagcatcca cctgctcaac aggaccctcc acgtcagcat 841 gttccaggtg gtccaggagc agtccaacag ggagtctgac ttgttctttt tggatcttca 901 gacgctccga gctggagacg agggctggct ggtgctggat gtcacagcag ccagtgactg 961 ctggttgctg aagcgtcaca aggacctggg actccgcctc tatgtggaga ctgaggacgg 1021 gcacagcgtg gatcctggcc tggccggcct gctgggtcaa cgggcccac gctcccaaca 1081 gcctttcgtg gtcactttct tcagggccag tccgagtccc atccgcaccc ctcgggcagt 1141 gaggccactg aggaggaggc aaccgaagaa aagcaacgag ctgccgcagg ccaaccgact 1201 cccagggatc tttgatgacg tccgcggctc ccacggccgg caggtctgcc gtcggcacga 1261 gctctacgtc agcttccagg accttggctg gctggactgg gtcatcgccc ccaaggcta
```

-continued

```
1321 ctcagcctat tactgtgagg gggagtgctc cttcccgctg gactcctgca tgaacgccac
1381 caaccacgcc atcctgcagt ccctggtgca cctgatgaag ccaaacgcag tcccaaggc
1441 gtgctgtgca cccaccaagc tgagcgccac ctctgtgctc tactatgaca gcagcaacaa
1501 cgtcatcctg cgcaagcacc gcaacatggt ggtcaaggcc tgcggctgcc actgagtcag
1561 cccgcccagc cctactgcag ccaccttct catctggatc gggccctgca gaggcagaaa
1621 acccttaaat gctgtcacag ctcaagcagg agtgtcaggg gccctcactc tcggtgccta
1681 cttcctgtca ggcttctggt cctttctcgg tacctctgtg cccctcccct ggggtttgtg
1741 gctgtcactc tgcccgacac tttggtggcc taaggcacac agcagcctca gagcctgtgc
1801 tgactgcact gtctggagtc agcacagaag tcctatctta ggacctgtca gactgtggct
1861 ggccccggat ggtctgaggt tggctgaccc gagcttttct ccattcacca gagggtttag
1921 gtgtgaggag aagggctctg cctcttccca ggtacaacac tggccatttc tgggcaaaat
1981 tggacacgct tatgttctca gcacagtgtg ttctgggatt cttctcattt ggtccaggt
2041 gcagttagca tattagaaaa agaataagct ggacatcccc acgaagccac tggggatttt
2101 tttttttttt ttccagatag agtctcactc tgtcacccag gctggagtgc agtggtgcaa
2161 tcctggctca ctgcaacctc tgcctcccag gttcaagcaa ttctcgtgcc tcagcctcct
2221 gagtagctgg gattacaggg gcccaccacc acgcccagct cattcttgta ttttttagtag
2281 agacggggtt tcaccatatc ggccaggctg gtcttgaact cctgacctca ggtgatccac
2341 ccgcccggcc tcccaaagtg ttgggatgac aggcatgagc caccgtgcct ggccactggg
2401 gatattttat gtcatgtgta ttcccttgcc ctgggcctgc cccttctcct gcctgggaaa
2461 gaggtatgac tcccacagga gcaaagaatc ctgggggctt ccagttccct ccaccatctc
2521 taccatgctg acccatttgg ggctcagcac tgagacagag gcaagaccag cagctccaac
2581 atgtagtgta ggctggcaca gagcaaatgc ccccgcagcc tgctccctt gcccatggct
2641 catgtcagta atcaacctac gtacctttcc cactgaacca ggacagggcc tccaggcctc
2701 agcacagaac tgcagacagc caccaccagg cattgtcaat aagacctcag ttccccctcc
2761 tgccccactg cagagcaatc cattccatcc aaagcagggt gactggcagt ctccggccag
2821 gcatggggca agggtgggga ctgccagtgt ttgcttgtgt ctaggagtta tgaacaagct
2881 ggccaccaaa attggcgtca ccctgggtgc ccaccagcgc tgtcctgtgt cttgggtctg
2941 tgagtcaaag aaaaggtccc tgtcccaggg agtgacaggc agtaattagg ctgagttggg
3001 tgggaggtt tgtctcggcc tccactgttc ccggaaaccg ctgttctcct tggaacagcc
3061 actgggagtt ggagtgttta tttgatttct gacttgctaa gcctgtaatt tacctgctgg
3121 aacagacaga gtccagctgc ccaaaccgtg tcattaaaag cagatcctgg gcccgcccca
3181 tccacaggca cagcctggca gagtggttcc acctccccat gggcccaagg atgcgcctct
3241 ctggagttca cgtgctgcac ccccaggag gggcctgggg agagctggtc cagcagcagg
3301 ggtggaggct ggggccacac tgcgggacag cagcccctcc acctggacca gggagggcct
3361 ccatgtgcaa gcgcagagga agagaccctc tcatgtacat aaagggtggg cccaggctgt
3421 ctggaagatg gtgagttccc cactagtcta aggcttcaag ctcagctagc agagattgga
3481 agaggcaatg gcctgagtgt taggagacag gtattctggt tccaactcag ccactgactt
3541 ggtgtcagga caagtcccct ttcttattca cgcttcagtt tctcatctgc aacatgagga
3601 cataggactc tttaattcca aaggctcttc caacccagag aacccatctg ccccatgac
3661 cttctcccag agcttgagac atggcctgag cccctgctg ccataggact tgggccctat
```

-continued

```
3721 ctgccattgc aggacctgat ttaacagctc tcttcttcca atactgggca gtagagtttc 3781 ggaaactgac aaatgtgtgg tctcttcagt gcccagtgtg taacctggca tggtttgggt 3841 gtgctaggag tttgtgaaat gaatgttttc aagacgcaaa cgctgctatg cccatcaggt 3901 gtgcacagca ggcctgagga tcatgatgag actccctttt tatgcagcaa agcacaaagt 3961 gtgacagtcg tggccttcct ggtggccaga cttctagcaa ctttagccac ccaccaaatg 4021 acatcacata cagaaggcct cagaaaggga ggaggtcgta aggacacaca gctgatgaag 4081 ggtcagtgct cagctatcaa ggtcatcttc tggcctggtt gcctcccaca gcccaggatg 4141 cattcaaggc tgcacatcag gagcataaat aagggtggtc agctcaggcc cactggctgc 4201 aacaagtagc cactgacagg gagtctgggg ccatttggtg cagaacaacc cccaacccag 4261 tggccatctt cacaactgca gcacagtgct ggccctaatg ccaggtgagc gtgcaaagtc 4321 ctgtttcttt gtctttacat agggaccggg cgatgcgctt tagagaaatt ccctattatt 4381 tcacaggaaa ggaggctgtg aaaggagag ggcaggtttt ggagccaagt cgacctggca 4441 tcaggtcctg gctgccttt tttttttttt tttaaagaca tacatggtct tgctttgtcg 4501 cccaggctgg agtgcagtgg cagtgtcatg gctcactgca gcctcaacct gctgggctca 4561 agcaatcctc ccacttcagc ccgagttgct gggatgacag gcacacgcca ccatacccag 4621 ctaattttta aatttttat agaaaccagg tctcactatg ttgcccaggc cggtcttaaa 4681 ctttgcccag gccagtcttg aactcctgag ctcaagcaat cctcctgcct cagcctccca 4741 aagtgctagg attacaggcg tgagccactt acccggcctc tgcctcttgt taatttgacc 4801 acatcatgta cctgctgtgc ccgttccttc ctccgtagaa gagggtgctg gtcctgccct 4861 tttgaggcct ccatgagggc caaatgtgcc atgggacact tagtgccatg cctgcgcaga 4921 cctgtggaat aaacagcaat tctgagcagg ctcattttaa agggacttgc aaatttgggc 4981 gttccttgtg tgccttcctc ataaaaccca ctcctcccag aatatgctta gaggtgctgc 5041 tgtatttacc tgagagctat gcttttcatc aaaaacctaa acgtgatcat ctcttggatg 5101 aggtgtggcc ctgcacactc gcctgctcgt ggaaggagtc tgggccagca gtgacccacg 5161 cgctagggtc tctgctgagg aagtggcagg tgtgcggccc tgccctggcc ccgtagtgag 5221 tgtggggccc acctgtgccc tcatgggcag ctgaaggggg agctttctac cccaggttcc 5281 tttccttact gaaaagtctt gagcaaacag ttgccgctct ccaccccctg cttttttaaaa 5341 aaaatttttt ctcacgtaag aaaatgttat ctgtgtgctg gggaaaattt tgaaaataac 5401 aaaaaccaga atacaaacac ccataatcaa tcacagagat aaccactgtt cataattcct 5461 tccagtcttc ttacttggca catatacatt tgtctttctt tatatatgac atatggatat 5521 tttacaaagt taggatccta ctctatgcac tgcttggtga tcggatctat tcaatgtaca 5581 aaatattttg aaagtttctg tgattaaatg ttctttgaaa acataaaaaa aaaaaaaaaa 5641 aa
```

At least about 31 related sequences have been identified and linked to the NCBI RefSeq entry for the human sequence.

Various BMP8a expression vectors are commercially available, some of which are linked to the above NCBI Ref. Seq. entry. For example, *Homo sapiens* bone morphogenetic protein 8a (BMP8A) as transfection-ready DNA (pCMV6-XL4, SKU SC307379); and other constructs are available from OriGene Technologies, Inc. (Rockville, Md.).

BMP8A (Human) Recombinant Protein (P01) (Cat. No. H00353500-P01) is available from Abnova (Taiwan, ROC). Such protein products may be suitable for formulating pharmaceutical composition comprising the ABI3BP protein.

Other commercially available resources linked to the human NCBI RefSeq entry include: siRNA and shRNA sequences from Santa Cruz Biotechnology (Santa Cruz, Calif.) or OriGen (Rockville, Md.), monoclonal antibody from R & D Systems (US, UK, or China), and other primer/probes for verifying expression level of constructs from Life Technologies Corp. (Grand Island, N.Y.).

C3 (Human Complement Component 3) (NCBI Reference Sequence: NM_000064.2 and NP_000055.2)

The complement system is an important mediator of natural and acquired immunity. It consists of approximately 30 proteins that can exhibit catalytic activity, function as regulators, or act as cellular surface receptors. These components normally circulate in inactive forms and are activated by the classical, alternative, or lectin pathways. Complement component 3 plays a central role in all 3 activation pathways (see Reis et al., *Scand. J. Immunol.* 63: 155-168, 2006).

De Bruijn and Fey (*Proc. Nat. Acad. Sci.* 82:708-712, 1985) presented the complete coding sequence of the C3 gene and the derived amino acid sequence. C3 is an acute phase reactant; increased synthesis of C3 is induced during acute inflammation. The liver is the main site of synthesis, although small amounts are also produced by activated monocytes and macrophages. A single chain precursor (pro-C3) of approximately 200 kD is found intracellularly; the cDNA shows that it comprises 1,663 amino acids. This is processed by proteolytic cleavage into alpha (C3a) and beta (C3b) subunits which in the mature protein are linked by disulfide bonds. Pro-C3 contains a signal peptide of 22 amino acid residues, the beta chain (645 residues) and the alpha chain (992 residues). The 2 chains are joined by 4 arginine residues that are not present in the mature protein. Human C3 has 79% identity to mouse C3 at the nucleotide level and 77% at the amino acid level.

The human C3 protein and cDNA sequences are listed below.

```
NCBI Reference Sequence: NP_000055.2:
                                                                  (SEQ ID NO: 9)
   1 mgptsgpsll lllthlpla lgspmysiit pnilrlesee tmvleahdaq gdvpvtvtvh 61 dfpgkklvls sektvltpat nhmgnvtfti panrefksek grnkfvtvqa tfgtqvvekv 121 vlvslqsgyl fiqtdktiyt pgstvlyrif tvnhkllpvg rtvmvnienp egipvkqdsl 181 ssqnqlgvlp lswdipelvn mgqwkirayy enspqqvfst efevkeyvlp sfevivepte 241 kfyyiynekg levtitarfl ygkkvegtaf vifgiqdgeq rislpeslkr ipiedgsgev 301 vlsrkvlldg vqnpraedlv gkslyvsatv ilhsgsdmvq aersgipivt spyqihftkt 361 pkyfkpgmpf dlmvfvtnpd gspayrvpva vqgedtvqsl tqgdgvakls inthpsqkpl 421 sitvrtkkqe lseaeqatrt mqalpystvg nsnnylhlsv lrtelrpget lnvnfllrmd 481 raheakiryy tylimnkgrl lkagrqvrep gqdlvvlpls ittdfipsfr lvayytliga 541 sgqrevvads vwvdvkdscv gslvvksgqs edrqpvpgqq mtlkiegdhg arvvlvavdk 601 gvfvlnkknk ltqskiwdvv ekadigctpg sgkdyagvfs dagltftsss gqqtaqrael 661 qcpqpaarrr rsvqltekrm dkvgkypkel rkccedgmre npmrfscqrr trfislgeac 721 kkvfldccny itelrrqhar ashlglarsn ldediiaeen ivsrsefpes wlwnvedlke 781 ppkngistkl mniflkdsit tweilavsms dkkgicvadp fevtvmqdff idlrlpysvv 841 rneqveirav lynyrqnqel kvrvellhnp afcslattkr rhqqtvtipp ksslsvpyvi 901 vplktglqev evkaavyhhf isdgvrkslk vvpegirmnk tvavrtldpe rlgregvqke 961 dippadlsdq vpdtesetri llqgtpvaqm tedavdaerl khlivtpsgc geqnmigmtp 1021 tviavhylde teqwekfgle krqgalelik kgytqqlafr qpssafaafv krapstwlta 1081 yvvkvfslav nliaidsqvl cgavkwlile kqkpdgvfqe dapvihqemi gglrnnnekd 1141 maltafvlis lqeakdicee qvnslpgsit kagdfleany mnlqrsytva iagyalaqmg 1201 rlkgpllnkf lttakdknrw edpgkqlynv eatsyallal lqlkdfdfvp pvvrwlneqr 1261 yyggggygstq atfmvfqala qyqkdapdhq elnldvslql psrsskithr ihwesasllr 1321 seetkenegf tvtaegkgqg tlsvvtmyha kakdqltcnk fdlkvtikpa petekrpqda 1381 kntmileict ryrgdqdatm sildismmtg fapdtddlkq langvdryis kyeldkafsd 1441 rntliiyldk vshseddcla fkvhqyfnve liqpgavkvy ayynleessct rfyhpekedg 1501 klnklcrdel crcaeencfi qksddkvtle erldkacepg vdyvyktrlv kvqlsndfde 1561 yimaieqtik sgsdevqvgq qrtfispikc realkleekk hylmwglssd fwgekpnlsy 1621 iigkdtwveh wpeedecqde enqkqcqdlg aftesmvvfg cpn NCBI Reference Sequence: NM_000064.2:
                                                                  (SEQ ID NO: 10)
   1 cactcctccc catcctctcc ctctgtccct ctgtccctct gaccctgcac tgtcccagca
```

-continued

```
  61 ccatgggacc cacctcaggt cccagcctgc tgctcctgct actaacccac ctcccctgg
 121 ctctggggag tcccatgtac tctatcatca cccccaacat cttgcggctg agagcgagg
 181 agaccatggt gctggaggcc cacgacgcgc aaggggatgt tccagtcact gttactgtcc
 241 acgacttccc aggcaaaaaa ctagtgctgt ccagtgagaa gactgtgctg acccctgcca
 301 ccaaccacat gggcaacgtc accttcacga tcccagccaa cagggagttc aagtcagaaa
 361 aggggcgcaa caagttcgtg accgtgcagg ccaccttcgg gacccaagtg gtggagaagg
 421 tggtgctggt cagcctgcag agcgggtacc tcttcatcca gacagacaag accatctaca
 481 cccctggctc cacagttctc tatcggatct tcaccgtcaa ccacaagctg ctacccgtgg
 541 gccggacggt catggtcaac attgagaacc cggaaggcat cccggtcaag caggactcct
 601 tgtcttctca gaaccagctt ggcgtcttgc ccttgtcttg ggacattccg aactcgtca
 661 acatgggcca gtggaagatc cgagcctact atgaaaactc accacagcag gtcttctcca
 721 ctgagtttga ggtgaaggag tacgtgctgc ccagtttcga ggtcatagtg gagcctacag
 781 agaaattcta ctacatctat aacgagaagg gcctggaggt caccatcacc gccaggttcc
 841 tctacgggaa gaaagtggag ggaactgcct ttgtcatctt cgggatccag gatggcgaac
 901 agaggatttc cctgcctgaa tccctcaagc gcattccgat tgaggatggc tcggggagg
 961 ttgtgctgag ccggaaggta ctgctggacg gggtgcagaa cccccgagca aagacctgg
1021 tggggaagtc tttgtacgtg tctgccaccg tcatcttgca ctcaggcagt gacatggtgc
1081 aggcagagcg cagcgggatc ccatcgtga cctctcccta ccagatccac ttcaccaaga
1141 cacccaagta cttcaaacca ggaatgccct ttgacctcat ggtgttcgtg acgaaccctg
1201 atggctctcc agcctaccga gtccccgtgg cagtccaggg cgaggacact gtgcagtctc
1261 taacccaggg agatggcgtg gccaaactca gcatcaacac acaccccagc cagaagccct
1321 tgagcatcac ggtgcgcacg aagaagcagg agctctcgga ggcagagcag gctaccagga
1381 ccatgcaggc tctgccctac agcaccgtgg gcaactccaa caattacctg catctctcag
1441 tgctacgtac agagctcaga cccggggaga ccctcaacgt caacttcctc ctgcgaatgg
1501 accgcgccca cgaggccaag atccgctact acacctacct gatcatgaac aagggcaggc
1561 tgttgaaggc gggacgccag gtgcgagagc ccggccagga cctggtggtg ctgcccctgt
1621 ccatcaccac cgacttcatc ccttccttcc gcctggtggc gtactacacg ctgatcggtg
1681 ccagcggcca gagggaggtg gtggccgact ccgtgtgggt ggacgtcaag gactcctgcg
1741 tgggctcgct ggtggtaaaa agcggccagt cagaagaccg gcagcctgta cctgggcagc
1801 agatgaccct gaagatagag ggtgaccacg gggcccgggt ggtactggtg gccgtggaca
1861 agggcgtgtt cgtgctgaat aagaagaaca aactgacgca gagtaagatc tgggacgtgg
1921 tggagaaggc agacatcggc tgcacccgg gcagtgggaa ggattacgcc ggtgtcttct
1981 ccgacgcagg gctgaccttc acgagcagca gtggccagca gaccgcccag agggcagaac
2041 ttcagtgccc gcagccagcc gcccgccgac gccgttccgt gcagctcacg gagaagcgaa
2101 tggacaaagt cggcaagtac cccaaggagc tgcgcaagtg ctgcgaggac ggcatgcggg
2161 agaaccccat gaggttctcg tgccagcgcc ggacccgttt catctccctg ggcgaggcgt
2221 gcaagaaggt cttcctggac tgctgcaact acatcacaga gctgcggcgg cagcacgcgc
2281 gggccagcca cctgggcctg gccaggagta acctggatga ggacatcatt gcagaagaga
2341 acatcgtttc ccgaagtgag ttcccagaga gctggctgtg gaacgttgag gacttgaaag
2401 agccaccgaa aaatggaatc tctacgaagc tcatgaatat attttttgaaa gactccatca
```

-continued

```
2461 ccacgtggga gattctggct gtgagcatgt cggacaagaa agggatctgt gtggcagacc
2521 ccttcgaggt cacagtaatg caggacttct tcatcgacct gcggctaccc tactctgttg
2581 ttcgaaacga gcaggtggaa atccgagccg ttctctacaa ttaccggcag aaccaagagc
2641 tcaaggtgag ggtggaacta ctccacaatc cagccttctg cagcctggcc accaccaaga
2701 ggcgtcacca gcagaccgta accatccccc ccaagtcctc gttgtccgtt ccatatgtca
2761 tcgtgccgct aaagaccggc ctgcaggaag tggaagtcaa ggctgctgtc taccatcatt
2821 tcatcagtga cggtgtcagg aagtccctga aggtcgtgcc ggaaggaatc agaatgaaca
2881 aaactgtggc tgttcgcacc ctggatccag aacgcctggg ccgtgaagga gtgcagaaag
2941 aggacatccc acctgcagac ctcagtgacc aagtcccgga caccgagtct gagaccagaa
3001 ttctcctgca agggacccca gtggcccaga tgacagagga tgccgtcgac gcggaacggc
3061 tgaagcacct cattgtgacc ccctcgggct gcggggaaca aacatgatc ggcatgacgc
3121 ccacggtcat cgctgtgcat tacctggatg aaacggagca gtgggagaag ttcggcctag
3181 agaagcggca gggggccttg gagctcatca agaaggggta cacccagcag ctggccttca
3241 gacaacccag ctctgccttt gcggccttcg tgaaacgggc acccagcacc tggctgaccg
3301 cctacgtggt caaggtcttc tctctggctg tcaacctcat cgccatcgac tcccaagtcc
3361 tctgcggggc tgttaaatgg ctgatcctgg agaagcagaa gcccgacggg gtcttccagg
3421 aggatgcgcc cgtgatacac caagaaatga ttggtggatt acggaacaac aacgagaaag
3481 acatggccct cacggccttt gttctcatct cgctgcagga ggctaaagat atttgcgagg
3541 agcaggtcaa cagcctgcca ggcagcatca ctaaagcagg agacttcctt gaagccaact
3601 acatgaacct acagagatcc tacactgtgg ccattgctgg ctatgctctg cccagatgg
3661 gcaggctgaa ggggcctctt cttaacaaat ttctgaccac agccaaagat aagaaccgct
3721 gggaggaccc tggtaagcag ctctacaacg tggaggccac atcctatgcc ctcttggccc
3781 tactgcagct aaaagacttt gactttgtgc ctcccgtcgt gcgttggctc aatgaacaga
3841 gatactacgg tggtggctat ggctctaccc aggccacctt catggtgttc caagccttgg
3901 ctcaatacca aaaggacgcc cctgaccacc aggaactgaa ccttgatgtg tccctccaac
3961 tgcccagccg cagctccaag atcacccacc gtatccactg gaatctgcc agcctcctgc
4021 gatcagaaga gaccaaggaa aatgagggtt tcacagtcac agctgaagga aaaggccaag
4081 gcaccttgtc ggtggtgaca atgtaccatg ctaaggccaa agatcaactc acctgtaata
4141 aattcgacct caaggtcacc ataaaaccag caccggaaac agaaaagagg cctcaggatg
4201 ccaagaacac tatgatcctt gagatctgta ccaggtaccg gggagaccag gatgccacta
4261 tgtctatatt ggacatatcc atgatgactg gctttgctcc agacacagat gacctgaagc
4321 agctggccaa tggtgttgac agatacatct ccaagtatga gctggacaaa gccttctccg
4381 ataggaacac cctcatcatc tacctggaca aggtctcaca ctctgaggat gactgtctag
4441 ctttcaaagt tcaccaatac tttaatgtag agcttatcca gcctggagca gtcaaggtct
4501 acgcctatta caacctggag gaaagctgta cccggttcta ccatccggaa aaggaggatg
4561 gaaagctgaa caagctctgc cgtgatgaac tgtgccgctg tgctgaggag aattgcttca
4621 tacaaaagtc ggatgacaag gtcaccctgg aagaacggct ggacaaggcc tgtgagccag
4681 gagtggacta tgtgtacaag acccgactgg tcaaggttca gctgtccaat gactttgacg
4741 agtacatcat ggccattgag cagaccatca gtcaggctc ggatgaggtg caggttggac
4801 agcagcgcac gttcatcagc cccatcaagt gcagagaagc cctgaagctg gaggagaaga
4861 aacactacct catgtggggt ctctcctccg atttctgggg agagaagccc aacctcagct
```

```
4921 acatcatcgg gaaggacact tgggtggagc actggcccga ggaggacgaa tgccaagacg 4981 aagagaacca gaaacaatgc caggacctcg gcgccttcac cgagagcatg gttgtctttg 5041 ggtgcccccaa ctgaccacac ccccattccc ccactccaga taaagcttca gttatatctc 5101 a
```

At least about 30 related sequences have been identified and linked to the NCBI RefSeq entry for the human sequence.

Various C3 expression vectors are commercially available, some of which are linked to the above NCBI Ref. Seq. entry. For example, Homo sapiens complement component 3 (C3) as transfection-ready DNA (pCMV6-XL6, SKU SC308721); and other constructs are available from OriGene Technologies, Inc. (Rockville, Md.).

C3 (Human) Native Protein (Cat. No. P4945) is available from Abnova (Taiwan, ROC). Such protein products may be suitable for formulating pharmaceutical composition comprising the C3 protein.

Other commercially available resources linked to the human NCBI RefSeq entry include: siRNA and shRNA sequences from Santa Cruz Biotechnology (Santa Cruz, Calif.) or OriGen (Rockville, Md.), monoclonal antibody from Abnova (Taiwan, ROC), and other primer/probes for verifying expression level of constructs from Life Technologies Corp. (Grand Island, N.Y.).

Ceruloplasmin or Caeruloplasmin (Human Ceruloplasmin (Ferroxidase) (CP)) (NCBI Reference Sequence: NM_000096.3 and NP_000087.1)

Ceruloplasmin is a ferroxidase enzyme that in humans is encoded by the CP gene, and is also known as CP-2.

Ceruloplasmin, a metalloprotein, is the major copper-carrying protein in the blood, and in addition plays a role in iron metabolism. Mutations in this gene cause aceruloplasminemia, which results in iron accumulation and tissue damage, and is associated with diabetes and neurologic abnormalities. Two transcript variants, one protein-coding and the other not protein-coding, have been found for this gene. The molecular weight of human ceruloplasmin is reported to be 151 kDa. It was first cloned in 1984 (Takahashi et al., 1984, *Proc. Natl. Acad. Sci. USA* 81(2):390-394; Koschinsky et al., 1986, *Proc. Natl. Acad. Sci. USA* 83(14): 5086-5090). Like any other plasma protein, levels drop in patients with hepatic disease due to reduced synthesizing capabilities. Low CP levels have been associated with Wilson disease (a rare copper storage disease), Menkes disease, overdose of Vitamin C, copper deficiency and aceruloplasminemia (Scheinberg et al., 1952, *Science* 116 (3018): 484-485; Gitlin, 1998, *Pediatr. Res.* 44:271-276). Elevated levels of CP have been associated with lymphoma, acute and chronic inflammation, rheumatoid arthritis, angina, Alzheimer's disease, schizophrenia and obsessive-compulsive disorder (Lutsenko et al., 2008, *Arch. Biochem. Biophys.* 476:22-32; Wolf et al., 2006, *Schizophr. Res.* 86(1-3):167-171; Virit et al., 2008, *Behav. Brain Funct.* 4:52).

The human CP protein and cDNA sequences are listed below.

```
NCBI Reference Sequence: NP_000087.1:
                                                  (SEQ ID NO: 13)
MKILILGIFLFLCSTPAWAKEKHYYIGIIETTWDYASDHGEKKLISVDTEHSNIYLQNGPDRIGRLYK

KALYLQYTDETFRTTIEKPVWLGFLGPIIKAETGDKVYVHLKNLASRPYTFHSHGITYYKEHEGAIY

PDNTTDFQRADDKVYPGEQYTYMLLATEEQSPGEGDGNCVTRIYHSHIDAPKDIASGLIGPLIICK

KDSLDKEKEKHIDREFVMFSWDENFSWYLEDNIKTYCSEPEKVDKDNEDFQESNRMYSVNGYTF

GSLPGLSMCAEDRVKWYLFGMGNEVDVHAAFFHGQALTNKNYRIDTINLFPATLFDAYMVAQNP

GEWMLSCQNLNHLKAGLQAFFQVQECNKSSSKDNIRGKHVRHYYIAAEEIIWNYAPSGIDIFTKEN

LTAPGSDSAVFFEQGTTRIGGSYKKLVYREYTDASFTNRKERGPEEEHLGILGPVIWAEVGDTIR

VTFHNKGAYPLSIEPIGVRFNKNNEGTYYSPNYNPQSRSVPPSASHVAPTETFTYEWTVPKEVGP

TNADPVCLAKMYYSAVDPTKDIFTGLIGPMKICKKGSLHANGRQKDVDKEFYLFPTVFDENESLLL

EDNIRMFTTAPDQVDKEDEDFQESNKMHSMNGFMYGNQPGLTMCKGDSVVWYLFSAGNEADV

HGIYFSGNTYLWRGERRDTANLFPQTSLTLHMWPDTEGTFNVECLTTDHYTGGMKQKYTVNQC

RRQSEDSTFYLGERTYYIAAVEVEWDYSPQREWEKELHHLQEQNVSNAFLDKGEFYIGSKYKKW

YRQYTDSTFRVPVERKAEEEHLGILGPQLHADVGDKVKIIFKNMATRPYSIHAHGVQTESSTVTPT

LPGETLTYVWKIPERSGAGTEDSACIPWAYYSTVDQVKDLYSGLIGPLIVCRRPYLKVFNPRRKLE

FALLFLVFDENESWYLDDNIKTYSDHPEKVNKDDEEFIESNKMHAINGRMFGNLQGLTMHVGDEV

NWYLMGMGNEIDLHTVHFHGHSFQYKHRGVYSSDVFDIFPGTYQTLEMFPRTPGIWLLHCHVTD

HIHAGMETTYTVLQNEDTKSG
```

-continued cDNA (NCBI Reference Sequence: NM_000096.3)
(SEQ ID NO: 14)

```
acaccctaat gcctccaaca ataactgttg acttttttatt ttcagtcaga gaagcctggc    61
aaccaagaac tgtttttttg gtggtttacg agaacttaac tgaattggaa aatatttgct   121
ttaatgaaac aatttactct tgtgcaacac taaattgtgt caatcaagca ataaggaag    181 aaagtcttat ttataaaatt gcctgctcct gattttactt catttcttct caggctccaa   241
gaaggggaaa aaaatgaaga ttttgatact tggtatttt ctgttttat gtagtacccc     301 agcctgggcg aaagaaaagc attattacat tggaattatt gaaacgactt gggattatgc   361
ctctgaccat ggggaaaaga aacttatttc tgttgacacg gaacattcca atatctatct   421
tcaaaatggc ccagatagaa ttgggagact atataagaag gcccttttatc ttcagtacac   481 agatgaaacc tttaggacaa ctatagaaaa accggtctgg cttgggtttt taggcctat    541 tatcaaagct gaaactggag ataaagttta tgtacactta aaaaaccttg cctctaggcc   601
ctacaccttt cattcacatg gaataactta ctataaggaa catgaggggg ccatctaccc   661
tgataacacc acagattttc aaagagcaga tgacaaagta tatccaggag agcagtatac   721
atacatgttg cttgccactg aagaacaaag tcctgggaaa ggagatggca attgtgtgac   781
taggatttac cattcccaca ttgatgctcc aaaagatatt gcctcaggac tcatcggacc   841
tttaataatc tgtaaaaaag attctctaga taagaaaaa gaaaacata ttgaccgaga    901 atttgtggtg atgttttctg tggtggatga aaatttcagc tggtacctag aagacaacat   961
taaaacctac tgctcagaac cagagaaagt tgacaaagac aacgaagact tccaggagag  1021
taacagaatg tattctgtga atggatacac ttttggaagt ctcccaggac tctccatgtg  1081
tgctgaagac agagtaaaat ggtaccttt tggtatgggt aatgaagttg atgtgcacgc   1141
agctttcttt cacgggcaag cactgactaa caagaactac cgtattgaca caatcaacct  1201 cttttcctgct accctgtttg atgcttatat ggtgcccag aaccctggag aatggatgct   1261
cagctgtcag aatctaaacc atctgaaagc cggtttgcaa gccttttcc aggtccagga   1321 gtgtaacaag tcttcatcaa aggataatat ccgtgggaag catgttagac actactacat  1381
tgccgctgag gaaatcatct ggaactatgc tccctctggt atagacatct tcactaaaga  1441
aaacttaaca gcacctggaa gtgactcagc ggtgttttt gaacaaggta ccacaagaat   1501
tggaggctct tataaaaagc tggtttatcg tgagtacaca gatgcctcct tcacaaatcg  1561
aaaggagaga ggccctgaag aagagcatct tggcatcctg ggtcctgtca tttgggcaga  1621
ggtgggagac accatcagag taaccttcca taacaaagga gcatatcccc tcagtattga  1681
gccgattggg gtgagattca ataagaacaa cgagggcaca tactattccc caaattacaa  1741
cccccagagc agaagtgtgc ctccttcagc ctcccatgtg gcacccacag aaacattcac  1801
ctatgaatgg actgtcccca agaagtagg acccactaat gcagatcctg tgtgtctagc   1861
taagatgtat tattctgctg tggatccac taaagatata ttcactgggc ttattgggcc   1921
aatgaaaata tgcaagaaag gaagtttaca tgcaaatggg agacagaaag atgtagacaa  1981
ggaattctat ttgttttccta cagtatttga tgagaatgag agtttactcc tggaagataa  2041
tattagaatg tttacaactg cacctgatca ggtggataag gaagatgaag actttcagga  2101
atctaataaa atgcactcca tgaatggatt catgtatggg aatcagccgg gtctcactat  2161
gtgcaaagga gattcggtcg tgtggtactt attcagcgcc ggaaatgagg ccgatgtaca  2221
tggaatatac ttttcaggaa acacatatct gtggagagga gaacggagag acacagcaaa  2281
cctcttccct caaacaagtc ttacgctcca catgtggcct gacacagagg ggacttttaa  2341
tgttgaatgc cttacaactg atcattacac aggcggcatg aagcaaaaat atactgtgaa  2401
```

-continued

```
ccaatgcagg cggcagtctg aggattccac cttctacctg ggagagagga catactatat    2461
cgcagcagtg gaggtggaat gggattattc cccacaaagg gagtgggaaa aggagctgca    2521
tcatttacaa gagcagaatg tttcaaatgc atttttagat aagggagagt tttacatagg    2581
ctcaaagtac aagaaagttg tgtatcggca gtatactgat agcacattcc gtgttccagt    2641
ggagagaaaa gctgaagaag aacatctggg aattctaggt ccacaacttc atgcagatgt    2701
tggagacaaa gtcaaaatta tctttaaaaa catggccaca aggccctact caatacatgc    2761
ccatggggta caaacagaga gttctacagt tactccaaca ttaccaggtg aaactctcac    2821
ttacgtatgg aaaatcccag aaagatctgg agctggaaca gaggattctg cttgtattcc    2881
atgggcttat tattcaactg tggatcaagt taaggacctc tacagtggat taattggccc    2941
cctgattgtt tgtcgaagac cttacttgaa agtattcaat cccagaagga aactggaatt    3001
tgcccttctg tttctagttt tgatgagaa tgaatcttgg tacttagatg acaacatcaa    3061
aacatactct gatcaccccg agaaagtaaa caaagatgat gaggaattca tagaaagcaa    3121
taaaatgcat gctattaatg gaagaatgtt tggaaaccta caaggcctca caatgcacgt    3181
gggagatgaa gtcaactggt atctgatggg aatgggcaat gaaatagact acacactgt    3241
acattttcac ggccatagct tccaatacaa gcacagggga gtttatagtt ctgatgtctt    3301
tgacattttc cctggaacat accaaacccc tagaaatgttt ccaagaacac ctggaatttg    3361
gttactccac tgccatgtga ccgaccacat tcatgctgga atggaaacca cttacaccgt    3421
tctacaaaat gaagacacca aatctggctg aatgaaataa attggtgata agtggaaaaa    3481
agagaaaaac caatgattca taacaatgta tgtgaaagtg taaaatagaa tgttactttg    3541
gaatgactat aaacattaaa agaagactgg aagcatacaa ctttgtacat ttgtggggga    3601
aaactattaa ttttttgcaa atggaaagat caacagacta tataatgata catgactgac    3661
acttgtacac taggtaataa aactgattca tacagtctaa tgatatcacc gctgttaggg    3721
ttttataaaa ctgcatttaa aaaaagatct atgaccagat attctcctgg gtgctcctca    3781
aaggaacact attaaggttc attgaaatgt tttcaatcat tgccttccca ttgatccttc    3841
taacatgctg ttgacatcac acctaatatt cagagggaat gggcaaggta tgagggaagg    3901
aaataaaaaa taaataaat aaatagaat gacacaaatt tgagttttgt gaacccctga    3961
acagatggtc ttaaggacgt tatctggaac tggagaaaag cagagttgag agacaattct    4021
atagattaaa tcctggtaag gacaaacatt gccattagaa gaaaagcttc aaaatagacc    4081
tgtggcagat gtcacatgag tagaatttct gcccagcctt aactgcattc agaggataat    4141
atcaatgaac taaacttgaa ctaaaaattt tttaaacaaa aagttataaa tgaagacaca    4201
tggttgtgaa tacaatgatg tatttcttta ttttcacata cactctagct aaaagagcaa    4261
gagtacacat caacaaaaat ggaaacaagg ctttggctga aaaaacatg catttgacaa    4321
atcatgttaa tagctagaca agaagaaagt tagctttgta aacttctact tcatttgatt    4381
cagagaaaca gagcatgagt tttcttaaaa gtaacaagaa aaggaacaaa aaaaatgagg    4441
tttgaaatct tttaccatgg caaaacatta acatctttct caaaaacata gagaaatctg    4501
gaaaaatcaa gaagataaaa ttctggacca gttagtgaca ttctttcaag catacttgta    4561
aaatgttttcc ttaaagtgtt cttgggatga aaatgattgt catgtctcca acaacagtga    4621
actgatgttg ttccttggaa taaaagtcaa tccccacctt aaaaaaaaaa aaaa
```

Various CP expression vectors are commercially available, some of which are linked to the above NCBI Ref. Seq. entry. For example, human CP as transfection-ready DNA (pCMV6-XL5, SKU SC315128); Myc-DDK-tagged ORF clone of *Homo sapiens* CP as transfection-ready DNA (pCMV6-Entry, SKU RC224598) and GFP-tagged as transfection-ready DNA (pCMV6-AC-GFP; OriGene Technologies, Inc., Rockville, Md., cat. no. RG224598)(Rockville, Md.).

CP (Human) isolated protein (P01) (Cat. No. 239799) is available from EMD Millipore (Billerica, Mass., USA) and Abnova (cat. no. P4942; Walnut, Calif., USA). Such protein products may be suitable for formulating pharmaceutical composition comprising the CP protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA) and many other suppliers, qPCR primers from OriGene Technologies (Rockville, Md.) and QIAGEN (Germantown, Md.), and other primer/probes for verifying expression level of constructs from QIAGEN (Germantown, Md.) and Ori-Gene Technologies (Rockville, Md.) other suppliers.

CXCL5 (Human Chemokine (C-X-C Motif) Ligand 5) (NCBI Reference Sequence: NM_002994.3 and NP_002985.1)

CXCL5, also known as epithelial-derived neutrophil-activating peptide 78 (ENA-78) or SCYB5. Protein encoded by this gene is an inflammatory chemokine that belongs to the CXC chemokine family. This chemokine is produced concomitantly with interleukin-8 (IL8) in response to stimulation with either interleukin-1 (ILD) or tumor necrosis factor-alpha (TNFA). This chemokine is a potent chemotaxin involved in neutrophil activation. CXCL5 is expressed in eosinophils (Chang et al. 1994, *J. Biol. Chem.* 269:25277-25282; Persson et al. 2003, *Clin. Exp. Allergy* 33:531-537). CXCL5 plays a role in reducing sensitivity to sunburn pain in some subjects, and is a "potential target which can be utilized to understand more about pain in other inflammatory conditions like arthritis and cystitis (Dawes et al. 2011, *Sci. Transl. Med.* 3(90):90ra60).

The human CXCL5 protein and cDNA sequences are listed below:

```
Protein (NCBI Reference Sequence: NP_002985.1)
                                                       (SEQ ID NO: 15)
MSLLSSRAARVPGPSSSLCALLVLLLLLTQPGPIASAGPAAAVLRELRCVCLQTTQGVHPKMISNLQV

FAIGPQCSKVEVVASLKNGKEICLDPEAPFLKKVIQKILDGGNKEN cDNA (NCBI Reference Sequence: NM_002994.3).
                                                       (SEQ ID NO: 16)
     gtgcagaagg cacgaggaag ccacagtgct ccggatcctc caatcttcgc tcctccaatc    61
tccgctcctc cacccagttc aggaacccgc gaccgctcgc agcgctctct tgaccactat   121
gagcctcctg tccagccgcg cggcccgtgt ccccggtcct tcgagctcct tgtgcgcgct   181
gttggtgctg ctgctgctgc tgacgcagcc agggcccatc gccagcgctg gtcctgccgc   241
tgctgtgttg agagagctgc gttgcgtttg tttacagacc acgcaaggag ttcatcccaa   301
aatgatcagt aatctgcaag tgttcgccat aggcccacag tgctccaagg tggaagtggt   361
agcctccctg aagaacggga aggaaatttg tcttgatcca gaagccccctt ttctaaagaa   421 agtcatccag aaaattttgg acggtggaaa caaggaaaac tgattaagag aaatgagcac   481
gcatggaaaa gtttcccagt cttcagcaga gaagttttct ggaggtctct gaacccaggg   541
aagacaagaa ggaaagattt tgttgttgtt tgtttatttg ttttttccagt agttagcttt   601 cttcctggat tcctcacttt gaagagtgtg aggaaaacct atgtttgccg cttaagcttt   661
cagctcagct aatgaagtgt ttagcatagt acctctgcta tttgctgtta ttttatctgc   721
tatgctattg aagttttggc aattgactat agtgtgagcc aggaatcact ggctgttaat   781 cttcaaagt gtcttgaatt gtaggtgact attatatttc caagaaatat tccttaagat   841
attaactgag aaggctgtgg atttaatgtg gaaatgatgt tcataagaa ttctgttgat   901 ggaaatacac tgttatcttc acttttataa gaaataggaa atattttaat gtttcttggg   961
gaatatgtta gagaatttcc ttactcttga ttgtgggata ctatttaatt atttcacttt  1021
agaaagctga gtgtttcaca ccttatctat gtagaatata tttccttatt cagaatttct  1081
aaaagtttaa gttctatgag ggctaatatc ttatcttcct ataattttag acattcttta  1141 tcttttttagt atggcaaact gccatcattt acttttaaac tttgatttta tatgctattt  1201
attaagtatt ttattaggag taccataatt ctggtagcta aatatatatt ttagatagat  1261
gaagaagcta gaaaacaggc aaattcctga ctgctagttt atatagaaat gtattcttt   1321
```

```
agtttttaaa gtaaaggcaa acttaacaat gacttgtact ctgaaagttt tggaaacgta    1381
ttcaaacaat ttgaatataa atttatcatt tagttataaa aatatatagc gacatcctcg    1441
aggccctagc atttctcctt ggatagggga ccagagagag cttggaatgt taaaaacaaa    1501
acaaaacaaa aaaaaacaag gagaagttgt ccaagggatg tcaattttt atccctctgt     1561 atgggttaga ttttccaaaa tcataatttg aagaaggcca gcatttatgg tagaatatat    1621
aattatatat aaggtggcca cgctggggca agttccctcc ccactcacag ctttggcccc    1681
tttcacagag tagaacctgg gttagaggat tgcagaagac gagcggcagc ggggagggca    1741
gggaagatgc ctgtcgggtt tttagcacag ttcatttcac tgggattttg aagcatttct    1801
gtctgaatgt aaagcctgtt ctagtcctgg tgggacacac tggggttggg ggtgggggaa    1861
gatgcggtaa tgaaaccggt tagtcagtgt tgtcttaata tccttgataa tgctgtaaag    1921
tttattttta caaatatttc tgtttaagct atttcacctt tgtttggaaa tccttccctt    1981
ttaaagagaa aatgtgacac ttgtgaaaag gcttgtagga aagctcctcc ctttttttct    2041
ttaaacsttt aaatgacaaa cctaggtaat taatggttgt gaatttctat ttttgcttg     2101 tttttaatga acatttgtct ttcagaatag gattctgtga taatatttaa atggcaaaaa    2161
caaaacataa ttttgtgcaa ttaacaaagc tactgcaaga aaaataaaac atttcttggt    2221
aaaaacgtat gtatttatat attatatatt tatatataat atatattata tatttagcat    2281
tgctgagctt tttagatgcc tattgtgtat cttttaaagg ttttgaccat tttgttatga    2341
gtaattacat atatattaca ttcactatat taaaattgta cttttttact atgtgtctca    2401
ttggttcata gtctttattt tgtcctttga ataaacatta aaagatttct aaacttcaaa    2461
aaaaaaaaaa aaaaa
```

Various CXCL5 expression vectors are commercially available, some of which are linked to the above NCBI Ref. Seq. entry. For example, human CCXCL5 as transfection-ready DNA (pCMV6-XL5, SKU SC118269); Myc-DDK-tagged ORF clone of *Homo sapiens* CXCL5 as transfection-ready DNA (pCMV6-Entry, SKU RC202707) and GFP-tagged as transfection-ready DNA (pCMV6-AC-GFP; OriGene Technologies, Inc., Rockville, Md., cat. no RG202707)(Rockville, Md.).

CXCL5 (Human) recombinant protein (Cat. No. TP302707) is available for example from OriGene Technologies (Rockville, Md., USA) and Abnova (cat. no. P3961; Walnut, Calif., USA) or ProSpec (Cat. No. CHM-331; East Brunswick, N.J., USA). Such protein products may be suitable for formulating pharmaceutical composition comprising the CXCL5 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA) and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

GLIPR1 (Human GLI Pathogenesis-Related 1 (GLIPR1)) (NCBI Reference Sequence: NM_006851.2 and NP_006842.2)

GLI pathogenesis-related 1 (GLIPR1), also known as glioma pathogenesis-related protein 1, RTVP1 or CRISP7, encodes a protein with similarity to both the pathogenesis-related protein (PR) superfamily and the cysteine-rich secretory protein (CRISP) family and was originally cloned from a human astrocytoma cell line (Murphy et al., 1995, *Gene* 159:131-135; Rich et al., 1997, *Gene* 180:125-130). Increased expression GLIPR1 is associated with myelomocytic differentiation in macrophage and decreased expression of this gene through gene methylation is associated with prostate cancer. GLIPR1 protein has been prescribed to have proapoptotic activities in prostate and bladder cancer cells and is thought to may be useful for treatment of cancer as tumor suppressor (Thompson, 2010, *Med. J.*, 51(4):479-483). Alternatively spliced variants which encode different protein isoforms have been described, by Xiang et al., 2007 (*Biochem. Biophys. Res. Commun.* 362:612-618).

The human GLIPR1 protein and cDNA sequences are listed below:

NCBI Reference Sequence: NP_006842.2)
(SEQ ID NO: 17)
MRVTLATIAWMVSFVSNYSHTANILPDIENEDFIKDCVRIHNKFRSEVKPTASDMLYMTWDPALAQIA

KAWASNCQFSHNTRLKPPHKLHPNFTSLGENIWTGSVPIFSVSSAITNWYDEIQDYDFKTRICKKVCG

HYTQWWADSYKVGCAVQFCPKVSGFDALSNGAHFICNYGPGGNYPTWPYKRGATCSACPNNDK

CLDNLCVNRQRDQVKRYYSVVYPGWPIYPRNRYTSLFLIVNSVILILSVIITILVQHKYPNLVLLD

NCBI Reference Sequence: NM_006851.2

(SEQ ID NO: 18)

```
agtgatgaac tcatgctctg ttctgttttc tcaaagctga agtcggctag gtttgcaaag    61
ctgtgggctg agcactcagg caatcacact ctcagaaact gcggcggctc tggactgcag   121
cctcccaagg ctccatgcca gacaaagcat gcgtgtcaca cttgctacaa tagcctggat   181
ggtttctttt gtctccaatt attcacacac agcaaatatt ttgccagata tcgaaaatga   241
agatttcatc aaagactgcg ttcgaatcca taacaagttc cgatcagagg tgaaaccaac   301
agccagtgat atgctataca tgacttggga cccagcacta gcccaaattg caaaagcatg   361
ggccagcaat tgccagtttt cacataatac acggctgaag ccaccccaca agctgcaccc   421
aaacttcact tcactgggag agaacatctg gactgggtct gtgcccattt tttctgtgtc   481
ttccgccatc acaaactggt atgacgaaat ccaggactat gacttcaaga ctcggatatg   541
caaaaaagtc tgtggccact acactcaggt tgtttgggca gatagttaca agttggctg    601
cgcagttcaa ttttgcccta agtttctgg ctttgacgct ctttccaatg gagcacattt    661
tatatgcaac tacggaccag gagggaatta cccaacttgg ccatataaga gaggagccac   721
ctgcagtgcc tgccccaata tgacaagtg tttggacaat ctctgtgtta accgacagcg    781
agaccaagtc aaacgttact actctgttgt atatccaggc tggcccatat atccacgtaa   841
cagatacact tctctcttc tcattgttaa ttcagtaatt ctaatactgt ctgttataat    901
taccattttg gtacagcaca agtaccctaa tttagttctt ttggactaat acaattcagg   961
aaagaaaaaa cccaaaaacc aacctcattc acatatggct ttttttttaa ccaataacaa  1021
ttaggtgtac ttctatttta aaacatttca gaaaaaaata tatgttatag caatactctt  1081
actcaaaaga agaaatttcc taactctatc agataaactc atctttagta taaataagca  1141
ttatttgcag gttgccacag gtggactttt agtaagtaac ctaacccatg tttcagcttc  1201
taaatctgca aaatgagcaa ggtacagtag cacatttta ggtgattctt agtaactcca    1261
gtagccttca ttagttaaaa acattattat ttttgcatg ctgcttcgac tctaaatatc    1321
tggttttccc tgtctttttg gtttactact tccccagatt cagaacagag gagtaactag   1381
gggatctgat tttagaggcc ttaattttct gttcatggac tgttaaaagt aaaaccaaac   1441
tttcaaaagg gataaaccta aatatttact tgttatcatt agagagggaa catcaaatgc   1501
tgggacatca ttactaacca atagcatcag acactggatt taatggataa tcacaatggt   1561
cgtaatgtat acaagactt atataccact ttctcgtata aatttttcaa aaaatacaat    1621
aataatataa tttataaaga acactcttct atgaacaacc accaccacca aaaaaaaaa    1681
aagccctcag aaaatttctc acaaataagg caactaatgc ctgatatctc aaaatccttt   1741
acaaaaggag atagttctag tcaaggagtt ttgggtatgt tactttttt tcttcttttt    1801
cttttcatct gcctccatct taagtgcaat ttcttcagct gtaagagctc ccagtttctt   1861
attctttgct ttcttaacct tttccttgat gctggccaca tcaattttag tttcagtaga   1921
agctagacaa attaaaagca caacacatgt aatactttag attttaccaa gtaaaacaaa   1981
gaatatatgt ttaacaaaga atatatgttt aaggcagtta acttcagagt attcttataa   2041
ttgaataatt gaaaggtgat cacagtataa aatataaaaa cacttgccta aagcagttag   2101
aaatttcttc agattaagat aaaacaaatc ataaaatact ttatatatta gtacaagtat   2161
acataaaaat ggcataaatg gcataattga accaattact ggattcaact atattaagac   2221
tatttcctta aatcctactt cagactaaat tattttacct acattctttt ccatattttg   2281
```

```
                                                -continued
gaacttctga gtcattattt tccatcttgc acattaaaat aatttaaaat tacatgtatc    2341
ccttctcaat aagtttaatc agctaaccct aagctagagg tcaaaatcta cttcctctaa    2401
tatcaaaacg aaaatttaaa gttttccaaa tattaattca atattaattg aatattcaat    2461
gaattaattc atttaatgtt agattaattc attgaatatt aattcaatga atgactaatt    2521
aatagtattt taacaagatt ttggtatatt taacaacatt ttggtaataa agacaataat    2581
ttgagagtgt gtggaagtcc ccctaataga agccaactat ctaatcaatg ccaaaagtgt    2641
gaacaaaata gagaaaggaa gcagtgaaaa agaatgcaac tttttcttac cattcaaagt    2701
acaggatcac agcataaaag aatcataaga taaaacatca aactacccag caacctgaga    2761
agcacagagt gttaaagcct ccaccgtgtg gagaaactaa attagggtaa ctagctattg    2821
agtatattga gtaccttcaa agcactcaac tgacaggttt tacagactgg aaattataat    2881
acttatgaca tttctacctt ttatataacc aataatctac catagaatgt agtattttta    2941
aagctattaa caagcaatat attaaaataa taatgtatta tatctgtttc tgacccagtc    3001
tatgtacaat attgctggtg agccctctcc cttcagtgtg tcactgttca ctttggaggg    3061
ttactttagg aagaggataa gtgttaccac aggggaaaaa aatgcagaag aggatgcatc    3121
agaagaaatg gcatgacaat gttttctctt agtgtctttt aaatactagg ttagtgcgaa    3181
agtgatttct gccatttaaa aaccacaatc actttcgcac taatagctcc tgaataagac    3241
ctgtcagcat cctttagtct aaggtgatga gaaatccatg ttaccgatat agaagccaaa    3301
ctctaagcca agatcacata aagagaagaa aaagtacaac ttctgataat tcctctttga    3361
gaggcatgac agcagagctc agggatcttc ttgcatttct acagaagatg cactggctgc    3421
cctgggtttg tatctttcac aacaaagagt cttttccaag cacagaccag aggtcaggag    3481
aggactgtca atccagtttg cactgaaata ggcattagct gcctctaaat tataaattat    3541
ctcagccatc ccttgtcctt aggattagta attaatgaaa tgctaagaga actgatgaaa    3601
agatacaact gtttcttaaa aagattcaga caaatttatt atgggtttac ttttcctaat    3661
taataaagac ttttacatca tagaaagcat taccttcctt aggtttcaca attggttttt    3721
ccttaggtgg aataaatgct ttgtttcttt cctcttgtct cttactgatg gcttctgctt    3781
gtttagccta cattaataaa taaaaaatat atcagtttaaa tgtatttata gttaaataat    3841
tcaagtatct atgaactttg ctattcatgt gagccagaca taaagtgccg tacctttatt    3901
gcttccaaaa aaaaaaaaaa aaaa
```

Various GLIPR1 expression vectors are commercially available, some of which are linked to the above NCBI Ref. Seq. entry. For example, human GLIPR1 as transfection-ready DNA (pCMV6-XL5, SKU SC108517); Myc-DDK-tagged ORF clone of *Homo sapiens* GLIPR1 as transfection-ready DNA (pCMV6-Entry, SKU RC216882) and GFP-tagged as transfection-ready DNA (pCMV6-AC-GFP; OriGene Technologies, Inc., Rockville, Md., cat. no. RG216882)(Rockville, Md.).

GLIPR1 (Human) recombinant protein is available for example from Abnova (cat. no. H00011010-Q01; Walnut, Calif., USA). Such protein products may be suitable for formulating pharmaceutical composition comprising the GLIPR1 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA) and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

IGFBP3 (Human Insulin-Like Growth Factor Binding Protein 3 (IGFBP3)) (NCBI Reference Sequence: NM_001013398.1 and NP_001013416.1)

IGFBP3 here interchangeable used IGBP3, BP3 or BP-53 is a member of the insulin-like growth factor-binding protein (IGFBP) family and encodes a protein with an IGFBP domain and a thyroglobulin type-I domain (Wood et al., 1988, *Mol. Endocr.* 2:1176-1185). The protein forms a ternary complex with insulin-like growth factor acid-labile subunit (IGFALS) and either insulin-like growth factor (IGF) I or II. In this form, it circulates in the plasma, prolonging the half-life of IGFs and altering their interaction with cell surface receptors. Alternate transcriptional splice variants, encoding different isoforms, have been characterized (Cubbage et al. 1990, *J. Biol. Chem.* 265:12642-12649).

It has been found IGFBP3 is active in the unglycosyalted form, and also as a truncated form (SEQ ID NO: 20). IGFBP3 protein levels decrease during the progression of prostate cancer from benign to metastatic disease (Miyake et al. 2000, *Cancer Res.* 60:3058-3064). Recombinant IGF-1 with IGFBP-3 (mecasermin rinfabate) is used for treatment of growth failure in children, and amyotrophic lateral sclerosis.

The human IGFBP3 protein and cDNA sequences are listed below:

```
Protein NCBI Reference Sequence: NP_001013416.1
                                                    (SEQ ID NO: 19)
MQRARPTLWAAALTLLVLLRGPPVARAGASSAGLGPVVRCEPCDARALAQCAPPPAVCAELVREPGCG

CCLTCALSEGQPCGIYTERCGSGLRCQPSPDEARPLQALLDGRGLCVNASAVSRLRAYLLPAPPAPGEP

PAPGNASESEEDRSAGSVESPSVSSTHRVSDPKFHPLHSKIIIIKKGHAKDSQRYKVDYESQSTDTQNF

SSESKRETEYGPCRREMEDTLNHLKFLNVLSPRGVHIPNCDKKGFYKKKQCRPSKGRKRGFCWCVDKYG

QPLPGYTTKGKEDVHCYSMQSK

Mature protein (29 kD, active as unglycosylated protein):
                                                    (SEQ ID NO: 20)
GASSAGLGPWRCEPCDARALAQCAPPPAVCAELVREPGCGCCLTCALSEGQPCGIYTERCGSGLRCQP

SPDEARPLQALLDGRGLCVNASAVSRLRAYLLPAPPAPGNASESEEDRSAGEVESPSVSSTHRVSDPKFH

PLHSKIIIIKKGHAKDSQRYKVDYESQSTDTQNFSSESKRETEYGPCRREMEDTLNHLKFLNVLSPRGV

HIPNCDKKGFYKKKQCRPSKGRKRGFCWCVDKYGQPLPGYTTKGKEDVHCYSMQSK

NCBI Reference Sequence: NM_001013398.1
                                                    (SEQ ID NO: 21)
agatgcgagc actgcggctg ggcgctgagg atcagccgct tcctgcctgg attccacagc    61
ttcgcgccgt gtactgtcgc cccatccctg cgcgcccagc ctgccaagca gcgtgccccg   121
gttgcaggcg tcatgcagcg ggcgcgaccc acgctctggg ccgctgcgct gactctgctg   181
gtgctgctcc gcgggccgcc ggtggcgcgg gctggcgcga gtcggcgggg cttgggtccc   241
gtggtgcgct gcgagccgtg cgacgcgcgt gcactggccc agtgcgcgcc tccgccgcc    301 gtgtgcgcgg agctggtgcg cgagccgggc tgcggctgct gcctgacgtg cgcactgagc   361
gagggccagc cgtgcggcat ctacaccgag cgctgtggct ccggccttcg ctgccagccg   421
tcgcccgacg aggcgcgacc gctgcaggcg ctgctggacg gccgcgggct ctgcgtcaac   481
gctagtgccg tcagccgcct gcgcgcctac ctgctgccag cgccgccagc tccaggtgag   541
ccgcccgcgc caggaaatgc tagtgagtcg gaggaagacc gcagcgccgg cagtgtggag   601
agcccgtccg tctccagcac gcaccgggtg tctgatccca agttccaccc cctccattca   661
aagataatca tcatcaagaa agggcatgct aaagacagcc agcgctacaa agttgactac   721
gagtctcaga gcacagatac ccagaacttc tcctccgagt ccaagcggga gacagaatat   781
ggtccctgcc gtagagaaat ggaagacaca ctgaatcacc tgaagttcct caatgtgctg   841
agtccagggg tgtacacat tcccaactgt gacaagaagg gattttataa gaaaaagcag   901
tgtcgccctt ccaaaggcag gaagcggggc ttctgctggt gtgtggataa gtatgggcag   961
cctctcccag gctacaccac caaggggaag gaggacgtgc actgctacag catgcagagc  1021
aagtagacgc ctgccgcaag gttaatgtgg agctcaaata tgccttattt tgcacaaaag  1081
actgccaagg acatgaccag cagctggcta cagcctcgat ttatatttct gtttgtggtg  1141
aactgatttt ttttaaacca aagtttagaa agaggttttt gaatgcctta tggtttcttt  1201
gaatggtaaa cttgagcatc ttttcacttt ccagtagtca gcaaagagca gtttgaattt  1261
tcttgtcgct tcctatcaaa atattcagag actcgagcac agcacccaga cttcatgcgc  1321
ccgtggaatg ctcaccacat gttggtcgaa gcggccgacc actgactttg tgacttaggc  1381
ggctgtgttg cctatgtaga gaacacgctt caccccact ccccgtacag tgcgcacagg   1441
ctttatcgag aataggaaaa cctttaaacc ccggtcatcc ggacatccca acgcatgctc  1501
```

```
ctggagctca cagccttctg tggtgtcatt tctgaaacaa gggcgtggat ccctcaacca    1561
agaagaatgt ttatgtcttc aagtgacctg tactgcttgg ggactattgg agaaaataag    1621
gtggagtcct acttgtttaa aaaatatgta tctaagaatg ttctagggca ctctgggaac    1681
ctataaaggc aggtatttcg ggccctcctc ttcaggaatc ttcctgaaga catggcccag    1741
tcgaaggccc aggatggctt ttgctgcggc cccgtggggt aggagggaca gagagacagg    1801
gagagtcagc ctccacattc agaggcatca caagtaatgg cacaattctt cggatgactg    1861
cagaaaatag tgttttgtag ttcaacaact caagacgaag cttatttctg aggataagct    1921
ctttaaaggc aaagctttat tttcatctct catcttttgt cctccttagc acaatgtaaa    1981
aaagaatagt aatatcagaa caggaaggag gaatggcttg ctggggagcc catccaggac    2041
actgggagca catagagatt cacccatgtt tgttgaactt agagtcattc tcatgctttt    2101
ctttataatt cacacatata tgcagagaag atatgttctt gttaacattg tatacaacat    2161
agccccaaat atagtaagat ctatactaga taatcctaga tgaaatgtta gagatgctat    2221
atgatacaac tgtggccatg actgaggaaa ggagctcacg cccagagact gggctgctct    2281
cccggaggcc aaacccaaga aggtctggca aagtcaggct cagggagact ctgccctgct    2341
gcagacctcg gtgtggacac acgctgcata gagctctcct tgaaaacaga ggggtctcaa    2401
gacattctgc ctacctatta gctttctttt attttttaa cttttggggg ggaaaagtat     2461
ttttgagaag tttgtcttgc aatgtattta taaatagtaa ataaagtttt taccattaaa    2521
aaaatatctt tccctttgtt attgaccatc tctgggcttt gtatcactaa ttattttatt    2581
ttattatata ataattattt tattataata aaatcctgaa aggggaaaat aaaaaaaa
```

Various IGFBP3 expression vectors are commercially available, some of which are linked to the above NCBI Ref. Seq. entry. For example, human IGFBP3 as transfection-ready DNA (pCMV6-XL5, SKU SC119779 transcript variant 2 and SC301776 transcript variant 1); Myc-DDK-tagged ORF clone of Homo sapiens IGFBP3 as transfection-ready DNA (pCMV6-Entry, SKU RC209150 transcript variant 2 and RC216898 transcript variant 1) and GFP-tagged as transfection-ready DNA (pCMV6-AC-GFP; OriGene Technologies, Inc., Rockville, Md., cat. no. RG209150 transcript variant 2 and RG216898 transcript variant 1)(Rockville, Md.).

IGFBP3 (Human) recombinant protein is available for example from Abnova (cat. no. P4128; Walnut, Calif., USA), ProSpec (Cat. No. CYT-300; East Brunswick, N.J., USA), or R&D Systems (Cat. No. 675-B3-025). Such protein products may be suitable for formulating pharmaceutical composition comprising the IGFBP3 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

IGFBP6 (Human Insulin-Like Growth Factor Binding Protein 6 (IGFBP6)) (NCBI Reference Sequence: NM_002178.2 and NP_002169.1)

IGFBP6 was cloned by Kiefer et al. 1991 (*Biochem. Biophys. Res. Commun.* 176:219-225) and Shimasaki et al. 1991 (*Mol. Endocr.* 5: 938-948). IGFBP6 codes for a deduced 216-amino acid protein with a calculated molecular mass of 22,847 Da. A single 1.3-kb IGFBP6 mRNA was detected by Northern blot analysis in all rat tissues examined, indicating that this binding protein is ubiquitous. In the human keratinocyte cell line HaCat secretes IGFBP6 as an autocrine growth inhibitor. Recombinant IGFBP6 was also shown to inhibit growth of HaCat cells and other keratinocyte cell lines (Kato et al. 1995, *J. Biol. Chem.* 270:12373-12379).

The human IGFBP6 protein and cDNA sequences are listed below:

```
NCBI Reference Sequence: NP_002169.1
                                                        (SEQ ID NO: 22)
MTPHRLLPPLLLLLALLLAASPGGALARCPGCGQGVQAGCPGGCVEEEDGGSPAEGCAEAEGCLRREG

QECGVYTPNCAPGLQCHPPKDDEAPLRALLLGRGRCLPARAPAVAEENPKESKPQAGTARPQDVNRRDQ

QRNPGTSTTPSQPNSAGVQDTEMGPCRRHLDSVLQQLQTEVYRGAQTLYVPNCDHRGFYRKRQCRSS

QGQRRGPCWCVDRMGKSLPGSPDGNGSSSCPTGSSG

NCBI Reference Sequence: NM_002178.2
```

-continued (SEQ ID NO: 23)

```
gcggcggcgg gcagcagctg cgctgcgact gctctggaag gagaggacgg ggcacaaacc    61
ctgaccatga ccccccacag gctgctgcca ccgctgctgc tgctgctagc tctgctgctc   121
gctgccagcc caggaggcgc cttggcgcgg tgcccaggct gcgggcaagg ggtgcaggcg   181
ggttgtccag ggggctgcgt ggaggaggag gatgggtggg cgccagccga gggctgcgcg   241
gaagctgagg gctgtctcag gagggagggg caggagtgcg gggtctacac ccctaactgc   301
gccccaggac tgcagtgcca tccgcccaag gacgacgagg cgcctttgcg ggcgctgctg   361
ctcggccgag gccgctgcct tccggcccgc gcgcctgctg ttgcagagga gaatcctaag   421
gagagtaaac cccaagcagg cactgcccgc ccacaggatg tgaaccgcag agaccaacag   481
aggaatccag gcacctctac cacgccctcc cagcccaatt ctgcgggtgt ccaagacact   541
gagatgggcc catgccgtag acatctggac tcagtgctgc agcaactcca gactgaggtc   601
taccgagggg ctcaaacact ctacgtgccc aattgtgacc atcgaggctt ctaccggaag   661
cggcagtgcc gctcctccca ggggcagcgc cgaggtccct gctggtgtgt ggatcggatg   721
ggcaagtccc tgccagggtc tccagatggc aatggaagct cctcctgccc cactgggagt   781
agcggctaaa gctgggggat agaggggctg cagggccact ggaaggaaca tggagctgtc   841
atcactcaac aaaaaaccga ggccctcaat ccaccttcag gccccgcccc atgggcccct   901
caccgctggt tggaaagagt gttggtgttg gctggggtgt caataaagct gtgcttgggg   961
tcgctgaaaa aaaaaaaaaa
```

At least about 9 related sequences have been identified and linked to the NCBI RefSeq entry for the human sequence.

Various IGFBP6 expression vectors are commercially available, some of which are linked to the above NCBI Ref. Seq. entry. For example, human IGFBP6 as transfection-ready DNA (pCMV6-XL5, SKU SC122620); Myc-DDK-tagged ORF clone of *Homo sapiens* IGFBP6 as transfection-ready DNA (pCMV6-Entry, SKU RC204060) and GFP-tagged as transfection-ready DNA (pCMV6-AC-GFP; OriGene Technologies, Inc., Rockville, Md., cat. no. RG204060)(Rockville, Md.).

IGFBP6 (Human) recombinant protein is available for example from Abnova (cat. no. H00003489-P01; Walnut, Calif., USA), ProSpec (Cat. No. CYT-258; East Brunswick, N.J., USA), or R&D Systems (Cat. No. 876-B6-025). Such protein products may be suitable for formulating pharmaceutical composition comprising the IGFBP6 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

LGALS1 (Human Lectin, Galactoside-Binding, Soluble, 1 (LGALS1)) (NCBI Reference Sequence: NM_002305.3 and NP_002296.1)

LGALS1 (lectin, galactoside-binding, soluble, 1) is also known as galectin-1, GBP, or GALL The protein is 135 amino acids in length (Gitt and Barondes, 1986, *Proc. Nat. Acad. Sci. USA* 83:7603-7607; Sakaguchi et al., 2006 *Proc.* *Nat. Acad. Sci. USA* 103:7112-7117). LGALS1 can be found in the nucleus, the cytoplasm, the cell surface and in the extracellular space. Galectins in general lack a traditional signal sequence, but are still secreted across the plasma membrane, but requires a functional glycan binding site. Galectin 1 contains a single carbohydrate recognition domain through which it can bind glycans both as a monomer and as a homodimer. Dimers are non-covenantly bound and will spontaneously disassociate in low concentration (Cho and Cummings, 1995, *JBC* 270: 5198-5206). LGALS1 does not bind glycans when oxidized. LGALS1 is thought to play a role in the immunosuppression required for a successful pregnancy (Munoz-Suano et al., 2011, *Immunol. Rev.* 241:20-38). LGALS1 is expressed by the endometrial stromal cells throughout the menstrual cycle, however significantly increases during implantation. LGALS1 induces the differentiation of dendritic cells towards a phenotype which dampens T helper 1 cells and T helper 17 cells and dampens inflammation via interleukin-10 and interleukin-27 (Ilarregui et al., 2009, *Nat. Immunol.* 10:981-991). LGALS1 has been shown to protect from inflammation-induced neurodegeneration (Starossom et al., 2012, *Immunity* 37:249-263), to control cardiac inflammation during acute myocardial infarction (Seropian et al., 2013, *Am. J. Pathol.* 182: 29-40).

The term "LGALS1" as used herein refers to a human protein or a species homologue of higher eukaryotic origin, preferably to the human protein as described in Tsai et al., 2008, (*J. Immunol.*, 181:4570-4579), more preferably to the protein having the SEQ ID NO: 27, or the protein having the NCBI Ref. Seq accession No. NP_002296.1, GI:4504981, or being encoded by the nucleotide sequence having the NCBI Ref. Seq. accession No. NM_002305.3, or functional homologs thereof, e.g. proteins comprising deletions, modifications such as amino acid exchanges, additions etc. which are functionally comparable with the wildtype sequence, or isoforms thereof.

The human LGALS1protein and cDNA sequences are listed below.

NCBI Reference Sequence: NP_002296.1

(SEQ ID NO: 27)
MACGLVASNLNLKPGECLRVRGEVAPDAKSFVLNLGKDSNNLCLHFNPRFNAHGDANTIVCNSKDGGA

WGTEQREAVFPFQPGSVAEVCITFDQANLTVKLPDGYEFKFPNRLNLEAINYMAADGDFKIKCVAFD

NCBI Reference Sequence: NM_002305.3

(SEQ ID NO: 28)
```
agttaaaagg gtgggagcgt ccgggggccc atctctctcg ggtggagtct tctgacagct  61
ggtgcgcctg cccgggaaca tcctcctgga ctcaatcatg gcttgtggtc tggtcgccag  121
caacctgaat ctcaaacctg gagagtgcct tcgagtgcga ggcgaggtgg ctcctgacgc  181
taagagcttc gtgctgaacc tgggcaaaga cagcaacaac ctgtgcctgc acttcaaccc  241
tcgcttcaac gcccacggcg acgccaacac catcgtgtgc aacagcaagg acggcgggc  301 ctgggggacc gagcagcggg aggctgtctt tcccttccag cctggaagtg ttgcagaggt  361
gtgcatcacc ttcgaccagg ccaacctgac cgtcaagctg ccagatggat acgaattcaa  421
gttccccaac cgcctcaacc tggaggccat caactacatg gcagctgacg gtgacttcaa  481
gatcaaatgt gtggcctttg actgaaatca gccagcccat ggcccccaat aaaggcagct  541
gcctctgctc cctctgaaaa aaaaaaaaa aaaaaaaaa aaaaaa
```

Various LGALS1 expression vectors are commercially available, some of which are linked to the above NCBI Ref. Seq. entry. For example, human LGALS1 as transfection-ready DNA (pCMV6-XL5, SKU SC118705); Myc-DDK-tagged ORF clone of *Homo sapiens* LGALS1 as transfection-ready DNA (pCMV6-Entry, SKU RC204674) and GFP-tagged as transfection-ready DNA (pCMV6-AC-GFP; OriGene Technologies, Inc., Rockville, Md., cat. no. RG204674)(Rockville, Md.).

LGALS1 (Human) recombinant protein is available for example from OriGene Technologies (cat no. TP304674), Abnova (cat. no. P4390; Walnut, Calif., USA), ProSpec (Cat. No. CYT-544; East Brunswick, N.J., USA), or R&D Systems (Cat. No. 1152-GA). Such protein products may be suitable for formulating pharmaceutical composition comprising the LGALS1 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

LTBP1 (Human Latent Transforming Growth Factor Beta Binding Protein 1 (LTBP1)) (NCBI Reference Sequence: NM_206943.2 and NP_996826.2)

Kanzaki et al., 1990 (*Cell* 61:1051-1061) cloned a cDNA encoding human LTBP1, the structure of human LTBP1 resembles fibrillin in that it includes 16 epidermal growth factor-like repeats and 3 copies of a novel 8-cysteine motif. LTBP1 protein targets latent complexes of transforming growth factor beta 1 (TGF-beta 1) to the extracellular matrix, where the latent cytokine is subsequently activated by several different mechanisms. Alternatively spliced transcript variants encoding different isoforms have been identified (Saharinen et al., 2000, *Mol. Biol. Cell,* 11:2691-2704).

The human LTBP1 protein and cDNA sequences are listed below.

```
NCBI Reference Sequence: NP_996826.2
                                                              (SEQ ID NO: 29)
MAGAWLRWGLLLWAGLLASSAHGRLRRITYWHPGPGLAAGALPLSGPPRSRTFNVALNARYSRSSAA

AGAPSRASPGVPSERTRRTSKPGGAALQGLRPPPPPPPEPARPAVPGGQLHPNPGGHPAAAPFTKQG

RQWRSKVPQETQSGGGSRLQVHQKQQLQGVNVCGGRCCHGWSKAPGSQRCTKPSCVPPCQNGGM

CLRPQLCVCKPGTKGKACETIAAQDTSSPVFGGQSPGAASSWGPPEQAAKHTSSKKADTLPRVSPVA

QMTLTLKPKPSVGLPQQIHSQVTPLSSQSWIHHGQTQEYVLKPKYFPAQKGISGEQSTEGSFPLRYVQ

DQVAAPFQLSNHTGRIKWFTPSICKVTCTKGSCQNSCEKGNTTTLISENGHAADTLTATNFRVVICHLPC

MNGGQCSSRDKCQCPPNFTGKLCQIPVHGASVPKLYQHSQQPGKALGTHVIHSTHTLPLTVTSQQGV

KVKFPPNIVNIHVKHPPEASVQIHQVSRIDGPTGQKTKEAQPGQSQVSYQGLPVQKTQTIHSTYSHQQV

IPHVYPVAAKTQLGRCFQETIGSQCGKALPGLSKQEDCCGTVGTSWGFNKCQKCPKKPSYHGYNQM

MECLPGYKRVNNTFCQDINECQLQGVCPNGECLNTMGSYRCTCKIGFGPDPTFSSCVPDPPVISEEKG

PCYRLVSSGRQCMHPLSVHLTKQLCCCSVGKAWGPHCEKCPLPGTAAFKEICPGGMGYTVSGVHRRR

PIHHHVGKGPVFVKPKNTQPVAKSTHPPPLPAKEEPVEALTFSREHGPGVAEPEVATAPPEKEIPSLDQE

KTKLEPGQPQLSPGISTIHLHPQFPWIEKTSPPVPVEVAPEASTSSASQVIAPTQVTEINECTVNPDIC

GAGHCINLPVRYTCICYEGYRFSEQQRKCVDIDECTQVQHLCSQGRCENTEGSFLCICPAGFMASEEG

TNCIDVDECLRPDVCGEGHCVNTVGAFRCEYCDSGYRMTQRGRCEDIDECLNPSTCPDEQCVNSPGSYQC

VPCTEGFRGWNGQCLDVDECLEPNVCANGDCSNLEGSYMCSCHKGYTRTPDHKHCRDIDECQQGNL

CVNGQCKNTEGSFRCTCGQGYQLSAAKDQCEDIDECQHRHLCAHGQCRNTEGSFQCVCDQGYRAS

GLGDHCEDINECLEDKSVCQRGDCINTAGSYDCTCPDGFQLDDNKTCQDINECEHPGLCGPQGECLNT

EGSFHCVCQQGFSISADGRTCEDIDECVNNTVCDSHGFCDNTAGSFRCLCYQGFQAPQDGQGCVDV

NECELLSGVCGEAFCENVEGSFLCVCADENQEYSPMTGQCRSRTSTDLDVDVDQPKEEKKECYYNLN

DASLCDNVLAPNVTKQECCCTSGAGWGDNCEIFPCPVLGTAEFTEMCPKGKGFVPAGESSSEAGGEN

YKDADECLLFGQEICKNGFCLNTRPGYECYCKQGTYYDPVKLQCFDMDECQDPSSCIDGQCVNTEG

SYNCFCTHPMVLDASEKRCIRPAESNEQIEETDVYQDLCWEHLSDEYVCSRPLVGKQTTYTECCCLYG

EAWGMQCALCPLKDSDDYAQLCNIPVTGRRQPYGRDALVDFSEQYTPEADPYFIQDRFLNSFEELQA

EECGILNGCENGRCVRVQEGYTCDCFDGYHLDTAKMTCVDVNECDELNNRMSLCKNAKCINTDGSYK

CLCLPGYVPSDKPNYCTPLNTALNLEKDSDLE

NCBI Reference Sequence: NM_206943.2
                                                              (SEQ ID NO: 30)
            ggtcgcgccc gctggggccc gcgatggcgg gggcctggct caggtggggg ctcctgctct    61
gggcagggct cctcgcgtcc tcggcgcacg gccggctgcg gaggatcacc tacgtggtgc   121
acccgggccc cggcctggca gccggcgcct tgccctgag  cgggcccccg cgttcgcgga   181
cattcaacgt cgcgctcaac gccaggtaca gccgcagctc ggcggctgcc ggcgccccca   241
gccgtgcctc ccccggggtc ccctcggaga ggacccggcg cacgagcaag ccgggcggcg   301
cggccctgca ggggctcaga ccgccgccgc cgccgccgcc ggagcctgcg cgtcccgcgg   361 tccccgcgg  gcagctccac cccaatcccg gcggccaccc ggcagccgcc ccgttcacca   421
aacaaggcag gcaagttgtg cgctccaagg tgccgcagga cccagagc   ggcggaggct   481 ctaggctgca ggttcaccag aagcagcagc tgcagggggt caatgtctgt ggagggcggt   541
gctgtcatgg ctggagtaag gcccctggct cccagaggtg caccaaacct agctgtgttc   601
```

```
cgccatgtca gaatggaggg atgtgtctcc ggccacaact ctgtgtgtgt aaaccaggga    661
ccaagggcaa agcctgtgaa acaatagctg cccaggacac ctcgtcacca gtctttggag    721
ggcagagtcc tggggctgct tcctcgtggg gccctcctga gcaagcagca aagcatactt    781
catctaagaa ggcagacact ctaccaagag tcagccctgt ggcccagatg accttaaccc    841
tcaagccgaa gccttcagtg ggactccccc agcagataca ttctcaagtg actcctcttt    901
cttcccagag tgtggtgatt caccatggcc agacccagga atacgtgctc aagcccaagt    961
actttccagc ccagaagggg atttcaggag agcagtccac tgaaggttct ttccctttaa   1021
gatatgtgca ggatcaagtt gcggcacctt ttcagctgag taaccacact ggccgcatca   1081
aggtggtctt tactccgagc atctgtaaag tgacctgcac caagggcagc tgtcagaaca   1141
gctgtgagaa ggggaacacc accactctca ttagtgagaa tggtcatgct gccgacaccc   1201
tgacggccac gaacttccga gtggtaattt gccatcttcc atgtatgaat ggtggccagt   1261
gcagttcaag ggacaaatgt cagtgccctc caaatttcac aggaaaactt tgtcagatcc   1321
cagtccatgg tgccagcgtg cctaaacttt atcagcattc ccagcagcca ggcaaggcgt   1381
tggggacgca tgtcatccat tcaacacata ccttgcctct gaccgtgact agccagcaag   1441
gagtcaaagt gaaatttcct cctaacatag tcaatatcca tgtgaaacat cctcctgaag   1501
cttccgtcca gatacatcag gtttcaagaa ttgatggccc aacaggccag aagacaaaag   1561
aagctcaacc aggccaatcc caagtctcgt accaagggct tcctgtccag aagacccaga   1621
ccatacattc cacatactcc caccagcagg tcattcctca cgtctacccc gtggctgcta   1681
agacacagct tggccggtgc ttccaggaaa ccattgggtc acagtgtggc aaagcgctcc   1741
ctggcctttc aaagcaagag gactgctgtg gaactgtggg tacctcctgg gctttaaca   1801 aatgccagaa atgccccaag aaaccatctt atcatggata caaccaaatg atggaatgcc   1861
taccgggtta taagcgggtt aacaacacct tttgccaaga tattaatgaa tgtcagctac   1921
aaggtgtatg ccctaatggt gagtgtttga ataccatggg cagctatcga tgtacctgca   1981
aaataggatt tgggccggat cctaccttt caagttgtgt tcctgatccc cctgtgatct   2041
cggaagagaa agggccctgt taccgacttg tcagttctgg aagacagtgt atgcaccctc   2101
tgtctgttca cctcaccaag cagctctgct gttgtagtgt gggcaaggcc tggggcccac   2161
actgtgagaa atgtcccctt ccaggcacag ctgcttttaa ggaaatctgt cctggtggaa   2221
tgggttatac ggtttctggc gttcatagac gcaggccaat ccatcaccat gtaggtaaag   2281
gacctgtatt tgtcaagcca agaacactc aacctgttgc taaaagtact catcctccac   2341
ctctcccagc caaggaagag ccagtggagg ccctgacctt ctcccgggaa cacgggccag   2401
gagtggcgga gccagaagtg gcaactgcac cccctgaaaa ggaaataccdt tcattggatc   2461 aagagaaaac caaacttgag cctggtcaac cccagctgtc tccaggcatt tccactattc   2521
atctgcatcc acagtttcca gtagtgattg aaaaaacatc acctcctgtg cctgttgaag   2581
tagctcctga agcttctacg tctagtgcca gccaagtgat tgctcctact caagtgacag   2641
aaatcaatga atgtactgtg aaccctgata tctgtggagc aggacactgc attaacctac   2701
cagtgagata tacctgtata tgctacgagg gctacaggtt cagtgaacaa cagaggaaat   2761
gtgtggatat tgatgagtgt actcaggtcc aacacctctg ctcccagggc cgctgtgaaa   2821
acaccgaggg aagtttcttg tgcatttgcc cagcaggatt tatggccagt gaggagggta   2881
ctaactgcat agatgttgac gaatgcctga ggccggacgt ctgtggggag gggcactgtg   2941
tcaatactgt gggggccttc cggtgtgaat actgtgacag cggtaccgc atgactcaga   3001 gaggccgttg tgaggatatt gatgaatgtt tgaatccaag cacttgtcca gatgagcagt   3061
```

-continued

```
gtgtgaattc tcctggatct taccagtgcg ttccctgcac agaaggattc cgaggctgga    3121
atggacagtg ccttgatgtg gacgagtgcc tggaaccaaa cgtctgcgca aatggtgatt    3181
gttccaacct tgaaggctcc tacatgtgtt catgccacaa aggctatacc cggactccgg    3241
accacaagca ctgtagagat attgatgaat gtcagcaagg gaatctatgt gtaaacgggc    3301
agtgcaaaaa taccgagggc tccttcaggt gcacctgtgg acaggggtac cagctgtcgg    3361
cagctaaaga ccagtgtgaa gacattgatg aatgccagca ccgtcatctc tgtgctcatg    3421
ggcagtgcag gaacactgag ggctcttttc aatgtgtgtg tgaccagggt tacagagcat    3481
ctgggcttgg agaccactgt gaagatatca atgaatgctt ggaggacaag agtgtttgcc    3541
agagaggaga ctgcattaat actgcagggt cctatgattg tacttgtccg gatggatttc    3601
agctagatga caataaaaca tgtcaagata ttaatgaatg tgaacatcca gggctctgtg    3661
gtccgcaagg ggagtgccta aacacagagg gttctttcca ttgtgtctgc cagcagggtt    3721
tctcaatctc tgcagatggc cgtacgtgtg aagatattga tgaatgtgta acaacactg    3781
tttgtgacag tcacgggttt tgtgacaata cagctggctc cttccgctgc ctctgttatc    3841
agggctttca gccccacag gatgggcaag ggtgtgtgga tgtgaatgaa tgtgaactgc    3901
tcagtggggt gtgtggtgaa gccttctgtg aaaacgtgga agggtccttc ctgtgcgtgt    3961
gtgctgatga aaaccaagag tacagcccca tgactgggca gtgccgctcc cggacctcca    4021
cagatttaga tgtagatgta gatcaaccca agaagaaaa gaaagaatgc tactataatc    4081
tcaatgacgc cagtctctgt gataatgtgt tggcccccaa tgtcacgaaa caagaatgct    4141
gctgtacatc aggcgcggga tggggagata actgcgaaat cttcccctgc ccggtcttgg    4201
gaactgctga gttcactgaa atgtgtccca aagggaaagg ttttgtgcct gctggagaat    4261
catcttctga agctggtggt gagaactata agatgcaga tgaatgccta cttttttggac    4321
aagaaatctg caaaaatggt ttctgtttga cactcggcc tgggtatgaa tgctactgta    4381
agcaagggac gtactatgat cctgtgaaac tgcagtgctt tgatatggat gaatgtcaag    4441
accccagtag ttgtattgat ggccagtgtg ttaatacaga gggctcttac aactgcttct    4501
gtactcaccc catggtcctg gatgcgtcag aaaaaagatg tatacgaccg gctgagtcaa    4561
acgaacaaat agaagaaact gatgtctacc aagatttgtg ctgggaacat ctgagtgatg    4621
aatacgtgtg tagccggcct cttgtgggca agcagacaac gtacactgag tgctgctgtc    4681
tgtatggaga ggcctggggc atgcagtgtg ccctctgccc cctgaaggat tcagatgact    4741
atgctcagct gtgtaacatc cccgtgacgg gacgccggca gccatatgga cgggacgcct    4801
tggttgactt cagtgaacag tatactccag aagccgatcc ctacttcatc caagaccgtt    4861
ttctaaatag ctttgaggag ttacaggctg aggaatgcgg catcctcaat ggatgtgaaa    4921
atggtcgctg tgtgagggtc caggaaggtt acacctgcga ttgctttgat gggtatcact    4981
tggatacggc caagatgacc tgtgtcgatg taaatgaatg cgatgagttg aacaaccgga    5041
tgtctctctg caagaatgcc aagtgcatta acaccgatgg ttcctacaag tgtttgtgtc    5101
tgccaggcta cgtgccttct gacaagccaa actactgcac tccgttgaat accgccttga    5161
atttagagaa agacagtgac ctggagtgaa acagaatcta cataacctaa gcccatatac    5221
tctgcactgt gtaaaggaaa agggagaaat gtattatact tgagacattg cacctacccc    5281
ggaaggctgg aaatacagaa acagcatgga attgcaagtc ctctgaagac aatgagagga    5341
tttaggatga gcccgatagg tgtggcagac caaatggaca tttctctaaa aaaccagtat    5401
atatagtctg ttcatatgta aaattcaatg gaagagaggt ggaacagtgc tgttatttta    5461
```

```
                                          -continued
aacagaaggt tgtattatta tgttgttttg ttttttact attgcttgat taaatttggc  5521
atttaaatag tggtggaaat attttatata attttcattt tttggttgtg cagttccttg  5581
gctactgttt ttcttttact tcagttttt aaaaatctca aatgaaaaag tcttcgatac  5641
aatattgtta agctgtatta taagtattgt tacacagggt tatgcaattc ccggcctgga  5701
gcatttttga aattcaaatt gtctgtcctg tggagcaggc agtgattttg ttccaaaact  5761
ttgtatacac atttggagaa aagtacttta tattttcagt gttttgtctg attttaatgt  5821
ccgttcttag ccaagctgct agcaggtgtt aattggatcc ctttccttca ctgaaatgga  5881
agagtttata agcttacgtt agtattgtaa tatgtaaagt aagcccaaca aaaattttta  5941
aaaatttgat gatccccaat atatctacca ttgtatgtta aataaatcac cattttttgta  6001 gaaaaaattc tacctgagag taattgtcaa tgagtacatg tgtataagtt gtatcccact  6061
ctccccactt ttatctttc cagtggtctt ctgttaatgt agtgtctttt acaagttaat  6121
cattaaattt gttagatctt gttatgggct aaaaaaaaaa aaaaaaa
```

Additional isoforms can be found at NCBI under the references NM_000627.3; NP_000618.3 (latent-transforming growth factor beta-binding protein 1 isoform LTBP-1S precursor); NM_001166265.1; NP_001159737.1 (latent-transforming growth factor beta-binding protein 1 isoform 3 precursor); NM_001166264.1; NP_001159736.1 (latent-transforming growth factor beta-binding protein 1 isoform 4 precursor); NM_001166266.1; NP_001159738.1 (latent-transforming growth factor beta-binding protein 1 isoform 5 precursor).

Various LTBP1 expression vectors are commercially available, some of which are linked to the above NCBI Ref. Seq. entry. For example, human LTBP1 as transfection-ready DNA (pCMV6-XL5, SKU SC308336 transcript variant 1; SC119796 transcript variant 2; SC327309 transcript variant 3; SC327710 transcript variant 4; SC327304 transcript variant 5); Myc-DDK-tagged ORF clone of Homo sapiens LTBP1 as transfection-ready DNA (pCMV6-Entry, SKU RC220132 transcript variant 1 and RC218088 transcript variant 2) and GFP-tagged as transfection-ready DNA (pCMV6-AC-GFP; OriGene Technologies, Inc., Rockville, Md., cat. no. RG220132 transcript variant 1 and RG218088 transcript variant 2)(Rockville, Md.).

LTBP1 (Human) recombinant protein is available for example from Abnova (cat. no. H00004052-Q01; Human LTBP1 partial ORF (NP_000618, 403 aa-500 aa; Walnut, Calif., USA). Such protein products may be suitable for formulating pharmaceutical composition comprising the LTBP1 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

MSMB (Human Microseminoprotein, Beta-(MSMB)) (NCBI Reference Sequence: NM_002443.3 & NP_002434.1, NM_138634.2 & NP_619540.1)

MSMB (microseminoprotein, beta-) is also known as MSP; PSP; IGBF; MSPB; PN44; PRPS; HPC13; PSP57; prostate secretory protein 94; PSP94; PSP-94.

The protein encoded by this gene is a member of the immunoglobulin binding factor family. It is synthesized by the epithelial cells of the prostate gland and secreted into the seminal plasma and has a concentration in seminal plasma of 0.5 to 1 mg/mL (Valtonen-André et al., 2008, J. Androl. 29:330-337). This protein has inhibin-like activity. It may have a role as an autocrine paracrine factor in uterine, breast and other female reproductive tissues. The expression of the encoded protein is found to be decreased in prostate cancer. Two alternatively spliced transcript variants encoding different isoforms are described for this gene. Variant PSP94 encodes the full-length isoform (a), while variant PSP57 lacks an alternate coding exon compared to variant PSP94, that causes a frameshift. The resulting isoform (b) has a shorter and distinct C-terminus compared to isoform a (PSP94) (Mbikay et al., 1987, DNA 6:23-29). MSMB protein inhibits growth of cancer cells in an experimental model of prostate cancer (Garde et al., 1993, Prostate 22:225-233; Shukeir et al., 2003, Cancer Res. 63:2072-2078; Pathak et al., 2010, Asian J. Androl. 12:677-689).

The human MSMB protein and cDNA sequences are listed below.

```
NCBI Reference Sequence NP_002434.1 (transcript variant PSP94)
                                                    (SEQ ID NO: 31)
MNVLLGSVVIFATFVTLCNASCYFIPNEGVPGDSTRKCMDLKGNKHPINSEWQTDNCETC.TCYETEI

SCCTLVSTPVGYDKDNCQRIFKKEDCKYIWEKKDPKKTCSVSEWII

NCBI Reference Sequence: NP_619540.1 (transcript variant PSP57)
                                                    (SEQ ID NO: 32)
MNVLLGSVVIFATFVTLCNASCYFIPNEGVPGDSTRMFLHLWVMTKTTAKESSRRRTASISWWRRRTQ

KRPVLSVN
```

```
NCBI Reference Sequence: NM_002443.3 (transcript variant PSP94)
                                                            (SEQ ID NO: 33)
gtacctgtct ataaggagtc ctgcttatca caatgaatgt tctcctgggc agcgttgtga    61
tctttgccac cttcgtgact ttatgcaatg catcatgcta tttcatacct aatgagggag   121
ttccaggaga ttcaaccagg aaatgcatgg atctcaaagg aaacaaacac ccaataaact   181
cggagtggca gactgacaac tgtgagacat gcacttgcta cgaaacagaa atttcatgtt   241 gcaccttgt ttctacacct gtgggttatg acaaagacaa ctgccaaaga atcttcaaga    301
aggaggactg caagtatatc gtggtggaga agaaggaccc aaaaaagacc tgttctgtca   361
gtgaatggat aatctaatgt gcttctagta ggcacagggc tcccaggcca ggcctcattc   421
tcctctggcc tctaatagtc aatgattgtg tagccatgcc tatcagtaaa aagatttttg   481
agcaaacact tgaaaaaaaa aaa

NCBI Reference Sequence: NM_138634.2 (transcript variant PSP57)
                                                            (SEQ ID NO: 34)
gtacctgtct ataaggagtc ctgcttatca caatgaatgt tctcctgggc agcgttgtga    61
tctttgccac cttcgtgact ttatgcaatg catcatgcta tttcatacct aatgagggag   121
ttccaggaga ttcaaccagg atgtttctac acctgtgggt tatgacaaag acaactgcca   181
aagaatcttc aagaaggagg actgcaagta tatcgtggtg gagaagaagg acccaaaaaa   241
gacctgttct gtcagtgaat ggataatcta atgtgcttct agtaggcaca gggctcccag   301
gccaggcctc attctcctct ggcctctaat agtcaatgat gtgtgtagcca tgcctatcag   361 taaaagatt tttgagcaaa cacttgaaaa aaaaaaa
```

Various MSMB expression vectors are commercially available, some of which are linked to the above NCBI Ref. Seq. entry. For example, human MSMB as transfection-ready DNA (pCMV6-XL5, SKU SC109457 transcript variant PSP57 and SC111654 transcript variant PSP94); Myc-DDK-tagged ORF clone of *Homo sapiens* MSMB as transfection-ready DNA (pCMV6-Entry, SKU RC216174 variant PSP57 and RC202704 transcript variant PSP94) and GFP-tagged as transfection-ready DNA (pCMV6-AC-GFP; OriGene Technologies, Inc., Rockville, Md., cat. no. RG216174 transcript variant PSP57 and RG202704 transcript variant PSP94)(Rockville, Md.).

MSMB (Human) recombinant protein is available for example from OriGene Technologies (cat no. TP302704), Abnova (cat. no. H00004477-P01; Walnut, Calif., USA), or R&D Systems (Cat. No. 3780-PS-050). Such protein products may be suitable for formulating pharmaceutical composition comprising the MSMB protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

OLFM4 (Human Olfactomedin 4 (OLFM4)) (NCBI Reference Sequence: NM_006418.4 and NP_006409.3)

OLFM4 (olfactomedin 4) also known as antiapoptotic protein GW 112; G-CSF-stimulated clone 1 protein; GC1; OLM4; OlfD; hGC-1; hOLfD; UNQ362; bA209J19.1 was originally cloned from human myeloblasts and found to be selectively expressed in inflamed colonic epithelium (Shinozaki et al. (2001, Gut 48: 623-239). The deduced 510-amino acid protein has an N-terminal signal sequence, a C-terminal olfactomedin (OLFM1; 605366)-like domain, and 6 evenly distributed potential N-glycosylation sites. The predicted mature protein contains 490 amino acids. GC1 shares high amino acid sequence similarity and predicted secondary structure with olfactomedin. Northern blot analysis detected a 2.8-kb GC1 transcript in small intestine, colon, prostate, bone marrow, and stomach, but not in other tissues examined. GC1 was expressed in myeloid lineage cell lines, but not in erythroid or megakaryocytic lineage cell lines. GC1 expressed in transfected 293 cells had an apparent molecular mass of about 64 kD, which was reduced to 54 kD following N-glycanase treatment (Zhang et al. 2002, *Gene* 283:83-93). OLFM4 has a role in RA-regulated cell growth, differentiation, and apoptosis (Liu et al. 2010, *Proc. Nat. Acad. Sci. USA* 107:11056-11061). Further, OLFM4 is involved in host defense against *H. pylori* infection acting through NOD1- and NOD2-mediated NFKB activation and subsequent cytokine and chemokine production, which in turn inhibit host immune responses and contribute to the persistence of *H. pylori* colonization (Liu et al. 2010).

The human OLFM4 protein and cDNA sequences are listed below.

NCBI Reference Sequence: NP_006409.3

(SEQ ID NO: 35)

MRPGLSFLLALLFFLGQAAGDLGDVGPPIPSPGFSSFPGVDSSSSFSSSSRSGSSSSRSLGSGGSVSQLFSNFTGSVDDR

GTCQCSVSLPDTTFPVDRVERLEFTAHVLSQKFEKELSKVREYVQLISVYEKKLLNLTVRIDIMEKDTISYTELDFELIK

VEVKEMEKLVIQLKESFGGSSEIVDQLEVEIRNMTLLVEKLETLDKNNVLAIRREIVALKTKLKECEASKDQNTPVVHPP

PTPGSCGHGGWNISKPSWQLNWRGFSYLYGAWGRDYSPQHPNKGLYWVAPLNTDGRLLEYYRLYNTLDDLLLYINARE

LRITYGQGSGTAVYNNNMYVNMYNTGNIARVNLTTNTIAVTQTLPNAAYNNRFSYANVAWQDIDFAVDENGLWVIYSTEA

STGNMVISKLNDTTLQVLNTWYTKQYKPSASNAFMVCGVLYATRTMNTRTEEIFYYYDTNTGKEGKLDIVMHKMQEKVQS

INYNPFDQKLYVYNDGYLLNYDLSVLQKPQ

NCBI Reference Sequence: NM_006418.4

(SEQ ID NO: 36)

```
   1 ttttcctaca tgctggccat ggggaaatca ccactgggca ctataagaag cccctgggct   61
     ctctgcagag ccagcggctc cagctaagag acaagatga ggcccggcct ctcatttctc  121
     ctagcccttc tgttcttcct tggccaagct gcagggggatt tgggggatgt gggacctcca  181
     attcccagcc ccggcttcag ctctttccca ggtgttgact ccagctccag cttcagctcc  241
     agctccaggt cgggctccag ctccagccgc agcttaggca gcggaggttc tgtgtcccag  301
     ttgttttcca atttcaccgg ctccgtggat gaccgtggga cctgccagtg tctgtttcc   361
     ctgccagaca ccaccttttcc cgtggacaga gtggaacgct tggaattcac agctcatgtt  421
     cttttctcaga agtttgagaa agaactttcc aaagtgaggg aatatgtcca attaattagt  481
     gtgtatgaaa agaaactgtt aaacctaact gtccgaattg acatcatgga gaaggatacc  541
     atttcttaca ctgaactgga cttcgagctg atcaaggtag aagtgaagga gatggaaaaa  601
     ctggtcatac agctgaagga gagttttggt ggaagctcag aaattgttga ccagctggag  661
     gtggagataa gaaatatgac tctcttggta gagaagcttg agacactaga caaaaacaat  721
     gtccttgcca ttcgccgaga atcgtggct ctgaagacca agctgaaaga gtgtgaggcc  781
     tctaaagatc aaaacacccc tgtcgtccac cctcctccca ctccagggag ctgtggtcat  841
     ggtggtgtgg tgaacatcag caaaccgtct gtggttcagc tcaactggag agggttttct  901
     tatctatatg gtgcttgggg tagggattac tctccccagc atccaaacaa aggactgtat  961
     tgggtggcgc cattgaatac agatgggaga ctgttggagt attatagact gtacaacaca 1021
     ctggatgatt tgctattgta tataaatgct cgagagttgc ggatcaccta tggccaaggt 1081
     agtggtacag cagtttacaa caacaacatg tacgtcaaca tgtacaacac cgggaatatt 1141
     gccagagtta acctgaccac caacacgatt gctgtgactc aaactctccc taatgctgcc 1201
     tataataacc gcttttcata tgctaatgtt gcttggcaag atattgactt tgctgtggat 1261
     gagaatggat tgtgggttat ttattcaact gaagccagca ctggtaacat ggtgattagt 1321
     aaactcaatg acaccacact tcaggtgcta aacacttggt ataccaagca gtataaacca 1381
     tctgcttcta acgccttcat ggtatgtggg gttctgtatg ccacccgtac tatgaacacc 1441
     agaacagaag agatttttta ctattatgac acaaacacag ggaaagaggg caaactagac 1501
     attgtaatgc ataagatgca ggaaaaagtg cagagcatta actataaccc ttttgaccag 1561
     aaactttatg tctataacga tggttacctt ctgaattatg atctttctgt cttgcagaag 1621
     ccccagtaag ctgtttagga gttagggtga aagagaaaat gtttgttgaa aaaatagtct 1681
     tctccactta cttagatatc tgcagggggtg tctaaaagtg tgttcatttt gcagcaatgt 1741
     ttaggtgcat agttctacca cactagagat ctaggacatt tgtcttgatt tggtgagttc 1801
```

```
tcttgggaat catctgcctc ttcaggcgca tttttgcaata aagtctgtct agggtgggat    1861
tgtcagaggt ctaggggcac tgtgggccta gtgaagccta ctgtgaggag gcttcactag    1921
aagccttaaa ttaggaatta aggaacttaa aactcagtat ggcgtctagg gattctttgt    1981
acaggaaata ttgcccaatg actagtcctc atccatgtag caccactaat tcttccatgc    2041
ctggaagaaa cctggggact tagttaggta gattaatatc tggagctcct cgagggacca    2101
aatctccaac tttttttttcc cctcactagc acctggaatg atgctttgta tgtggcagat   2161
aagtaaattt ggcatgctta tatattctac atctgtaaag tgctgagttt tatggagaga    2221
ggccttttta tgcattaaat tgtacatggc aaataaatcc cagaaggatc tgtagatgag    2281
gcacctgctt tttcttttct ctcattgtcc accttactaa aagtcagtag aatcttctac    2341
ctcataactt ccttccaaag gcagctcaga agattagaac cagacttact aaccaattcc    2401 acccccacc aacccccttc tactgcctac tttaaaaaaa ttaatagttt tctatggaac    2461
tgatctaaga ttagaaaaat taattttctt taatttcatt atgaactttt atttacatga    2521
ctctaagact ataagaaaat ctgatggcag tgacaaagtg ctagcattta ttgttatcta    2581
ataaagacct tggagcatat gtgcaactta tgagtgtatc agttgttgca tgtaattttt    2641
gcctttgttt aagcctggaa cttgtaagaa aatgaaaatt taattttttt ttctaggacg    2701
agctatagaa aagctattga gagtatctag ttaatcagtg cagtagttgg aaaccttgct    2761
ggtgtatgtg atgtgcttct gtgcttttga atgactttat catctagtct ttgtctattt    2821
ttcctttgat gttcaagtcc tagtctatag gattggcagt ttaaatgctt tactccccct    2881
tttaaaataa atgattaaaa tgtgctttga aaaagtcaa aaaaaaaaa aaaaa
```

Various OLFM4 expression vectors are commercially available, some of which are linked to the above NCBI Ref. Seq. entry. For example, human OLFM4 as transfection-ready DNA (pCMV6-XL5, SKU SC108914); Myc-DDK-tagged ORF clone of *Homo sapiens* OLFM4 as transfection-ready DNA (pCMV6-Entry, SKU RC214942) and GFP-tagged as transfection-ready DNA (pCMV6-AC-GFP; OriGene Technologies, Inc., Rockville, Md., cat. no. RG214942)(Rockville, Md.).

OLFM4 (Human) recombinant protein is available for example from Abnova (cat. no. H00010562-P01; Walnut, Calif., USA). Such protein products may be suitable for formulating pharmaceutical composition comprising the OLFM4 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

PLUNC (Human BPI Fold Containing Family A, Member 1 (BPIFA1)) (NCBI Reference Sequence: NM_016583.3 & NP_057667.1; NCBI Reference Sequence: NM_130852.2 & NP_570913.1; NM_001243193.1 & NP_001230122.1)

PLUNC also known as BPI fold containing family A, member 1 (BPIFA1); LUNX; NASG; SPURT; SPLUNC1; bA49G10.5 was cloned in mouse by Weston et al. 1999 (*J. Biol. Chem.* 274:13698-13703) and in human by Bingle and Bingle (*Biochim. Biophys. Acta* 1493: 363-367, 2000). PLUNC is specifically expressed in the upper airways and nasopharyngeal regions. The exact biological function of this gene is not known, however, it has been suggested to be involved in inflammatory responses to irritants in the upper airways. It may also serve as a potential molecular marker for detection of micrometastasis in non-small-cell lung cancer. Multiple transcript variants resulting from alternative splicing in the 3' UTR have been detected, but the full-length nature of only three are known (Iwao et al. 2001, *Int. J. Cancer* 91:433-437). Recombinant PLUNC can inhibit ENaC activity in human bronchial epithelial cultures (Garcia-Caballero et al. 2009, *Proc. Nat. Acad. Sci. USA* 106:11412-11417)

The human PLUNC protein and cDNA sequences are listed below.

```
NCBI Reference Sequence: NP_057667.1; transcript variant 1
                                                         (SEQ ID NO: 37)
MFQTGGLIVFYGLLAQTMAQFGGLPVPLDQTLPLNVNPALPLSPTGLAGSLTNALSNGLLSGGLLGILENLPLLDILKPG

GGTSGGLLGGLLGKVTSVIPGLNNIIDIKVTDPQLLELGLVQSPDGHRLYVTIPLGIKLQVNTPLVGASLLRLAVKLDIT

AEILAVRDKQERIHLVLGDCTHSPGSLQISLLDGLGPLPIQGLLDSLTGILNKVLPELVQGNVCPLVNEVLRGLDITLVH

DIVNMLIHGLQFVIKV
```

NCBI Reference Sequence: NP_570913.1, transcript variant 2
(SEQ ID NO: 38)
MFQTGGLIVFYGLLAQTMAQFGGLPVPLDQTLPLNVNPALPLSPTGLAGSLTNALSNGLLSGGLLGILENLPLLDILKPG

GGTSGGLLGGLLGKVTSVIPGLNNIIDIKVTDPQLLELGLVQSPDGHRLYVTIPLGIKLQVNTPLVGASLLRLAVKLDIT

AEILAVRDKQERIHLVLGDCTHSPGSLQISLLDGLGPLPIQGLLDSLTGILNKVLPELVQGNVCPLVNEVLRGLDITLVH

DIVNMLIHGLQFVIKV

NCBI Reference Sequence: NP_001230122.1, BPI fold-containing family A member 1
precursor, transcript variant 3
(SEQ ID NO: 39)
MFQTGGLIVFYGLLAQTMAQFGGLPVPLDQTLPLNVNPALPLSPTGLAGSLTNALSNGLLSGGLLGILENLPLLDILKPG

GGTSGGLLGGLLGKVTSVIPGLNNIIDIKVTDPQLLELGLVQSPDGHRLYVTIPLGIKLQVNTPLVGASLLRLAVKLDIT

AEILAVRDKQERIHLVLGDCTHSPGSLQISLLDGLGPLPIQGLLDSLTGILNKVLPELVQGNVCPLVNEVLRGLDITLVH

DIVNMLIHGLQFVIKV

NCBI Reference Sequence: NM_016583.3, transcript variant 1
(SEQ ID NO: 40)

```
  1 gagtgggga gagagaggag accaggacag ctgctgagac ctctaagaag tccagatact    61
    aagagcaaag atgtttcaaa ctgggggcct cattgtcttc tacgggctgt tagcccagac   121
    catggcccag tttgaggcc tgcccgtgcc cctgaccag accctgccct tgaatgtgaa    181
    tccagccctg cccttgagtc ccacaggtct tgcaggaagc ttgacaaatg ccctcagcaa   241
    tggcctgctg tctggggcc tgtttgggcat tctggaaaac cttccgctcc tggacatcct   301
    gaagcctgga ggaggtactt ctggtggcct ccttggggga ctgcttggaa aagtgacgtc   361
    agtgattcct ggcctgaaca acatcattga cataaaggtc actgaccccc agctgctgga   421
    acttggcctt gtgcagagcc ctgatggcca ccgtctctat gtcaccatcc ctctcggcat   481
    aaagctccaa gtgaatacgc ccctggtcgg tgcaagtctg ttgaggctgg ctgtgaagct   541
    ggacatcact gcagaaatct tagctgtgag agataagcag gagaggatcc acctggtcct   601
    tggtgactgc acccattccc ctggaagcct gcaaatttct ctgcttgatg gacttggccc   661
    cctccccatt caaggtcttc tggacagcct cacagggatc ttgaataaag tcctgcctga   721
    gttggttcag ggcaacgtgt gccctctggt caatgaggtt ctcagaggct ggacatcac    781
    cctggtgcat gacattgtta acatgctgat ccacggacta cagtttgtca tcaaggtcta   841
    agccttccag gaaggggctg gcctctgctg agctgcttcc cagtgctcac agatggctgg   901
    cccatgtgct ggaagatgac acagttgcct tctctccgag gaacctgccc cctctccttt   961
    cccaccaggc gtgtgtaaca tcccatgtgc ctcacctaat aaaatggctc ttcttctgca  1021
    tcaaaaaaaa aaaaa
```

NCBI Reference Sequence: NM_130852.2, transcript variant 2
(SEQ ID NO: 41)

```
  1 gagtgggga gagagaggag accaggacag ctgctgagac ctctaagaag tccagatact    61
    aagagcaaag atgtttcaaa ctgggggcct cattgtcttc tacgggctgt tagcccagac   121
    catggcccag tttgaggcc tgcccgtgcc cctgaccag accctgccct tgaatgtgaa    181
    tccagccctg cccttgagtc ccacaggtct tgcaggaagc ttgacaaatg ccctcagcaa   241
    tggcctgctg tctggggcc tgtttgggcat tctggaaaac cttccgctcc tggacatcct   301
    gaagcctgga ggaggtactt ctggtggcct ccttggggga ctgcttggaa aagtgacgtc   361
    agtgattcct ggcctgaaca acatcattga cataaaggtc actgaccccc agctgctgga   421
    acttggcctt gtgcagagcc ctgatggcca ccgtctctat gtcaccatcc ctctcggcat   481
    aaagctccaa gtgaatacgc ccctggtcgg tgcaagtctg ttgaggctgg ctgtgaagct   541
    ggacatcact gcagaaatct tagctgtgag agataagcag gagaggatcc acctggtcct   601
```

```
                                                  -continued
tggtgactgc  acccattccc  ctggaagcct  gcaaatttct  ctgcttgatg  gacttggccc   661
cctccccatt  caaggtcttc  tggacagcct  cacagggatc  ttgaataaag  tcctgcctga   721
gttggttcag  ggcaacgtgt  gccctctggt  caatgaggtt  ctcagaggct  tggacatcac   781
cctggtgcat  gacattgtta  acatgctgat  ccacggacta  cagtttgtca  tcaaggtcta   841
agccttccag  gaagggggctg  gcctctgctg  agctgggtct  tcccccaaca  gaactatttc   901
ttgctgctca  atccatttcc  tctggcccag  cttcccagtg  ctcacagatg  gctggcccat   961
gtgctggaag  atgacacagt  tgccttctct  ccgaggaacc  tgcccctct   cctttcccac   1021 caggcgtgtg  taacatccca  tgtgcctcac  ctaataaaat  ggctcttctt  ctgcatcaaa   1081 aaaaaaaaaa

NCBI Reference Sequence: NM_001243193.1, BPI fold-containing family A member 1
precursor, transcript variant 3
                                                          (SEQ ID NO: 42)
gagtggggga  gagagaggag  accaggacag  ctgctgagac  ctctaagaag  tccagatact   61
aagagcaaag  atgtttcaaa  ctgggggcct  cattgtcttc  tacgggctgt  tagcccagac   121
catggcccag  tttggaggcc  tgcccgtgcc  cctggaccag  accctgccct  tgaatgtgaa   181
tccagccctg  cccttgagtc  ccacaggtct  tgcaggaagc  ttgacaaatg  ccctcagcaa   241
tggcctgctg  tctggggggcc  tgttgggcat  tctggaaaac  cttccgctcc  tggacatcct   301
gaagcctgga  ggaggtactt  ctggtggcct  ccttgggggga  ctgcttggaa  aagtgacgtc   361
agtgattcct  ggcctgaaca  acatcattga  cataaaggtc  actgaccccc  agctgctgga   421
acttggcctt  gtgcagagcc  ctgatggcca  ccgtctctat  gtcaccatcc  ctctcggcat   481
aaagctccaa  gtgaatacgc  ccctggtcgg  tgcaagtctg  ttgaggctgg  ctgtgaagct   541
ggacatcact  gcagaaatct  tagctgtgag  agataagcag  gagaggatcc  acctggtcct   601
tggtgactgc  acccattccc  ctggaagcct  gcaaatttct  ctgcttgatg  gacttggccc   661
cctccccatt  caaggtcttc  tggacagcct  cacagggatc  ttgaataaag  tcctgcctga   721
gttggttcag  ggcaacgtgt  gccctctggt  caatgaggtt  ctcagaggct  tggacatcac   781
cctggtgcat  gacattgtta  acatgctgat  ccacggacta  cagtttgtca  tcaaggtcta   841
agccttccag  gaagggggctg  gcctctgctg  agctgaacta  tttcttgctg  ctcaatccat   901
ttcctctggc  ccagcttccc  agtgctcaca  gatggctggc  ccatgtgctg  gaagatgaca   961
cagttgcctt  ctctccgagg  aacctgcccc  ctctcctttc  ccaccaggcg  tgtgtaacat   1021
cccatgtgcc  tcacctaata  aaatggctct  tcttctgcat  caaaaaaaaa  aaaa
```

At least about 3 related sequences have been identified and linked to the NCBI RefSeq entry for the human sequence.

Various PLUNC expression vectors are commercially available, some of which are linked to the above NCBI Ref. Seq. entry. For example, human PLUNC as transfection-ready DNA (pCMV6-XL5, SKU SC122850 transcript variant 1; SC305921 transcript variant 2); Myc-DDK-tagged ORF clone of Homo sapiens PLUNC as transfection-ready DNA (pCMV6-Entry, SKU RC213322 transcript variant 1; RC203060 transcript variant 2) and GFP-tagged as transfection-ready DNA (pCMV6-AC-GFP; OriGene Technologies, Inc., Rockville, Md., cat. no. RG213322 transcript variant 1; RG203060 transcript variant 2)(Rockville, Md.).

PLUNC (Human) recombinant protein is available for example from OriGene Technologies (cat no. TP313322 for transcript variant 1 and TP303060 for transcript variant 2); Abnova (cat. no. H00051297-P01; Walnut, Calif., USA). Such protein products may be suitable for formulating pharmaceutical composition comprising the PLUNC protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

PPBP (Human Pro-Platelet Basic Protein (Chemokine (C-X-C Motif) Ligand 7) (PPBP)) (NCBI Reference Sequence: NM_002704.3 and NP_002695.1)

PPBP (pro-platelet basic protein (chemokine (C-X-C motif) ligand 7), also known as PBP; TC1; TC2; TGB; LDGF; MDGF; TGB1; B-TG1; CTAP3; CXCL7; NAP-2; SCYB7; THBGB; LA-PF4; THBGB1; Beta-TG; CTAPIII; CTAP-III.

The protein encoded by this gene is a platelet-derived growth factor that belongs to the CXC chemokine family. This growth factor is a potent chemoattractant and activator of neutrophils. It has been shown to stimulate various cellular processes including DNA synthesis, mitosis, glycolysis, intracellular cAMP accumulation, prostaglandin E2 secretion, and synthesis of hyaluronic acid and sulfated glycosaminoglycan. It also stimulates the formation and secretion of plasminogen activator by synovial cells (Castor et al., 1983, Proc. Nat. Acad. Sci. USA 80: 765-769; Castor et al., 1985, Biochemistry 24: 1762-1767). PPBP is the precursor of the 2 platelet alpha-granule proteins, platelet basic protein (PBP) and connective tissue-activating peptide III (CTAP3). Upon platelet activation they are released and further processed in plasma to beta-thromboglobulin (TGB) and neutrophil-activating peptide-2 (NAP2).

The human PPBP protein and cDNA sequences are listed below.

Various PPBP expression vectors are commercially available, some of which are linked to the above NCBI Ref. Seq. entry. For example, human PPBP as transfection-ready DNA (pCMV6-XL4, SKU SC118473); Myc-DDK-tagged ORF clone of *Homo sapiens* PPBP as transfection-ready DNA (pCMV6-Entry, SKU RC207018) and GFP-tagged as transfection-ready DNA (pCMV6-AC-GFP; OriGene Technologies, Inc., Rockville, Md., cat. no. RG207018)(Rockville, Md.).

PPBP (Human) recombinant protein is available for example from OriGene Technologies (cat no. TP307018), Abnova (cat. no. H00005473-P01, P3656 and P4070; Walnut, Calif., USA), or R&D Systems (Cat. No. 393-NP). Such protein products may be suitable for formulating pharmaceutical composition comprising the PPBP protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.)

```
NCBI Reference Sequence: NP_002695.1
                                                        (SEQ ID NO: 43)
MSLRLDTTPSCNSARPLHALQVLLLLSLLLTALASSTKGQTKRNLAKGKEESLDSDLYAELRCMCIK

TTSGIHPKNIQSLEVIGKGTHCNQVEVIATLKDGRKICLDPDAPRIKKIVQKKLAGDESAD

NCBI Reference Sequence: NM_002704.3
                                                        (SEQ ID NO: 44)
   1 acttatctgc agacttgtag gcagcaactc accctcactc agaggtcttc tggttctgga     61 aacaactcta gctcagcctt ctccaccatg agcctcagac ttgataccac cccttcctgt    121 aacagtgcga gaccacttca tgccttgcag gtgctgctgc ttctgtcatt gctgctgact    181 gctctggctt cctccaccaa aggacaaact aagagaaact tggcgaaagg caaagaggaa    241 agtctagaca gtgacttgta tgctgaactc cgctgcatgt gtataaagac aacctctgga    301 attcatccca aaaacatcca aagtttggaa gtgatcggga aaggaaccca ttgcaaccaa    361 gtcgaagtga tagccacact gaaggatggg aggaaaatct gcctggaccc agatgctccc    421 agaatcaaga aaattgtaca gaaaaaattg gcaggtgatg aatctgctga ttaatttgtt    481 ctgtttctgc caaacttctt taactcccag gaagggtaga attttgaaac cttgatttc     541 tagagttctc atttattcag gatacctatt cttactgtat taaaatttgg atatgtgttt    601 cattctgtct caaaaatcac attttattct gagaaggttg gttaaaagat ggcagaaaga    661 agatgaaaat aaataagcct ggtttcaacc ctctaattct tgcctaaaca ttggactgta    721 ctttgcattt ttttctttaa aaatttctat tctaacacaa cttggttgat ttttcctggt    781 ctactttatg gttattagac atactcatgg gtattattag atttcataat ggtcaatgat    841 aataggaatt acatggagcc caacagagaa tatttgctca atacattttt gttaatatat    901 ttaggaactt aatggagtct ctcagtgtct tagtcctagg atgtcttatt taaaatactc    961 cctgaaagtt tattctgatg tttattttag ccatcaaaca ctaaaataat aaattggtga   1021 atatgaatct tataaactgt ggttagctgg tttaaagtga atatatttgc cactagtaga   1081 acaaaaatag atgatgaaaa tgaattaaca tatctacata gttataattc tatcattaga   1141 atgagcctta taaataagta caatatagga cttcaacctt actagactcc taattctaaa   1201 ttctactttt ttcatcaaca gaactttcat tcattttta aaccctaaaa cttatacccca  1261 cactattctt acaaaaatat tcacatgaaa taaaaatttg ctattga
``` and QIAGEN (Germantown, Md.), and other primer/probes for verifying expression level of constructs from QIAGEN (Germantown, Md.) and OriGene Technologies (Rockville, Md.) other suppliers.

SERPINA3 (Human Serpin Peptidase Inhibitor, Clade A (Alpha-1 Antiproteinase, Antitrypsin), Member 3 (SERPINA3)) (NCBI Reference Sequence: NM_001085.4 and NP_001076.2)

SERPINA3 (serpin peptidase inhibitor, clade A), also known as alpha-1 antiproteinase, alpha-1-antichymotrypsin; AACT, antitrypsin, member 3; antichymotrypsin, alpha-1; ACT; GIG24; GIG25. SERPINA3 is a plasma protease inhibitor synthesized in the liver. It is a single glycopeptide chain of about 68 KD and belongs to the class of serine protease inhibitors. In man, the normal serum level is about one-tenth that of alpha-1-antitrypsin, with which it shares nucleic acid and protein sequence homology (Chandra et al., 1983, Biochemistry 22: 5055-5061). Both are major acute phase reactants; their concentrations in plasma increase in response to trauma, surgery, and infection. Deficiency of SERPINA3 has been associated with liver disease. Mutations have been identified in patients with Parkinson disease and chronic obstructive pulmonary disease (Munoz et al., Neurology 52:297-301, 1999). SERPINA3 may have a function in wound healing (Hoffmann et al. 2011, J. Biol. Chem. 286:28889-28901).

The human SERPINA3 protein and cDNA sequences are listed below.

NCBI Reference Sequence: NP_001076.2
(SEQ ID NO: 45)

MERMLPLLALGLLAAGFCPAVLCHPNSPLDEENLTQENQDRGTHVDLGLASANVDFAFSLYKQLVLKA

PDKNVIFSPLSISTALAFLSLGAHNTTLTEILKGLKFNLTETSEAEIHQSFQHLLRTLNQSSDELQLSMGN

AMFVKEQLSLLDRFTEDAKRLYGSEAFATDFQDSAAAKKLINDYVKNGTRGKITDLIKDLDSQTMMVL

VNYIFFKAKWEMPFDPQDTHQSRFYLSKKKWVMVPMMSLHHLTIPYFRDEELSCTWELKYTGNASAL

FILPDQDKMEEVEAMLLPETLKRWRDSLEFREIGELYLPKFSISRDYNLNDILLQLGIEEAFTSKADLSG

ITGARNLAVSQWHKAVLDVFEEGTEASAATAVKITLLSALVETRTIVRFNRPFLMIIVPTDTQNIFFMSK

VTNPKQA

NCBI Reference Sequence: NM_001085.4
(SEQ ID NO: 46)

```
   1 attcatgaaa atccactact ccagacagac ggctttggaa tccaccagct acatccagct    61
     ccctgaggca gagttgagaa tggagagaat gttacctctc ctggctctgg ggctcttggc   121
     ggctgggttc tgccctgctg tcctctgcca cccaacagc ccacttgacg aggagaatct   181
     gacccaggag aaccaagacc gagggacaca cgtggacctc ggattagcct ccgccaacgt   241
     ggacttcgct ttcagcctgt acaagcagtt agtcctgaag gccctgata agaatgtcat   301
     cttctcccca ctgagcatct ccaccgcctt ggccttcctg tctctggggg cccataatac   361
     caccctgaca gagattctca aaggcctcaa gttcaacctc acggagactt ctgaggcaga   421
     aattcaccag agcttccagc acctcctgcg caccctcaat cagtccagcg atgagctgca   481
     gctgagtatg ggaaatgcca tgtttgtcaa agagcaactc agtctgctgg acaggttcac   541
     ggaggatgcc aagaggctgt atggctccga ggcctttgcc actgactttc aggactcagc   601
     tgcagctaag aagctcatca cgactacgt gaagaatgga actaggggga aaatcacaga   661
     tctgatcaag gaccttgact cgcagacaat gatggtcctg gtgaattaca tcttctttaa   721
     agccaaatgg gagatgccct ttgaccccca agatactcat cagtcaaggt tctacttgag   781
     caagaaaaag tgggtaatgg tgcccatgat gagtttgcat cacctgacta taccttactt   841
     ccgggacgag gagctgtcct gcaccgtggt ggagctgaag tacacaggca atgccagcgc   901
     actcttcatc ctccctgatc aagacaagat ggaggaagtg gaagccatgc tgctcccaga   961
     gaccctgaag cggtggagag actctctgga gttcagagag ataggtgagc tctacctgcc   1021
     aaagttttcc atctcgaggg actataacct gaacgacata cttctccagc tgggcattga   1081
     ggaagccttc accagcaagg ctgacctgtc agggatcaca ggggccagga acctagcagt   1141
     ctcccaggtg gtccataagg ctgtgcttga tgtatttgag gagggcacag aagcatctgc   1201
     tgccacagca gtcaaaatca cctccttc tgcattagtg gagacaagga ccattgtgcg   1261
     tttcaacagg cccttcctga tgatcattgt ccctacagac acccagaaca tcttcttcat   1321
     gagcaaagtc accaatccca agcaagccta gagcttgcca tcaagcagtg gggctctcag   1381
```

```
taaggaactt ggaatgcaag ctggatgcct gggtctctgg gcacagcctg gcccctgtgc    1441
accgagtggc catggcatgt gtggccctgt ctgcttatcc ttggaaggtg acagcgattc    1501
cctgtgtagc tctcacatgc acaggggccc atggactctt cagtctggag ggtcctgggc    1561
ctcctgacag caataaataa tttcgttgga aaaaaaaaaa aaaaaaaaaa aaaaaaaaaa    1621 aaaaaaaaa
```

Various SERPINA3 expression vectors are commercially available, some of which are linked to the above NCBI Ref. Seq. entry. For example, human SERPINA3 as transfection-ready DNA (pCMV6-XL5, SKU SC119471); Myc-DDK-tagged ORF clone of *Homo sapiens* SERPINA3 as transfection-ready DNA (pCMV6-Entry, SKU RC200509) and GFP-tagged as transfection-ready DNA (pCMV6-AC-GFP; OriGene Technologies, Inc., Rockville, Md., cat. no. RG200509)(Rockville, Md.).

SERPINA3 (Human) recombinant protein is available for example from, Abnova (cat. no. H00000012-P01; Walnut, Calif., USA), or R&D Systems (Cat. No. 1295-PI-010). Such protein products may be suitable for formulating pharmaceutical composition comprising the SERPINA3 protein. Native protein isolated from human plasma is available from Abnova (cat. no. P4947).

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

TNFSF15 (Human Tumor Necrosis Factor (Ligand) Superfamily, Member 15 (TNFSF15)) (NCBI Reference Sequence: NM_005118.3 and NP_005109.2; NM_001204344.1 & NP_001191273.1) Tumor necrosis factor ligand superfamily, member 15 (TNFSF15) is a member of the TNF superfamily, and is also known as TL1; TL1A; VEGI; VEGI192A. TNFSF15 is abundantly expressed in endothelial cells, but is not expressed in either B or T cells. The expression of this protein is inducible by TNF and IL-1 alpha. This cytokine is a ligand for receptor TNFRSF25 and decoy receptor TNFRSF21/DR6. It can activate NF-kappaB and MAP kinases, and acts as an autocrine factor to induce apoptosis in endothelial cells. TNFSF15 is also found to inhibit endothelial cell proliferation, and thus may function as an angiogenesis inhibitor. Two transcript variants encoding different isoforms have been found for this gene (Tan et al., 1997, *Gene* 204:35-46; Zhai et al., 1999, FASEB 13:181-189; Migone et al., 2002, *Immunity* 16:479-492). TNFSF15 may be involved in autoimmune diseases and tumorigenesis (Sethi et al., 2009, *Adv. Exp. Med. Biol.* 647:207-215). Recently it has been shown that TNFSF15 can induce proinflammatory cytokines in inflammatory bowel disease (Jin et al., 2012, *Mucosal. Immunol.*, doi: 10.1038/mi.2012.124).

The human TNFSF15 protein and cDNA sequences are listed below.

```
NCBI Reference Sequence: NP_005109.2; isoform VEGI-251 precursor; transcript
variant 1:
                                                            (SEQ ID NO: 47)
MAEDLGLSFGETASVEMLPEHGSCRPKARSSSARWALTCCLVLLPFLAGLTTYLLVSQLRAQGEACVQFQALKGQEFAPS

HQQVYAPLRADGDKPRAHLTVVRQTPTQHFKNQFPALHWEHELGLAFTKNRMNYTNKFLLIPESGDYFIYSQVTFRGMTS

ECSEIRQAGRPNKPDSITWITKVTDSYPEPTQLLMGTKSVCEVGSNWFQPIYLGAMFSLQEGDKLMVNVSDISLVDYTK

EDKTFFGAFLL

NCBI Reference Sequence: NP_001191273.1, isoform VEGI192A precursor, transcript
variant 2:
                                                            (SEQ ID NO: 48)
MQLTKGRLHFSHPLSHTKHISPFVTDAPLRADGDKPRAHLTWRQTPTQHFKNQFPALHWEHELGLAFTKNRMNYTNKFL

LIPESGDYFIYSQVTFRGMTSECSEIRQAGRPNKPDSITWITKVTDSYPEPTQLLMGTKSVCEVGSNWFQPIYLGAMFS

LQEGDKLMVNVSDISLVDYTKEDKTFFGAFLL

NCBI Reference Sequence: NM_005118.3; isoform VEGI-251 precursor; transcript
variant 1:
                                                            (SEQ ID NO: 49)
  1 ggaaaaggga aggaggagac tgagtgatta agtcacccac tgtgagagct ggtcttctat    61 ttaatggggg ctctctctgc ccaggagtca gaggtgcctc caggagcagc aggagcatgg   121 ccgaggatct gggactgagc tttggggaaa cagccagtgt ggaaatgctg ccagagcacg   181 gcagctgcag gcccaaggcc aggagcagca gcgcacgctg ggctctcacc tgctgcctgg   241 tgttgctccc cttccttgca ggactcacca catacctgct tgtcagccag ctccgggccc   301
```

-continued

```
agggagaggc ctgtgtgcag ttccaggctc taaaaggaca ggagtttgca ccttcacatc    361
agcaagttta tgcacctctt agagcagacg gagataagcc aagggcacac ctgacagttg    421
tgagacaaac tcccacacag cactttaaaa atcagttccc agctctgcac tgggaacatg    481
aactaggcct ggccttcacc aagaaccgaa tgaactatac caacaaattc ctgctgatcc    541
cagagtcggg agactacttc atttactccc aggtcacatt ccgtgggatg acctctgagt    601
gcagtgaaat cagacaagca ggccgaccaa acaagccaga ctccatcact gtggtcatca    661
ccaaggtaac agacagctac cctgagccaa cccagctcct catgggacc aagtctgtat     721 gcgaagtagg tagcaactgg ttccagccca tctacctcgg agccatgttc tccttgcaag    781 aagggacaa gctaatggtg aacgtcagtg acatctcttt ggtggattac acaaaagaag     841
ataaaacctt ctttggagcc ttcttactat aggaggagag caaatatcat tatatgaaag    901
tcctctgcca ccgagttcct aattttctt gttcaaatgt aattataacc aggggttttc     961
ttggggccgg gagtaggggg cattccacag ggacaacggt ttagctatga aatttggggc    1021
ccaaaatttc acacttcatg tgccttactg atgagagtac taactgaaa aaggctgaag     1081 agagcaaata tattattaag atgggttgga ggattggcga gtttctaaat attaagacac    1141
tgatcactaa atgaatggat gatctactcg ggtcaggatt gaaagagaaa tatttcaaca    1201
ccttcctgct atacaatggt caccagtggt ccagttattg ttcaatttga tcataaattt    1261
gcttcaattc aggagctttg aaggaagtcc aaggaaagct ctagaaaaca gtataaactt    1321
tcagaggcaa aatccttcac caattttttcc acatactttc atgccttgcc taaaaaaat    1381 gaaaagagag ttggtatgtc tcatgaatgt tcacacagaa ggagttggtt ttcatgtcat    1441
ctacagcata tgagaaaagc tacctttctt ttgattatgt acacagatat ctaaataagg    1501
aagtatgagt ttcacatgta tatcaaaaat acaacagttg cttgtattca gtagagtttt    1561
cttgcccacc tattttgtgc tgggttctac cttaacccag aagacactat gaaaaacaag    1621
acagactcca ctcaaaattt atatgaacac cactagatac ttcctgatca aacatcagtc    1681
aacatactct aaagaataac tccaagtctt ggccaggcgc agtggctcac acctgtaatc    1741
ccaacacttt gggaggccaa ggtgggtgga tcatctaagg ccgggagttc aagaccagcc    1801
tgaccaacgt ggagaaaccc catctctact aaaaatacaa aattagccgg gcgtggtagc    1861
gcatggctgt aatcctggct actcaggagg ccgaggcaga agaattgctt gaactgggga    1921
ggcagaggtt gcggtgagcc cagatcgcgc cattgcactc cagcctgggt aacaagagca    1981
aaactctgtc caaaaaaaaa aaaataaaat aataactcca agcctttaaa aaatatcatc    2041
tgaaactgtt acatcagatt tctggcactc tactgactgt ggaagatagc cagctgactg    2101
gaagatagcc agctgattag ttccctgaag aaacctgaag acagatacct ggttaactag    2161
atcaactaca ctgccaactt gtttgatgct gagagacaat ggacttattc catggggaa     2221 gggaaaaaag aagtcaatca ccaaatctga agaagttaac ctagatcttt gaggtttgat    2281
ttgcaacttt atatgcagag tattatgtgg gtattttccc ttaaaatatt caagggatt     2341 tacatatggg attagctaat gagcctagcc aagaccttcc ctggaggaca ggctggtcat    2401
tgcggaggtc ccttctgtgc ttcagtgggt tcatatcctc tagtccgtat gattttccta    2461
cgctaatatg tcaaggcag gagaggcagc tctgttctcc tagcctttgt tgacttgtct     2521
gcaaagcagg aatctgccca tttgtttcca aggagcaaat gagctcatga gaatgaaaga    2581
tgttaacttc atgcattctg tgccatctga gcatttcggt attatatgac tggtgaccct    2641
tggcccgtat tataaatgct tcctatcctg ggagacctca tggatgagtc tgagaggaaa    2701
tttggcacca aaatcactct cactctggtt tccagtagac tatagaggca gagaggcatt    2761
```

-continued

```
tgagaggctc ctgagcaaag tgtccagtgt agcaggagca cttcattaat atttattgag    2821
ttataattaa ataaaaatta atttctgatt tctcagtttg gaggttaagg ctctaaatat    2881
attttctaac ctctgctagg ctaacttaag ccaggccttt ttcttgcctt ccctttctca    2941
aaacagtcag cacagactca gtgggagcac agaggagtgt ggtcacctcc acctggctca    3001
ccagagtctt catagaggaa gtgaagcctg gaagaaactg ggcgggcccc agatgaccac    3061
agggaaaggg catctcagat ggaggaatta cccttgactt aaagcagaaa agaaagattt    3121
ctcagtaact ccaaaacttg cttgatagga gaatattccc tcaaccaatt cctaggacaa    3181
tatttattgg tagatcaaga atgtttcctc aataactcta gtctagctcc atgatcagaa    3241
ctaacaccca ttaaaaacat aaaatgttct ttctgaaccg tcttcatgg tgcgtgagag     3301 caccaagcag ctttggtatg caggaggagt tttgcacaga agagtggcct gctcaaacct    3361
gcccactgtt ctgtaggtga tctggtggat ctggaaattt atcccaagac aggaatttcc    3421
taatattcga agacatttga ggctttggga aattctctgc tgtgcattta tttggctcct    3481
gtcataagct tgttttttaa agaatgtatc atagctcaag tttttactgc tgattttgtt    3541
aaattctgta tagtatattt tttacggaaa ggcacagtca gacattccta atagggctca    3601
tgtcagaact tctgttccca aggcattatc tccatagcaa aaattagtgc actgttttca    3661
aaagtgaggt gggaaaatgc ttttaagatc atgtgatgtt cccctaaaag gggttaatgg    3721
ggtgtattca gggtttggga gggaggaaga agcatgcttt agaaaacagt aaatttaggg    3781
agaaaatgct ttgttggtta aatgtcactc aaaaggctga attcaaatca attccacaaa    3841
catttactga gtacctactg cccctgggga cacagagata aattatttag tctcagacac    3901
actcattcta acttcccagc acctctactg tctgcagatt ctttaattta ttttggttgt    3961
attagctaat taattcgtaa actttaggca catggatcta ttctcattat gaaaatggat    4021
gccatttgat taaggctgat gactaacaaa atgatttgtg tttactcgaa gtgttttttt    4081
aaaaatagct actcaaggat agttttccat aaatcaagaa ggtaaaaaag ttcccatttt    4141
ttattgtaga atccattatt taaactacat gtagagacag gttattattt gctatattca    4201
agtttggtca tcaataccct taaaaatatt agaattttat ggatgaccca gaaatgcttt    4261
gaaaatctgt gttcctcagc aaatacagag accatgatca aaatgcacag aatcactaac    4321
attttgatgc tagcatggtt tcagtctatt tggcagaaca gaattgatta tgctactaaa    4381
atttcttttt cttttttttt tttttttttt ttgagacaga gtcttgcttt gtcacccagg    4441
ctgaagtgca gtggcaggat ctcagttcac tgcaacctct gcctcccagg ttcacgccat    4501
tctcctgctt cagcctcccg agtagctggg actacaggct cccaccacca tgcccggcta    4561
attttttgca ttttagtag acgggggtt tcaccgtgtt agccaggatg gtctcgatct     4621
cctgacctcg tgatccgccc gcctcagcct ccaaagtgc tgggattaca ggcgtgagcc     4681
actgtgcccg gactctgatt tttttttac taaggtacag taagaaaagg gaaagtgta     4741 cgttttcact tcctgaaata tgtcaggttg aatcaataat agagcacacc agaactcttg    4801
gctccatttc aacctaaact attcagttct catcacccca gaggaaattc cgcctctgtg    4861
ctggtcagta atccccctgg attataaaag tttaactaac tcactgtgca caaggcacgg    4921
ccattgccaa cattctcttg caaggtattt tcccaagccc ttacccaatt ctgttccat     4981 gattgtgaca ttggggatta attctgcaag acagaactgt ttatattctg taccttaaaa    5041
acacatgcaa acatctcttg ccttaagatt tctgctttc ctatggccca gagtcctaga    5101
agtgttttga tatttgtagc agaattttca agtgtacatc cttatcctgg atattaacat    5161
```

-continued

```
ttttgcatca tattggcagc tggacctaca gagaatttag tagactgtta acctaataag    5221
ccttgaatcc ttttgcacca gtggtgagag aatgtggatc agagccatca cctccatgcc    5281
ccgtcaccct ctaacaacca catttacaac ttccccagct ctgagacaca cttgcctcca    5341
ccccttccat caccccattt taagatgaaa ataccacacc agcctggaag gaagaagtta    5401
cttgcccagg gccacatagt gagttaaggg ctgatctaga gctaggaagc tgtcttcctg    5461
aaccataatc ctggactctt ctaacctctc tactcatcgc aaatagagtt catttagtg    5521 atttgaagga agatgggaca agtattttca aacacctgta ggacaacatg gaagtgggag    5581
gagacttcta ctgtagctcc ccagagaaga gagctagggc tacagagttg cagttacaag    5641
gttgccctct ctggcttgat ccccaaagga attttctact ccaaaataga attttctag    5701 gatgctattt ctcagtccct ggagatactc aaacaaaggg cttgtcacaa gggttttgt    5761 agaagctatt cttcacagag gttggggag agattaagcc aaaggatctc tgaggtcttt    5821
ttcaaatcta taattatgtg gccttttgtt cattgacttc catgtgttct agttgatcat    5881
tacaaacctg gcaggccttc tcaaggggttc agtaattagc tgtcatttcc catttgtcca    5941
gagagtgtcc aacacaaat accccctaaga tcttggccaa tagagaaatg tcatggaatt    6001
ttagaaatga cagtatctgc ggagtttatt ccaagttata tcatttcaaa gatgaagaaa    6061
cccaggctca gagggagcca tcacatccac accctgtcac ccttcgtggc cagtgccaga    6121
cagtagctag ttggatgcta aaagtagaat ttagatatct taacaataag cccagcagtc    6181
tttcaacttc attcgtaaat cattttttgtt ttgagcatct gtcacgtggc agcacttgcc    6241
tggatactgg agagctgaga aggaatgcga caggcaagtc ctactctcac agtgtataca    6301
ttcaggagga acaagacaca cagtgccaag taaataaagt agctgaactt catcaaatga    6361
ttttattctt aaagtcatta aagcatgtaa tgttcccctt tttttgtttc aggggtgtac    6421
agattgaaga agtgtaggtg tttatgtggt tttagtgaca aaccccatgt gctttcattg    6481
attttatgtt ttatgttaaa acatcaaccg caaggtaaaa tgcatattgt atgttgttgg    6541
atacgtactt aactggtatg catcccatgt ctttgggtac tagtgtatga attctaatct    6601
ctgtaaatga aatgttgtat gtgttaatat atttaataga tgtaacttaa taaactggca    6661
ttgaagactg aagaattttc acactgtcaa aaaaaaaaa aaaaa
```

NCBI Reference Sequence: NM_001204344.1; isoform VEGI192A
precursor, transcript variant 2:

(SEQ ID NO: 50)
```
atgcaactca caagggccg tcttcatttc agtcacccctt tgtctcatac aaagcacatt      61
tctccttttg ttacagatgc acctcttaga gcagacggag ataagccaag gcacacctg     121 acagttgtga gacaaactcc cacacagcac tttaaaaatc agttcccagc tctgcactgg     181
gaacatgaac taggcctggc cttcaccaag aaccgaatga actataccaa caattcctg     241 ctgatcccag agtcgggaga ctacttcatt tactcccagg tcacattccg tgggatgacc     301
tctgagtgca gtgaaatcag acaagcaggc cgaccaaaca agccagactc catcactgtg     361
gtcatcacca aggtaacaga cagctaccct gagccaaccc agctcctcat ggggaccaag     421
tctgtatgcg aagtaggtag caactggttc cagcccatct acctcggagc catgttctcc     481
ttgcaagaag gggacaagct aatggtgaac gtcagtgaca tctctttggt ggattacaca     541
aaagaagata aaaccttctt ggagccttc ttactatagg aggagagcaa atatcattat     601
atgaaagtcc tctgccaccg agttcctaat tttctttgtt caaatgtaat tataaccagg     661
ggttttcttg gggccgggag taggggggcat tccacaggga caacggttta gctatgaaat     721
ttggggccca aaatttcaca cttcatgtgc cttactgatg agagtactaa ctggaaaaag     781
```

-continued

```
gctgaagaga gcaaatatat tattaagatg ggttggagga ttggcgagtt tctaaatatt    841
aagacactga tcactaaatg aatggatgat ctactcgggt caggattgaa agagaaatat    901
ttcaacacct tcctgctata caatggtcac cagtggtcca gttattgttc aatttgatca    961
taaatttgct tcaattcagg agctttgaag gaagtccaag gaaagctcta gaaaacagta   1021
taaactttca gaggcaaaat ccttcaccaa tttttccaca tactttcatg ccttgcctaa   1081
aaaaaatgaa aagagagttg gtatgtctca tgaatgttca cacagaagga gttggttttc   1141
atgtcatcta cagcatatga gaaaagctac ctttcttttg attatgtaca cagatatcta   1201
aataaggaag tatgagtttc acatgtatat caaaaataca acagttgctt gtattcagta   1261
gagttttctt gcccacctat tttgtgctgg gttctacctt aacccagaag acactatgaa   1321
aaacaagaca gactccactc aaaatttata tgaacaccac tagatacttc ctgatcaaac   1381
atcagtcaac atactctaaa gaataactcc aagtcttggc caggcgcagt ggctcacacc   1441
tgtaatccca cactttggg aggccaaggt gggtggatca tctaaggccg ggagttcaag   1501
accagcctga ccaacgtgga gaacccccat ctctactaaa aatacaaaat tagccgggcg   1561
tggtagcgca tggctgtaat cctggctact caggaggccg aggcagaaga attgcttgaa   1621
ctggggaggc agaggttgcg gtgagcccag atcgcgccat tgcactccag cctgggtaac   1681
aagagcaaaa ctctgtccaa aaaaaaaaaa ataaataat aactccaagc ctttaaaaaa   1741
tatcatctga aactgttaca tcagatttct ggcactctac tgactgtgga agatagccag   1801
ctgactggaa gatagccagc tgattagttc cctgaagaaa cctgaagaca gatacctggt   1861
taactagatc aactacactg ccaacttgtt tgatgctgag agacaatgga cttattccat   1921
gggggaaggg aaaaaagaag tcaatcacca aatctgaaga agttaaccta gatctttgag   1981
gtttgatttg caactttata tgcagagtat tatgtgggta ttttccctta aaatattcaa   2041
agggatttac atatgggatt agctaatgag cctagccaag accttccctg gaggacaggc   2101
tggtcattgc ggaggtccct tctgtgcttc agtgggttca tatcctctag tccgtatgat   2161
tttcctacgc taatatgtca agggcaggag aggcagctct gttctcctag cctttgttga   2221
cttgtctgca aagcaggaat ctgcccattt gtttccaagg agcaaatgag ctcatgagaa   2281
tgaaagatgt taacttcatg cattctgtgc catctgagca tttcggtatt atatgactgg   2341
tgacccttgg cccgtattat aaatgcttcc tatcctggga gacctcatgg atgagtctga   2401
gaggaaattt ggcaccaaaa tcactctcac tctggtttcc agtagactat agaggcagag   2461
aggcatttga gaggctcctg agcaaagtgt ccagtgtagc aggagcactt cattaatatt   2521
tattgagtta taattaaata aaaattaatt tctgatttct cagtttggag gttaaggctc   2581
taaatatatt ttctaacctc tgctaggcta acttaagcca ggccttttc ttgccttccc   2641 tttctcaaaa cagtcagcac agactcagtg ggagcacaga ggagtgtggt cacctccacc   2701
tggctcacca gagtcttcat agaggaagtg aagcctggaa gaaactgggc gggcccaga   2761 tgaccacagg gaaagggcat ctcagatgga ggaattaccc ttgacttaaa gcagaaaaga   2821
aagatttctc agtaactcca aaacttgctt gataggagaa tattccctca accaattcct   2881
aggacaatat ttattggtag atcaagaatg tttcctcaat aactctagtc tagctccatg   2941
atcagaacta acacccatta aaaacataaa atgttctttc tgaaccggtc ttcatggtgc   3001
gtgagagcac caagcagctt tggtatgcag gaggagtttt gcacagaaga gtggcctgct   3061
caaacctgcc cactgttctg taggtgatct ggtggatctg gaaatttatc ccaagacagg   3121
aatttcctaa tattcgaaga catttgaggc tttgggaaat tctctgctgt gcatttattt   3181
ggctcctgtc ataagcttgt ttttaaaga atgtatcata gctcaagttt ttactgctga   3241
```

-continued

```
ttttgttaaa ttctgtatag tatatttttt acggaaaggc acagtcagac attcctaata    3301
gggctcatgt cagaacttct gttcccaagg cattatctcc atagcaaaaa ttagtgcact    3361
gttttcaaaa gtgaggtggg aaaatgcttt taagatcatg tgatgttccc ctaaaagggg    3421
ttaatggggt gtattcaggg tttgggaggg aggaagaagc atgctttaga aaacagtaaa    3481
tttagggaga aaatgctttg ttggttaaat gtcactcaaa aggctgaatt caaatcaatt    3541
ccacaaacat ttactgagta cctactgccc ctggggacac agagataaat tatttagtct    3601
cagacacact cattctaact tcccagcacc tctactgtct gcagattctt taatttattt    3661
tggttgtatt agctaattaa ttcgtaaact ttaggcacat ggatctattc tcattatgaa    3721
aatggatgcc atttgattaa ggctgatgac taacaaaatg atttgtgttt actcgaagtg    3781
ttttttaaa aatagctact caaggatagt tttccataaa tcaagaaggt aaaaaagttc     3841
ccattttta ttgtagaatc cattatttaa actacatgta gagacaggtt attatttgct     3901
atattcaagt ttggtcatca ataccttaa aaatattaga atttatgga tgacccagaa     3961
atgctttgaa aatctgtgtt cctcagcaaa tacagagacc atgatcaaaa tgcacagaat    4021
cactaacatt ttgatgctag catggtttca gtctatttgg cagaacagaa ttgattatgc    4081
tactaaaatt tcttttctt ttttttttt tttttttttg agacagagtc ttgctttgtc     4141
acccaggctg aagtgcagtg gcaggatctc agttcactgc aacctctgcc tcccaggttc    4201
acgccattct cctgcttcag cctcccgagt agctgggact acaggctccc accaccatgc    4261
ccggctaatt ttttgcattt ttagtagaga cggggtttca ccgtgttagc caggatggtc    4321
tcgatctcct gacctcgtga tccgcccgcc tcagccttcc aaagtgctgg gattacaggc    4381
gtgagccact gtgcccggac tctgattttt tttttactaa ggtacagtaa gaaaagggaa    4441
aagtgtacgt tttcacttcc tgaaatatgt caggttgaat caataataga gcacaccaga    4501
actcttggct ccatttcaac ctaaactatt cagttctcat caccccagag gaaattccgc    4561
ctctgtgctg gtcagtaatc cccctggatt ataaaagttt aactaactca ctgtgcacaa    4621
ggcacggcca ttgccaacat tctcttgcaa ggtattttcc caagccctta cccaattctg    4681
tttccatgat tgtgacattg gggattaatt ctgcaagaca gaactgttta tattctgtac    4741
cttaaaaaca catgcaaaca tctcttgcct taagatttct ggctttccta tggcccagag    4801
tcctagaagt gttttgatat ttgtagcaga attttcaagt gtacatcctt atcctggata    4861
ttaacatttt tgcatcatat tggcagctgg acctacagag aatttagtag actgttaacc    4921
taataagcct tgaatccttt tgcaccagtg gtgagagaat gtggatcaga gccatcacct    4981
ccatgccccg tcaccctcta acaaccacat ttacaacttc cccagctctg agacacactt    5041
gcctccaccc cttccatcac cccattttaa gatgaaaata ccacaccagc ctggaaggaa    5101
gaagttactt gcccagggcc acatagtgag ttaagggctg atctagagct aggaagctgt    5161
cttcctgaac cataatcctg gactcttcta acctctctac tcatcgcaaa tagagttcat    5221
tttagtgatt tgaaggaaga tgggacaagt attttcaaac acctgtagga caacatggaa    5281
gtgggaggag acttctactg tagctcccca gagaagagag ctagggctac agagttgcag    5341
ttacaaggtt gccctctctg gcttgatccc caaaggaatt ttctactcca aaatagaatt    5401
tttctaggat gctatttctc agtccctgga gatactcaaa caaagggctt gtcacaaggg    5461
ttttgtaga agctattctt cacagaggtt gggggagaga ttaagccaaa ggatctctga    5521
ggtctttttc aaatctataa ttatgtggcc ttttgttcat tgacttccat gtgttctagt    5581
tgatcattac aaacctggca ggccttctca agggttcagt aattagctgt catttcccat    5641
```

```
                                     -continued
ttgtccagag agtgtccaac acaaaatacc cctaagatct tggccaatag agaaatgtca   5701
tggaatttta gaaatgacag tatctgcgga gtttattcca agttatatca tttcaaagat   5761
gaagaaaccc aggctcagag ggagccatca catccacacc ctgtcaccct tcgtggccag   5821
tgccagacag tagctagttg gatgctaaaa gtagaattta gatatcttaa caataagccc   5881
agcagtcttt caacttcatt cgtaaatcat ttttgttttg agcatctgtc acgtggcagc   5941
acttgcctgg atactggaga gctgagaagg aatgcgacag gcaagtccta ctctcacagt   6001
gtatacattc aggaggaaca agacacacag tgccaagtaa ataaagtagc tgaacttcat   6061
caaatgattt tattcttaaa gtcattaaag catgtaatgt tcccctttt  ttgtttcagg   6121 ggtgtacaga ttgaagaagt gtaggtgttt atgtggtttt agtgacaaac cccatgtgct   6181
ttcattgatt ttatgtttta tgttaaaaca tcaaccgcaa ggtaaaatgc atattgtatg   6241
ttgttggata cgtacttaac tggtatgcat cccatgtctt tgggtactag tgtatgaatt   6301
ctaatctctg taaatgaaat gttgtatgtg ttaatatatt taatagatgt aacttaataa   6361
actggcattg aagactgaag aattttcaca ctgtcaaaaa aaaaaaaaaa aa
```

Various TNFSF15 expression vectors are commercially available, some of which are linked to the above NCBI Ref. Seq. entry. For example, human TNFSF15 as transfection-ready DNA (pCMV6-XL6, SKU SC312650); Myc-DDK-tagged ORF clone of Homo sapiens TNFSF15 as transfection-ready DNA (pCMV6-Entry, SKU RC212177) and GFP-tagged as transfection-ready DNA (pCMV6-AC-GFP; OriGene Technologies, Inc., Rockville, Md., cat. no. RG212177)(Rockville, Md.).

TNFSF15 (Human) recombinant protein is available for example from Abnova (cat. no. H00009966; Walnut, Calif., USA), or R&D Systems (Cat. No. 1319-TL-). Such protein products may be suitable for formulating pharmaceutical composition comprising the TNFSF15 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

FN1 (Fibronectin 1)

Fibronectin 1 (FN1), is also known as FN; CIG; FNZ; MSF; ED-B; FINC; GFND; LETS; GFND2. The gene encodes fibronectin, a glycoprotein present in a soluble dimeric form in plasma, and in a dimeric or multimeric form at the cell surface and in extracellular matrix. Fibronectin is involved in cell adhesion and migration processes including embryogenesis, wound healing, blood coagulation, host defense, and metastasis. The gene has three regions subject to alternative splicing, with the potential to produce 20 different transcript variants. However, the full-length nature of some variants has not been determined (Kornblihtt et al. 1983, Proc. Nat. Acad. Sci. USA 80:3218-3222; Muro et al., 2003, J. Cell. Biol. 162:149-160). Two types of fibronectin are present in vertebrates: a soluble plasma fibronectin (formerly called "cold-insoluble globulin," or CIg) is a major protein component of blood plasma (300 μg/ml) and is produced in the liver by hepatocytes, and a insoluble cellular fibronectin is a major component of the extracellular matrix. It is secreted by various cells, primarily fibroblasts, as a soluble protein dimer and is then assembled into an insoluble matrix in a complex cell-mediated process.

Fibronectin plays a major role in cell adhesion, growth, migration, and differentiation, and it is important for processes such as wound healing and embryonic development. Altered fibronectin expression, degradation, and organization has been associated with a number of pathologies, including cancer and fibrosis. Fibronectin has profound effects on wound healing (Grinnell et al. 1981, J. Inv. Derm. 76:181-189).

The human FN1 protein and cDNA sequences are listed below.

```
NCBI Reference Sequence: NP_997639.1; fibronectin isoform 6 preproprotein
                                                                    (SEQ ID NO: 51)
MLRGPGPGLLLLAVQCLGTAVPSTGASKSKRQAQQMVQPQSPVAVSQSKPGCYDNGKHYQINQQWERTYLGNALVCTCYG

GSRGFNCESKPEAEETC.FDKYTGNTYRVGDTYERPKDSMIWDCTCIGAGRGRISCTIANRCHEGGQSYKIGDTWRRPHE

TGGYMLECVCLGNGKGEWTCKPIAEKCFDHAAGTSYWGETWEKPYQGWMMVDCTCLGEGSGRITCTSRNRCNDQDTRTS

YRIGDTWSKKDNRGNLLQCICTGNGRGEWKCERHTSVQTTSSGSGPFTDVRAAVYQPQPHPQPPPYGHCVTDSGVVYSVG

MQWLKTQGNKQMLCTCLGNGVSCQETAVTQTYGGNSNGEPCVLPFTYNGRTFYSCTTEGRQDGHLWCSTTSNYEQDQKYS

FCTDHTVLVQTRGGNSNGALCHFPFLYNNHNYTDCTSEGRRDNMKWCGTTQNYDADQKFGFCPMAAHEEICTTNEGVMYR

IGDQWDKQHDMGHMMRCTCVGNGRGEWTCIAYSQLRDQCIVDDITYNVNDTFHKRHEEGHMLNCTCFGQGRGRWKCDPVD
```

-continued

QCQDSETGTFYQIGDSWEKYVHGVRYQCYCYGRGIGEWHCQPLQTYPSSSGPVEVFITETPSQPNSHPIQWNAPQPSHIS

KYILRWRPKNSVGRWKEATIPGHLNSYTIKGLKPGWYEGQLISIQQYGHQEVTRFDFTTTSTSTPVTSNTVTGETTPFS

PLVATSESVTEITASSFWSWVSASDTVSGFRVEYELSEEGDEPQYLDLPSTATSVNIPDLLPGRKYIVNVYQISEDGEQ

SLILSTSQTTAPDAPPDPTVDQVDDTSIWRWSRPQAPITGYRIVYSPSVEGSSTELNLPETANSVTLSDLQPGVQYNIT

IYAVEENQESTPWIQQETTGTPRSDTVPSPRDLQFVEVTDVKVTIMWTPPESAVTGYRVDVIPVNLPGEHGQRLPISRN

TFAEVTGLSPGVTYYFKVFAVSHGRESKPLTAQQTTKLDAPTNLQFVNETDSTVLVRWTPPRAQITGYRLTVGLTRRGQP

RQYNVGPSVSKYPLRNLQPASEYTVSLVAIKGNQESPKATGVFTTLQPGSSIPPYNTEVTETTIVITWTPAPRIGFKLGV

RPSQGGEAPREVTSDSGSIWSGLTPGVEYVYTIQVLRDGQERDAPIVNKWTPLSPPTNLHLEANPDTGVLTVSWERST

TPDITGYRITTTPTNGQQGNSLEEWHADQSSCTFDNLSPGLEYNVSVYTVKDDKESVPISDTIIPAVPPPTDLRFTNIG

PDTMRVTWAPPPSIDLTNFLVRYSPVKNEEDVAELSISPSDNAVVLTNLLPGTEYWSVSSVYEQHESTPLRGRQKTGLD

SPTGIDFSDITANSFTVHWIAPRATITGYRIRHHPEHFSGRPREDRVPHSRNSITLTNLTPGTEYWSIVALNGREESPL

LIGQQSTVSDVPRDLEVVAATPTSLLISWDAPAVTVRYYRITYGETGGNSPVQEFTVPGSKSTATISGLKPGVDYTITVY

AVTGRGDSPASSKPISINYRTEIDKPSQMQVTDVQDNSISVKWLPSSSPVTGYRVTTTPKNGPGPTKTKTAGPDQTEMTI

EGLQPTVEYWSVYAQNPSGESQPLVQTAVTTIPAPTDLKFTQVTPTSLSAQWTPPNVQLTGYRVRVTPKEKTGPMKEIN

LAPDSSSWVSGLMVATKYEVSVYALKDTLTSRPAQGVVTTLENVSPPRRARVTDATETTITISWRTKTETITGFQVDAV

PANGQTPIQRTIKPDVRSYTITGLQPGTDYKIYLYTLNDNARSSPWIDASTAIDAPSNLRFLATTPNSLLVSWQPPRAR

ITGYIIKYEKPGSPPREWPRPRPGVTEATITGLEPGTEYTIYVIALKNNQKSEPLIGRKKTGQEALSQTTISWAPFQDT

SEYIISCHPVGTDEEPLQFRVPGTSTSATLTGLTRGATYNIIVEALKDQQRHKVREEWTVGNSVNEGLNQPTDDSCFDP

YTVSHYAVGDEWERMSESGFKLLCQCLGFGSGHFRCDSSRWCHDNGVNYKIGEKWDRQGENGQMMSCTCLGNGKGEFKCD

PHEATCYDDGKTYHVGEQWQKEYLGAICSCTCFGGQRGWRCDNCRRPGGEPSPEGTTGQSYNQYSQRYHQRTNTNVNCPI

ECFMPLDVQADREDSRE

NCBI Reference Sequence: NM_212474.1; fibronectin
isoform 6 preproprotein (SEQ ID NO: 52)

```
   1 gcccgcgccg gctgtgctgc acaggggggag gagagggaac cccaggcgcg agcgggaaga    61
     ggggacctgc agccacaact tctctggtcc tctgcatccc ttctgtccct ccacccgtcc   121
     ccttccccac cctctggccc ccaccttctt ggaggcgaca acccccggga ggcattagaa   181
     gggattttc  ccgcaggttg cgaagggaag caaacttggt ggcaacttgc ctcccggtgc   241
     gggcgtctct cccccaccgt ctcaacatgc ttaggggtcc ggggcccggg ctgctgctgc   301
     tggccgtcca gtgcctgggg acagcggtgc cctccacggg agcctcgaag agcaagaggc   361
     aggctcagca aatggttcag ccccagtccc cggtggctgt cagtcaaagc aagcccggtt   421
     gttatgacaa tggaaaacac tatcagataa atcaacagtg ggagcggacc tacctaggca   481
     atgcgttggt ttgtacttgt tatggaggaa gccgaggttt taactgcgag agtaaacctg   541
     aagctgaaga acttgctttt gacaagtaca ctgggaacac ttaccgagtg ggtgacactt   601
     atgagcgtcc taaagactcc atgatctggg actgtacctg catcggggct gggcgaggga   661
     gaataagctg taccatcgca aaccgctgcc atgaaggggg tcagtcctac aagattggtg   721
     acacctggag gagaccacat gagactggtg ttacatgtt  agagtgtgtg tgtcttggta   781
     atggaaaagg agaatggacc tgcaagccca gctgagaa   gtgttttgat catgctgctg   841
     ggacttccta tgtggtcgga gaaacgtggg agaagcccta ccaggctgg  atgatggtag   901
     attgtacttg cctgggagaa ggcagcggac gcatcacttg cacttctaga aatagatgca   961
     acgatcagga cacaaggaca tcctatagaa ttggagacac ctggagcaag aaggataatc  1021
     gaggaaacct gctccagtgc atctgcacag gcaacggccg aggagagtgg aagtgtgaga  1081
```

-continued

```
ggcacacctc tgtgcagacc acatcgagcg gatctggccc cttcaccgat gttcgtgcag   1141
ctgtttacca accgcagcct cacccccagc ctcctcccta tggccactgt gtcacagaca   1201
gtggtgtggt ctactctgtg gggatgcagt ggctgaagac acaaggaaat aagcaaatgc   1261
tttgcacgtg cctgggcaac ggagtcagct gccaagagac agctgtaacc cagacttacg   1321
gtggcaactc aaatggagag ccatgtgtct taccattcac ctacaatggc aggacgttct   1381
actcctgcac cacagaaggg cgacaggacg gacatctttg gtgcagcaca acttcgaatt   1441
atgagcagga ccagaaatac tctttctgca cagaccacac tgttttggtt cagactcgag   1501
gaggaaattc caatggtgcc ttgtgccact tccccttcct atacaacaac cacaattaca   1561
ctgattgcac ttctgagggc agaagagaca acatgaagtg gtgtgggacc acacagaact   1621
atgatgccga ccagaagttt gggttctgcc ccatggctgc ccacgaggaa atctgcacaa   1681
ccaatgaagg ggtcatgtac cgcattggag atcagtggga taagcagcat gacatgggtc   1741
acatgatgag gtgcacgtgt gttgggaatg gtcgtgggga tggacatgc attgcctact   1801 cgcagcttcg agatcagtgc attgttgatg acatcactta caatgtgaac gacacattcc   1861
acaagcgtca tgaagagggg cacatgctga actgtacatg cttcggtcag ggtcgggca   1921 ggtggaagtg tgatcccgtc gaccaatgcc aggattcaga gactgggacg ttttatcaaa   1981
ttggagattc atgggagaag tatgtgcatg tgtcagata ccagtgctac tgctatggcc   2041
gtggcattgg ggagtggcat tgccaacctt tacagaccta tccaagctca agtggtcctg   2101
tcgaagtatt tatcactgag actccgagtc agcccaactc ccaccccatc cagtggaatg   2161
caccacagcc atctcacatt tccaagtaca ttctcaggtg gagacctaaa aattctgtag   2221
gccgttggaa ggaagctacc ataccaggcc acttaaactc ctacaccatc aaaggcctga   2281
agcctggtgt ggtatacgag ggccagctca tcagcatcca gcagtacggc caccaagaag   2341
tgactcgctt tgacttcacc accaccagca ccagcacacc tgtgaccagc aacaccgtga   2401
caggagagac gactcccttt tctcctcttg tggccacttc tgaatctgtg accgaaatca   2461
cagccagtag ctttgtggtc tcctgggtct cagcttccga caccgtgtcg ggattccggg   2521
tggaatatga gctgagtgag gagggagatg agccacagta cctggatctt ccaagcacag   2581
ccacttctgt gaacatccct gacctgcttc ctggccgaaa atacattgta aatgtctatc   2641
agatatctga ggatgggag cagagtttga tcctgtctac ttcacaaaca acagcgcctg   2701
atgcccctcc tgacccgact gtggaccaag ttgatgacac ctcaattgtt gttcgctgga   2761
gcagacccca ggctcccatc acagggtaca gaatagtcta ttcgccatca gtagaaggta   2821
gcagcacaga actcaacctt cctgaaactg caaactccgt caccctcagt gacttgcaac   2881
ctggtgttca gtataacatc actatctatg ctgtggaaga aaatcaagaa agtacacctg   2941
ttgtcattca acaagaaacc actggcaccc cacgctcaga tacagtgccc tctcccaggg   3001
acctgcagtt tgtggaagtg acagacgtga aggtcaccat catgtggaca ccgcctgaga   3061
gtgcagtgac cggctaccgt gtggatgtga tccccgtcaa cctgcctggc gagcacgggc   3121
agaggctgcc catcagcagg aacacctttg cagaagtcac cgggctgtcc cctggggtca   3181
cctattactt caaagtcttt gcagtgagcc atgggaggga gagcaagcct ctgactgctc   3241
aacagacaac caaactggat gctcccacta acctccagtt tgtcaatgaa actgattcta   3301
ctgtcctggt gagatggact ccacctcggg cccagataac aggataccga ctgaccgtgg   3361
gccttacccg aagaggacag cccaggcagt acaatgtggg tcctctcgtc tccaagtacc   3421
cactgaggaa tctgcagcct gcatctgagt acaccgtatc cctcgtggcc ataaagggca   3481
accaagagag ccccaaagcc actggagtct ttaccacact gcagcctggg agctctattc   3541
```

-continued

```
caccttacaa caccgaggtg actgagacca ccattgtgat cacatggacg cctgctccaa    3601
gaattggttt taagctgggt gtacgaccaa gccagggagg agaggcacca cgagaagtga    3661
cttcagactc aggaagcatc gttgtgtccg gcttgactcc aggagtagaa tacgtctaca    3721
ccatccaagt cctgagagat ggacaggaaa gagatgcgcc aattgtaaac aaagtggtga    3781
caccattgtc tccaccaaca aacttgcatc tggaggcaaa ccctgacact ggagtgctca    3841
cagtctcctg ggagaggagc accaccccag acattactgg ttatagaatt accacaaccc    3901
ctacaaacgg ccagcaggga aattctttgg aagaagtggt ccatgctgat cagagctcct    3961
gcacttttga taacctgagt cccggcctgg agtacaatgt cagtgtttac actgtcaagg    4021
atgacaagga aagtgtccct atctctgata ccatcatccc agctgttcct cctcccactg    4081
acctgcgatt caccaacatt ggtccagaca ccatgcgtgt cacctgggct ccaccccat    4141 ccattgattt aaccaacttc ctggtgcgtt actcacctgt gaaaaatgag gaagatgttg    4201
cagagttgtc aatttctcct tcagacaatg cagtggtctt aacaaatctc ctgcctgta    4261 cagaatatgt agtgagtgtc tccagtgtct acgaacaaca tgagagcaca cctcttagag    4321
gaagacagaa aacaggtctt gattcccaa ctggcattga cttttctgat attactgcca    4381
actcttttac tgtgcactgg attgctcctc gagccaccat cactggctac aggatccgcc    4441
atcatcccga gcacttcagt gggagacctc gagaagatcg ggtgccccac tctcggaatt    4501
ccatcaccct caccaacctc actccaggca cagagtatgt ggtcagcatc gttgctctta    4561
atggcagaga ggaaagtccc ttattgattg gccaacaatc aacagtttct gatgttccga    4621
gggacctgga agttgttgct gcgaccccca ccagcctact gatcagctgg gatgctcctg    4681
ctgtcacagt gagatattac aggatcactt acggagagac aggaggaaat agccctgtcc    4741
aggagttcac tgtgcctggg agcaagtcta cagctaccat cagcggcctt aaacctggag    4801
ttgattatac catcactgtg tatgctgtca ctggccgtgg agacagcccc gcaagcagca    4861
agccaatttc cattaattac cgaacagaaa ttgacaaacc atcccagatg caagtgaccg    4921
atgttcagga caacagcatt agtgtcaagt ggctgccttc aagttcccct gttactggtt    4981
acagagtaac caccactccc aaaaatggac caggaccaac aaaaactaaa actgcaggtc    5041
cagatcaaac agaaatgact attgaaggct tgcagcccac agtggagtat gtggttagtg    5101
tctatgctca gaatccaagc ggagagagtc agcctctggt tcagactgca gtaaccacta    5161
ttcctgcacc aactgacctg aagttcactc aggtcacacc cacaagcctg agcgcccagt    5221
ggacaccacc caatgttcag ctcactggat atcgagtgcg ggtgaccccc aaggagaaga    5281
ccggaccaat gaaagaaatc aaccttgctc ctgacagctc atccgtggtt gtatcaggac    5341
ttatggtggc caccaaatat gaagtgagtg tctatgctct taaggacact ttgacaagca    5401
gaccagctca gggagttgtc accactctgg agaatgtcag cccaccaaga agggctcgtg    5461
tgacagatgc tactgagacc accatcacca ttagctggag aaccaagact gagacgatca    5521
ctggcttcca agttgatgcc gttccagcca atggccagac tccaatccag agaaccatca    5581
agccagatgt cagaagctac accatcacag gtttacaacc aggcactgac tacaagatct    5641
acctgtacac cttgaatgac aatgctcgga gctcccctgt ggtcatcgac gcctccactg    5701
ccattgatgc accatccaac ctgcgtttcc tggccaccac acccaattcc ttgctggtat    5761
catggcagcc gccacgtgcc aggattaccg gctacatcat caagtatgag aagcctgggt    5821
ctcctcccag agaagtggtc cctcggcccc gcctggtgt cacagaggct actattactg    5881
gcctggaacc gggaaccgaa tatacaattt atgtcattgc cctgaagaat aatcagaaga    5941
```

-continued

```
gcgagccct   gattggaagg   aaaaagacag   gacaagaagc   tctctctcag   acaaccatct   6001
catgggcccc  attccaggac   acttctgagt   acatcatttc   atgtcatcct   gttggcactg   6061
atgaagaacc  cttacagttc   agggttcctg   gaacttctac   cagtgccact   ctgacaggcc   6121
tcaccagagg  tgccacctac   aacatcatag   tggaggcact   gaaagaccag   cagaggcata   6181
aggttcggga  agaggttgtt   accgtgggca   actctgtcaa   cgaaggcttg   aaccaaccta   6241
cggatgactc  gtgctttgac   ccctacacag   tttcccatta   tgccgttgga   gatgagtggg   6301
aacgaatgtc  tgaatcaggc   tttaaactgt   tgtgccagtg   cttaggcttt   ggaagtggtc   6361
atttcagatg  tgattcatct   agatggtgcc   atgacaatgg   tgtgaactac   aagattggag   6421
agaagtggga  ccgtcaggga   gaaaatggcc   agatgatgag   ctgcacatgt   cttgggaacg   6481
gaaaaggaga  attcaagtgt   gaccctcatg   aggcaacgtg   ttatgatgat   gggaagacat   6541
accacgtagg  agaacagtgg   cagaaggaat   atctcggtgc   catttgctcc   tgcacatgct   6601
ttggaggcca  gcggggctgg   cgctgtgaca   actgccgcag   acctgggggt   gaacccagtc   6661
ccgaaggcac  tactggccag   tcctacaacc   agtattctca   gagataccat   cagagaacaa   6721
acactaatgt  taattgccca   attgagtgct   tcatgccttt   agatgtacag   gctgacagag   6781
aagattcccg  agagtaaatc   atctttccaa   tccagaggaa   caagcatgtc   tctctgccaa   6841
gatccatcta  aactggagtg   atgttagcag   acccagctta   gagttcttct   ttctttctta   6901
agcccttgc   tctggaggaa   gttctccagc   ttcagctcaa   ctcacagctt   ctccaagcat   6961
caccctggga  gtttcctgag   ggttttctca   taaatgaggg   ctgcacattg   cctgttctgc   7021
ttcgaagtat  tcaataccgc   tcagtatttt   aaatgaagtg   attctaagat   ttggtttggg   7081
atcaatagga  aagcatatgc   agccaaccaa   gatgcaaatg   ttttgaaatg   atatgaccaa   7141
aattttaagt  aggaaagtca   cccaaacact   tctgctttca   cttaagtgtc   tggcccgcaa   7201
tactgtagga  acaagcatga   tcttgttact   gtgatatttt   aaatatccac   agtactcact   7261
ttttccaaat  gatcctagta   attgcctaga   aatatctttc   tcttacctgt   tatttatcaa   7321
tttttcccag  tattttttata  cggaaaaaat   tgtattgaaa   acacttagta   tgcagttgat   7381
aagaggaatt  tggtataatt   atggtgggtg   attatttttt   atactgtatg   tgccaaagct   7441
ttactactgt  ggaaagacaa   ctgttttaat   aaaagattta   cattccacaa   cttgaagttc   7501
atctatttga  tataagacac   cttcggggga   aataattcct   gtgaatattc   tttttcaatt   7561
cagcaaacat  ttgaaaatct   atgatgtgca   agtctaattg   ttgatttcag   tacaagattt   7621
tctaaatcag  ttgctacaaa   aactgattgg   tttttgtcac   ttcatctctt   cactaatgga   7681
gatagcttta  cactttctgc   tttaatagat   ttaagtggac   cccaatattt   attaaaattg   7741
ctagtttacc  gttcagaagt   ataatagaaa   taatctttag   ttgctctttt   ctaaccattg   7801
taattcttcc  cttcttccct   ccaccttcc   ttcattgaat   aaacctctgt   tcaaagagat   7861
tgcctgcaag  ggaaataaaa   atgactaaga   tattaaaaaa   aaaaaaaaa   aa
```

Various FN1 expression vectors are commercially available, some of which are linked to the above NCBI Ref. Seq. entry. For example, human FN1 as transfection-ready DNA (pCMV6-XL5 or pCMV6-XL, SKU SC308634; SC12686; SC308635; SC308636; SC308637; SC308640); Myc-DDK-tagged ORF clone of *Homo sapiens* FN1 as transfection-ready DNA (pCMV6-Entry, SKU RC224503; RC212860) and GFP-tagged as transfection-ready DNA (pCMV6-AC-GFP; OriGene Technologies, Inc., Rockville, Md., cat. no. RG224503; RG224603), and other variants (Rockville, Md.).

FN1 (Human) recombinant protein is available for example from Abnova (cat. no. H00002335-P01; Walnut, Calif., USA), or R&D Systems (Cat. No. 1918-FN; ACFP4305). Such protein products may be suitable for formulating pharmaceutical composition comprising the FN1 protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.)

and QIAGEN (Germantown, Md.), and other primer/probes for verifying expression level of constructs from QIAGEN (Germantown, Md.) and OriGene Technologies (Rockville, Md.) other suppliers.

4. Pro-Inflammatory Genes

Using the screening methods of the invention, certain genes have been identified as potential pro-inflammatory genes in that their expression level (e.g., expression as measured by mRNA expression) is dramatically increased after contacting the test cells by a proinflammatory cytokine (e.g., IL-13), as compared to untreated control (see fold increase in Tables 3 and 4 below). Thus inhibiting the expression of the subject pro-inflammatory genes may antagonize the function of the pro-inflammatory cytokine, such that at least one adverse phenotype induced by the pro-inflammatory cytokine is inhibited or reversed.

Certain genes identified by the various screening assays of the invention as being pro-inflammatory are listed in the two tables below (Tables 3 and 4), with the genes in bold representing those common to both assays (stem cell-based assay vs. differentiated structures-based assay). Other genes of particular interest as being pro-inflammatory are italicized. The expression fold increase after IL-13 treatment, either over 3, 5, and 13 days for isolated upper airway stem cells, or over 2, 5, and 7 days for differentiated cells in air-liquid interface (ALI), as compared to time-matched untreated control cells, are listed in the $1^{st}$ to the $3^{rd}$ column after each gene name.

In general, antagonists of these pro-inflammatory genes may encode RNA-based therapeutic reagents (e.g., siRNA, miRNA, shRNA, antisense, ribozyme etc.) or protein-based reagents (e.g., antibody to the proteins encoded by the pro-inflammatory genes, or dominant negative versions of the proteins encoded by the pro-inflammatory genes) that may be formulated as pharmaceutical compositions for treating inflammatory diseases, disorders, or abnormal conditions.

For antibody-based therapeutic agents, existing or commercially available antibodies against the protein encoded by the pro-inflammatory genes may be used as antagonist. Alternatively, new antibodies may be produced based on the protein encoded by the pro-inflammatory genes. Methods of producing antibodies, including mouse antibodies, human-mouse chimeric antibodies, humanized antibodies, or fully human antibodies, or there antigen-binding portions are well known in the art.

For example, chimeric antibodies, in which the variable regions of the antibody chains are murine-derived and the constant regions of the antibody chains are human-derived, have been described (see Knight, *Mol. Immunol.* 30:1443-1453, 1993; PCT Publication No. WO 92/16553). Additionally, humanized antibodies, in which the hypervariable domains of the antibody variable regions are murine-derived but the remainder of the variable regions and the antibody constant regions are human-derived, have also been prepared (see PCT Publication No. WO 92/11383). Entirely human antibody theoretically does not elicit HAMA (host against murine antibody) reaction, even if used for prolonged periods. Human monoclonal autoantibodies can be prepared using standard human hybridoma techniques (see Boyle et al., *Cell. Immunol.* 152:556-568, 1993; Boyle et al., *Cell. Immunol.* 152:569-581, 1993; European Patent Application Publication No. 614 984 A2). Fully human monoclonal antibodies can be prepared using humanized transgenic mouse models or in vitro approaches (see Lonberg 1995, *Int. Rev. Immunol.* 13:65-93; Schwimmer et al. 2013, *J. Immunol. Methods*, doi: 10.1016/j.jim.2013.02.010; U.S. Pat. No. 7,605,237.

The term "antigen-binding portion" of an antibody, as used herein, refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., *Science* 242:423-426, 1988; and Huston et al., *Proc. Natl. Acad. Sci. USA* 85:5879-5883, 1988). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., *Proc. Natl. Acad. Sci. USA* 90:6444-6448, 1993; Poljak et al., *Structure* 2:1121-1123, 1994).

The human sequences of these pro-inflammatory genes are described individually below for the representative pro-inflammatory genes of the invention. These sequences can be used as query sequences to identify additional homologs from other species using, for example, standard sequence comparison software in public or proprietary sequence databases, including BLASTp or BLASTn searches in NCBI sequences databases (such as the non-redundant sequence database, or sequence databases for specific model organisms including mouse, rat, bovine, zebrafish, gorilla, *Drosophila*, etc.).

In general, these homologs or fragments thereof sharing at least about 40%, 50%, 60%, 70%, 80%, 85%, 90%, 95%, 97%, 99% protein sequence identity may replace the human protein for use in producing the RNA- or protein-based pharmaceutical composition of the invention described above. The effectiveness of any of the therapeutic agents can be verified or tested based on their effectiveness in inhibiting the function of the pro-inflammatory genes in the assays of the invention, e.g., assay to determine the extent of inhibition on the adverse inflammatory phenotype caused by the pro-inflammatory genes in the ALI differentiated upper airway stem cells of the invention.

Certain genes identified by two different assays of the invention as being pro-inflammatory are listed in the two tables below, with the genes in bold representing those common to both assays (stem cell-based assay vs. differentiated structures-based assay). Other genes of particular interest as being pro-inflammatory are italicized. The expression fold increase after IL-13 treatment, either over 3, 5, and 13 days for isolated upper airway stem cells, or over 2, 5, and 7 days for differentiated cells in air-liquid interface (ALI), as compared to time-matched untreated control cells, are listed after each gene.

TABLE 3

Representative Pro-Inflammatory Genes
and Expression Fold Increase - Differentiated Cells
Genes Upregulated in Differentiated Cells

|  | Day 2* | Day 5* | Day 7* |
|---|---|---|---|
| ITLN1 | 19.0 | 22.0 | 110.0 |
| DPP4 | 3.0 | 4.3 | 13.0 |
| TCN1 | 6.0 | 6.0 | 12.0 |
| CA2 | 3.0 | 4.5 | 9.0 |
| TIMP1 | 3.0 | 8.0 | 8.0 |
| *CD200R1* | 2.0 | 2.7 | 8.0 |
| SERPINB2 | 4.0 | 3.5 | 7.0 |
| ST6GAL1 | 2.0 | 3.0 | 6.0 |
| GGH | 4.0 | 2.5 | 5.0 |
| CST1 | 1.0 | 5.0 | 5.0 |
| *PLA2G7* | 3.0 | 2.9 | 4.0 |
| CCL26 | 3.0 | 4.0 | 4.0 |
| *SAA4* | 1.0 | 2.0 | 4.0 |
| POSTN | 3.0 | 2.0 | 4.0 |
| *ANG* | 3.0 | 2.5 | 4.0 |
| *SPINK5* | 3.0 | 2.0 | 4.0 |
| SAA1 | 2.0 | 2.2 | 4.0 |
| CST2 | 1.0 | 3.0 | 3.0 |
| AGR2 | 2.0 | 2.0 | 3.0 |
| TNFSF10 | 2.0 | 3.0 | 3.0 |
| *TFF1* | 1.0 | 3.0 | 3.0 |
| *C20orf114* | 1.0 | 3.0 | 3.0 |
| PDCD1LG2 | 2.0 | 3.0 | 3.0 |
| CLCA4 | 1.0 | 1.0 | 2.0 |
| STATH | 1.0 | 2.0 | 2.0 |
| PTHLH | 1.0 | 1.2 | 2.0 |
| C5orf53 | 1.0 | 1.0 | 2.0 |
| KITLG | 2.0 | 1.0 | 2.0 |
| *SULF1* | 2.0 | 2.0 | 2.0 |
| TMPRSS2 | 2.0 | 2.0 | 2.0 |
| CF1 | 2.0 | 1.0 | 2.0 |
| SPINK4 | 1.0 | 2.0 | 2.0 |
| AZGP1 | 1.0 | 2.0 | 2.0 |
| FAM3B | 2.0 | 1.3 | 2.0 |
| PIGR | 1.0 | 2.0 | 2.0 |
| CLU | 1.0 | 1.3 | 2.0 |
| *EPGN* | 2.0 | 1.0 | −2.0 |
| FGF2 | 2.0 | 1.0 | −3.0 |
| CCL20 | 3.0 | 3.0 | 1.0 |
| KL | 3.0 | 1.5 | 1.6 |
| CD55 | 3.0 | 2.4 | 3.0 |
| *SMPDL3B* | 2.4 | 1.0 | 1.0 |
| DEFB128 | 2.0 | 1.0 | 1.0 |
| OVOS2 | 2.0 | 1.6 | 1.0 |
| CFI | 2.0 | 1.0 | 2.0 |
| DEFB118 | 2.0 | 1.0 | 1.0 |

*Days 2, 5, and 7: IL-13 was added on Day 0 to cells differentiated in ALI culture for 25 days, and expression fold increase for each listed gene was measured at Days 2, 5, and 7.

TABLE 4

Representative Pro-Inflammatory Genes
and Expression Fold Increase - Stem Cells
Genes Up-regulated in Isolated Stem Cells

|  | Day 3^ | Day 5^ | Day 13^ |
|---|---|---|---|
| ITLN1 | 62.8 | 99.9 | 76.4 |
| POSTN | 51.9 | 30.4 | 29.7 |
| DPP4 | 18.2 | 13.7 | 8.3 |
| CCL26 | 16.9 | 7.9 | 2.8 |
| SERPINB2 | 10.5 | 21.5 | 13.1 |
| CA2 | 8.2 | 9.1 | 2.4 |
| *FETUB* | 6.3 | 2.3 | 5.4 |
| TCN1 | 6.1 | 16.6 | 6.9 |
| GGH | 4.5 | 8.4 | 2.3 |

TABLE 4-continued

Representative Pro-Inflammatory Genes
and Expression Fold Increase - Stem Cells
Genes Up-regulated in Isolated Stem Cells

|  | Day 3^ | Day 5^ | Day 13^ |
|---|---|---|---|
| CST1 | 4.0 | 9.6 | 83.8 |
| STATH | 4 | 1.9 | 1.0 |
| *SULF1* | 3.9 | 1.9 | 1.3 |
| TMPRSS2 | 3.6 | 2.0 | 2.2 |
| KITLG | 3.5 | 3.3 | 2.9 |
| LOXL4 | 3.1 | 2.0 | 2.9 |
| CST2 | 3.0 | 4.1 | 8.5 |
| ST6GAL1 | 2.3 | 3.3 | 2.8 |
| LIPH | 2.3 | 2.2 | 2.7 |
| TNFSF10 | 2.2 | 4.7 | 4.5 |
| PIP | 2.0 | 4.5 | 3.9 |
| THBS1 | 2.0 | 2.2 | 4.5 |
| DNAJC10 | 2 | 3.2 | 1.8 |
| F3 | 1.9 | 2.9 | 1.5 |
| PAPPA | 1.8 | 1.4 | 4.2 |
| TIMP1 | 1.7 | 6.9 | 7.6 |
| LIFR | 1.7 | 2.4 | 2.3 |
| PDCD1LG2 | 1.7 | 2.2 | 2.0 |
| PTHLH | 1.7 | 3.8 | 4.3 |
| AGR2 | 1.7 | 3.4 | 1.0 |
| TFPI2 | 1.6 | 3.5 | 1.5 |
| CST3 | 1.5 | 2.1 | 2.6 |
| LRRC17 | 1.5 | 4 | 2.8 |
| CTSS | 1.5 | 2.1 | 1.0 |
| EDN1 | 1.2 | 1.8 | 2.7 |
| PLA2G12A | 1.2 | 2.7 | 1.0 |
| FST | 1.2 | 2.2 | 1.7 |
| IL32 | 1.2 | 2 | 1.7 |
| IL1B | 1.0 | 1.2 | 2.7 |
| PLAU | 1.0 | 1.2 | 2.8 |
| PLAUR | 1.0 | 1.6 | 2.0 |
| PRRG1 | 1.0 | 1.2 | 2.7 |
| PSAP | 1.0 | 1.2 | 2.6 |
| SDF2 | 1.0 | 1.2 | 2.7 |
| SERPINB1 | 1.0 | 1.2 | 2.3 |

^Days 3, 5, and 13: IL-13 was added on Day 0 to upper airway stem cells in ALI culture, and expression fold increase for each listed gene was measured at Days 3, 5, and 13.

In certain embodiments, the invention provides pharmaceutical compositions that can be used to treat inflammatory diseases, comprising one or more antagonists of the pro-inflammatory genes selected from the group consisting of: any one or more of the pro-inflammatory genes listed in Tables 3 and 4, such as AGR2, ANG, C20orf114, CA2, CCL26, CD200R1, CST1, CST2, DEFB118, DPP4, EPGN, FETUB, GGH, ITLN1, KITLG, PDCD1LG2, PLA2G7, POSTN, PTHLH, SAA4, SERPINB2, SMPDL3B, SPINK5, ST6GAL1, STATH, SULF1, TCN1, TFF1, TIMP1, TMPRSS2, TNFSF10.

Representative pro-inflammatory genes are further described below.

AGR2 (Human Anterior Gradient 2 Homolog (*Xenopus laevis*)) (NCBI Reference Sequence: NM_006408.3 and NP_006399.1)

AGR2 was cloned as a gene differentially expressed in ER-positive breast carcinomas that might contribute to its less aggressive phenotype compared to ER-negative tumors. See Kuang et al. (*Nucleic Acids Res.* 26:1116-1123, 1998) and Thompson and Weigel (*Biochem. Biophys. Res. Commun.* 251:111-116, 1998). AGR2 is apparently a homolog of the frog secreted cement gland anterior gradient protein AG2. The deduced 175-amino acid soluble AGR2 protein, which is 91% identical to the mouse protein and 47% identical to the frog protein, contains a signal peptide. Northern blot analysis revealed strongest expression of 0.9- and 1.6-kb AGR2 transcripts in lung and in all ER-positive breast carcinoma lines tested; weaker expression was also detected in pancreas. RNA dot blot analysis detected strong expression in trachea, lung, stomach, colon, prostate, and small intestine, with lower expression in other tissues.

The human AGR2 protein and cDNA sequences are listed below.

```
NCBI Reference Sequence: NP_006399.1:
                                                        (SEQ ID NO: 53)
   1 mekipvsafl llvalsytla rdttvkpgak kdtkdsrpkl pqtlsrgwgd qliwtqtyee 61 alyksktsnk plmiihhlde cphsqalkkv faenkeiqkl aeqfvllnlv yettdkhlsp 121 dgqyvprimf vdpsltvrad itgrysnrly ayepadtall ldnmkkalkl lktel NCBI Reference Sequence: NM_006408.3:
                                                        (SEQ ID NO: 54)
   1 aatcacttgg ggaaaggaag gttcgtttct gagttagcaa caagtaaatg cagcactagt 61 gggtgggatt gaggtatgcc ctggtgcata aatagagact cagctgtgct ggcacactca 121 gaagcttgga ccgcatccta gccgccgact cacacaaggc aggtgggtga ggaaatccag 181 agttgccatg gagaaaattc cagtgtcagc attcttgctc cttgtggccc tctcctacac 241 tctggccaga gataccacag tcaaacctgg agccaaaaag gacacaaagg actctcgacc 301 caaactgccc cagaccctct ccagaggttg gggtgaccaa ctcatctgga ctcagacata 361 tgaagaagct ctatataaat ccaagacaag caacaaaccc ttgatgatta ttcatcactt 421 ggatgagtgc ccacacagtc aagctttaaa gaaagtgttt gctgaaaata aagaaatcca 481 gaaattggca gagcagtttg tcctcctcaa tctggtttat gaaacaactg acaaacacct 541 tttctcctgat ggccagtatg tccccaggat tatgtttgtt gacccatctc tgacagttag 601 agccgatatc actggaagat attcaaatcg tctctatgct tacgaacctg cagatacagc 661 tctgttgctt gacaacatga agaaagctct caagttgctg aagactgaat tgtaaagaaa 721 aaaaatctcc aagcccttct gtctgtcagg ccttgagact tgaaaccaga agaagtgtga 781 gaagactggc tagtgtggaa gcatagtgaa cacactgatt aggttatggt ttaatgttac 841 aacaactatt ttttaagaaa aacaagtttt agaaatttgg tttcaagtgt acatgtgtga 901 aaacaatatt gtatactacc atagtgagcc atgattttct aaaaaaaaaa ataaatgttt 961 tgggggtgtt ctgttttctc caaaaaaaaa aaaaaa
```

At least about 36 related sequences have been identified and linked to the NCBI RefSeq entry for the human sequence. These sequences may be used to design antisense RNA or ribozyme that either target the conserved regions of the related sequences, or target unique regions of a specific sequence.

Various AGR2 RNAi reagents are commercially available, some of which are linked to the above NCBI Ref. Seq. entry. See, for example, AGR2—Human, 4 unique 29mer shRNA constructs in retroviral untagged vector (Cat. No. TR314890) and AGR2 (Human)—3 unique 27mer siRNA duplexes—2 nmol each (Cat. No. SR307173) (OriGene Technologies, Inc., Rockville, Md.); AGR2 Pre-design Chimera RNAi (Cat. No. H00010551-R01) (Abnova, Taiwan, ROC).

Various anti-AGR2 antibodies are commercially available, some of which are linked to the above NCBI Ref. Seq. entry. See, for example, AGR2 monoclonal antibody (MOD, clone 1E5 (Cat. No. H00010551-M01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

CCL2 (Human Chemokine (C-C Motif) Ligand 2) (NCBI Reference Sequence: NM_002982.3 and NP_002973.1)

CCL2 (C-C motif) ligand 2), also referred to as monocyte chemotactic protein-1 (MCP-1) and small inducible cytokine A2, and also known as HC11; MCAF; MCP1; MCP-1; SCYA2; GDCF-2; SMC-CF; HSMCR30, is a small cytokine that belongs to the CC chemokine family. CCL2 recruits monocytes, memory T cells, and dendritic cells to the sites of inflammation produced by either tissue injury or infection (Carr et al. 1994, *PNAS USA* 91:3652-3656; Xu et al., 1996, *Leukoc. Biol.* 60:365-371). Members of this CXC subfamily are characterized by two cysteines separated by a single amino acid.

The CCL2 protein precursor contains a signal peptide of 23 amino acids. In turn, the mature CCL2 is 76 amino acids long (Yoshimura et al. 1989, *FEBS Letters* 244:487-493; Furutani, Y et al. 1989, *BBRC* 159:249-255). The CCL2 predicted weight is 11.025 kiloDaltons (kDa). CCL2 is anchored in the plasma membrane of endothelial cells by glycosaminoglycan side chains of proteoglycans. CCL2 is primarily secreted by monocytes, macrophages and dendritic cells. Platelet derived growth factor is a major inducer of CCL2 gene. To become activated CCL2 protein has to be cleaved by metalloproteinase MMP-12. The receptors that bind CCL2 are CCR2 and CCR4.

CCL2 exhibits a chemotactic activity for monocytes and basophils. However, it does not attract neutrophils or eosinophils. After deletion of the N-terminal residue, CCL2 loses its attractivity for basophils and becomes a chemoattractant of eosinophils. Basophils and mast cells that are treated with CCL2 releases their granules to the intercellular space. This effect can be also potentiated by a pre-treatment with IL-3 or even by other cytokines (Conti et al., 1995, *Immunol.* 86:434-440; Bischoff et al., 1992, *J. Exp. Med.* 175:1271-1275). CCL2 augments monocyte anti-tumor activity and it is essential for formation of granulomas.

CCL2 can be found at the sites of tooth eruption and bone degradation. In the bone, CCL2 is expressed by mature osteoclasts and osteoblasts and it is under control of nuclear factor κB (NFκB). In the human osteoclasts, CCL2 and RANTES (regulated on activation normal T cell expressed and secreted). Both MCP-1 and RANTES induce formation of TRAP-positive, multinuclear cells from M-CSF-treated monocytes in the absence of RANKL, but produced osteoclasts that lacked cathepsin K expression and resorptive capacity. It is proposed that CCL2 and RANTES act as autocrine loop in human osteoclast differentiation (Kim et al., 2005, *J. Biol. Chem.* 280:16163-16169).

The CCL2 chemokine is also expressed by neurons, astrocytes and microglia (Banisadr et al. 2005, *J. Comp. Neur.* 489:275-292).

CCL2 is implicated in pathogeneses of several diseases characterized by monocytic infiltrates, such as psoriasis, rheumatoid arthritis and atherosclerosis (Xia and Sui, 2009, *Expert Opin. Ther. Patents* 19:295-303). For example, administration of anti-CCL2 antibodies in a model of glomerulonephritis reduces infiltration of macrophages and T cells, reduces crescent formation, as well as scarring and renal impairment (Lloyd et al., 1997, *J. Exp. Med.*, 185:1371-1138). There is evidence that CCL2 is involved in the neuroinflammatory processes, e.g. various diseases of the central nervous system (CNS), epilepsy, brain ischemia, Alzheimer's disease, experimental autoimmune encephalomyelitis (EAE) and traumatic brain injury (Gerard and Rollins, 2001, *Nature Immun.* 2:108-115; Foresti et al., 2009, *J. Neuroinflamm.*, 6:40; Fabene et al., 2010, *J. Neuroimmun.* 224:22-27; Kim et al., 1995, *J. Neuroimmun.* 56:127-134; Hickman and Khoury, 2010 *CNS & Neurol Disorders Drug Targets* 9(2):68-173; Ransohoff et al. 1993, *FASEB* 7:592-600; Semple et al. 2009, *J. Cereb. Blood Flow & Met.* 30:769-782. It has been further implicated in vascular complications of type 2 diabetes and insulin resistance in obesity (Liu et al. 2012, *J. Endocrinol. Invest.* 35:585-589; Cai et al. 2011, *PLoS ONE* 6 (5):e19559).

Treatment with melatonin in old mice with age related liver inflammation decreased the mRNA expression of TNF-α, IL-1β, HO (HO-1 and HO-2), iNOS, CCL2, NF-κB1, NF-κB2 and NKAP in old male mice. The protein expression of TNF-α, IL-1β was also decreased and IL-10 increased with melatonin treatment (Cuesta et al. 2010, *Exp. Gerontol.* 45:950-956).

The human CCL2 protein and cDNA sequences are listed below.

```
NCBI Reference Sequence: NP_002973.1:
                                                    (SEQ ID NO: 11)
MKVSAALLCLLLIAATFIPQGLAQPDAINAPVTCCYNFTNRKISVQRLASYRRITSSKCPKEAVIF

KTIVAKEICADPKQKWVQDSMDHLDKQTQTPKT

NCBI Reference Sequence: NM_002982.3:
                                                    (SEQ ID NO: 12)
    gaggaaccga gaggctgaga ctaacccaga aacatccaat tctcaaactg aagctcgcac    61
tctcgcctcc agcatgaaag tctctgccgc ccttctgtgc ctgctgctca tagcagccac   121
cttcattccc caagggctcg ctcagccaga tgcaatcaat gcccagtca cctgctgtta   181 taacttcacc aataggaaga tctcagtgca gaggctcgcg agctatagaa gaatcaccag   241
cagcaagtgt cccaaagaag ctgtgatctt caagaccatt gtggccaagg agatctgtgc   301 tgacccaag cagaagtggg ttcaggattc catggaccac ctggacaagc aaacccaaac    361
tccgaagact tgaacactca ctccacaacc caagaatctg cagctaactt attttcccct   421
agctttcccc agacaccctg ttttatttta ttataatgaa ttttgtttgt tgatgtgaaa   481
cattatgcct taagtaatgt taattcttat ttaagttatt gatgttttaa gtttatcttt   541
catggtacta gtgttttta gatacagaga cttggggaaa ttgcttttcc tcttgaacca    601
cagttctacc cctgggatgt tttgagggtc tttgcaagaa tcattaatac aaagaatttt    661
ttttaacatt ccaatgcatt gctaaaatat tattgtggaa atgaatattt tgtaactatt   721
acaccaaata aatatatttt tgtacaaaaa aaaaaaaaaa
```

At least about 53 related sequences have been identified and linked to the NCBI RefSeq entry for the human sequence.

Various CCL2 expression vectors are commercially available, some of which are linked to the above NCBI Ref. Seq. entry. For example, human CCL2 GFP-tagged as transfection-ready DNA (pCMV6-AC-GFP; OriGene Technologies, Inc., Rockville, Md., cat. no. RG202180); Myc-DDK-tagged ORF clone of *Homo sapiens* CCL2 as transfection-ready DNA (pCMV6-Entry, SKU RC202180) and CCL2 as transfection-ready DNA NM_002982 (pCMV6-XL5) available from OriGene Technologies, Inc. (Rockville, Md.).

CCL2 (Human) Recombinant Protein (P01) (Cat. GF012) is available from EMD Millipore (Billerica, Mass., USA); R&D Systems (cat. no. 279-MC; Minneapolis, Minn., USA) and many other suppliers. Such protein products may be suitable for formulating pharmaceutical composition comprising the CCL2 protein.

Other commercially available resources linked to the human NCBI RefSeq entry include: siRNA and shRNA sequences from EMD Millipore (Billerica, Mass., USA) or OriGene Technologies (Rockville, Md.), monoclonal antibody from OriGen (Rockville, Md.), ThermoFisher (Rockford, Ill. USA) and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

Interleukin-1 Alpha (Human Interleukin 1, Alpha (IL1A)) (NCBI Reference Sequence: NM_000575.3 and NP_000566.3)

IL1A here interchangeable used with IL-1α, IL-1A, IL1-ALPHA, or IL1-alpha, is also known as pro-interleukin-1-alpha, IL1F1, fibroblast-activating factor (FAF), lymphocyte-activating factor (LAF), B-cell-activating factor (BAF), leukocyte endogenous mediator (LEM), epidermal cell-derived thymocyte-activating factor (ETAF), serum amyloid A inducer of hepatocyte-stimulating factor (HSP), catabolin, hemopoetin-1 (H-1), endogenous pyrogen (EP), osteoclast-activating factor (OAF), and proteolysis-inducing factor (PIF). IL1A is 1 of 2 structurally distinct forms of IL1. IL1A protein is synthesized by a variety of cell types, including activated macrophages, keratinocytes, stimulated B lymphocytes, and fibroblasts, and are potent mediators of inflammation and immunity (Lord et al., 1991, *J. Clin. Invest.* 87:1312-1321). Expression of the C-terminal 159 amino acids of human IL1-alpha in *E. coli* produces IL1A biologic activity, thus being synthesized as large precursors that are processed (March et al. 1985, *Nature* 315:641-647; Mosley et al. 1987, *J. Biol. Chem.* 262:2941-2944). IL1A polymorphisms has been associated with periodontitis (Diehl et al. 1999, *J. Periodont.* 70:418-430), Alzheimer Disease (Du et al. 2000, *Neurology* 55:480-484; Grimaldi et al. 2000, *Ann. Neurol.* 47:361-365 and Nicoll et al. 2000, *Ann. Neurol.* 47:365-368), osteomyelitis (Asensi et al. 2003, *Am. J. Med. Genet.* 119A:132-136) and renal disease (Bensen et al. 2003, *Genomics* 82:194-217). IL-1α has been administered to patients, e.g. treatment with 50 ng/kg IL-la from day zero of autologous bone marrow or stem cells transfer resulted in an earlier recovery of thrombocytopenia compared with historical controls (Smith et al., 1993, *N. Engl. J. Med.* 328 (11):756-61). IL1A stimulates fibroblasts proliferation and may accelerate wound healing (Chedid et al., 1994, *J. Biol. Chem.* 8; 269:10753-10757).

The human IL1A protein and cDNA sequences are listed below:

```
NCBI Reference Sequence: NP_000566.3
                                                        (SEQ ID NO: 24)
MAKVPDMFEDLKNCYSENEEDSSSIDHLSLNQKSFYHVSYGPLHEGCMDQSVSLSISETSKTSKLTFKESMVWATNGKV

LKKRRLSLSQSITDDDLEAIANDSEEEIIKPRSAPFSFLSNVKYNFMRIIKYEFILNDALNQSIIRANDQYLTAAALHNL

DEAVKFDMGAYKSSKDDAKITVILRISKTQLYVTAQDEDQPVLLKEMPEIPKTITGSETNLLFFWETHGTKNYFTSVAHP

NLFIATKQDYWVCLAGGPPSITDFQILENQA

Mature Protein: GenBank Reference: CAA39086.1
                                                        (SEQ ID NO: 25)
SAPFSFLSNVKYNFMRIIKYEFILNDALNQSIIRANDQYLTAAALHNLDEAVKFDMGAYKSSKDDAKITVILRISKTQLY

VTAQDEDQPVLLKEMPEIPKTITGSETNLLFFWETHGTKNYFTSVAHPNLFIATKQDYWVCLAGGPPSITDFQILENQA

NCBI Reference Sequence: NM_000575.3
                                                        (SEQ ID NO: 26)
           accaggcaac accattgaag gctcatatgt aaaaatccat gccttccttt ctcccaatct    61
ccattcccaa acttagccac tggcttctgg ctgaggcctt acgcatacct cccggggctt   121
gcacacacct tcttctacag aagacacacc ttgggcatat cctacagaag accaggcttc   181
tctctggtcc ttggtagagg gctactttac tgtaacaggg ccagggtgga gagttctctc   241
ctgaagctcc atcccctcta taggaaatgt gttgacaata ttcagaagag taagaggatc   301
aagacttctt tgtgctcaaa taccactgtt ctcttctcta ccctgcccta accaggagct   361
tgtcacccca aactctgagg tgatttatgc cttaatcaag caaacttccc tcttcagaaa   421
agatggctca ttttccctca aaagttgcca ggagctgcca agtattctgc caattcaccc   481
tggagcacaa tcaacaaatt cagccagaac acaactacag ctactattag aactattatt   541
attaataaat tcctctccaa atctagcccc ttgacttcgg atttcacgat ttctcccttc   601
ctcctagaaa cttgataagt ttcccgcgct tcccttttc taagactaca tgtttgtcat    661
cttataaagc aaaggggtga ataaatgaac caaatcaata acttctggaa tatctgcaaa   721
caacaataat atcagctatg ccatctttca ctattttagc cagtatcgag ttgaatgaac   781
atagaaaaat acaaaactga attcttccct gtaaattccc cgttttgacg acgcacttgt   841
agccacgtag ccacgcctac ttaagacaat tacaaaaggc gaagaagact gactcaggct   901
taagctgcca gccagagagg gagtcatttc attggcgttt gagtcagcaa agaagtcaag   961
```

```
atggccaaag ttccagacat gtttgaagac ctgaagaact gttacagtga aaatgaagaa  1021
gacagttcct ccattgatca tctgtctctg aatcagaaat ccttctatca tgtaagctat  1081
ggcccactcc atgaaggctg catggatcaa tctgtgtctc tgagtatctc tgaaacctct  1141
aaaacatcca agcttacctt caaggagagc atggtggtag tagcaaccaa cgggaaggtt  1201
ctgaagaaga gacggttgag tttaagccaa tccatcactg atgatgacct ggaggccatc  1261
gccaatgact cagaggaaga aatcatcaag cctaggtcag caccttttag cttcctgagc  1321
aatgtgaaat acaactttat gaggatcatc aaatacgaat tcatcctgaa tgacgccctc  1381
aatcaaagta taattcgagc caatgatcag tacctcacgg ctgctgcatt acataatctg  1441
gatgaagcag tgaaatttga catgggtgct tataagtcat caaaggatga tgctaaaatt  1501
accgtgattc taagaatctc aaaaactcaa ttgtatgtga ctgcccaaga tgaagaccaa  1561
ccagtgctgc tgaaggagat gcctgagata cccaaaacca tcacaggtag tgagaccaac  1621
ctcctcttct tctgggaaac tcacggcact aagaactatt tcacatcagt tgcccatcca  1681
aacttgttta ttgccacaaa gcaagactac tgggtgtgct tggcaggggg gccaccctct  1741
atcactgact ttcagatact ggaaaaccag gcgtaggtct ggagtctcac ttgtctcact  1801
tgtgcagtgt tgacagttca tatgtaccat gtacatgaag aagctaaatc ctttactgtt  1861
agtcatttgc tgagcatgta ctgagccttg taattctaaa tgaatgttta cactctttgt  1921
aagagtggaa ccaacactaa catataatgt tgttatttaa agaacaccct atattttgca  1981
tagtaccaat cattttaatt attattcttc ataacaattt taggaggacc agagctactg  2041
actatggcta ccaaaaagac tctacccata ttacagatgg gcaaattaag gcataagaaa  2101
actaagaaat atgcacaata gcagttgaaa caagaagcca cagacctagg atttcatgat  2161
ttcatttcaa ctgtttgcct tctactttta agttgctgat gaactcttaa tcaaatagca  2221
taagtttctg ggacctcagt tttatcattt tcaaaatgga gggaataata cctaagcctt  2281
cctgccgcaa cagtttttta tgctaatcag ggaggtcatt ttggtaaaat acttcttgaa  2341
gccgagcctc aagatgaagg caaagcacga aatgttattt tttaattatt atttatatat  2401
gtatttataa atatatttaa gataattata atatactata tttatgggaa ccccttcatc  2461
ctctgagtgt gaccaggcat cctccacaat agcagacagt gttttctggg ataagtaagt  2521
ttgatttcat taatacaggg cattttggtc caagttgtgc ttatcccata gccaggaaac  2581
tctgcattct agtacttggg agacctgtaa tcatataata aatgtacatt aattaccttg  2641
agccagtaat tggtccgatc tttgactctt ttgccattaa acttacctgg gcattcttgt  2701
ttcaattcca cctgcaatca agtcctacaa gctaaaatta gatgaactca actttgacaa  2761
ccatgagacc actgttatca aaactttctt ttctggaatg taatcaatgt ttcttctagg  2821
ttctaaaaat tgtgatcaga ccataatgtt acattattat caacaatagt gattgataga  2881
gtgttatcag tcataactaa ataaagcttg caacaaaatt ctctgacaaa aaaaaaaaa  2941 aaa
```

Various IL1A expression vectors are commercially available, some of which are linked to the above NCBI Ref. Seq. entry. For example, human IL1A as transfection-ready DNA (pCMV6-XL5, SKU SC324639); Myc-DDK-tagged ORF clone of *Homo sapiens* IL1A as transfection-ready DNA (pCMV6-Entry, SKU RC202084) and GFP-tagged as transfection-ready DNA (pCMV6-AC-GFP; OriGene Technologies, Inc., Rockville, Md., cat. no. RG202084)(Rockville, Md.).

IL1A (Human) recombinant protein is available for example from Abnova (cat. no. P3627; Walnut, Calif., USA), ProSpec (Cat. No. CYT-253; East Brunswick, N.J., USA), or R&D Systems (Cat. No. 200-LA). Such protein products may be suitable for formulating pharmaceutical composition comprising the IL1A protein.

Other commercially available resources linked to the human NCBI RefSeq entry include: siRNA and shRNA sequences from EMD Millipore (Billerica, Mass., USA), Abnova or OriGene Technologies (Rockville, Md.), monoclonal antibody from OriGene Technologies (Rockville, Md.), Abnova or ThermoFisher (Rockford, Ill. USA), R&D Systems (Minneapolis, Minn.), and many other suppliers, qPCR primers from OriGene Technologies (Rockville, Md.) and QIAGEN (Germantown, Md.), and other primer/probes for verifying expression level of constructs from QIAGEN (Germantown, Md.) and OriGene Technologies (Rockville, Md.) other suppliers.

ANG (Human Angiogenin, Ribonuclease, RNase A Family, 5 (ANG)) (NCBI Reference Sequence: NM_001145.4 and NP_006399.1)

At least about 40 related sequences have been identified and linked to the NCBI RefSeq entry for the human sequence. These sequences may be used to design antisense RNA or ribozyme that either target the conserved regions of the related sequences, or target unique regions of a specific sequence.

Various ANG RNAi reagents are commercially available, some of which are linked to the above NCBI Ref. Seq. entry. See, for example, ANG—Human, 4 unique 29mer shRNA constructs in retroviral untagged vector (Cat. No. TR316443) and ANG (Human)—3 unique 27mer siRNA duplexes—2 nmol each (Cat. No. SR300197) (OriGene Technologies, Inc., Rockville, Md.); ANG Pre-design Chimera RNAi (Cat. No. H00000283-R01) (Abnova, Taiwan, ROC).

Various anti-ANG antibodies are commercially available, some of which are linked to the above NCBI Ref. Seq. entry. See, for example, ANG monoclonal antibody (M05), clone 2A7 (Cat. No. H00000283-M05) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

C20orf114 (Human BPI Fold Containing Family B, Member 1 (BPIFB1)) (NCBI Reference Sequence: NM_033197.2 and NP_149974.2)

At least about 14 related sequences have been identified and linked to the NCBI RefSeq entry for the human sequence. These sequences may be used to design antisense RNA or ribozyme that either target the conserved regions of the related sequences, or target unique regions of a specific sequence.

Various C20orf114 RNAi reagents are commercially available, some of which are linked to the above NCBI Ref. Seq. entry. See, for example, C20orf114—Human, 4 unique 29mer shRNA constructs in retroviral untagged vector (Cat. No. TR305966) and C20orf114 (Human)—3 unique 27mer siRNA duplexes—2 nmol each (Cat. No. SR314220) (OriGene Technologies, Inc., Rockville, Md.).

Various anti-C20orf114 antibodies are commercially available, some of which are linked to the above NCBI Ref. Seq. entry. See, for example, C20orf114 monoclonal antibody (Cat. No. H00092747-M) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

CA2 (Human Carbonic Anhydrase II) (NCBI Reference Sequence: NM_000067.2 and NP_000058.1)

At least about 32 related sequences have been identified and linked to the NCBI RefSeq entry for the human sequence. These sequences may be used to design antisense RNA or ribozyme that either target the conserved regions of the related sequences, or target unique regions of a specific sequence.

Various CA2 RNAi reagents are commercially available, some of which are linked to the above NCBI Ref. Seq. entry. See, for example, CA2—Human, 4 unique 29mer shRNA constructs in retroviral untagged vector (Cat. No. TR314258) and CA2 (Human)—3 unique 27mer siRNA duplexes—2 nmol each (Cat. No. SR300530) (OriGene Technologies, Inc., Rockville, Md.).

Various anti-CA2 antibodies are commercially available, some of which are linked to the above NCBI Ref. Seq. entry. See, for example, CA2 monoclonal antibody (Cat. No. H00000760-M) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

CCL26 (Human Chemokine (C-C Motif) Ligand 26) (NCBI Reference Sequence: NM_006072.4 and NP_006063.1)

At least about 18 related sequences have been identified and linked to the NCBI RefSeq entry for the human sequence. These sequences may be used to design antisense RNA or ribozyme that either target the conserved regions of the related sequences, or target unique regions of a specific sequence.

Various CCL26 RNAi reagents are commercially available, some of which are linked to the above NCBI Ref. Seq. entry. See, for example, CCL26—Human, 4 unique 29mer shRNA constructs in retroviral untagged vector (Cat. No. TR319888) and CCL26 (Human)—3 unique 27mer siRNA duplexes—2 nmol each (Cat. No. SR307010) (OriGene Technologies, Inc., Rockville, Md.).

Various anti-CCL26 antibodies are commercially available, some of which are linked to the above NCBI Ref. Seq. entry. See, for example, Human CCL26/Eotaxin-3 MAb (Clone 115002) (Cat. No. MAB653) (R & D Systems, US, UK, and China).

Other commercially available resources linked to the human NCBI RefSeq entry include: expression clones, protein and peptides, cDNA clones, and gene expression assay reagents that may be generally related to the design and use of the antagonists of the target gene.

CD200R1 (Human CD200 Receptor 1 (CD200R1), Transcript Variant 1) (NCBI Reference Sequence: NM_138806.3 and NP_620161.1)

At least about 33 related sequences have been identified and linked to the NCBI RefSeq entry for the human sequence. These sequences may be used to design antisense RNA or ribozyme that either target the conserved regions of the related sequences, or target unique regions of a specific sequence.

Various CD200R1 RNAi reagents are commercially available, some of which are linked to the above NCBI Ref. Seq. entry. See, for example, CD200R1—Human, 4 unique 29mer shRNA constructs in retroviral untagged vector (Cat. No. TR305521) and CD200R1 (Human)—3 unique 27mer siRNA duplexes—2 nmol each (Cat. No. SR315129) (OriGene Technologies, Inc., Rockville, Md.).

Various anti-CD200R1 antibodies are commercially available, some of which are linked to the above NCBI Ref. Seq. entry. See, for example, CD200r (Cat. No. MA1-35931) (Thermal Scientific Pierce Antibodies, Rockford, Ill.).

Other commercially available resources linked to the human NCBI RefSeq entry include: expression clones, protein and peptides, cDNA clones, and gene expression assay reagents that may be generally related to the design and use of the antagonists of the target gene.

CST1 (Human Cystatin SN) (NCBI Reference Sequence: NM_001898.2 and NP_001889.2)

At least about 16 related sequences have been identified and linked to the NCBI RefSeq entry for the human sequence. These sequences may be used to design antisense RNA or ribozyme that either target the conserved regions of the related sequences, or target unique regions of a specific sequence.

Various CST1 RNAi reagents are commercially available, some of which are linked to the above NCBI Ref. Seq. entry. See, for example, CST1—Human, 4 unique 29mer shRNA constructs in retroviral untagged vector (Cat. No. TR319832) and CST1 (Human)—3 unique 27mer siRNA duplexes—2 nmol each (Cat. No. SR301040) (OriGene Technologies, Inc., Rockville, Md.).

Various anti-CST1 antibodies are commercially available, some of which are linked to the above NCBI Ref. Seq. entry. See, for example, CST1 monoclonal antibody (Cat. No. H00001469-M) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

CST2 (Human Cystatin SA) (NCBI Reference Sequence: NM_001322.2 and NP_001313.1)

At least about 16 related sequences have been identified and linked to the NCBI RefSeq entry for the human sequence. These sequences may be used to design antisense RNA or ribozyme that either target the conserved regions of the related sequences, or target unique regions of a specific sequence.

Various CST2 RNAi reagents are commercially available, some of which are linked to the above NCBI Ref. Seq. entry. See, for example, CST2—Human, 4 unique 29mer shRNA constructs in retroviral untagged vector (Cat. No. TR319831) and CST2 (Human)—3 unique 27mer siRNA duplexes—2 nmol each (Cat. No. SR301041) (OriGene Technologies, Inc., Rockville, Md.).

Various anti-CST2 antibodies are commercially available, some of which are linked to the above NCBI Ref. Seq. entry. See, for example, Purified CST2 (Cystatin SA) mouse monoclonal antibody, Clone 1D6 (Cat. No. TA504259) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

DEFB128 (Human Defensin, Beta 128) (NCBI Reference Sequence: NM_001037732.1 and NP_001032821.1)

At least about 8 related sequences have been identified and linked to the NCBI RefSeq entry for the human sequence. These sequences may be used to design antisense RNA or ribozyme that either target the conserved regions of the related sequences, or target unique regions of a specific sequence.

Various DEFB128 RNAi reagents are commercially available, some of which are linked to the above NCBI Ref. Seq. entry. See, for example, DEFB128—Human, 4 unique 29mer shRNA constructs in retroviral untagged vector (Cat. No. TR313508) and DEFB128 (Human)—3 unique 27mer siRNA duplexes—2 nmol each (Cat. No. SR316712) (OriGene Technologies, Inc., Rockville, Md.).

Various anti-DEFB128 antibodies are commercially available, some of which are linked to the above NCBI Ref. Seq. entry. See, for example, beta-defensin 128 (V-13) (Cat. No. sc-85539) (Santa Cruz Biotechnology, Santa Cruz, Calif.).

Other commercially available resources linked to the human NCBI RefSeq entry include: expression clones, protein and peptides, cDNA clones, and gene expression assay reagents that may be generally related to the design and use of the antagonists of the target gene.

DEFB118 (Human Defensin, Beta 118) (NCBI Reference Sequence: NM_054112.2 and NP_473453.1)

At least about 18 related sequences have been identified and linked to the NCBI RefSeq entry for the human sequence. These sequences may be used to design antisense RNA or ribozyme that either target the conserved regions of the related sequences, or target unique regions of a specific sequence.

Various DEFB118 RNAi reagents are commercially available, some of which are linked to the above NCBI Ref. Seq. entry. See, for example, DEFB118—Human, 4 unique 29mer shRNA constructs in retroviral untagged vector (Cat. No. TR305047) and DEFB118 (Human)—3 unique 27mer siRNA duplexes—2 nmol each (Cat. No. SR314627) (OriGene Technologies, Inc., Rockville, Md.).

Various anti-DEFB118 antibodies are commercially available, some of which are linked to the above NCBI Ref. Seq. entry. See, for example, DEFB118 polyclonal antibody (Cat. No. PAB23961) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

DPP4 (Human Dipeptidyl-Peptidase 4) (NCBI Reference Sequence: NM_001935.3 and NP_001926.2)

At least about 34 related sequences have been identified and linked to the NCBI RefSeq entry for the human sequence. These sequences may be used to design antisense RNA or ribozyme that either target the conserved regions of the related sequences, or target unique regions of a specific sequence.

Various DPP4 RNAi reagents are commercially available, some of which are linked to the above NCBI Ref. Seq. entry. See, for example, DPP4—Human, 4 unique 29mer shRNA constructs in retroviral untagged vector (Cat. No. TR313382) and DPP4 (Human)—3 unique 27mer siRNA duplexes—2 nmol each (Cat. No. SR301258) (OriGene Technologies, Inc., Rockville, Md.).

Various anti-DPP4 antibodies are commercially available, some of which are linked to the above NCBI Ref. Seq. entry. See, for example, CD26, Mouse Anti-Human, (FITC) (Cat. No. CD2601) (Life Technologies Inc., Grand Island, N.Y.).

Other commercially available resources linked to the human NCBI RefSeq entry include: expression clones, protein and peptides, cDNA clones, and gene expression assay reagents that may be generally related to the design and use of the antagonists of the target gene.

EPGN (Mouse Epithelial Mitogen Homolog (Mouse)) (NCBI Reference Sequence: NM_001013442.1 and NP_001013460.1)

Various EPGN RNAi reagents are commercially available, some of which are linked to the above NCBI Ref. Seq. entry. See, for example, EPGN—Human, 4 unique 29mer shRNA constructs in retroviral untagged vector (Cat. No. TR315228) and EPGN (Human)—3 unique 27mer siRNA duplexes—2 nmol each (Cat. No. SR316824) (OriGene Technologies, Inc., Rockville, Md.).

Various anti-EPGN antibodies are commercially available, some of which are linked to the above NCBI Ref. Seq. entry. See, for example, EPGN polyclonal antibody (Cat. No. PAB21933) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

FETUB (Human Fetuin B) (NCBI Reference Sequence: NM_014375.2 and NP_055190.2)

At least about 20 related sequences have been identified and linked to the NCBI RefSeq entry for the human sequence. These sequences may be used to design antisense RNA or ribozyme that either target the conserved regions of the related sequences, or target unique regions of a specific sequence.

Various FETUB RNAi reagents are commercially available, some of which are linked to the above NCBI Ref. Seq. entry. See, for example, FETUB—Human, 4 unique 29mer shRNA constructs in retroviral untagged vector (Cat. No. TR313004) and FETUB (Human)—3 unique 27mer siRNA duplexes—2 nmol each (Cat. No. SR308924) (OriGene Technologies, Inc., Rockville, Md.).

Various anti-FETUB antibodies are commercially available, some of which are linked to the above NCBI Ref. Seq. entry. See, for example, FETUB monoclonal antibody (Cat. No. H00026998-M) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

GGH (Human Gamma-Glutamyl Hydrolase (Conjugase, Folylpolygammaglutamyl Hydrolase)) (NCBI Reference Sequence: NM_003878.2 and NP_003869.1)

At least about 16 related sequences have been identified and linked to the NCBI RefSeq entry for the human sequence. These sequences may be used to design antisense RNA or ribozyme that either target the conserved regions of the related sequences, or target unique regions of a specific sequence.

Various GGH RNAi reagents are commercially available, some of which are linked to the above NCBI Ref. Seq. entry. See, for example, GGH—Human, 4 unique 29mer shRNA constructs in retroviral untagged vector (Cat. No. TR312784) and GGH (Human)—3 unique 27mer siRNA duplexes—2 nmol each (Cat. No. SR305832) (OriGene Technologies, Inc., Rockville, Md.).

Various anti-GGH antibodies are commercially available, some of which are linked to the above NCBI Ref. Seq. entry. See, for example, GGH monoclonal antibody (Cat. No. H00008836-M) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

ITLN1 (Human Intelectin 1 (Galactofuranose Binding)) (NCBI Reference Sequence: NM_017625.2 and NP_060095.2)

The human ITLN1 protein and cDNA sequences are listed below.

```
NCBI Reference Sequence: NP_060095.2:
                                                                    (SEQ ID NO: 55)
MNQLSFLLFLIATTRGWSTDEANTYFKEWTCSSSPSLPRSCKEIKDECPSAFDGLYFLRTENGVIYQTFCDMTSGGGGWT

LVASVHENDMRGKCTVGDRWSSQQGSKAVYPEGDGNWANYNTFGSAEAATSDDYKNPGYYDIQAKDLGIWHVPNKSPMQH

WRNSSLLRYRTDTGFLQTLGHNLFGIYQKYPVKYGEGKCWTDNGPVIPVVYDFGDAQKTASYYSPYGQREFTAGFVQFRV

FNNERAANALCAGMRVTGCNTEHHCIGGGGYFPEASPQQCGDFSGFDWSGYGTHVGYSSSREITEAAVLLFYR

GenBank Sequence: EU832610.1
                                                                    (SEQ ID NO: 56)
       gtacaaaaaa gcaggctcca ccatgaacca actcagcttc ctgctgtttc tcatagcgac      61
caccagagga tggagtacag atgaggctaa tacttacttc aaggaatgga cctgttcttc     121
gtctccatct ctgcccagaa gctgcaagga aatcaaagac gaatgtccta gtgcatttga     181
tggcctgtat tttctccgca ctgagaatgg tgttatctac cagaccttct gtgacatgac     241
ctctgggggt ggcggctgga ccctggtggc cagcgtgcac gagaatgaca tgcgtgggaa     301
gtgcacggtg ggcgatcgct ggtccagtca gcagggcagc aaagcagtct acccagaggg     361
ggacggcaac tgggccaact acaacacctt tggatctgca gaggcggcca cgagcgatga     421
ctacaagaac cctggctact acgacatcca ggccaaggac ctgggcatct ggcacgtgcc     481
caataagtcc cccatgcagc actggagaaa cagctccctg ctgaggtacc gcacggacac     541
tggcttcctc cagacactgg gacataatct gtttggcatc taccagaaat atccagtgaa     601
atatggagaa ggaaagtgtt ggactgacaa cggcccggtg atccctgtgg tctatgattt     661
tggcgacgcc cagaaaacag catcttatta ctcaccctat ggccagcggg aattcactgc     721
gggatttgtt cagttcaggg tatttaataa cgagagagca gccaacgcct tgtgtgctgg     781
aatgagggtc accggatgta acactgagca ccactgcatt ggtggaggag gatactttcc     841
```

```
                                      -continued
agaggccagt ccccagcagt gtggagattt ttctggtttt gattggagtg gatatggaac   901
tcatgttggt tacagcagca gccgtgagat aactgaggca gctgtgcttc tattctatcg   961
ttgaatccac ccagctttct tgtac
```

At least about 23 related sequences have been identified and linked to the NCBI RefSeq entry for the human sequence. These sequences may be used to design antisense RNA or ribozyme that either target the conserved regions of the related sequences, or target unique regions of a specific sequence.

Various ITLN1 RNAi reagents are commercially available, some of which are linked to the above NCBI Ref. Seq. entry. See, for example, ITLN1—Human, 4 unique 29mer shRNA constructs in retroviral untagged vector (Cat. No. TR303870) and ITLN1 (Human)—3 unique 27mer siRNA duplexes—2 nmol each (Cat. No. SR310784) (OriGene Technologies, Inc., Rockville, Md.).

Various anti-ITLN1 antibodies are commercially available, some of which are linked to the above NCBI Ref. Seq. entry. See, for example, ITLN1 monoclonal antibody, clone 17 (Cat. No. MAB9975) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

KITLG (Human KIT Ligand) (NCBI Reference Sequence: NM_000899.4 and NP_000890.1)

At least about 42 related sequences have been identified and linked to the NCBI RefSeq entry for the human sequence. These sequences may be used to design antisense RNA or ribozyme that either target the conserved regions of the related sequences, or target unique regions of a specific sequence.

Various KITLG RNAi reagents are commercially available, some of which are linked to the above NCBI Ref. Seq. entry. See, for example, KITLG—Human, 4 unique 29mer shRNA constructs in retroviral untagged vector (Cat. No. TR311889) and KITLG (Human)—3 unique 27mer siRNA duplexes—2 nmol each (Cat. No. SR302889) (OriGene Technologies, Inc., Rockville, Md.).

Various anti-KITLG antibodies are commercially available, some of which are linked to the above NCBI Ref. Seq. entry. See, for example, KITLG monoclonal antibody (M01), clone 3E10 (Cat. No. H00004254-M01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

PDCD1LG2 (Human Programmed Cell Death 1 Ligand 2) (NCBI Reference Sequence: NM_025239.3 and NP_079515.2)

At least about 29 related sequences have been identified and linked to the NCBI RefSeq entry for the human sequence. These sequences may be used to design antisense RNA or ribozyme that either target the conserved regions of the related sequences, or target unique regions of a specific sequence.

Various PDCD1LG2 RNAi reagents are commercially available, some of which are linked to the above NCBI Ref. Seq. entry. See, for example, PDCD1LG2—Human, 4 unique 29mer shRNA constructs in retroviral untagged vector (Cat. No. TR317544) and PDCD1LG2 (Human)—3 unique 27mer siRNA duplexes—2 nmol each (Cat. No. SR312920) (OriGene Technologies, Inc., Rockville, Md.).

Various anti-PDCD1LG2 antibodies are commercially available, some of which are linked to the above NCBI Ref. Seq. entry. See, for example, PDCD1LG2 monoclonal antibody (M06), clone 7D5 (Cat. No. H00080380-M06) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

PLA2G7 (Human Phospholipase A2, Group VII (Platelet-Activating Factor Acetylhydrolase, Plasma)) (NCBI Reference Sequence: NM_001168357.1 and NP_001161829.1)

At least about 25 related sequences have been identified and linked to the NCBI RefSeq entry for the human sequence. These sequences may be used to design antisense RNA or ribozyme that either target the conserved regions of the related sequences, or target unique regions of a specific sequence.

Various PLA2G7 RNAi reagents are commercially available, some of which are linked to the above NCBI Ref. Seq. entry. See, for example, PLA2G7—Human, 4 unique 29mer shRNA constructs in retroviral GFP vector (Cat. No. TG310385) and PLA2G7 (Human)—3 unique 27mer siRNA duplexes—2 nmol each (Cat. No. SR305319) (OriGene Technologies, Inc., Rockville, Md.).

Various anti-PLA2G7 antibodies are commercially available, some of which are linked to the above NCBI Ref. Seq. entry. See, for example, PLA2G7 monoclonal antibody (M01), clone 5B9 (Cat. No. H00007941-M01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

POSTN (Human Periostin, Osteoblast Specific Factor) (NCBI Reference Sequence: NM_006475.2 and NP_006466.2)

At least about 72 related sequences have been identified and linked to the NCBI RefSeq entry for the human sequence. These sequences may be used to design antisense RNA or ribozyme that either target the conserved regions of the related sequences, or target unique regions of a specific sequence.

Various POSTN RNAi reagents are commercially available, some of which are linked to the above NCBI Ref. Seq. entry. See, for example, POSTN—Human, 4 unique 29mer shRNA constructs in retroviral untagged vector (Cat. No. TR310280) and ITLN1 (Human)—3 unique 27mer siRNA duplexes—2 nmol each (Cat. No. SR310784) (OriGene Technologies, Inc., Rockville, Md.).

Various anti-POSTN antibodies are commercially available, some of which are linked to the above NCBI Ref. Seq. entry. See, for example, Purified Periostin (Periostin) mouse monoclonal antibody, clone 1A1 (Cat. No. TA500070) (OriGene Tech., Inc., Rockville, Md.).

Other commercially available resources linked to the human NCBI RefSeq entry include: expression clones, protein and peptides, cDNA clones, and gene expression assay reagents that may be generally related to the design and use of the antagonists of the target gene.

PTHLH (Human Parathyroid Hormone-Like Hormone) (NCBI Reference Sequence: NM_198965.1 and NP_945316.1)

At least about 45 related sequences have been identified and linked to the NCBI RefSeq entry for the human sequence. These sequences may be used to design antisense RNA or ribozyme that either target the conserved regions of the related sequences, or target unique regions of a specific sequence.

Various PTHLH RNAi reagents are commercially available, some of which are linked to the above NCBI Ref. Seq. entry. See, for example, PTHLH—Human, 4 unique 29mer shRNA constructs in retroviral untagged vector (Cat. No. TR310073) and PTHLH (Human)—3 unique 27mer siRNA duplexes—2 nmol each (Cat. No. SR303874) (OriGene Technologies, Inc., Rockville, Md.).

Various anti-PTHLH antibodies are commercially available, some of which are linked to the above NCBI Ref. Seq. entry. See, for example, PTHLH monoclonal antibody (M01), clone 3H1-5G8 (Cat. No. H00005744-M01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

SAA4 (Human Serum Amyloid A4, Constitutive) (NCBI Reference Sequence: NM_006512.3 and NP_006503.2)

At least about 16 related sequences have been identified and linked to the NCBI RefSeq entry for the human sequence. These sequences may be used to design antisense RNA or ribozyme that either target the conserved regions of the related sequences, or target unique regions of a specific sequence.

Various SAA4 RNAi reagents are commercially available, some of which are linked to the above NCBI Ref. Seq. entry. See, for example, SAA4—Human, 4 unique 29mer shRNA constructs in retroviral untagged vector (Cat. No. TR318894) and SAA4 (Human)—3 unique 27mer siRNA duplexes—2 nmol each (Cat. No. SR304228) (OriGene Technologies, Inc., Rockville, Md.).

Various anti-SAA4 antibodies are commercially available, some of which are linked to the above NCBI Ref. Seq. entry. See, for example, SAA4 polyclonal antibody (A01) (Cat. No. H00006291-A01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

SERPINB2 (Human Serpin Peptidase Inhibitor, Clade B (Ovalbumin), Member 2) (NCBI Reference Sequence: NM_001143818.1 and NP_001137290.1)

At least about 43 related sequences have been identified and linked to the NCBI RefSeq entry for the human sequence. These sequences may be used to design antisense RNA or ribozyme that either target the conserved regions of the related sequences, or target unique regions of a specific sequence.

Various SERPINB2 RNAi reagents are commercially available, some of which are linked to the above NCBI Ref. Seq. entry. See, for example, SERPINB2—Human, 4 unique 29mer shRNA constructs in retroviral untagged vector (Cat. No. TR309533) and SERPINB2 (Human)—3 unique 27mer siRNA duplexes—2 nmol each (Cat. No. SR303346) (OriGene Technologies, Inc., Rockville, Md.).

Various anti-SERPINB2 antibodies are commercially available, some of which are linked to the above NCBI Ref. Seq. entry. See, for example, SERPINB2 monoclonal antibody (M08), clone 3A9 (Cat. No. H00005055-M08) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

SMPDL3B (Human Sphingomyelin Phosphodiesterase, Acid-Like 3B) (NCBI Reference Sequence: NM_014474.2 and NP_055289.2)

At least about 14 related sequences have been identified and linked to the NCBI RefSeq entry for the human sequence. These sequences may be used to design antisense RNA or ribozyme that either target the conserved regions of the related sequences, or target unique regions of a specific sequence.

Various SMPDL3B RNAi reagents are commercially available, some of which are linked to the above NCBI Ref. Seq. entry. See, for example, SMPDL3B—Human, 4 unique 29mer shRNA constructs in retroviral untagged vector (Cat. No. TR309229) and SMPDL3B (Human)—3 unique 27mer siRNA duplexes—2 nmol each (Cat. No. SR309070) (OriGene Technologies, Inc., Rockville, Md.).

Various anti-SMPDL3B antibodies are commercially available, some of which are linked to the above NCBI Ref. Seq. entry. See, for example, SMPDL3B (Acid Sphingomyelinase-like Phosphodiesterase 3b, ASM-like Phosphodiesterase 3b, ASML3B) (Cat. No. 51014-63T) (US Biological, Salem, Mass.).

Other commercially available resources linked to the human NCBI RefSeq entry include: expression clones, protein and peptides, cDNA clones, and gene expression assay reagents that may be generally related to the design and use of the antagonists of the target gene.

SPINK5 (Human Serine Peptidase Inhibitor, Kazal Type 5) (NCBI Reference Sequence: NM_001127698.1 and NP_001121170.1)

At least about 47 related sequences have been identified and linked to the NCBI RefSeq entry for the human sequence. These sequences may be used to design antisense RNA or ribozyme that either target the conserved regions of the related sequences, or target unique regions of a specific sequence.

Various SPINK5 RNAi reagents are commercially available, some of which are linked to the above NCBI Ref. Seq. entry. See, for example, SPINK5—Human, 4 unique 29mer shRNA constructs in retroviral untagged vector (Cat. No. TR309144) and SPINK5 (Human)—3 unique 27mer siRNA duplexes—2 nmol each (Cat. No. SR307522) (OriGene Technologies, Inc., Rockville, Md.).

Various anti-SPINK5 antibodies are commercially available, some of which are linked to the above NCBI Ref. Seq. entry. See, for example, SPINK5 polyclonal antibody (Cat. No. PAB20549) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

ST6GAL1 (Human ST6 Beta-Galactosamide Alpha-2,6-Sialyltranferase 1) (NCBI Reference Sequence: NM_173216.2 and NP_775323.1)

At least about 29 related sequences have been identified and linked to the NCBI RefSeq entry for the human sequence. These sequences may be used to design antisense RNA or ribozyme that either target the conserved regions of the related sequences, or target unique regions of a specific sequence.

Various ST6GAL1 RNAi reagents are commercially available, some of which are linked to the above NCBI Ref. Seq. entry. See, for example, ST6GAL1—Human, 4 unique 29mer shRNA constructs in retroviral untagged vector (Cat. No. TR309074) and ST6GAL1 (Human)—3 unique 27mer siRNA duplexes—2 nmol each (Cat. No. SR304371) (OriGene Technologies, Inc., Rockville, Md.).

Various anti-ST6GAL1 antibodies are commercially available, some of which are linked to the above NCBI Ref. Seq. entry. See, for example, ST6GAL1 monoclonal antibody, clone LN1 (Cat. No. MAB6959) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

STATH (Human Statherin) (NCBI Reference Sequence: NM_003154.2 and NP_003145.1)

At least about 19 related sequences have been identified and linked to the NCBI RefSeq entry for the human sequence. These sequences may be used to design antisense RNA or ribozyme that either target the conserved regions of the related sequences, or target unique regions of a specific sequence.

Various STATH RNAi reagents are commercially available, some of which are linked to the above NCBI Ref. Seq. entry. See, for example, STATH—Human, 4 unique 29mer shRNA constructs in retroviral untagged vector (Cat. No. TR318818) and STATH (Human)—3 unique 27mer siRNA duplexes—2 nmol each (Cat. No. SR304627) (OriGene Technologies, Inc., Rockville, Md.).

Various anti-STATH antibodies are commercially available, some of which are linked to the above NCBI Ref. Seq. entry. See, for example, STATH polyclonal antibody (Cat. No. PAB24343) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

SULF1 (Human Sulfatase 1) (NCBI Reference Sequence: NM_001128205.1 and NP_001121677.1)

At least about 40 related sequences have been identified and linked to the NCBI RefSeq entry for the human sequence. These sequences may be used to design antisense RNA or ribozyme that either target the conserved regions of the related sequences, or target unique regions of a specific sequence.

Various SULF1 RNAi reagents are commercially available, some of which are linked to the above NCBI Ref. Seq. entry. See, for example, SULF1—Human, 4 unique 29mer shRNA constructs in retroviral GFP vector (Cat. No. TG309018) and SULF1 (Human)—3 unique 27mer siRNA duplexes—2 nmol each (Cat. No. SR308097) (OriGene Technologies, Inc., Rockville, Md.).

Various anti-SULF1 antibodies are commercially available, some of which are linked to the above NCBI Ref. Seq. entry. See, for example, SULF1 monoclonal antibody (M01A), clone 1A4 (Cat. No. H00023213-M01A) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

TCN1 (Human Transcobalamin I (Vitamin B12 Binding Protein, R Binder Family)) (NCBI Reference Sequence: NM_001062.3 and NP_001053.2)

At least about 17 related sequences have been identified and linked to the NCBI RefSeq entry for the human sequence. These sequences may be used to design antisense RNA or ribozyme that either target the conserved regions of the related sequences, or target unique regions of a specific sequence.

Various TCN1 RNAi reagents are commercially available, some of which are linked to the above NCBI Ref. Seq. entry. See, for example, TCN1—Human, 4 unique 29mer shRNA constructs in retroviral GFP vector (Cat. No. TG308899) and TCN1 (Human)—3 unique 27mer siRNA duplexes—2 nmol each (Cat. No. SR304756) (OriGene Technologies, Inc., Rockville, Md.).

Various anti-TCN1 antibodies are commercially available, some of which are linked to the above NCBI Ref. Seq. entry. See, for example, TCN1 polyclonal antibody (A01) (Cat. No. H00006947-A01) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

TFF1 (Human Trefoil Factor 1) (NCBI Reference Sequence: NM_003225.2 and NP_003216.1)

At least about 22 related sequences have been identified and linked to the NCBI RefSeq entry for the human sequence. These sequences may be used to design antisense RNA or ribozyme that either target the conserved regions of the related sequences, or target unique regions of a specific sequence.

Various TFF1 RNAi reagents are commercially available, some of which are linked to the above NCBI Ref. Seq. entry. See, for example, TFF1—Human, 4 unique 29mer shRNA constructs in retroviral untagged vector (Cat. No. TR318799) and TFF1 (Human)—3 unique 27mer siRNA duplexes—2 nmol each (Cat. No. SR304797) (OriGene Technologies, Inc., Rockville, Md.).

Various anti-TFF1 antibodies are commercially available, some of which are linked to the above NCBI Ref. Seq. entry. See, for example, TFF1 monoclonal antibody (M02), clone 3H5 (Cat. No. H00007031-M02) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

TIMP1 (Human TIMP Metallopeptidase Inhibitor 1) (NCBI Reference Sequence: NM_003254.2 and NP_003245.1)

At least about 43 related sequences have been identified and linked to the NCBI RefSeq entry for the human sequence. These sequences may be used to design antisense RNA or ribozyme that either target the conserved regions of the related sequences, or target unique regions of a specific sequence.

Various TIMP1 RNAi reagents are commercially available, some of which are linked to the above NCBI Ref. Seq. entry. See, for example, TIMP1—Human, 4 unique 29mer shRNA constructs in retroviral untagged vector (Cat. No. TR308814) and TIMP1 (Human)—3 unique 27mer siRNA duplexes—2 nmol each (Cat. No. SR304837) (OriGene Technologies, Inc., Rockville, Md.).

Various anti-TIMP1 antibodies are commercially available, some of which are linked to the above NCBI Ref. Seq. entry. See, for example, TIMP1 monoclonal antibody, clone 6F6a (Cat. No. MAB9574) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

TMPRSS2 (Human Transmembrane Protease, Serine 2) (NCBI Reference Sequence: NM_001135099.1 and NP_001128571.1)

At least about 52 related sequences have been identified and linked to the NCBI RefSeq entry for the human sequence. These sequences may be used to design antisense RNA or ribozyme that either target the conserved regions of the related sequences, or target unique regions of a specific sequence.

Various TMPRSS2 RNAi reagents are commercially available, some of which are linked to the above NCBI Ref. Seq. entry. See, for example, TMPRSS2—Human, 4 unique 29mer shRNA constructs in retroviral untagged vector (Cat. No. TR308745) and TMPRSS2 (Human)—3 unique 27mer siRNA duplexes—2 nmol each (Cat. No. SR304872) (OriGene Technologies, Inc., Rockville, Md.).

Various anti-TMPRSS2 antibodies are commercially available, some of which are linked to the above NCBI Ref. Seq. entry. See, for example, TMPRSS2 monoclonal antibody (M05), clone 2F4 (Cat. No. H00007113-M05) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

TNFSF10 (Human Tumor Necrosis Factor (Ligand) Superfamily, Member 10) (NCBI Reference Sequence: NM_003810.3 and NP_003801.1)

At least about 40 related sequences have been identified and linked to the NCBI RefSeq entry for the human sequence. These sequences may be used to design antisense RNA or ribozyme that either target the conserved regions of the related sequences, or target unique regions of a specific sequence.

Various TNFSF10 RNAi reagents are commercially available, some of which are linked to the above NCBI Ref. Seq. entry. See, for example, TNFSF10—Human, 4 unique 29mer shRNA constructs in retroviral untagged vector (Cat. No. TR308728) and TNFSF10 (Human)—3 unique 27mer siRNA duplexes—2 nmol each (Cat. No. SR305761) (OriGene Technologies, Inc., Rockville, Md.).

Various anti-TNFSF10 antibodies are commercially available, some of which are linked to the above NCBI Ref. Seq. entry. See, for example, TNFSF10 monoclonal antibody, clone RIK-2 (Cat. No. MAB10903) (Abnova, Taiwan, ROC).

Other commercially available resources linked to the human NCBI RefSeq entry include: expression clones, protein and peptides, cDNA clones, and gene expression assay reagents that may be generally related to the design and use of the antagonists of the target gene.

5. Delivery of Protein Therapeutic Agents

In accordance with the present invention, determination of acceptable protocols to administer an agent, composition or formulation, including the route of administration and the effective amount of an agent to be administered to an individual, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, intestinal, intra-luminal, and parenteral routes. Preferred parenteral routes can include, but are not limited to, subcutaneous, intradermal, intravenous, intramuscular, intraarterial, intrathecal and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). Ex vivo refers to performing part of the administration step outside of the patient. Preferred routes of administration for protein-based therapeutic agent such as antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, for example, Stribling et al., *Proc. Natl. Acad. Sci. USA* 189:11277-11281, 1992, which is incorporated herein by reference in its entirety).

Carriers suitable for aerosol delivery are known in the art or described herein.

According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein (excessive) inflammatory response is occurring or is expected to occur. Preferred pharmaceutically acceptable carriers are capable of maintaining an agent used in a formulation of the invention in a form that, upon arrival of the agent at the target site in a patient, the agent is capable of acting on its target (e.g., a cell or tissue that is showing signs of cellular stress or symptoms of (excessive) inflammatory response), preferably resulting in a therapeutic benefit to the patient. A delivery vehicle for a protein or agent can include a liposome.

Suitable excipients of the present invention include excipients or formularies that transport or help transport, but do not specifically target a composition to a cell or tissue (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

Formulations of the present invention can be sterilized by conventional methods and/or lyophilized.

One type of pharmaceutically acceptable carrier includes a controlled release formulation that is capable of slowly releasing a composition of the present invention into an individual. As used herein, a controlled release formulation comprises an agent of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other suitable carriers include any carrier that can be bound to or incorporated with the agent that extends that half-life of the agent to be delivered. Such a carrier can include any suitable protein carrier or even a fusion segment that extends the half-life of a protein when delivered in vivo. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of an inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is referred to as a "targeting delivery vehicle." Targeting delivery vehicles of the present invention are capable of delivering a formulation, including an inhibitory agent, to a target site in a patient. A "target site" refers to a site in a patient to which one desires to deliver a therapeutic formulation. For example, a target site can be any cell or tissue which is targeted by direct injection or delivery using liposomes or other delivery vehicles. A delivery vehicle of the present invention can be modified to target to a particular site in an individual, thereby targeting and making use of the agent at that site (e.g., the lung for inflammatory lung disease). Suitable modifications include manipulating the chemical formula of the lipid portion of the delivery vehicle and/or introducing into the vehicle a compound capable of specifically targeting a delivery vehicle to a preferred site, for example, a preferred cell or tissue type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands.

Devices for delivery of aerosolized formulations include, but are not limited to, pressurized metered dose inhalers (MDI), dry powder inhalers (DPI), and metered solution devices (MSI), and include devices that are nebulizers and inhalers. Oral delivery can be performed by complexing a therapeutic composition of the present invention to a carrier capable of withstanding degradation by digestive enzymes in the gut of an individual. Examples of such carriers, include plastic capsules or tablets, such as those known in the art. Administration of a composition locally within the area of a target cell refers to injecting the composition centimeters and preferably, millimeters from the target cell or tissue.

In humans, it is known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods.

Finally, one of skill in the art will readily be capable of converting an animal dosage (e.g., a dosage determined in animal model study) to a human dosage using alometric scaling. For example, essentially, a scale of dosage from mouse to human is based on the clearance ratio of a compound and the body surface of the mouse. The conversion for mg/kg is $\frac{1}{12}$th of the "no observed adverse event level" (NOEL) to obtain the concentration for human dosage. This calculation assumes that the elimination between mouse and human is the same, which is believed to be the case for antibodies, for example.

A preferred single dose of an agent, including proteins, small molecules and antibodies, for use in any method described herein, comprises between about 0.01 $\mu g \times kg^{-1}$ and about 10 $mg \times kg^{-1}$ body weight of an individual. Another single dose of an agent comprises between about 1 $\mu g \times kg^{-1}$ and about 10 $mg \times kg^{-1}$ body weight of an individual. Another single dose of an agent comprises between about 5 $\mu g \times kg^{-1}$ and about 7 $mg \times kg^{-1}$ body weight of an individual. Another single dose of an agent comprises between about 10 $\mu g \times kg^{-1}$ and about 5 $mg \times kg^{-1}$ body weight of an individual. Another single dose of an agent comprises between about 0.1 $mg \times kg^{-1}$ and about 5 $mg \times kg^{-1}$ body weight of an animal, if the an agent is delivered by aerosol. Another single dose of an agent comprises between about 0.1 $\mu g \times kg^{-1}$ and about 10 $\mu g \times kg^{-1}$ body weight of an individual, if the agent is delivered parenterally.

In one embodiment, an appropriate single dose of a protein:liposome complex of the present invention is from about 0.1 μg to about 100 μg per kg body weight of the patient to which the complex is being administered. In another embodiment, an appropriate single dose is from about 1 μg to about 10 μg per kg body weight. In another embodiment, an appropriate single dose of protein:lipid complex is at least about 0.1 μg of protein:lipid complex, or at least about 1 μg of protein:lipid complex, or at least about 10 μg of protein:lipid complex, or at least about 50 μg of protein:lipid complex, or at least about 100 μg of protein:lipid complex.

A preferred single dose of an antibody comprises between about 1 $ng \times kg^{-1}$ and about less than 1 $mg \times kg^{-1}$ body weight of an individual. Another single dose of an antibody comprises between about 20 $ng \times kg^{-1}$ and about 600 $\mu g \times kg^{-1}$ body weight of the individual. Another single dose of an antibody, particularly when the antibody formulation is delivered by nebulization, comprises between about 20 $ng \times kg^{-1}$ and about 600 $\mu g \times kg^{-1}$ body weight of the individual, or between about 20 $ng \times kg^{-1}$ and about 500 $\mu g \times kg^{-1}$, or between about 20 $ng \times kg^{-1}$ and about 400 $\mu g \times kg^{-1}$, or between about 20 $ng \times kg^{-1}$ and about 300 $\mu g \times kg^{-1}$, or between about 20 $ng \times kg^{-1}$ and about 200 $\mu g \times kg^{-1}$, or between about 20 $ng \times kg^{-1}$ and about 100 $\mu g \times kg^{-1}$, or between about 20 $ng \times kg^{-1}$ and about 50 $\mu g \times kg^{-1}$ body weight of the individual.

In another embodiment, the protein or antibody is administered at a dose of less than about 500 μg antibody per milliliter of formulation, or less than about 250 μg protein or antibody per milliliter of formulation, or less than about 100

μg protein or antibody per milliliter of formulation, or less than about 50 μg protein or antibody per milliliter of formulation, or less than about 40 μg protein or antibody per milliliter of formulation, or less than about 30 μg protein or antibody per milliliter of formulation, or less than about 20 μg protein or antibody per milliliter of formulation, or less than about 10 μg protein or antibody per milliliter of formulation, or between about 5 μg protein or antibody, or about 10 μg protein or antibody per milliliter of formulation.

With particular regard to the method of the invention, an effective amount of an agent, and particularly a liposome, protein, antibody, drug or combination thereof, to administer to an individual is an amount that measurably inhibits (or prevents) histological damage, including oxidative damage or cell death, in the individual as compared to in the absence of administration of the agent. A suitable single dose of an inhibitory agent to administer to an individual is a dose that is capable of reducing or preventing at least one symptom, type of injury, or resulting damage, from inflammatory response in an individual when administered one or more times over a suitable time period. Suitable doses of proteins, liposomes, antibodies and other agents, including for various routes of administration, are described in detail above. In one aspect, an effective amount of an agent that inhibits inflammatory response to administer to an individual comprises an amount that is capable of inhibiting at least one symptom or damage caused by the inflammatory response without being toxic to the individual.

One of skill in the art will be able to determine that the number of doses of an agent to be administered to an individual is dependent upon the extent of the inflammatory response and/or the anticipated or observed physiological damage associated with the inflammatory response, as well as the response of an individual patient to the treatment. The clinician will be able to determine the appropriate timing for delivery of the agent in a manner effective to reduce the symptom(s) associated with the inflammatory response in the individual. Preferably, the agent is delivered within 48 hours, and more preferably 36 hours, and more preferably 24 hours, and more preferably within 12 hours, and more preferably within 6 hours, 5 hours, 4 hours, 3 hours, 2 hours, or 1 hour, or even minutes after the recognition of an inflammatory response in an individual; after an event that causes the inflammatory response in an individual or that is predicted to cause the inflammatory response in an individual, which can include administration prior to the development of any symptoms of the inflammatory response in the individual. In one embodiment, the agent is administered concomitantly with (at the same time or within minutes or hours of) conventional therapy for the inflammatory response, such as an NSAID. In one embodiment, the agent is administered as soon as it is recognized (i.e. immediately) by the patient or clinician that the patient may suffer from the inflammatory response, is suffering from the inflammatory response, or will suffer from the inflammatory response. Preferably, such administrations are given until signs of reduction of physiological damage or reduction of the symptoms appear, or until the potential for physiological damage due to the inflammatory response has diminished or is eliminated, and/or as needed until any symptoms are gone or arrested.

Numerous protein-based therapeutic agents have been successfully delivered through various route to treat a variety of diseases, and hundreds of more bioengineered proteins and peptides are undergoing clinical investigation. These protein-based therapeutic agents include growth factors, hormones, monoclonal antibodies, cytokines and anti-infective agents, among others. Most proteins and peptides currently on the market are injectable, including I.V. injection (e.g., the human-mouse chimeric anti-TNFα monoclonal antibody infliximab) and subcutaneous (s.c.) injection (e.g., the human anti-TNFα monoclonal antibody adalimumab). Alternative routes for protein therapeutic delivery include nasal delivery and inhalation.

The nasal cavity has limited surface area available for drug absorption (about 180 $cm^2$). In the lung, however, a much larger surface area is available for drug absorption (about 75 $m^2$), and the alveolar epithelium is very thin (about 0.1-0.5 mm thick), thereby permitting rapid drug absorption. The alveoli can be effectively targeted for drug absorption by delivering the drug as an aerosol, with mass median aerodynamic diameter (MMAD) less than 5 mm. An added benefit is that the first-pass metabolism of the gastrointestinal tract is avoided.

Optimal management of most diseases requires accurate dosing of the therapeutic compound. Suitable devices commercially available for pulmonary drug administration are developed to achieve local effects of the drug in the conducting airways, and are particularly useful for treating inflammatory lung diseases, such as asthma and COPD. These devices include nebulizers, metered-dose inhalers (MDIs) and dry-powder inhalers (DPIs). With minor or no modification, most of these devices can be readily used for pulmonary peptide and protein administration.

MDIs utilize propellants (e.g., chlorofluorocarbons and hydrofluoroalkanes) to atomize the drug solution, resulting in a more uniform spray than that achieved with nebulizers. A even more promising alternative to MDIs and nebulizers is the DPI, in which the biopharmaceutical formulation can be delivered in dry form. Like MDIs, most DPIs that are currently approved are made for pulmonary drug administration of locally acting drugs for the management of asthma and chronic obstructive pulmonary diseases (COPDs), such as antiasthmatic agents. Examples of such devices include the Turbohaler (AstraZeneca, Wilmington, Del., USA), Diskhaler (GlaxoSmithKline, Research Triangle Park, N.C., USA), Diskus (i.e., Accuhaler in some countries, such as UK; GlaxoSmithKline), Rotahaler (Glaxo-SmithKline) and Aerolizer (Novartis Pharma, Basel, Switzerland).

Drug delivery to the lower respiratory tract are also achievable from these DPI devices. For example, the AKITA system (InAmed GmbH, Gauting, Germany) is a fully electronically controlled device that makes use of vital patient parameters, such as inhalation flow rate, inhaled volume and inhalation duration, among others, to control the exact dose of the drug administered to the patient. Thus this device is particularly suited for drugs that are very expensive and drugs for which accurate dosing is critical.

Newer devices have also been developed for pulmonary delivery, such as those from Inhale Therapeutics (San Carlos, Calif., USA), Aradigm Corporation (Hayward, Calif., USA), and Dura Pharmaceuticals (San Diego, Calif., USA). For example, the Inhale Therapeutics device (Inhance) mechanically compresses a fixed volume of air in order to aerosolize a pre-metered and sealed dose of the drug into a chamber. The patient inhales the drug within 10 s, during a slow and deep breath. This simple inhalation technique eliminates the complex motor co-ordination that is often required with MDIs, DPIs and nebulizers. The device from Dura Pharmaceuticals (Spiros motorized blisterdisk) relies on a battery-powered motor/impeller, which is actuated by the patient's breath to aerosolize a pre-metered dose of drug in the chamber. The patient inhales deeply through a mouthpiece that turns on the motor. As with the Inhance device, patient motor co-ordination is not required. The AERx delivery system (Aradigm Corporation) converts large molecules (e.g., proteins and peptides) into fine-particle aerosols at the time of use. The device has unique features, such as computer-controlled processes and an electronic compliance monitoring system.

Numerous protein-based drugs have been successfully delivered through inhalation, including pulmonary delivery of metabolic hormones, including insulin, calcitonin, growth hormones, somatostatin, TSH and FSH, to humans and experimental animals, as reported in References 15 (published in 1971) to 52 of Agu et al. (*Respiratory Research* 2(4):198-209, 2001). The US FDA approved an inhalable insulin formulation Exubera in 2006 (manufactured by Pfizer in collaboration with Nektar Therapeutics) that is licensed for use by both type 1 and type 2 diabetics.

In another example, Folksson and coworkers (Folksson et al., *Acta Physiol. Scand.* 139:347-354, 1990; and Folkesson et al., *Acta Physiol. Scand.* 147:173-178, 1993) reported that high plasma concentrations of an analogue of vasopressin (1-deamino-8-D-arginine vasopressin [dDAVP]) could be attained following administration via the lung by instillation, demonstrating that proteins and peptides may traverse the lung epithelium via different routes that are differently affected during postnatal development.

Additional studies have shown that a systemic response may be achieved following pulmonary administration of certain macromolecules. This has been demonstrated for immunoglobulins, CsA, r-huG-CSF, pancreatic islet autoantigen insulin and interferons.

Specifically, delivery of specific antibodies or immunoglobulin constructs to the respiratory tract is useful for prophylaxis or active treatment of local or systemic disorders. Folkesson et al. (*Acta Physiol. Scand.* 139:347-354, 1990) showed the possibility of systemic delivery of immunoglobulins via the lung, which may be especially efficient during inflammation. Bot et al. (*Pharm. Res.* 17:275-283, 2000) demonstrated pulmonary delivery of human immunoglobulin (MMAD4.6 mm) using microparticles (Pulmospheres, Alliance Pharmaceutical Corporation, San Diego, Calif., USA) as a platform for delivery. Installation of nonaqueous human immunoglobulin formulated in Pulmospheres to the respiratory tract of BALB/c mice resulted in systemic biodistribution. The formulation triggered enhanced local and systemic immune responses against xenotypic epitopes, and was associated with receptor-mediated loading of alveolar macrophages. Thus, local and systemic delivery of immunoglobulins via the respiratory mucosa may be used to trigger or modulate immune responses.

In yet another example, high plasma concentrations of recombinant-methionyl interferon consensus (rCon-IFN) and interferon-a have been attained following pulmonary administration to animals.

In certain embodiments, pulmonary drug delivery may be performed in the presence or co-administration of absorption enhancers and enzyme inhibitors, which alleviates limitations on delivery efficiency due to physical barriers and enzymatic degradation. This approach has been shown to improve the bioavailabilities and pharmacodynamic response of biotherapeutic agents, including insulin, calcitonin and others.

In certain embodiments, the protein-based therapeutics are delivered in the form of microparticles. The human lung has efficient mechanisms to remove deposited particles by mucociliary clearance and phagocytosis. When peptide and protein drugs are formulated using microparticles as vehicles, the influence of these clearance mechanisms may be attenuated, and more efficient absorption and a sustained therapeutic effect may result. See Edwards et al (*Science* 276:1868-1871, 1997), demonstrating that the inhalation of large porous insulin particles (formulated with poly[lactic acid-co-glycolic acid]) resulted in elevated systemic levels of insulin and suppressed systemic glucose levels for 96 h, whereas small, nonporous insulin particles had this effect for only 4 h. Also see Kawashima et al. (*J. Contr. Rel.* 62:279-287, 1999), reporting that the pulmonary delivery of insulin with nebulized DL-lactide/glycocholide copolymer nanospheres resulted in prolonged hypoglycaemia (48 h) as compared with the nebulized aqueous solution (6 h). The observed prolonged insulin concentrations and hypoglycaemic effect in these studies was attributed to the sustained release of insulin from the polymers.

In certain embodiments, enhancement of pulmonary absorption is achieved using liposomes as carriers. See Liu et al. (*Pharm. Res.* 10:228-232, 1993), reporting that intratracheal administration of insulin liposomes (dipalmitoylphosphatidyl choline:cholesterol, 7:2) led to facilitated pulmonary uptake of insulin and enhanced hypoglycaemic effect. The ability of liposomes to promote pulmonary drug absorption may be further controlled or adjusted, depending on the concentration, charge and acyl chain length of the phospholipid (see Li et al., *Pharm. Res.* 13:76-79, 1996).

In certain embodiments, polyethyleneglycol may be used for systemic delivery of protein based therapeutic agents of the invention through pulmonary delivery. See Niven et al. (*J. Contr. Rel.* 32:177-189, 1994), showing that pulmonary absorption of polyethylene glycolated r-huG-CSF in rat generated a more intense response and extended white blood cell response, as compared with r-huG-CSF alone.

According to the present invention, the methods of the present invention are suitable for use in an individual that is a member of the Vertebrate class, Mammalia, including, without limitation, primates (human and non-human), livestock and domestic pets (e.g., a companion animal). Most typically, an individual will be a human individual. The term "individual" can be interchanged with the term "subject" or "patient" and refers to the subject of a method according to the invention. Accordingly, an individual can include a healthy, normal (non-diseased) individual, but is most typically an individual who has or is at risk of developing the inflammatory response or a symptom or indicator thereof as described herein.

6. Delivery of Nucleic Acid Therapeutic Agents

Pro-inflammatory genes identified by the methods of the invention may be responsible for a range of inflammatory diseases, disorders or abnormal conditions. Thus inhibiting one or more functions of the identified pro-inflammatory genes may treat, prevent, retard the progression, or alleviate a symptom of the inflammatory diseases, disorders or abnormal conditions.

There are numerous art-recognized methods for antagonizing the function of a target gene by delivering a nucleic acid based therapeutic agent comprising a nucleic acid construct. Some of the non-limiting examples are provided in this section, including transfection and infection (e.g., by a viral vector) by various types of nucleic acid constructs.

A nucleic acid construct in general comprises a nucleic acid molecule of interest, and is generally capable of directing the expression of the encompassed nucleic acid molecule of interest in the cells into which it has been introduced. To inhibit the function of a target gene in a target cell, the nucleic acid construct may encode a polynucleotide based antagonist of the target gene, such as an siRNA, miRNA, shRNA, antisense sequence, aptamer, ribozyme etc. The nucleic acid construct may also encode a protein based antagonist of the target gene product, such as an antibody to the target gene product, a functional fragment of the antibody, a binding protein to the target gene product that antagonizes the function of the target gene product, or a dominant negative version of the target gene product. For example, the nucleic acid construct may encode a defective transcription factor that competes for the same binding site as the wildtype transcription factor (as the target gene), but lacks transcription activation domain. The nucleic acid construct may also encode a defective cell surface receptor that competes for the same ligand as the wildtype receptor (as the target gene), but lacks cytoplasmic signaling domain. The nucleic acid construct may also encode a defective ligand or secreted protein or cytokine that competes for the same receptor as the wildtype ligand/cytokine (as the target gene), but lacks the ability to activate the receptor; or encode a defective monomer that forms a non-functional multimer with the wildtype monomer.

Thus in certain embodiments, the nucleic acid construct is an expression vector wherein a nucleic acid molecule encoding a gene product, such as a polypeptide (e.g., antibody or functional fragment, dominant negative etc.) or a nucleic acid (e.g., an siRNA, miRNA, shRNA, antisense sequence, aptamer, rybozyme etc.), that antagonizes the expression of a target gene is operably linked to a promoter capable of directing expression of the nucleic acid molecule in the target cells.

The term "expression vector" generally refers to a nucleic acid molecule that is capable of effecting expression of a gene/nucleic acid molecule it contains in a cell compatible with such sequences. These expression vectors typically include at least suitable promoter sequences and optionally, transcription termination signals. A nucleic acid or DNA or nucleotide sequence encoding a polypeptide is incorporated into a DNA/nucleic acid construct capable of introduction into and expression in a target cell.

A DNA construct prepared for introduction into a particular cell typically include a replication system recognized by the cell, an intended DNA segment encoding a desired polypeptide or polynucleotide, and transcriptional and/or translational initiation and termination regulatory sequences operably linked to the polypeptide- or the polynucleotide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading phase. However, enhancers need not be contiguous with a coding sequence whose transcription they control. Linking is accomplished by ligation at convenient restriction sites or at adapters or linkers inserted in lieu thereof.

The selection of an appropriate promoter sequence generally depends upon the host cell selected for the expression of a DNA segment. Examples of suitable promoter sequences include eukaryotic promoters well known in the art (see, e.g., Sambrook and Russell, *Molecular Cloning: A Laboratory Manual, Third Edition,* 2001). A transcriptional regulatory sequence typically includes a heterologous enhancer or promoter that is recognized by the cell. Suitable promoters include the CMV promoter. An expression vector includes the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) *Nature* 334: 31-36.

Some aspects of the invention concern the use of a nucleic acid construct or expression vector comprising a nucleotide sequence as defined above, wherein the vector is a vector that is suitable for gene therapy. Vectors that are suitable for gene therapy are known in the art, such as those described in Anderson (*Nature* 392: 25-30, 1998); Walther and Stein (*Drugs* 60:249-271, 2000); Kay et al. (*Nat. Med.* 7:33-40, 2001); Russell (*J. Gen. Virol.* 81:2573-2604, 2000); Amado and Chen (*Science* 285:674-676, 1999); Federico (*Curr. Opin. Biotechnol.* 10:448-453, 1999); Vigna and Naldini (*J. Gene Med.* 2:308-16, 2000); Marin et al. (*Mol. Med. Today* 3:396-403, 1997); Peng and Russell (*Curr. Opin. Biotechnol.* 10:454-457, 1999); Sommerfelt (*J. Gen. Virol.* 80:3049-3064, 1999); Reiser (*Gene Ther.* 7:910-913, 2000); and references cited therein (all incorporated by reference). Examples include integrative and non-integrative vectors such as those based on retroviruses, adenoviruses (AdV), adeno-associated viruses (AAV), lentiviruses, pox viruses, alphaviruses, and herpes viruses.

A particularly suitable gene therapy vector includes an Adenoviral (Ad) and Adeno-associated virus (AAV) vector. These vectors infect a wide number of dividing and non-dividing cell types. In addition, adenoviral vectors are capable of high levels of transgene expression. However, because of the episomal nature of the adenoviral and AAV vectors after cell entry, these viral vectors are most suited for therapeutic applications requiring only transient expression of the transgene (Russell, *J. Gen. Virol.* 81:2573-2604, 2000; Goncalves, *Virol J.* 2(1):43, 2005) as indicated above. Preferred adenoviral vectors are modified to reduce the host response as reviewed by Russell (2000, supra). Safety and efficacy of AAV gene transfer has been extensively studied in humans with encouraging results in the liver, muscle, CNS, and retina (Manno et al., *Nat. Medicine,* 2006; Stroes et al., *ATVB,* 2008; Kaplitt, Feigin, *Lancet,* 2009; Maguire, Simonelli et al., *NEJM* 2008; Bainbridge et al. *NEJM,* 2008).

AAV2 is the best characterized serotype for gene transfer studies both in humans and experimental models. AAV2 presents natural tropism towards skeletal muscles, neurons, vascular smooth muscle cells and hepatocytes. Other examples of adeno-associated virus-based non integrative vectors include AAV1, AAV3, AAV4, AAV5, AAV 6, AAV7, AAV8, AAV9, AAV 10, AAV11 and pseudotyped AAV. The use of non-human serotypes, like AAV8 and AAV9, might be useful to overcome these immunological responses in subjects, and clinical trials have commenced (see ClinicalTrials dot gov Identifier: NCT00979238). For gene transfer into a liver cell, an adenovirus serotype 5 or an AAV serotype 2, 7 or 8 have been shown to be effective vectors and therefore a preferred Ad or AAV serotype (Gao, *Molecular Therapy* (2006) 13:77-87).

An exemplary retroviral vector for application in the present invention is a lentiviral based expression construct. Lentiviral vectors have the unique ability to infect non-dividing cells (Amado and Chen, *Science* 285:674-676, 1999). Methods for the construction and use of lentiviral based expression constructs are described in U.S. Pat. Nos. 6,165,782, 6,207,455, 6,218,181, 6,277,633, and 6,323,031, and in Federico (*Curr. Opin. Biotechnol.* 10:448-453, 1999) and Vigna et al. (*J. Gene Med.* 2:308-316, 2000).

Generally, gene therapy vectors will be as the expression vectors described above in the sense that they comprise a nucleotide sequence encoding a gene product (e.g., a polypeptide or polynucleotide) of the invention to be expressed, whereby a nucleotide sequence is operably linked to the appropriate regulatory sequences as indicated above. Such regulatory sequence will at least comprise a promoter sequence. Suitable promoters for expression of a nucleotide sequence encoding a polypeptide from gene therapy vectors include, e.g., cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter and the herpes simplex virus thymidine kinase promoter. Additional suitable promoters are described below.

Several inducible promoter systems have been described that may be induced by the administration of small organic or inorganic compounds. Such inducible promoters include those controlled by heavy metals, such as the metallothionine promoter (Brinster et al., *Nature* 296:39-42, 1982; Mayo et al., *Cell* 29:99-108, 1982), RU-486 (a progesterone antagonist) (Wang et al., *Proc. Natl. Acad. Sci. USA* 91:8180-8184, 1994), steroids (Mader and White, *Proc. Natl. Acad. Sci. USA* 90:5603-5607, 1993), tetracycline (Gossen and Bujard, *Proc. Natl. Acad. Sci. USA* 89:5547-5551, 1992; U.S. Pat. No. 5,464,758; Furth et al., *Proc. Natl. Acad. Sci. USA* 91:9302-9306, 1994; Howe et al., *J. Biol. Chem.* 270:14168-14174, 1995; Resnitzky et al., *Mol. Cell. Biol.* 14:1669-1679, 1994; Shockett et al., *Proc. Natl. Acad. Sci. USA* 92:6522-6526, 1995) and the tTAER system that is based on the multi-chimeric transactivator composed of a tetR polypeptide, as activation domain of VP 16, and a ligand binding domain of an estrogen receptor (Yee et al., 2002, U.S. Pat. No. 6,432,705).

Suitable promoters for nucleotide sequences encoding small RNAs for knock down of specific genes by RNA interference (see below) include, in addition to the above mentioned polymerase II promoters, polymerase III promoters. The RNA polymerase III (pol III) is responsible for the synthesis of a large variety of small nuclear and cytoplasmic non-coding RNAs including 5S, U6, adenovirus VA1, Vault, telomerase RNA, and tRNAs. The promoter structures of a large number of genes encoding these RNAs have been determined and it has been found that RNA pol III promoters fall into three types of structures (for a review see Geiduschek and Tocchini-Valentini, *Annu. Rev. Biochem.* 57:873-914, 1988; Willis, *Eur. J. Biochem.* 212:1-11, 1993; Hernandez, *J. Biol. Chem.* 276:26733-26736, 2001). Particularly suitable for expression of siRNAs are the type 3 of the RNA pol III promoters, whereby transcription is driven by cis-acting elements found only in the 5'-flanking region, i.e., upstream of the transcription start site. Upstream sequence elements include a traditional TATA box (Mattaj et al., *Cell* 55:435-442, 1988), proximal sequence element and a distal sequence element (DSE; Gupta and Reddy, *Nucleic Acids Res.* 19:2073-2075, 1991). Examples of genes under the control of the type 3 pol III promoter are U6 small nuclear RNA (U6 snRNA), 7SK, Y, MRP, HI and telomerase RNA genes (see, e.g., Myslinski et al., *Nucl. Acids Res.* 21:2502-2509, 2001).

A gene therapy vector may optionally comprise a second or one or more further nucleotide sequence coding for a second or further polypeptide. A second or further polypeptide may be a (selectable) marker polypeptide that allows for the identification, selection and/or screening for cells containing the expression construct. Suitable marker proteins for this purpose are, e.g., the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russell, *Molecular Cloning: A Laboratory Manual* (3rd edition), Cold Spring Harbor Laboratory, Cold Spring Harbor Laboratory Press, New York, 2001.

Alternatively, a second or further nucleotide sequence may encode a polypeptide that provides for fail-safe mechanism that allows a subject from the transgenic cells to be cured, if deemed necessary. Such a nucleotide sequence, often referred to as a suicide gene, encodes a polypeptide that is capable of converting a prodrug into a toxic substance that is capable of killing the transgenic cells in which the polypeptide is expressed. Suitable examples of such suicide genes include, e.g., the *E. coli* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see, e.g., Clair et al., *Antimicrob. Agents Chemother.* 31:844-849, 1987).

For knock down of expression of a specific polypeptide, a gene therapy vector or other expression construct is used for the expression of a desired nucleotide sequence that preferably encodes an RNAi agent, i.e., an RNA molecule that is capable of RNA interference or that is part of an RNA molecule that is capable of RNA interference. Such RNA molecules are referred to as siRNA (short interfering RNA, including, e.g., a short hairpin RNA).

A desired nucleotide sequence comprises an antisense code DNA coding for the antisense RNA directed against a region of the target gene mRNA, and/or a sense code DNA coding for the sense RNA directed against the same region of the target gene mRNA. In a DNA construct of the invention, an antisense and sense code DNAs are operably linked to one or more promoters as herein defined above that are capable of expressing an antisense and sense RNAs, respectively. "siRNA" includes a small interfering RNA that is a short-length double-stranded RNA that is not toxic in mammalian cells (Elbashir et al., *Nature* 411:494-498, 2001; Caplen et al., *Proc. Natl. Acad. Sci. USA* 98:9742-9747, 2001). The length is not necessarily limited to 21 to 23 nucleotides. There is no particular limitation in the length of siRNA as long as it does not show toxicity. "siRNAs" can be, e.g., at least about 15, 18 or 21 nucleotides and up to 25, 30, 35 or 49 nucleotides long. Alternatively, the double-stranded RNA portion of a final transcription product of siRNA to be expressed can be, e.g., at least about 15, 18 or 21 nucleotides, and up to 25, 30, 35 or 49 nucleotides long.

"Antisense RNA" is preferably an RNA strand having a sequence complementary to a target gene mRNA, and thought to induce RNAi by binding to the target gene mRNA.

"Sense RNA" has a sequence complementary to the antisense RNA, and annealed to its complementary antisense RNA to form siRNA.

The term "target gene" in this context includes a gene whose expression is to be silenced due to siRNA to be expressed by the present system, and can be arbitrarily selected. As this target gene, for example, genes whose sequences are known but whose functions remain to be elucidated, and genes whose expressions are thought to be causative of diseases are preferably selected. A target gene may be one whose genome sequence has not been fully elucidated, as long as a partial sequence of mRNA of the gene having at least 15 nucleotides or more, which is a length capable of binding to one of the strands (antisense RNA strand) of siRNA, has been determined Therefore, genes, expressed sequence tags (ESTs) and portions of mRNA, of which some sequence (preferably at least 15 nucleotides) has been elucidated, may be selected as the "target gene" even if their full length sequences have not been determined.

The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. A non-pairing portions can be contained to the extent that they do not interfere with siRNA formation.

The "bulge" used herein may comprise 1 to 2 non-pairing nucleotides, and the double-stranded RNA region of siRNAs in which two RNA strands pair up contains preferably 1 to 7, more preferably 1 to 5 bulges.

The term "mismatch" as used herein may be contained in the double-stranded RNA region of siRNAs in which two RNA strands pair up, preferably 1 to 7, more preferably 1 to 5, in number. In certain mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, a double-stranded RNA region of siRNAs in which two RNA strands pair up may contain both bulge and mismatched, which sum up to, preferably 1 to 7, more preferably 1 to 5 in number. Such non-pairing portions (mismatches or bulges, etc.) can suppress the below-described recombination between antisense and sense code DNAs and make the siRNA expression system as described below stable. Furthermore, although it is difficult to sequence stem loop DNA containing no non-pairing portion in the double-stranded RNA region of siR-NAs in which two RNA strands pair up, the sequencing is enabled by introducing mismatches or bulges as described above. Moreover, siRNAs containing mismatches or bulges in the pairing double-stranded RNA region have the advantage of being stable in *E. coli* or animal cells.

The terminal structure of siRNA may be either blunt or cohesive (overhanging) as long as siRNA enables to silence the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is necessarily the cut off structure at both ends as described above, and may have a stem-loop structure in which ends of one side of double-stranded RNA are connected by a linker RNA (a "shRNA"). The length of the double-stranded RNA region (stem-loop portion) can be, e.g., at least 15, 18 or 21 nucleotides and up to 25, 30, 35 or 49 nucleotides long. Alternatively, the length of the double-stranded RNA region that is a final transcription product of siRNAs to be expressed is, e.g., at least 15, 18 or 21 nucleotides and up to 25, 30, 35 or 49 nucleotides long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA, snRNA or viral RNA, or an artificial RNA molecule.

To express antisense and sense RNAs from the antisense and sense code DNAs respectively, a DNA construct of the present invention comprise a promoter as defined above. The number and the location of the promoter in the construct can in principle be arbitrarily selected as long as it is capable of expressing antisense and sense code DNAs. As a simple example of a DNA construct of the invention, a tandem expression system can be formed, in which a promoter is located upstream of both antisense and sense code DNAs. This tandem expression system is capable of producing siRNAs having the aforementioned cut off structure on both ends. In the stem-loop siRNA expression system (stem expression system), antisense and sense code DNAs are arranged in the opposite direction, and these DNAs are connected via a linker DNA to construct a unit. A promoter is linked to one side of this unit to construct a stem-loop siRNA expression system. Herein, there is no particular limitation in the length and sequence of the linker DNA, which may have any length and sequence as long as its sequence is not the termination sequence, and its length and sequence do not hinder the stem portion pairing during the mature RNA production as described above. As an example, DNA coding for the above-mentioned tRNA and such can be used as a linker DNA.

In both cases of tandem and stem-loop expression systems, the 5' end may be have a sequence capable of promoting the transcription from the promoter. More specifically, in the case of tandem siRNA, the efficiency of siRNA production may be improved by adding a sequence capable of promoting the transcription from the promoters at the 5' ends of antisense and sense code DNAs. In the case of stem-loop siRNA, such a sequence can be added at the 5' end of the above-described unit. A transcript from such a sequence may be used in a state of being attached to siRNA as long as the target gene silencing by siRNA is not hindered. If this state hinders the gene silencing, it is preferable to perform trimming of the transcript using a trimming means (for example, ribozyme as are known in the art). It will be clear to the skilled person that an antisense and sense RNAs may be expressed in the same vector or in different vectors. To avoid the addition of excess sequences downstream of the sense and antisense RNAs, it is preferred to place a terminator of transcription at the 3' ends of the respective strands (strands coding for antisense and sense RNAs). The terminator may be a sequence of four or more consecutive adenine (A) nucleotides.

All patent and literature references cited in the present specification are hereby incorporated by reference in their entirety.

7. Combination Therapy

In certain embodiments, a gene product of a subject anti-inflammatory gene (e.g., a protein encoded by the anti-inflammatory gene), or an antagonist of a subject pro-inflammatory gene (e.g., an RNAi therapeutic agent or an antibody against the pro-inflammatory gene product), or "an anti-inflammatory therapeutic agent of the invention," may be used in combination with one or more second therapeutic agents, such as a known anti-inflammatory therapeutic agent, to treat one or more inflammatory disease, disorder, or otherwise abnormal condition as described herein above.

In addition to the inflammatory diseases, disorders, or otherwise abnormal conditions described above, additional treatable inflammatory diseases, disorders, or otherwise abnormal conditions include, but are not limited to, a disorder chosen from one or more of: autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, vasculitis, multiple sclerosis, autoimmune thyroiditis, dermatitis (including atopic dermatitis and eczematous dermatitis), myasthenia gravis, inflammatory bowel disease (IBD), Crohn's disease, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); septicemia; transplant rejection and allergy.

In one embodiment, the inflammatory disease, disorder, or otherwise abnormal condition is an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

The combination therapy can include one or more anti-inflammatory therapeutic agent of the invention co-formulated with, and/or co-administered with, one or more additional therapeutic agents, e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more detail herein.

Examples of preferred additional therapeutic agents that can be co-administered and/or co-formulated with one or more anti-inflammatory therapeutic agent of the invention include, but are not limited to, one or more of: TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; TNF enzyme antagonists, e.g., TNFα converting enzyme (TACE) inhibitors); antagonists of IL-12, IL-15, IL-17, IL-18, IL-21/IL-21R; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Examples of preferred additional therapeutic agents that can be co-administered and/or co-formulated with one or more anti-inflammatory therapeutic agent of the invention include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™); methotrexate, leflunomide, or a sirolimus (rapamycin) or an analog thereof, e.g., CCI-779.

Additional second therapeutic agents for treating rheumatoid arthritis include: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); 55 kdTNFR-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); TNF-bp/s-TNFR (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or 1ck inhibitor (inhibitor of the tyrosine kinase zap-70 or 1ck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclophosphamide; cyclosporine; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine.

Additional second therapeutic agents for treating inflammatory bowel disease include: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-TL-1β monoclonal antibodies; anti-IL-6 monoclonal antibodies; growth factors; elastase inhibitors; pyridinyl-imidazole compounds; CDP-571/BAY-10-3356 (humanized anti-TNFα; antibody; Celitech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNFR-IgG (55 kD TNF receptor-IgG fusion protein; Hoffmann-LaRoche); interleukin-10 (SCH 52000; Schering Plough); IL-4; IL-10 and/or IL-4 agonists (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

Additional second therapeutic agents for treating multiple sclerosis include: corticosteroids; prednisolone; methylprednisolone; azathioprine; cyclophosphamide; cyclosporine; methotrexate; 4-aminopyridine; tizanidine; interferon-β1 a (Avonex®; Biogen); interferon-β 1b (Betaseron®; Chiron/Berlex); Copolymer 1 (Cop-1; Copaxone®; Teva Pharmaceutical Industries, Inc.); hyperbaric oxygen; intravenous immunoglobulin; clabribine; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNFR-IgG (55 kD TNF receptor-IgG fusion protein; Hoffmann-LaRoche); IL-10; IL-4; and IL-10 and/or IL-4 agonists (e.g., agonist antibodies).

Additional second therapeutic agents for treating sepsis include: hypertonic saline solutions; antibiotics; intravenous gamma globulin; continuous hemofiltration; carbapenems (e.g., meropenem); antagonists of cytokines such as TNFα, IL-1β, IL-6 and/or IL-8; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNFR-IgG (55 kD TNF receptor-IgG fusion protein; Hoffmann-LaRoche); Cytokine Regulating Agents (CRAs) HP228 and HP466 (Houghten Pharmaceuticals, Inc.); SK&F 107647 (low molecular peptide; SmithKline Beecham); tetravalent guanylhydrazone CNI-1493 (Picower Institute); Tissue Factor Pathway Inhibitor (TFPI; Chiron); PHP (chemically modified hemoglobin; APEX Bioscience); iron chelators and chelates, including diethylenetriamine pentaacetic acid-iron (III) complex (DTPA iron (III); Molichem Medicines); lisofylline (synthetic small molecule methylxanthine; Cell Therapeutics, Inc.); PGG-Glucan (aqueous soluble β1,3glucan; Alpha-Beta Technology); apolipoprotein A-1 reconstituted with lipids; chiral hydroxamic acids (synthetic antibacterials that inhibit lipid A biosynthesis); anti-endotoxin antibodies; E5531 (synthetic lipid A antagonist; Eisai America, Inc.); rBPI21 (recombinant N-terminal fragment of human Bactericidal/Permeability-Increasing Protein); and Synthetic Anti-Endotoxin Peptides (SAEP; BiosYnth Research Laboratories).

Additional second therapeutic agents for treating adult respiratory distress syndrome (ARDS) include: anti-IL-8 antibodies; surfactant replacement therapy; CDP-571/BAY-10-3356 (humanized anti-TNFα antibody; Ceiltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; *J. Invest. Med.* (1996) Vol. 44, 235A); and 55 kdTNFR-IgG (55 kD TNF receptor-IgG fusion protein; Hoffmann-LaRoche).

In another aspect, the invention provides compositions, e.g., pharmaceutical compositions, which include a pharmaceutically acceptable carrier and at least one anti-inflammatory therapeutic agent of the invention, plus at least one of the second therapeutic agent referenced above, such as a one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more herein.

In another aspect, the invention features a method of decreasing, inhibiting or reducing an acute phase response in a subject, or at least one symptom of the inflammatory disease, disorder, or otherwise abnormal condition, the method includes administering to the subject an anti-inflammatory therapeutic agent of the invention in an amount sufficient to decrease, inhibit or reduce the acute phase response in the subject. In one embodiment, the subject is a mammal, e.g., a human suffering from an inflammatory disease, disorder, or otherwise abnormal condition, including, e.g., respiratory disorders, inflammatory disorders and autoimmune disorders. In one embodiment, the anti-inflammatory therapeutic agent of the invention is administered locally, e.g., topically, subcutaneously, or other administrations that are not in the general circulation.

The subject method can be used on cells in vitro (e.g., in a cell-free system), in culture, e.g. in vitro or ex vivo. Alternatively, the method can be performed on cells present in a subject, e.g., as part of an in vivo (e.g., therapeutic or prophylactic) protocol.

In a related aspect, kits comprising an anti-inflammatory therapeutic agent of the invention (e.g., in the form of a pharmaceutical composition), and optionally one or more second therapeutic agent identified above, are also within the scope of the invention.

The following examples are offered for illustrative purposes only, and are not intended to limit the scope of the present invention in any way.

EXAMPLES

Example 1: Cloning of Human Airway Stem Cells

Human (upper) airway stem cells can be isolated and clonally expanded according to the method described in the co-pending co-owned application filed on the same day (Mar. 15, 2013), entitled "Isolation of Non-Embryonic Stem Cells and Uses Thereof," as U.S. Provisional Application No. 61/792,027 (incorporated herein by reference). Also see Section 2 above.

In this experiment, human airway biopsy was digested with 2 mg/mL collagenase type IV (Gibco, cat. no. 17104-109), and epithelial cells were isolated and cultivated onto a feeder layer of lethally irradiated 3T3-J2 cells (originally from the Howard Green laboratory of Harvard Medical School, Boston, Mass.) in CFAD media based on the previously described methods for epidermal stem cells and airway epithelial stem cells (see Barrandon and Green, *Proc. Natl. Acad. Sci. USA* 84:2302-2306, 1987; Kumar et al., *Cell* 147:525-538, 2011; Senoo et al. 2007, *Cell* 129:523-536). CFAD culture medium contains three volumes of Dulbecco's minimal essential medium (DMEM) (Gibco/Invitrogen), one volume of F10 (Ham's) (Gibco), 5 µg/mL of insulin (Sigma), $2 \times 10^{-9}$ M triiodothyronin (T3, Sigma), 0.4 µg/mL of hydrocortisone (Calbiochem), $10^{-10}$ M cholera toxin (ICN), $1.8 \times 10^{-5}$ M adenine (Sigma), 5 µg/mL of transferrin (Sigma), 1% nonessential amino acids (Gibco), 1% sodium pyruvate (Gibco), 1% penicillin-streptomycin (Gibco), 1% glutamine (Gibco), 0.2% fungizone (Gibco), 10% fetal bovine serum. A single colony derived from a single isolated stem cell was expanded as pedigree cell line.

Example 2: Screening Methods Using Sensitized Test Cells from an Asthma Patient

Figure 19:
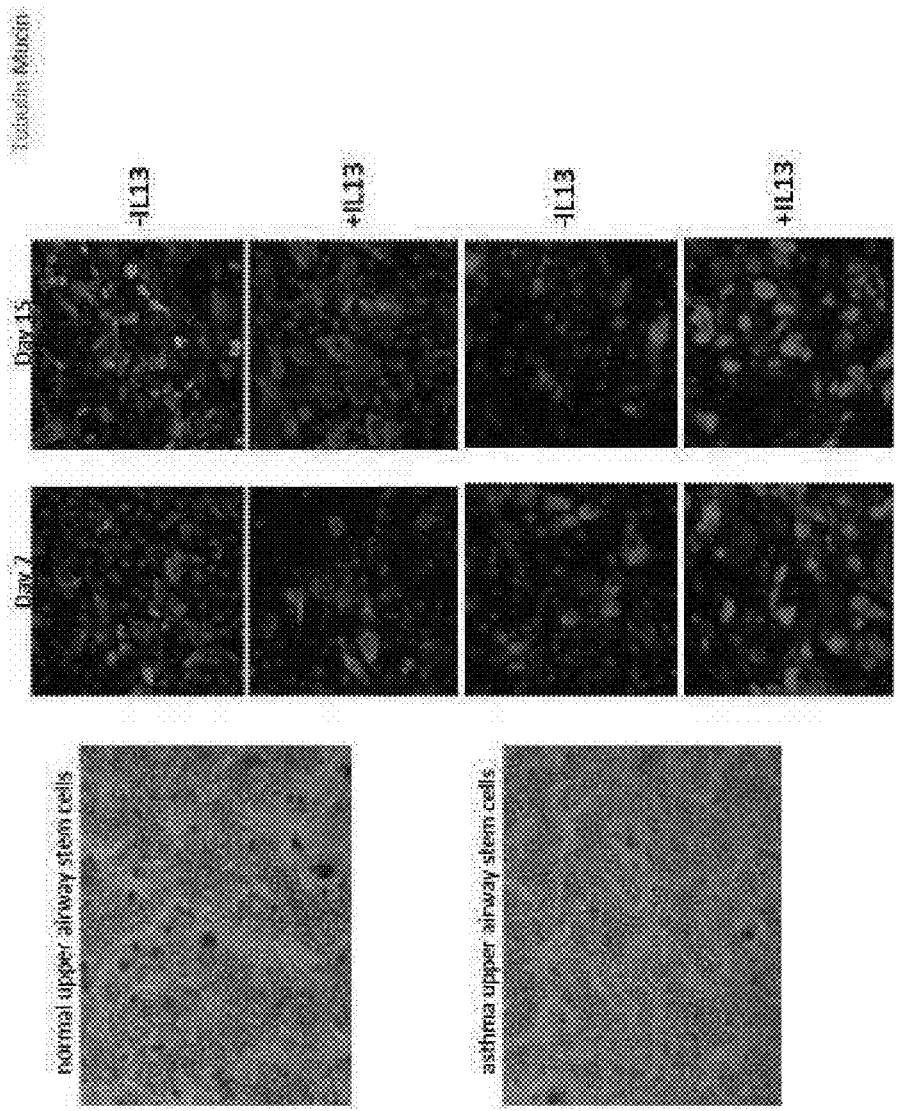
FIG. 19 shows that a pedigree cell line established based on an isolated upper airway stem cell from an asthma patient exhibit enhanced sensitivity to IL-13 treatment. Normal upper airway stem cells differentiate into both ciliated cells and goblet cells in about 13 days in the absence of IL-13 treatment. However, stem cells isolated from the asthma patient have extremely limited or no ability to form ciliated cells. Based on microarray-based expression level analysis, even without IL-13 treatment, on Day 13, AMTN expression is already 35-fold lower in cells differentiated from the patient pedigree cell line, as compared to normally differentiated cells. Meanwhile, in the same differentiated cells from the patient pedigree cell line, TCN1 expression is already 45-fold higher than normal. Consistent with this observation, Asthma stem cells are more susceptible to IL-13 treatment, and give rise to goblet cell metaplasia much faster and stronger compared to normal upper airway epithelial stem cells.

Upper airway stem cells were isolated using the methods of the invention from an asthma patient. Microarray analysis revealed that, without IL-13 treatment, in about 13 days, normal upper airway stem cells differentiate into both ciliated cells and goblet cells. However, Asthma patient stem cells have extremely limited or no ability to form ciliated cells. Based on the microarray data, AMTN expression in the patient cells was already 35-fold lower, and TCN1 expression in the patient was already 45-fold higher compared to normal control at day 13. Consistently with this observation, Asthma stem cells were more susceptible to IL-13 treatment, and gave rise to goblet cell metaplasia much faster and stronger than normal upper airway epithelial stem cells. See FIG. 19.

Note that on Day 15, without IL-13 treatment, normal upper airway stem cells differentiate into both goblet cells and ciliated cells. IL-13 treatment led to hypertrophy and hyperplasia of the goblet cells.

In contrast, in asthma upper airway stem cell differentiated cells, there was nearly no visible ciliated cell differentiation, as indicated by the lack of tubulin expression, a marker for the ciliated cells. Upon IL-13 treatment, the asthma patient derived epithelia showed much stronger or pronounced goblet cell hypertrophy and hyperplasia, as evidenced by prominent mucin staining.

The data presented in this example demonstrates that Asthma patient's upper airway stem cells are particularly more susceptible to IL-13 treatment, which is consistent with the fact that the relevant genes, such as AMTN, are already aberrantly expressed in these cells pre IL-13 treatment. Therefore, these cells, although having been cultured in the same medium as normal TBEC in the absence of other cell types (such as immune cells) for a long period of time, still retain a "memory" of their disease state. This evidence further supports the importance of correcting epithelial stem cells in the asthma patients due to their activated intrinsic pathways for inflammatory phenotype. On the other hand, treating aberrant immune system alone will not automatically correct the diseased epithelial cells derived from such stem cells.

Example 3: In Vitro Differentiation Assays for Human and Rat Cells

Air-liquid interface culture of upper airway epithelial cells was performed as described (Schmidt et al., *Toxicol. Lett.* 88:75-79, 1996; Kumar et al, supra, both incorporated by reference). Briefly, upper airway stem cells were cultured on Transwell plates (Corning) coated with irradiated 3T3-J2 feeder cells in the presence of CFAD medium (a base medium). At confluence, the medium on the inserts was removed and the medium outside the insert was changed to differentiation medium (DMEM/F12 1:1, 50 mg/mL penicillin; 50 mg/mL streptomycin; Fungizone 2.5 mg/mL (GIBCO); 10 ng/mL cholera toxin, retinoic acid $10^{-7}$ M; 10% Knockout SR serum replacement (GIBCO)).

Example 4: Differentiation of Liver Stem Cells in MATRIGEL™

Liver stem cells were digested by 0.05% trypsin for 30 to 60 seconds. The epithelial stem cells were separated from the irradiated 3T3-J2 fibroblast feeder, and the trypsin was neutralized by the serum containing medium.

The liver epithelial stem cells were then plated on the MATRIGEL™ basement membrane matrix (BD) coated tissue culture plates, and grown in the presence of the growth medium (CFAD+1 µM Jagged-1+100 ng/mL Noggin+125 ng/mL R-Spondin-1+2.5 µM Rock inhibitor+2 µM SB431542+10 mM Nicotinamide).

After 3 to 5 days, the growth medium was changed to differentiation medium (HBM Basal Medium (Lonza, cat. no. CC-3199) and Hepatocyte Culture Medium HCM™ SingleQuots™ Kit (Lonza, cat. no. CC-4182). The differentiation medium was changed every 2 days. After about 10 days, the differentiation structures were harvested for sectioning, IHC (immunohistochemistry), IF (immunofluorescent) staining, and/or RNA collection.

The isolated liver stem cell differentiated into organized structures in MATRIGEL™ basement membrane matrix (BD) under the conditions described (data not shown). IF (immunofluorescent) staining of the differentiated structure shows that the differentiated cells expressed the hallmark liver marker genes such as albumin, HNF-1α (hepatocyte nuclear factor 1 alpha) and alpha-fetoprotein (AFP), demonstrating that the liver stem cells have differentiated into mature liver cells.

Example 5: Differentiation of Barrett's Esophagus Stem Cell and Gastric Cardia Stem Cell Barrett's esophagus and gastric cardia cells were digested by 0.05% trypsin for 30 to 60 seconds. The epithelial stem cells were separated from the irradiated (3T3-J2) fibroblast feeder and the trypsin was neutralized by the serum containing medium. The epithelial stem cells were then plated on the MATRIGEL™ basement membrane matrix (BD) coated tissue culture plates and grown in the presence of the growth medium (advanced F12/DMEM, 10 mM Hepes, pen/strep, N2, B27, EGF 50 ng/mL, FGF10 100 ng/mL, Wnt3a 100 ng/mL, R-Spondin 1 (125 ng/mL), SB431542 2 μM, SB203580 10 μM, Nicotinamide 10 mM, Noggin 100 ng/ml, Y27632 2.5 μM). After 3 to 5 days, the growth medium was changed to differentiation medium (advanced F12/DMEM, 10 mM Hepes, pen/strep, N2, B27, EGF 50 ng/mL, FGF10 100 ng/mL, Wnt3a 100 ng/mL, R-Spondin 1 (125 ng/mL), Noggin 100 ng/mL, DBZ 10 μM). The differentiation medium was changed every 2 days. After 2 weeks, the differentiation structures were harvested for sectioning, immunohistochemistry (IHC), immunofluorescence (IF) staining and RNA collection.

Example 6: Differentiation of Small Intestine Stem Cells on Air Liquid Interface Isolated small intestine stem cells can be differentiated on air-liquid interface (ALI) with collagen and 3T3-J2 insert according to the method described in the example.

About $1 \times 10^5$ 3 T3-J2 cells were first plated on each well of a Transwell-COL plate (Collagen coated transwell, 24 well plate, Cat. 3495, Corning Inc.). About 700 μL of 3T3 growth Medium was added to the outside chamber of each well, and about 200 μL of 3T3 growth medium (DMEM Invitrogen cat. no. 11960, high glucose (4.5 g/L), no L-glutamine, no sodium pyruvate; 10% bovine calf serum, not heat inactivated; 1% penicillin-streptomycin and 1% L-glutamine) was added to the inside chamber of each well.

The day after, 3T3 cells were washed once with the CFAD medium (see Example 1), then intestine stem cell clones were transferred onto the transwell. Each outside chamber of the transwell plate was filled by about 700 μL of stem cell growth medium (CFAD+1 μM Jagged-1+100 ng/mL Noggin+125 ng/mL R-Spondin-1+2.5 μM Rock inhibitor), and each inside chamber of the transwell was filled by 200 μL of stem cell growth medium.

The stem cell growth medium was changed about every 1-2 days, both inside and outside of each transwell insert. After confluence was reached (roughly 8-10 days for intestinal stem cells), the medium was change to differentiation medium (stem cell growth medium plus 2 μM GSK3 inhibitor), with about 700 μL of differentiation medium in the outside chamber of each transwell, but with no medium in the inside chambers. The differentiated structure was formed in about one month.

Example 7: Secreted Protein Production

Expression vectors were purchased from OpenBioSystems, Thermo Fisher Scientific. Plasmid vectors encoding the various secreted proteins were transfected into 293T cells using Lipofectamine method based on manufacture's recommendation (Invitrogen). Conditioned medium was collected 48-72 hrs. after transfection, and was filtered through Milipore Amicon ultra centrifugal filters to enrich protein concentration for proteins with molecular weight in the range of between 3 to 50 kDa. The expression of the secreted protein in the conditioned medium was also examined by Western blot.

Protein concentration in the concentrated conditioned medium was quantified by standard Bradford protein assay. Typically, final protein concentration for the concentrated conditioned medium was between 30 ng/mL to 50 ng/mL.

The conditioned medium was diluted 1:5 with differentiation medium before being used to treat ALI culture.

Example 8: IL-13 and Secreted Factors Treatment

The upper airway epithelial stem cells or differentiated structures are treated with IL-13 (10-20 ng/mL) in the absence or presence of the conditioned medium containing secreted factor(s). Total RNA from around 100,000 cells was collected at various time points using Trizol reagent (Invitrogen) according to the manufacture's recommendation. RNA concentration was measured by Nanodrop Spectroscopy (Thermo Fisher Scientific Inc.).

Example 9: Microarray and Bioinformatics

RNA obtained from various time points of air-liquid interface (ALI) assays was amplified using the WT Pico RNA Amplification System (NuGEN Technologies Inc., Catalog #3300-12, 3300-60), the WT-Ovation Exon Module, and the Encore Biotin Module (NuGEN Technologies, Inc.), and hybridized onto GeneChip human Exon 1.0 ST Array (Affymetrix, Inc.) according to the respective manufactures' recommendations. GeneChip operating software was used to process all the Cel files and calculate probe intensity values.

To validate sample quality, probe hybridization ratios were calculated using Affymetrix Expression Console software. The intensity values were log 2-transformed, and imported into the Partek Genomics Suite 6.5 (beta). Exons were summarized to genes and a 1-way ANOVA analysis was performed to identify differentially expressed genes. P values and fold-change were calculated for each analysis.

Example 10: Whole-Mount Immunofluorescence

The ALI culture was washed with PBS and fixed by 4% PFA for 20 mins. at room temperature. The fixed structures were washed with PBS and blocked by TBST (Tris Buffered Saline with Tween 20) with 0.1% Triton and 5% BSA for one hour. The structures were then incubated with the primary antibody, e.g., anti-acetylated alpha tubulin (Sigma) and anti-Muc5Ac (Santa Cruz), at 1:500 dilution for one hour, washed with PBS and then incubated with the Alexa Fluro® 488 donkey anti-mouse IgG (H+L) and Alexa Fluro® 594 donkey anti-rabbit IgG (H+L) secondary antibodies for one hour. After washing, the VECTASHIELD mounting medium was added, and 3D images were taken by Zeiss LCM510 confocal microscope.

Figure 15:
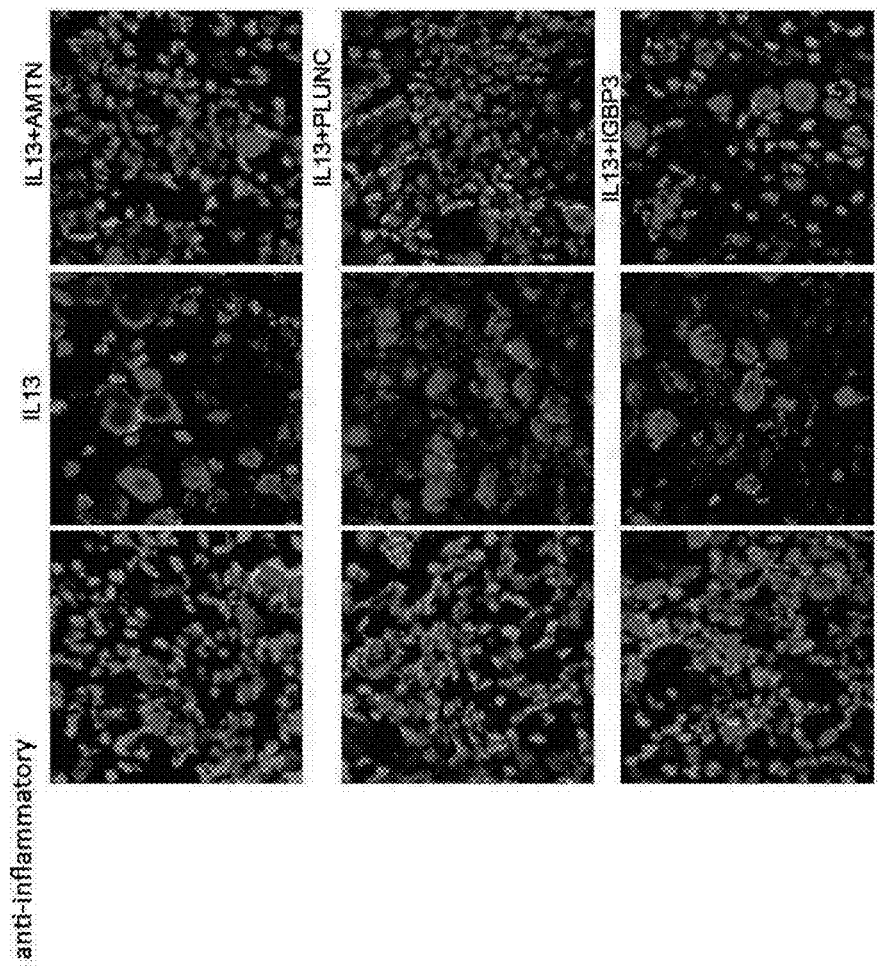
FIGS. 15 and 16 show examples of anti-inflammatory effects of several anti-inflammatory proteins identified using the methods of the invention. Preparations of the selected anti-inflammatory proteins were generated by transfecting 293T cells with expression vectors encoding AMTN, PLUNC, IGBP3 (IGFBP3), TGFbeta1, TGFbeta2 or SERPINA3, respectively. Conditioned media containing these secreted proteins were collected. Cells from the upper airway stem cell pedigree cell lines were seeded on the transwell membrane and grown to confluency prior to exposure to an air-liquid interface (ALI) to induce differentiation. After 25 days, the cells adopted a differentiated, upper airway epithelium morphology. IL-13 or IL-13 with condition medium (of expressed anti-inflammatory proteins) were added into the cell culture medium. The middle panel shows that 7 days following these treatments, IL-13 induced goblet cell hyperplasia and hypertrophy phenotype. However, IL-13+conditioned medium shows different degrees of a rescue phenotype. AMTN and SERPINA3 show the most significant rescue phenotype. PLUNC, IGBP3, TGFbeta1 and TGFbeta2 also show a trend of reversing the IL-13 phenotype.
Figure 16:
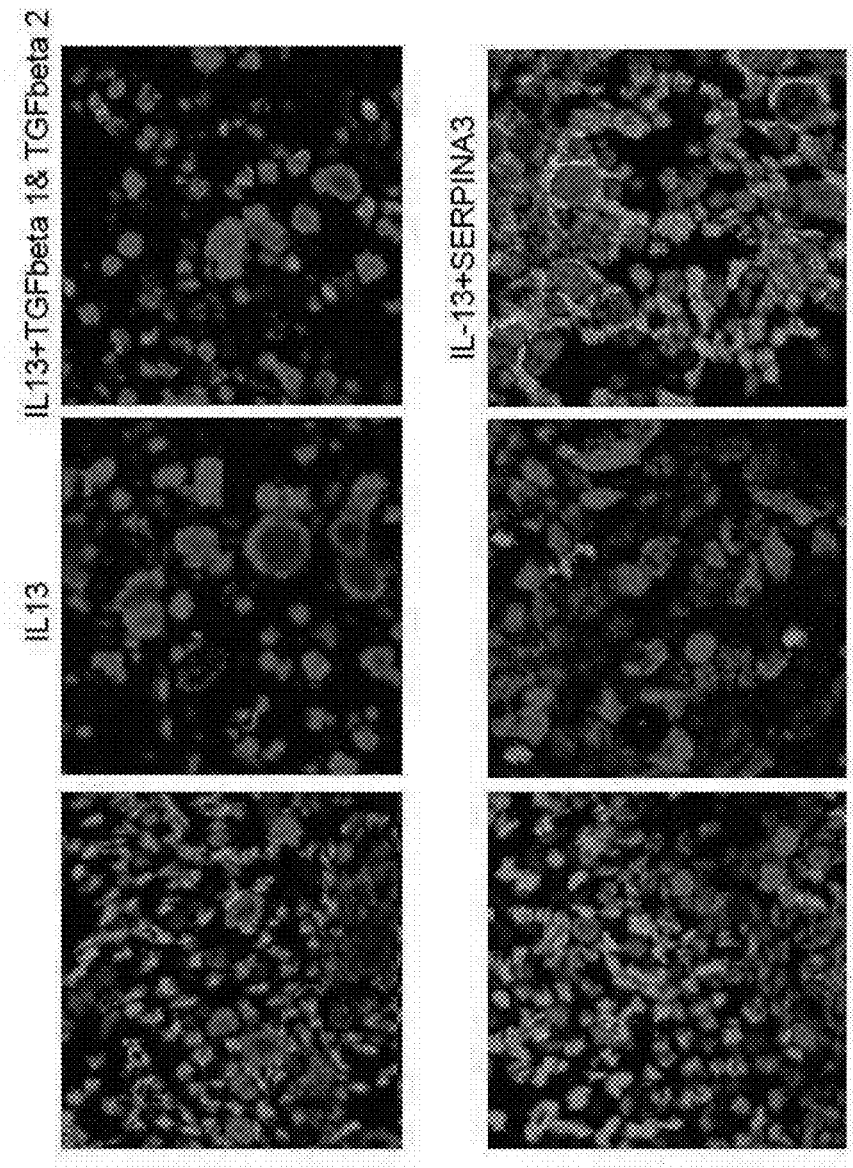
Figure 18:
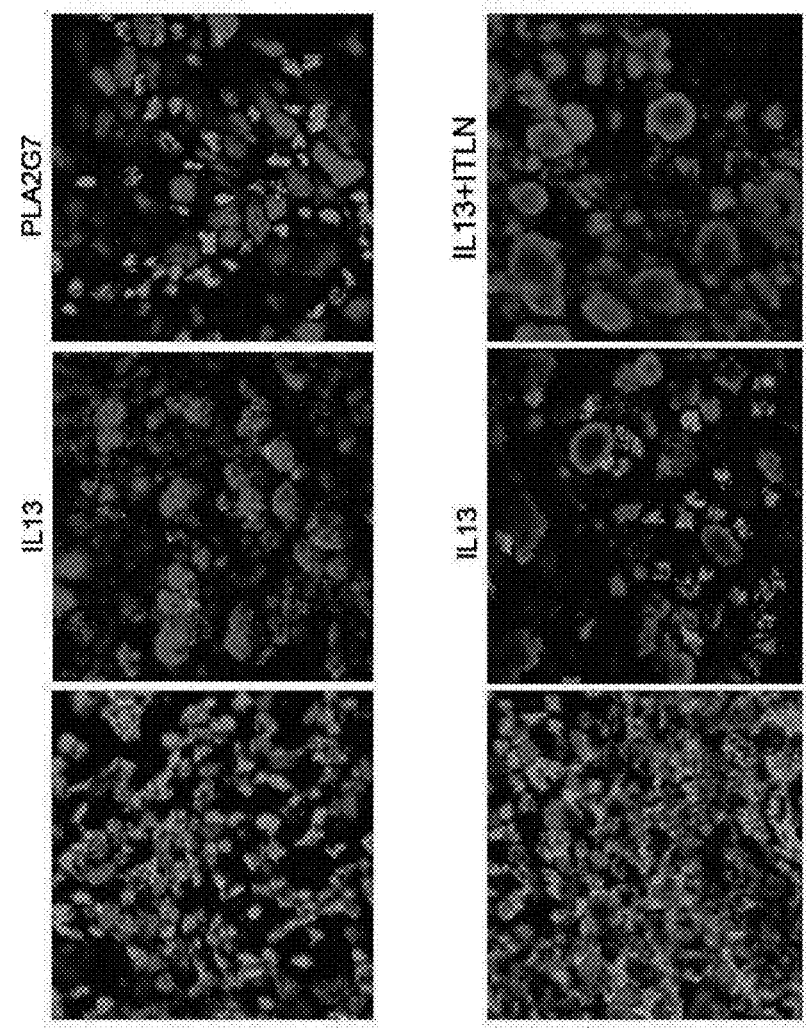
FIG. 18 shows examples of pro-inflammatory effects of several identified proteins. The 293T cells were transfected with expression vectors for PLA2G7 and ITLN, respectively. The conditioned media containing these secreted proteins were collected. 25-day differentiated ALI were treated with IL-13 or IL-13 plus conditioned media, or condition medium alone. The middle panel shows that 7 days following these treatments, IL-13 induced goblet cell hyperplasia and hypertrophy phenotype. PLA3G7 conditioned medium treatment displays the similar IL-13 mediated phenotype in the absence of IL-13. IL-13+ITLN conditioned medium shows a much more severe goblet cell hyperplasia and hypertrophy phenotype.

Example 11: Treatment of Upper Airway Epithelial Stem Cells with Anti-Inflammatory Proteins Conditioned media was prepared from transfected 293T cells expressing AMTN, PLUNC, IGFBP3, TGFbeta1, TGFbeta2 or SERPINA3. Cells from the upper airway stem cell pedigree cell lines were seeded on the transwell membrane and grown to confluency prior to exposure to an air-liquid interface (ALI) to induce differentiation. After 25 days, the cells adopted a differentiated, upper airway epithelium morphology. IL-13 or IL-13 with condition medium (of expressed anti-inflammatory proteins) were added into the cell culture medium to the Day 25 differentiated structures. The middle panels showed that 7 days following these treatments, IL-13 induced goblet cell hyperplasia and hypertrophy phenotype. However, when the differentiated structures were contacted by IL-13 and the various conditioned media (e.g., IL-13+AMTN conditioned medium, IL-13+SERPINA3 conditioned medium, etc.), different degrees of a rescue was observed. AMTN and SERPINA3 showed the most significant rescue phenotype, with almost complete suppression of the inflammatory phenotype compared to structure treated by IL-13 only. When using PLUNC, IGBP3, TGFbeta1 or TGFbeta2 conditioned medium, a trend of reversing the IL-13 phenotype has also been observed (see FIGS. 15 and 16).

The phenotype rescue results are somewhat surprising, especially with respect to certain identified anti-inflammatory genes such as AMTN, for which no existing literature Applicants are aware of appears to suggest a role of such genes in anti-inflammatory pathways.

Example 12: Screening Methods Using Intestinal Stem Cells

Human intestinal stem cells can be isolated and clonally expanded according to the method described in the co-pending co-owned application filed on the same day (Mar. 15, 2013), entitled "Isolation of Non-Embryonic Stem Cells and Uses Thereof," as U.S. Provisional Application No. 61/792,027 (incorporated herein by reference).

For example, fresh human intestinal biopsies are washed vigorously in cold wash buffer (F12:DMEM 1:1; 1.0% penicillin-streptomycin; 0.1% fungizone and 2.5 ml of 100 µg/ml gentamycin) for three times and followed once by cold PBS. The biopsy is minced and soaked in digestion medium (BD Cell Recovery Solution cat. no. 354253) and incubated at 4° C. for 8-12 hours with gentle shaking. The digested tissues are washed five more times with 30 ml cold wash buffer each. After the final wash, the samples are spun down and resuspended in modified growth medium and seeded on the feeder. The modified growth medium for human adult intestine epithelial stem cells consists of basic growth medium (DMEM:F12 in a ratio 3:1; 10% FBS (not heat inactivated); 1.35 mM L-glutamine; 5 µg/ml insulin; $2\times10^{-9}$ M T3 (3,3',5-Triiodo-L-Thyronine); $1\times10^{-10}$ M cholera enterotoxin; 400 ng/ml hydrocortisone; 24.3 µg/ml adenine; 10 ng/ml EGF) and the following factors: of 2.5 µM rock inhibitor (R)-(+)-trans-N-(4-Pyridyl)-4-(1-aminoethyl)-cyclohexanecarboxamide (Y-27632, Rho Kinase Inhibitor VI, Calbiochem, cat. no. 688000); 125 ng/ml R-spondin 1 protein (R&D, cat. no. 4645-RS); 100 ng/ml noggin protein (Peprotech, cat. no. 120-10c); 1 µM Jagged-1 peptide (188-204) (AnaSpec Inc., cat. no. 61298); 2 µM SB431542: 4-(4-(benzo[d][1,3]dioxol-5-yl)-5-(pyridin-2-yl)-1H-imidazol-2-yl)benzamide (Cayman chemical company, cat. no. 13031); 10 mM nicotinamide (Sigma, cat. no. N0636-100G). After three to four days the first epithelial cell colonies are detectable. Then cells were trypsinized with warm 0.25% trypsin (Invitrogen, cat. no 25200056) for 10 min, neutralized, resuspended in the modified growth medium, passed through 40 micron cell strainer and seeded as single cells onto a new plate containing a 3T3-J2 feeder layer. The medium is changed every two days. Three days later, individual clones of adult human epithelial stem cells are observed. A single colony is picked using a cloning ring and expanded to develop a pedigree cell line, i.e., a cell line that has been derived from a single cell.

The pedigreed cell lines are cultured in the presence of IL-13 or TNF-α to induce an inflammatory phenotype in comparison to untreated cells. The culture in presence of the pro-inflammatory protein is for 1 day, 5 days, or up to 21 days. RNA will be isolated and analyzed either by microarray analysis (e.g., Affymetrix) or RNA-Seq to identify differences in gene expression between the two groups. Standard bioinformatics tools will be applied to rank the genes. Genes that are upregulated will be further analyzed regarding their pro-inflammatory potential and genes that are downregulated regarding their anti-inflammatory activities. Such can be done for example by treating the IL-13 culture with the protein and see if the phenotype can be reverted to the untreated stage, or if a more severe inflammatory phenotype is detectable.

Alternatively, the intestinal epithelial stem cells are first differentiated, e.g., into an intestine-like structure as described containing enterocytes, goblet cells and enteroendocrine cells, and/or Paneth cells. For the differentiation a non-cellular matrix, such as collagen or Matrigel, or an appropriate feeder cell layer may be included, or the cells may be co-cultured with other cells.

Such differentiated cells can then be treated with IL-13 or TNF-α (or other pro-inflammatory cytokine of interest) for 1 day, 5 days, up to 21 days to induce an inflammatory phenotype, for control untreated cells will be cultured. At specific time points RNA will be isolated and analyzed either by microarray analysis (e.g., Affymetrix) or RNA-Seq to identify differences in gene expression between the two groups (treated vs. control). Standard bioinformatics tools will be applied to rank the genes. Genes that are upregulated will be further analyzed regarding their pro- as well as anti-inflammatory potential and genes that are downregulated regarding their pro- and anti-inflammatory activities. Such can be done for example by treating the IL-13 stimulated culture with the identified protein and see if the 11-13 induced phenotype can be reverted to the untreated stage, or if a more severe inflammatory phenotype is detectable.

I claim:

1. A method of identifying a target gene which may be useful for treating an inflammatory disease in a human subject, the method comprising:
   a) providing a population of test cells, said test cells are:
      1) a clonal expansion of a single epithelial stem cell isolated from said human subject and are capable of propagating for at least about 20 (30, 40, 50, 60, 70, 100, 150, 200, 250, 300, 350, 400 or more) doublings while maintaining a multipotent phenotype; or
      2) differentiated from said clonal expansion of said single epithelial stem cell isolated from said human subject;
   wherein said single epithelial stem cell is an adult stem cell isolated from an adult tissue from said human subject according to a method comprising the steps of:
      (1) culturing dissociated epithelial cells from said adult tissue, in contact with a first population of lethally irradiated feeder cells and a basement membrane matrix, to form epithelial cell clones, in a medium comprising: (i) a Notch agonist; (ii) a ROCK (Rho Kinase) inhibitor; (iii) a Bone Morphogenetic Protein (BMP) antagonist; (iv) a Wnt agonist; (v) a mitogenic growth factor; and, (vi) insulin or IGF; the medium optionally further comprising at least one of: (vii) a TGFβ signaling pathway inhibitor; and, (viii) nicotinamide or an analog, precursor, or mimic thereof;
      (2) isolating single cells from said epithelial cell clones; and
      (3) culturing isolated single cells from step (2) individually to form single cell clones, in contact with a second population of lethally irradiated feeder cells and a second basement membrane matrix in the medium; wherein each of the single cell clones represents a clonal expansion of said adult stem cell, thereby isolating said adult stem cell;
   b) contacting the test cells with a pro-inflammatory cytokine associated with the inflammatory disease; and
   c) identifying one or more genes the expression level of which has been modulated upon contacting the pro-inflammatory cytokine, as compared to that of control test cells not contacted by the pro-inflammatory cytokine;
   wherein said one or more genes identified in step c) are target gene(s) which may be useful for treating the inflammatory disease in said human subject.

2. The method of claim 1, wherein the pro-inflammatory cytokine is IL-4, IL-5, IL-6, IL-10, IL-13, TNFα, IL-8, IL-10, IL-11, IL-17 (IL-17A, IL-17B, IL-17C, IL-17D, IL-17E, IL-17F), or IL-1 (IL-1α, IL-1β, IL-18, IL-33, IL-36α, IL-36β, IL-36γ).

3. The method of claim 1, wherein the single epithelial stem cell is isolated from a subject predisposed to the inflammatory disease, or has the inflammatory disease.

4. The method of claim 1, wherein the single epithelial stem cell is isolated from upper airway of the respiratory system, small intestine, or colon.

5. The method of claim 1, further comprising:
   d) determining the effect of contacting a second population of test cells with both the pro-inflammatory cytokine and gene expression products of said one or more genes,
   wherein said one or more genes are identified as anti-inflammatory if at least one inflammatory phenotype induced by the pro-inflammatory cytokine is alleviated.

6. The method of claim 5, wherein said test cells are a clonal expansion of a single upper airway epithelial stem cell, or are upper airway epithelial cells differentiated therefrom, and wherein said at least one inflammatory phenotype comprises goblet cell hyperplasia, goblet cell hypertrophy, and/or ciliated cell deciliation.

7. The method of claim 5, wherein in step d), the second population of test cells are contacted by the pro-inflammatory cytokine and the gene expression products of said one or more genes substantially simultaneously.

8. The method of claim 5, wherein in step d), the second population of test cells are first contacted by the pro-inflammatory cytokine to produce at least one inflammatory phenotype, before being contacted by the gene expression products of said one or more genes.

9. The method of claim 5, wherein said second population of test cells are a second population of epithelial cells differentiated from said clonal expansion of said single epithelial stem cell.

10. The method of claim 1, wherein the test cells are upper airway epithelial cells differentiated in air-liquid interface (ALI) cultures.

11. The method of claim 10, wherein the test cells are differentiated in ALI cultures while in contact with a fibroblast feeder layer.

12. The method of claim 1, wherein in step c), gene expression level is determined by quantitating mRNA expression.

13. The method of claim 12, wherein gene expression level is determined by microarray or real-time PCR.

14. The method of claim 1, wherein step c) comprises identifying one or more genes the expression level of which is decreased upon contacting the pro-inflammatory cytokine.

15. The method of claim 1, wherein step c) comprises identifying one or more genes the expression level of which is increased upon contacting the pro-inflammatory cytokine.

16. The method of claim 15, further comprising:
d) contacting a second population of test cells with the pro-inflammatory cytokine, and determining the effect thereon of inhibiting a function of said one or more genes, wherein said one or more genes are identified as pro-inflammatory if at least one inflammatory phenotype induced by the pro-inflammatory cytokine is alleviated.

17. The method of claim 15, further comprising:
d) determining the effect of stimulating a function of said one or more genes in a second population of test cells, either in the presence or absence of the proinflammatory cytokine, wherein said one or more genes are identified as pro-inflammatory if at least one inflammatory phenotype is induced or enhanced in the test cells.

18. The method of claim 16, wherein said test cells are a clonal expansion of a single upper airway epithelial stem cell, or are upper airway epithelial cells differentiated therefrom, and wherein said at least one inflammatory phenotype comprises goblet cell hyperplasia, goblet cell hypertrophy, and/or ciliated cell deciliation.

19. The method of claim 1, wherein the expression level of the target gene is increased or decreased by at least 2-fold, 3-fold, 5-fold, 10-fold, 20-fold, 50-fold, 100-fold or more compared to that of the control test cells.

20. The method of claim 1, wherein said medium comprises: 5 μg/mL insulin; 2 nM of (3,3',5-Triiodo-L-Thyronine); 400 ng/mL hydrocortisone; 24.3 μg/mL adenine; 10 ng/mL EGF; 10% fetal bovine serum (without heat inactivation); 1 μM Jagged-1; 100 ng/mL noggin; 125 ng/mL R-spondin 1; 2.5 μM Y-27632; and 1.35 mM L-glutamine in DMEM:F12 3:1 medium, optionally further comprising 0.1 nM cholera enterotoxin, 2 μM SB431542, and/or 10 mM nicotinamide.

21. A method of identifying a human subject suitable for therapeutic intervention, wherein the human subject has an inflammatory disease, or is predisposed to develop said inflammatory disease, the method comprising:
a) using the method of claim 1, identifying one or more pro-inflammatory genes or one or more anti-inflammatory genes as the target genes which may be useful for treating the inflammatory disease;
b) isolating, according to the method of claim 1, from a candidate subject a single epithelial stem cell capable of propagating at least about 20 (30, 40, 50, 60, 70, 100, 150, 200, 250, 300, 350, 400 or more) doublings while maintaining a multipotent phenotype;
c) determining the expression level of said pro-inflammatory genes or said anti-inflammatory genes in a clonal expansion of said single epithelial stem cell isolated from said candidate subject, or in cells differentiated from said clonal expansion; and,
d) identifying said candidate subject having increased expression of said pro-inflammatory genes or having decreased expression of said anti-inflammatory genes, as being suitable for therapeutic intervention that modulate the expression of said pro-inflammatory genes or said anti-inflammatory genes.

* * * * *

SEQUENCE LISTING

<160> NUMBER OF SEQ ID NOS: 56

<210> SEQ ID NO 1
<211> LENGTH: 209
<212> TYPE: PRT
<213> ORGANISM: Homo sapiens

<400> SEQUENCE: 1

Met Arg Ser Thr Ile Leu Leu Phe Cys Leu Leu Gly Ser Thr Arg Ser
1               5                   10                  15

Leu Pro Gln Leu Lys Pro Ala Leu Gly Leu Pro Pro Thr Lys Leu Ala
            20                  25                  30

Pro Asp Gln Gly Thr Leu Pro Asn Gln Gln Ser Asn Gln Val Phe
        35                  40                  45

Pro Ser Leu Ser Leu Ile Pro Leu Thr Gln Met Leu Thr Leu Gly Pro
    50                  55                  60

Asp Leu His Leu Asn Pro Ala Ala Gly Met Thr Pro Gly Thr Gln
65                  70                  75                  80

Thr His Pro Leu Thr Leu Gly Gly Leu Asn Val Gln Gln Gln Leu His
                85                  90                  95

Pro His Val Leu Pro Ile Phe Val Thr Gln Leu Gly Ala Gln Gly Thr
            100                 105                 110

Ile Leu Ser Ser Glu Glu Leu Pro Gln Ile Phe Thr Ser Leu Ile Ile
        115                 120                 125

His Ser Leu Phe Pro Gly Gly Ile Leu Pro Thr Ser Gln Ala Gly Ala
    130                 135                 140

Asn Pro Asp Val Gln Asp Gly Ser Leu Pro Ala Gly Gly Ala Gly Val
145                 150                 155                 160

Asn Pro Ala Thr Gln Gly Thr Pro Ala Gly Arg Leu Pro Thr Pro Ser
                165                 170                 175

Gly Thr Asp Asp Asp Phe Ala Val Thr Thr Pro Ala Gly Ile Gln Arg
            180                 185                 190

Ser Thr His Ala Ile Glu Glu Ala Thr Thr Glu Ser Ala Asn Gly Ile
        195                 200                 205

Gln

<210> SEQ ID NO 2
<211> LENGTH: 1072
<212> TYPE: DNA
<213> ORGANISM: Homo sapiens

<400> SEQUENCE: 2
aatttttcac cagagtaaac ttgagaaacc aactggacct tgagtattgt acattttgcc      60
tcgtggaccc aaaggtagca atctgaaaca tgaggagtac gattctactg ttttgtcttc     120
taggatcaac tcggtcatta ccacagctca aacctgcttt gggactccct cccacaaaac     180
tggctccgga tcagggaaca ctaccaaacc aacagcagtc aaatcaggtc tttccttctt     240
taagtctgat accattaaca cagatgctca cactgggggcc agatctgcat ctgttaaatc     300
ctgctgcagg aatgacacct ggtacccaga cccacccatt gaccctggga gggttgaatg     360
tacaacagca actgcaccca catgtgttac caattttttgt cacacaactt ggagcccagg     420
gcactatcct aagctcagag gaattgccac aaatcttcac gagcctcatc atccattcct     480
tgttcccggg aggcatcctg cccaccagtc aggcagggcc taatccagat gtccaggatg     540
gaagccttcc agcaggagga gcaggtgtaa atcctgccac ccagggaacc ccagcaggcc     600

```
gcctcccaac tcccagtggc acagatgacg actttgcagt gaccacccct gcaggcatcc      660
aaaggagcac acatgccatc gaggaagcca ccacagaatc agcaaatgga attcagtaag      720
ctgtttcaaa tttttcaac taagctgcct cgaatttggt gatacatgtg aatctttatc       780
attgattata ttatggaata gattgagaca cattggatag tcttagaaga aattaattct      840
taatttacct gaaatattc ttgaaatttc agaaatatg ttctatgtag agaatcccaa        900
cttttaaaaa caataattca atggataaat ctgtctttga aatataacat tatgctgcct      960
ggatgatatg catattaaaa catatttgga aaactggaaa aaaaaaaaaa aaaaaaaaa      1020 aaaaaaaaaa aaaaaaaaaa aaaaaaaaaa aaaaaaaaaa aaaaaaaaaa aa            1072
```

<210> SEQ ID NO 3
<211> LENGTH: 1075
<212> TYPE: PRT
<213> ORGANISM: Homo sapiens

<400> SEQUENCE: 3

```
Met Arg Gly Gly Lys Cys Asn Met Leu Ser Ser Leu Gly Cys Leu Leu
1               5                   10                  15

Leu Cys Gly Ser Ile Thr Leu Ala Leu Gly Asn Ala Gln Lys Leu Pro
            20                  25                  30

Lys Gly Lys Arg Pro Asn Leu Lys Val His Ile Asn Thr Thr Ser Asp
        35                  40                  45

Ser Ile Leu Leu Lys Phe Leu Arg Pro Ser Pro Asn Val Lys Leu Glu
    50                  55                  60

Gly Leu Leu Leu Gly Tyr Gly Ser Asn Val Ser Pro Asn Gln Tyr Phe
65                  70                  75                  80

Pro Leu Pro Ala Glu Gly Lys Phe Thr Glu Ala Ile Val Asp Ala Glu
                85                  90                  95

Pro Lys Tyr Leu Ile Val Val Arg Pro Ala Pro Pro Ser Gln Lys
            100                 105                 110

Lys Ser Cys Ser Gly Lys Thr Arg Ser Arg Lys Pro Leu Gln Leu Val
        115                 120                 125

Val Gly Thr Leu Thr Pro Ser Ser Val Phe Leu Ser Trp Gly Phe Leu
    130                 135                 140

Ile Asn Pro His His Asp Trp Thr Leu Pro Ser His Cys Pro Asn Asp
145                 150                 155                 160

Arg Phe Tyr Thr Ile Arg Tyr Arg Glu Lys Asp Lys Glu Lys Lys Trp
                165                 170                 175

Ile Phe Gln Ile Cys Pro Ala Thr Glu Thr Ile Val Glu Asn Leu Lys
            180                 185                 190

Pro Asn Thr Val Tyr Glu Phe Gly Val Lys Asp Asn Val Glu Gly Gly
        195                 200                 205

Ile Trp Ser Lys Ile Phe Asn His Lys Thr Val Val Gly Ser Lys Lys
    210                 215                 220

Val Asn Gly Lys Ile Gln Ser Thr Tyr Asp Gln Asp His Thr Val Pro
225                 230                 235                 240

Ala Tyr Val Pro Arg Lys Leu Ile Pro Ile Thr Ile Ile Lys Gln Val
                245                 250                 255

Ile Gln Asn Val Thr His Lys Asp Ser Ala Lys Ser Pro Glu Lys Ala
            260                 265                 270

Pro Leu Gly Gly Val Ile Leu Val His Leu Ile Ile Pro Gly Leu Asn
        275                 280                 285

Glu Thr Thr Val Lys Leu Pro Ala Ser Leu Met Phe Glu Ile Ser Asp
```

```
            290                 295                 300
Ala Leu Lys Thr Gln Leu Ala Lys Asn Glu Thr Leu Ala Leu Pro Ala
305                 310                 315                 320

Glu Ser Lys Thr Pro Glu Val Glu Lys Ile Ser Ala Arg Pro Thr Thr
                325                 330                 335

Val Thr Pro Glu Thr Val Pro Arg Ser Thr Lys Pro Thr Thr Ser Ser
                340                 345                 350

Ala Leu Asp Val Ser Glu Thr Thr Leu Ala Ser Ser Glu Lys Pro Trp
                355                 360                 365

Ile Val Pro Thr Ala Lys Ile Ser Glu Asp Ser Lys Val Leu Gln Pro
            370                 375                 380

Gln Thr Ala Thr Tyr Asp Val Phe Ser Ser Pro Thr Thr Ser Asp Glu
385                 390                 395                 400

Pro Glu Ile Ser Asp Ser Tyr Thr Ala Thr Ser Asp Arg Ile Leu Asp
                405                 410                 415

Ser Ile Pro Pro Lys Thr Ser Arg Thr Leu Glu Gln Pro Arg Ala Thr
                420                 425                 430

Leu Ala Pro Ser Glu Thr Pro Phe Val Pro Gln Lys Leu Glu Ile Phe
            435                 440                 445

Thr Ser Pro Glu Met Gln Pro Thr Thr Pro Ala Pro Gln Gln Thr Thr
            450                 455                 460

Ser Ile Pro Ser Thr Pro Lys Arg Arg Pro Arg Pro Lys Pro Pro Arg
465                 470                 475                 480

Thr Lys Pro Glu Arg Thr Thr Ser Ala Gly Thr Ile Thr Pro Lys Ile
                485                 490                 495

Ser Lys Ser Pro Glu Pro Thr Trp Thr Thr Pro Ala Pro Gly Lys Thr
                500                 505                 510

Gln Phe Ile Ser Leu Lys Pro Lys Ile Pro Leu Ser Pro Glu Val Thr
            515                 520                 525

His Thr Lys Pro Ala Pro Lys Gln Thr Pro Arg Ala Pro Pro Lys Pro
            530                 535                 540

Lys Thr Ser Pro Arg Pro Arg Ile Pro Gln Thr Gln Pro Val Pro Lys
545                 550                 555                 560

Val Pro Gln Arg Val Thr Ala Lys Pro Lys Thr Ser Pro Ser Pro Glu
                565                 570                 575

Val Ser Tyr Thr Thr Pro Ala Pro Lys Asp Val Leu Leu Pro His Lys
                580                 585                 590

Pro Tyr Pro Glu Val Ser Gln Ser Glu Pro Ala Pro Leu Glu Thr Arg
                595                 600                 605

Gly Ile Pro Phe Ile Pro Met Ile Ser Pro Ser Pro Ser Gln Glu Glu
            610                 615                 620

Leu Gln Thr Thr Leu Glu Thr Asp Gln Ser Thr Gln Glu Pro Phe
625                 630                 635                 640

Thr Thr Lys Ile Pro Arg Thr Thr Glu Leu Ala Lys Thr Thr Gln Ala
                645                 650                 655

Pro His Arg Phe Tyr Thr Thr Val Arg Pro Arg Thr Ser Asp Lys Pro
                660                 665                 670

His Ile Arg Pro Gly Val Lys Gln Ala Pro Arg Pro Ser Gly Ala Asp
            675                 680                 685

Arg Asn Val Ser Val Asp Ser Thr His Pro Lys Lys Pro Gly Thr
            690                 695                 700

Arg Arg Pro Pro Leu Pro Pro Arg Pro Thr His Pro Arg Lys Pro
705                 710                 715                 720
```

Leu Pro Pro Asn Asn Val Thr Gly Lys Pro Gly Ser Ala Gly Ile Ile
            725                 730                 735

Ser Ser Gly Pro Ile Thr Thr Pro Pro Leu Arg Ser Thr Pro Arg Pro
            740                 745                 750

Thr Gly Thr Pro Leu Glu Arg Ile Glu Thr Asp Ile Lys Gln Pro Thr
            755                 760                 765

Val Pro Ala Ser Gly Glu Glu Leu Glu Asn Ile Thr Asp Phe Ser Ser
770                 775                 780

Ser Pro Thr Arg Glu Thr Asp Pro Leu Gly Lys Pro Arg Phe Lys Gly
785                 790                 795                 800

Pro His Val Arg Tyr Ile Gln Lys Pro Asp Asn Ser Pro Cys Ser Ile
            805                 810                 815

Thr Asp Ser Val Lys Arg Phe Pro Lys Glu Glu Ala Thr Glu Gly Asn
            820                 825                 830

Ala Thr Ser Pro Pro Gln Asn Pro Pro Thr Asn Leu Thr Val Val Thr
            835                 840                 845

Val Glu Gly Cys Pro Ser Phe Val Ile Leu Asp Trp Glu Lys Pro Leu
            850                 855                 860

Asn Asp Thr Val Thr Glu Tyr Glu Val Ile Ser Arg Glu Asn Gly Ser
865                 870                 875                 880

Phe Ser Gly Lys Asn Lys Ser Ile Gln Met Thr Asn Gln Thr Phe Ser
            885                 890                 895

Thr Val Glu Asn Leu Lys Pro Asn Thr Ser Tyr Glu Phe Gln Val Lys
            900                 905                 910

Pro Lys Asn Pro Leu Gly Glu Gly Pro Val Ser Asn Thr Val Ala Phe
            915                 920                 925

Ser Thr Glu Ser Ala Asp Pro Arg Val Ser Glu Pro Val Ser Ala Gly
            930                 935                 940

Arg Asp Ala Ile Trp Thr Glu Arg Pro Phe Asn Ser Asp Ser Tyr Ser
945                 950                 955                 960

Glu Cys Lys Gly Lys Gln Tyr Val Lys Arg Thr Trp Tyr Lys Lys Phe
            965                 970                 975

Val Gly Val Gln Leu Cys Asn Ser Leu Arg Tyr Lys Ile Tyr Leu Ser
            980                 985                 990

Asp Ser Leu Thr Gly Lys Phe Tyr Asn Ile Gly Asp Gln Arg Gly His
            995                 1000                1005

Gly Glu Asp His Cys Gln Phe Val Asp Ser Phe Leu Asp Gly Arg
            1010                1015                1020

Thr Gly Gln Gln Leu Thr Ser Asp Gln Leu Pro Ile Lys Glu Gly
            1025                1030                1035

Tyr Phe Arg Ala Val Arg Gln Glu Pro Val Gln Phe Gly Glu Ile
            1040                1045                1050

Gly Gly His Thr Gln Ile Asn Tyr Val Gln Trp Tyr Glu Cys Gly
            1055                1060                1065

Thr Thr Ile Pro Gly Lys Trp
            1070                1075

<210> SEQ ID NO 4
<211> LENGTH: 4488
<212> TYPE: DNA
<213> ORGANISM: Homo sapiens

<400> SEQUENCE: 4
gtgcagccgc cgcctctgt cactgggaga cagtccactt aaatgcagct ccagggttgc      60

```
gaggcaccca ccagcatcat tccccatgcg aggtggcaaa tgcaacatgc tctccagttt      120
ggggtgtcta cttctctgtg gaagtattac actagccctg ggaaatgcac agaaattgcc      180
aaaaggtaaa aggccaaacc tcaaagtcca catcaatacc acaagtgact ccatcctctt      240
gaagttcttg cgtccaagtc caaatgtaaa gcttgaaggt cttctcctgg gatatgcag       300 caatgtatca ccaaaccagt acttccctct tcccgctgaa gggaaattca cagaagctat      360
agttgatgca gagccgaaat atctgatagt tgtgcgacct gctccacctc caagtcaaaa      420
gaagtcatgt tcaggtaaaa ctcgttctcg caaacctctg cagctggtgg ttggcactct      480
gacaccgagc tcggtcttcc tgtcctgggg tttcctcatc aacccacacc atgactggac      540
attgccaagt cactgtccca atgacagatt ttatacaatt cgctatcgag aaaaggataa      600
agaaaagaag tggattttc aaatctgtcc agccactgaa acaattgtgg aaaacctaaa       660
gcccaacaca gtttatgaat ttggagtgaa agacaatgtg aaggtggaa tttggagtaa       720 gattttcaat cacaagactg ttgttggaag taaaaaagta aatgggaaaa tccaaagtac      780
ctatgaccaa gaccacacag tgccagcata tgtcccaagg aaactaatcc aataacaat       840 catcaagcaa gtgattcaga atgttactca caaggattca gctaaatccc cagaaaaagc      900
tccactggga ggagtgatac tagtccacct tattattcca ggtcttaatg aaactactgt      960
aaaacttcct gcatccctaa tgtttgagat ttcagatgca ctcaagacac aattagctaa     1020
gaatgaaacc ttggcattac ctgccgaatc taaaacacca gaggttgaaa aatctcagc      1080 acgacccaca acagtgactc ctgaaacagt tccaagaagc actaaaccca ctacgtctag     1140
tgcattagat gtttcagaaa caacactggc ttcaagtgaa aagccatgga ttgtgcctac     1200
agctaaaata tctgaagatt ccaaagttct gcagcctcaa actgcaactt atgatgtttt     1260
ctcaagccct acaacatcag atgagcctga gatatcagat tcctacacag caacaagtga     1320
tcgtattctg gattctatcc cacctaaaac ttctagaact cttgaacagc aagggcaac      1380 actggctcca agtgaaacac catttgttcc tcaaaaactg gaaatctta ccagtccaga      1440 aatgcagcct acgacacctg ctccccagca aactacatct atcccttcta cacctaaacg     1500 acgccccgg cccaaaccgc caagaaccaa acctgaaaga accacaagtg ccggaacaat      1560
tacacctaaa atttctaaaa gccctgaacc tacatggaca acaccggctc ccggtaaaac     1620
acaatttatt tctctgaaac ctaaaatccc tctcagccca gaagtgacac acaccaaacc     1680
tgctcccaag cagacaccac gtgctcctcc taagccaaaa acatcaccac gcccaagaat     1740
cccacaaaca caaccagttc ctaaggtgcc ccagcgtgtt actgcaaaac caaaacgtc      1800 accaagtcca gaagtgtcat acaccacacc tgctccaaaa gatgtgctcc ttcctcataa     1860 accatacccct gaggtctctc agagcgaacc tgctcctcta gagacacgag gcatcccttt     1920
tatacccatg atttccccaa gtcctagtca agaggaacta cagaccactc tggaagaaac     1980
agaccaatcc acccaagaac cttttcacaac taagattcca cgaacaactg aactagcaaa     2040
gacaactcag gcgccacaca gatttttatac tactgtgagg cccagaacat ctgacaagcc     2100
acacatcaga cctggggtca agcaagcacc caggccatca ggtgctgata gaaatgtatc     2160
agtggactct acccaccca ctaaaaagcc agggactcgc cgcccaccct tgccacccag      2220
acctacacac ccacgaagaa aacctttacc accaaataat gtcactggaa agccaggaag     2280
tgcaggaatc atttcatcag gcccaataac tacaccaccc ctgaggtcaa cacccaggcc     2340
tactggaact cccttggaga gaatagagac agatataaag caaccaacag ttcctgcctc     2400
```

```
tggagaagaa ctggaaaata taactgactt tagctcaagc ccaacaagag aaactgatcc    2460
tcttgggaag ccaagattca aaggacctca tgtgcgatac atccaaaagc ctgacaacag    2520
tccctgctcc attactgact ctgtcaaacg gttccccaaa gaggaggcca cagaggggaa    2580
tgccaccagc ccaccacaga acccaccacc caacctcact gtggtcaccg tggaagggtg    2640
cccctcattt gtcatcttgg actgggaaaa gccactaaat gacactgtca ctgaatatga    2700
agttatatcc agagaaaatg ggtcattcag tgggaagaac aagtccattc aaatgacaaa    2760
tcagacattt tccacagtag aaaatctgaa accaaacacg agttatgaat tccaggtgaa    2820
acccaaaaac ccgcttggtg aaggcccggt cagcaacaca gtggcattca gtactgaatc    2880
agcggaccca agagtgagtg agccagtttc tgcaggaaga gatgccatct ggactgaaag    2940
acccttttaat tcagactctt actcagagtc taagggcaaa caatatgtca aaaggacatg    3000
gtataaaaaa tttgtaggag tgcagctgtg caactctctc agatacaaga tttacttgag    3060
cgactccctc acaggaaaat tttataacat aggtgatcag aggggccatg agaagatca    3120
ctgccagttt gtggattcat ttttagatgg acgcactggg cagcaactca cttctgacca    3180
gttaccaatc aaagaaggtt atttcagagc agttcgccag gaacctgtcc aatttggaga    3240
aataggtggt cacacccaaa tcaattatgt tcagtggtat gaatgtggga ctacaattcc    3300
tggaaaatgg tagatgctgc acaaagttac cttctgtttc atcattgcaa acaaaaatca    3360
ttgaaaatac tatgccgcat tcatttaaag ctattttgtt tactatgtat aaaagtctac    3420
aatctaatta atagcaatac tagatgttta ttattagaaa agattgctga gagtatttat    3480
caggttttac aaagtcattt taagaaagca agatactgat gttaacagaa taacattttt    3540
ggggaagctg gctccctatt catggtattt taagagatca tttgtatatt atttatcaca    3600
ctgttgtaat gatgttttga gatacttta taacaaaatt aacatcaaaa aggtatatac    3660
tttttaaaaa aaatttactt ttattgatgt gtactcttcc tattgatgag ttaattccat    3720
aaatctctac ttagtttaac ttattggatc aaattatctt cagcatgtat atctggggaa    3780
aaaaggtccg aattttcaca tttatattta aacttcaatt ttttatattt aaacttcaat    3840
ttttagcaa cagctgaata gctttgcgga ggagtttaat agttacacat tcatgctaat    3900
atacatttcc tttaaacatc cacaaattct taaaaagatt gaatcagtaa atttcatttc    3960
agctaaaaat ggagtctaat atattgtttc aaaagataca ttttaccca ccataaatgt    4020
tacaatatct gaatatgctt tgtcaaacta tcccttatg caatcgtctt catattgttt    4080
ttatgattct aatcaagctg tatgtagaga ctgaatgtga agtcaagtct gagcacaaaa    4140
agataatgca cgatgagatt gcctaccatt ttataggata tttactatgt attatacgt    4200
taagacctct atgaatgaat gtatcagaga atgtctttgt aactgtttaa ttcaatctgt    4260
aataaaaatc taactaacta actcatttat ttctattaaa aaggtattgt cctttaggcg    4320
gggaatggga atccttgctg cactgttgca gtcattctga aaggaccttt ccctgtactt    4380
acctttcaac atgcttcaat cttatcaacg ctacattttg tattttcaa acaagtataa    4440
attctgcaat aaagagatgt agtttttttt taaaaaaaaa aaaaaaaa            4488
```

<210> SEQ ID NO 5
<211> LENGTH: 189
<212> TYPE: PRT
<213> ORGANISM: Homo sapiens

<400> SEQUENCE: 5

Met Val Met Leu Leu Leu Leu Leu Ser Ala Leu Ala Gly Leu Phe Gly

```
              1               5                  10                 15
            Ala Ala Glu Gly Gln Ala Phe His Leu Gly Lys Cys Pro Asn Pro Pro
                            20                  25                  30

Val Gln Glu Asn Phe Asp Val Asn Lys Tyr Leu Gly Arg Trp Tyr Glu
                            35                  40                  45

Ile Glu Lys Ile Pro Thr Thr Phe Glu Asn Gly Arg Cys Ile Gln Ala
                        50                  55                  60

Asn Tyr Ser Leu Met Glu Asn Gly Lys Ile Lys Val Leu Asn Gln Glu
             65                 70                  75                  80

Leu Arg Ala Asp Gly Thr Val Asn Gln Ile Glu Gly Glu Ala Thr Pro
                                85                  90                  95

Val Asn Leu Thr Glu Pro Ala Lys Leu Glu Val Lys Phe Ser Trp Phe
                           100                 105                 110

Met Pro Ser Ala Pro Tyr Trp Ile Leu Ala Thr Asp Tyr Glu Asn Tyr
                           115                 120                 125

Ala Leu Val Tyr Ser Cys Thr Cys Ile Ile Gln Leu Phe His Val Asp
                       130                 135                 140

Phe Ala Trp Ile Leu Ala Arg Asn Pro Asn Leu Pro Pro Glu Thr Val
            145                 150                 155                 160

Asp Ser Leu Lys Asn Ile Leu Thr Ser Asn Asn Ile Asp Val Lys Lys
                           165                 170                 175

Met Thr Val Thr Asp Gln Val Asn Cys Pro Lys Leu Ser
                       180                 185

<210> SEQ ID NO 6
<211> LENGTH: 1148
<212> TYPE: DNA
<213> ORGANISM: Homo sapiens

<400> SEQUENCE: 6
tctctctcgc acacataccc acacacacac acacacacac acacgcgcgc gcgaaaacaa      60
tatctcattt cttcttcagg gagcagctgt gaaggaaatc gggggaggag gatggacaca     120
acatcccatc tttgtgtttc gatacagact aagcttttag gccaaccctc ctgactggat     180
gggggcggcg ggcgtggcat gcatgaaaag taaacatcag agacctgaag aagcttataa     240
aatagcttgg gagaggccag tcaccaagac aggcatctca aatcggctga ttctgcatct     300
ggaaactgcc ttcatcttga agaaaagct ccaggtccct tctccagcca cccagcccca     360
agatggtgat gctgctgctg ctgctttccg cactggctgg cctcttcggt gcggcagagg     420
gacaagcatt tcatcttggg aagtgcccca atcctccggt gcaggagaat tttgacgtga     480
ataagtatct cggaagatgg tacgaaattg agaagatccc aacaaccttt gagaatggac     540
gctgcatcca ggccaactac tcactaatgg aaaacggaaa gatcaaagtg ttaaaccagg     600
agttgagagc tgatggaact gtgaatcaaa tcgaaggtga agccaccca gttaacctca     660 cagagcctgc caagctggaa gttaagtttt cctggtttat gccatcggca ccgtactgga     720
tcctggccac cgactatgag aactatgccc tcgtgtattc ctgtacctgc atcatccaac     780
tttttcacgt ggattttgct tggatcttgg caagaaaccc taatctccct ccagaaacag     840
tggactctct aaaaaatatc ctgacttcta ataacttga tgtcaagaaa atgacggtca     900
cagaccaggt gaactgcccc aagctctcgt aaccaggttc tacagggagg ctgcacccac     960
tccatgttac ttctgcttcg ctttccccta cccccccccc ataaagacaa accaatcaac    1020
cacgacaaag gaagttgacc tgaacatgta accatgccc accctgttac cttgctagct    1080
```

```
gcaaaataaa cttgttgctg acctgctgtg ctcgcagtag attccaagtt aaaaaaaaaa    1140
aaaaaaaa                                                             1148
```

<210> SEQ ID NO 7
<211> LENGTH: 402
<212> TYPE: PRT
<213> ORGANISM: Homo sapiens

<400> SEQUENCE: 7

```
Met Ala Ala Arg Pro Gly Pro Leu Trp Leu Gly Leu Thr Leu Cys
1               5                   10                  15

Ala Leu Gly Gly Gly Gly Pro Gly Leu Arg Pro Pro Gly Cys Pro
            20                  25                  30

Gln Arg Arg Leu Gly Ala Arg Glu Arg Asp Val Gln Arg Glu Ile
        35                  40                  45

Leu Ala Val Leu Gly Leu Pro Gly Arg Pro Arg Ala Pro Pro
    50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                    85                  90                  95

Gln Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                    165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                    245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val Arg Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                    325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
```

```
              355                 360                 365
Pro Thr Lys Leu Ser Ala Thr Ser Val Leu Tyr Tyr Asp Ser Ser Asn
        370                 375                 380

Asn Val Ile Leu Arg Lys His Arg Asn Met Val Val Lys Ala Cys Gly
385                 390                 395                 400

Cys His

<210> SEQ ID NO 8
<211> LENGTH: 5642
<212> TYPE: DNA
<213> ORGANISM: Homo sapiens

<400> SEQUENCE: 8
ggtcgctgcc ggagctcgcc ggtcgcccct gcgctgcgcg gaccgcagcc acagccggac      60
tggtgggaac ggcggcgaca gacggattgg ctgacagtcc cagccctcag aacagccccg     120
gcctcgaagc gttggcgtct gcgtccgcgc cagcgtccgc ttgtcccgga gccggggcag     180
gtgcgcgcgg gggcgctcc agggaccgcg ctgaggccgc agacgccgcc cgccgagccc      240 cgcccccctgc tcgccgaact cagctccccg ttcgccgtcg gggcgtcccc gggcccaggg    300
gcggcggcgg agctgatgtg cgcccgctga gcgcccccgg cccgccatgg ccgcgcgccc    360
cggaccgctc tggcttctgg gcctgacgtt gtgcgcgctg gcggggggcg ccccggcct     420 gcgacccccg cccggctgtc cccagcgacg tctgggcgcg cgcgagcgcc gggacgtgca    480
gcgcgagatc ctggcggtgc tcgggctacc cgggcggccc cggccccgcg cgccacccgc    540
cgcctcccgc tgcccgcgt ccgcgccgct cttcatgctg gacctgtacc acgccatggc     600
tggcgacgac gacgaggacg gcgcgcccgc ggagcagcgc ctgggccgcg ccgacctggt    660
catgagcttc gtcaacatgg tggagcgaga ccgtgccctg gccaccagg agccccattg    720 gaaggagttc cgctttgacc tgacccagat cccggctggg gaggcggtca cagctgcgga    780
gttccggatt tacaaggtgc ccagcatcca cctgctcaac aggaccctcc acgtcagcat    840
gttccaggtg tccaggagc agtccaacag ggagtctgac ttgttctttt tggatcttca     900
gacgctccga gctggagacg agggctggct ggtgctggat gtcacagcag ccagtgactg    960
ctggttgctg aagcgtcaca aggacctggg actccgcctc tatgtggaga ctgaggacgg   1020
gcacagcgtg gatcctggcc tggcggcct gctgggtcaa cgggcccac gctcccaaca     1080 gcctttcgtg gtcactttct tcagggccag tccgagtccc atccgcaccc ctcgggcagt    1140
gaggccactg aggaggaggc aaccgaagaa aagcaacgag ctgccgcagg ccaaccgact    1200
cccagggatc tttgatgacg tccgcggctc ccacggccgg caggtctgcc gtcggcacga    1260
gctctacgtc agcttccagg accttggctg gctggactgg gtcatcgccc ccaaggcta    1320 ctcagcctat tactgtgagg gggagtgctc cttcccgctg gactcctgca tgaacgccac    1380
caaccacgcc atcctgcagt ccctggtgca cctgatgaag ccaaacgcag tcccaaggc    1440 gtgctgtgca cccaccaagc tgagcgccac ctctgtgctc tactatgaca gcagcaacaa    1500
cgtcatcctg cgcaagcacc gcaacatggt ggtcaaggcc tgcggctgcc actgagtcag    1560
cccgcccagc cctactgcag ccaccctttct catctggatc gggccctgca gaggcagaaa    1620
accctttaaa gctgtcacag ctcaagcagg agtgtcaggg ccctcactc tcggtgccta     1680 cttcctgtca ggcttctggt cctttctcgg tacctctgtg cccctcccct ggggtttgtg    1740
gctgtcactc tgcccgacac tttggtggcc taaggcacac agcagcctca gagcctgtgc    1800
tgactgcact gtctggagtc agcacagaag tcctatctta ggacctgtca gactgtggct    1860
```

```
ggccccggat ggtctgaggt tggctgaccc gagcttttct ccattcacca gagggtttag   1920
gtgtgaggag aagggctctg cctcttccca ggtacaacac tggccatttc tgggcaaaat   1980
tggacacgct tatgttctca gcacagtgtg ttctgggatt cttctcattt ggtccagggt   2040
gcagttagca tattagaaaa agaataagct ggacatcccc acgaagccac tggggatttt   2100
tttttttttt ttccagatag agtctcactc tgtcacccag gctggagtgc agtggtgcaa   2160
tcctggctca ctgcaacctc tgcctcccag gttcaagcaa ttctcgtgcc tcagcctcct   2220
gagtagctgg gattacaggg gcccaccacc acgcccagct cattcttgta tttttagtag   2280
agacggggtt tcaccatatc ggccaggctg gtcttgaact cctgacctca ggtgatccac   2340
ccgcccggcc tcccaaagtg ttgggatgac aggcatgagc caccgtgcct ggccactggg   2400
gatattttat gtcatgtgta ttcccttgcc ctgggcctgc cccttctcct gcctgggaaa   2460
gaggtatgac tcccacagga gcaaagaatc ctgggggctt ccagttccct ccaccatctc   2520
taccatgctg acccatttgg ggctcagcac tgagacagag gcaagaccag cagctccaac   2580
atgtagtgta ggctggcaca gagcaaatgc ccccgcagcc tgctccccct gcccatggct   2640
catgtcagta atcaacctac gtacctttcc cactgaacca ggacagggcc tccaggcctc   2700
agcacagaac tgcagacagc caccaccagg cattgtcaat aagacctcag ttccccctcc   2760
tgccccactg cagagcaatc cattccatcc aaagcagggt gactggcagt ctccggccag   2820
gcatggggca agggtgggga ctgccagtgt ttgcttgtgt ctaggagtta tgaacaagct   2880
ggccaccaaa attggcgtca ccctgggtgc ccaccagcgc tgtcctgtgt cttgggtctg   2940
tgagtcaaag aaaaggtccc tgtcccaggg agtgacaggc agtaattagg ctgagttggg   3000
tggggaggtt tgtctcggcc tccactgttc ccggaaaccg ctgttctcct tggaacagcc   3060
actgggagtt ggagtgttta tttgatttct gacttgctaa gcctgtaatt tacctgctgg   3120
aacagacaga gtccagctgc ccaaaccgtg tcattaaaag cagatcctgg gcccgcccca   3180
tccacaggca cagcctggca gagtggttcc acctccccat gggcccaagg atgcgcctct   3240
ctggagttca cgtgctgcac ccccagggag gggcctgggg agagctggtc cagcagcagg   3300
ggtggaggct ggggccacac tgcgggacag cagcccctcc acctggacca gggagggcct   3360
ccatgtgcaa gcgcagagga agagaccctc tcatgtacat aaagggtggg cccaggctgt   3420
ctggaagatg gtgagttccc cactagtcta aggcttcaag ctcagctagc agagattgga   3480
agaggcaatg gcctgagtgt taggagacag gtattctggt tccaactcag ccactgactt   3540
ggtgtcagga caagtcccct ttcttattca cgcttcagtt tctcatctgc aacatgagga   3600
cataggactc tttaattcca aaggctcttc caacccagag aacccatctg cccccatgac   3660
cttctcccag agcttgagac atggcctgag cccctgctg ccataggact tggggcctat   3720
ctgccattgc aggacctgat ttaacagctc tcttcttcca atactgggca gtagagtttc   3780
ggaaactgac aaatgtgtgg tctcttcagt gcccagtgtg taacctggca tggtttgggt   3840
gtgctaggag tttgtgaaat gaatgttttc aagacgcaaa cgctgctatg cccatcaggt   3900
gtgcacagca ggcctgagga tcatgatgag actccctttt tatgcagcaa agcacaaagt   3960
gtgacagtcg tggccttcct ggtggccaga cttctagcaa ctttagccac ccaccaaatg   4020
acatcacata cagaaggcct cagaaaggga ggaggtcgta aggacacaca gctgatgaag   4080
ggtcagtgct cagctatcaa ggtcatcttc tggcctggtt gcctcccaca gcccaggatg   4140
cattcaaggc tgcacatcag gagcataaat aagggtggtc agctcaggcc cactggctgc   4200
```

```
aacaagtagc cactgacagg gagtctgggg ccatttggtg cagaacaacc cccaacccag    4260
tggccatctt cacaactgca gcacagtgct ggccctaatg ccaggtgagc gtgcaaagtc    4320
ctgtttcttt gtcttacat agggaccggg cgatgcgctt tagagaaatt ccctattatt    4380
tcacaggaaa ggaggctgtg aaaggagag gcaggtttt ggagccaagt cgacctggca    4440
tcaggtcctg gctgccttt tttttttttt tttaaagaca tacatggtct tgctttgtcg    4500
cccaggctgg agtgcagtgg cagtgtcatg gctcactgca gcctcaacct gctgggctca    4560
agcaatcctc ccacttcagc ccgagttgct gggatgacag gcacacgcca ccatacccag    4620
ctaattttta aatttttat agaaaccagg tctcactatg ttgcccaggc cggtcttaaa    4680 cttgcccag gccagtcttg aactcctgag ctcaagcaat cctcctgcct cagcctccca    4740
aagtgctagg attacaggcg tgagccactt acccggcctc tgcctcttgt taatttgacc    4800
acatcatgta cctgctgtgc ccgttccttc ctccgtagaa gagggtgctg gtcctgccct    4860
tttgaggcct ccatgagggc caaatgtgcc atgggacact tagtgccatg cctgcgcaga    4920
cctgtggaat aaacagcaat tctgagcagg ctcattttaa agggacttgc aaatttgggc    4980
gttccttgtg tgccttcctc ataaaaccca ctcctcccag aatatgctta gaggtgctgc    5040
tgtatttacc tgagagctat gcttttcatc aaaaacctaa acgtgatcat ctcttggatg    5100
aggtgtggcc ctgcacactc gcctgctcgt ggaaggagtc tgggccagca gtgacccacg    5160
cgctagggtc tctgctgagg aagtggcagg tgtgcggccc tgccctggcc cgtagtgag    5220 tgtggggccc acctgtgccc tcatgggcag ctgaaggggg agctttctac cccaggttcc    5280
tttccttact gaaaagtctt gagcaaacag ttgccgctct ccaccccctg cttttaaaa    5340 aaaatttttt ctcacgtaag aaaatgttat ctgtgtgctg gggaaaattt tgaaaataac    5400
aaaaaccaga atacaaacac ccataatcaa tcacagagat aaccactgtt cataattcct    5460
tccagtcttc ttacttggca catatacatt tgtctttctt tatatatgac atatggatat    5520
tttacaaagt taggatccta ctctatgcac tgcttggtga tcggatctat tcaatgtaca    5580
aaatattttg aaagtttctg tgattaaatg ttctttgaaa acataaaaaa aaaaaaaaaa    5640
aa                                                                  5642
```

<210> SEQ ID NO 9
<211> LENGTH: 1663
<212> TYPE: PRT
<213> ORGANISM: Homo sapiens

<400> SEQUENCE: 9

```
Met Gly Pro Thr Ser Gly Pro Ser Leu Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110
```

-continued

```
Gly Thr Gln Val Val Glu Lys Val Leu Val Ser Leu Gln Ser Gly
            115                 120                 125
Tyr Leu Phe Ile Gln Thr Asp Lys Thr Ile Tyr Thr Pro Gly Ser Thr
130                 135                 140
Val Leu Tyr Arg Ile Phe Thr Val Asn His Lys Leu Leu Pro Val Gly
145                 150                 155                 160
Arg Thr Val Met Val Asn Ile Glu Asn Pro Glu Gly Ile Pro Val Lys
                165                 170                 175
Gln Asp Ser Leu Ser Ser Gln Asn Gln Leu Gly Val Leu Pro Leu Ser
            180                 185                 190
Trp Asp Ile Pro Glu Leu Val Asn Met Gly Gln Trp Lys Ile Arg Ala
        195                 200                 205
Tyr Tyr Glu Asn Ser Pro Gln Gln Val Phe Ser Thr Glu Phe Glu Val
    210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
            260                 265                 270
Phe Gly Ile Gln Asp Gly Glu Gln Arg Ile Ser Leu Pro Glu Ser Leu
        275                 280                 285
Lys Arg Ile Pro Ile Glu Asp Gly Ser Gly Glu Val Val Leu Ser Arg
    290                 295                 300
Lys Val Leu Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
            340                 345                 350
Tyr Gln Ile His Phe Thr Lys Thr Pro Lys Tyr Phe Lys Pro Gly Met
        355                 360                 365
Pro Phe Asp Leu Met Val Phe Val Thr Asn Pro Asp Gly Ser Pro Ala
    370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
    450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
        515                 520                 525
Phe Arg Leu Val Ala Tyr Tyr Thr Leu Ile Gly Ala Ser Gly Gln Arg
```

```
            530                 535                 540
Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
                595                 600                 605

Asn Lys Leu Thr Gln Ser Lys Ile Trp Asp Val Glu Lys Ala Asp
        610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
                645                 650                 655

Arg Ala Glu Leu Gln Cys Pro Gln Pro Ala Ala Arg Arg Arg Ser
                660                 665                 670

Val Gln Leu Thr Glu Lys Arg Met Asp Lys Val Gly Lys Tyr Pro Lys
                675                 680                 685

Glu Leu Arg Lys Cys Cys Glu Asp Gly Met Arg Glu Asn Pro Met Arg
690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Asn Ile Val Ser Arg Ser Glu Phe Pro
        755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Val Arg Asn Glu Gln Val Glu Ile Arg
                835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
                915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960
```

-continued

Asp Ile Pro Pro Ala Asp Leu Ser Asp Gln Val Pro Asp Thr Glu Ser
            965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
            995                 1000                1005

Gly Cys Gly Glu Gln Asn Met Ile Gly Met Thr Pro Thr Val Ile
        1010                1015                1020

Ala Val His Tyr Leu Asp Glu Thr Glu Gln Trp Glu Lys Phe Gly
        1025                1030                1035

Leu Glu Lys Arg Gln Gly Ala Leu Glu Leu Ile Lys Lys Gly Tyr
        1040                1045                1050

Thr Gln Gln Leu Ala Phe Arg Gln Pro Ser Ser Ala Phe Ala Ala
        1055                1060                1065

Phe Val Lys Arg Ala Pro Ser Thr Trp Leu Thr Ala Tyr Val Val
        1070                1075                1080

Lys Val Phe Ser Leu Ala Val Asn Leu Ile Ala Ile Asp Ser Gln
        1085                1090                1095

Val Leu Cys Gly Ala Val Lys Trp Leu Ile Leu Glu Lys Gln Lys
        1100                1105                1110

Pro Asp Gly Val Phe Gln Glu Asp Ala Pro Val Ile His Gln Glu
        1115                1120                1125

Met Ile Gly Gly Leu Arg Asn Asn Asn Glu Lys Asp Met Ala Leu
        1130                1135                1140

Thr Ala Phe Val Leu Ile Ser Leu Gln Glu Ala Lys Asp Ile Cys
        1145                1150                1155

Glu Glu Gln Val Asn Ser Leu Pro Gly Ser Ile Thr Lys Ala Gly
        1160                1165                1170

Asp Phe Leu Glu Ala Asn Tyr Met Asn Leu Gln Arg Ser Tyr Thr
        1175                1180                1185

Val Ala Ile Ala Gly Tyr Ala Leu Ala Gln Met Gly Arg Leu Lys
        1190                1195                1200

Gly Pro Leu Leu Asn Lys Phe Leu Thr Thr Ala Lys Asp Lys Asn
        1205                1210                1215

Arg Trp Glu Asp Pro Gly Lys Gln Leu Tyr Asn Val Glu Ala Thr
        1220                1225                1230

Ser Tyr Ala Leu Leu Ala Leu Leu Gln Leu Lys Asp Phe Asp Phe
        1235                1240                1245

Val Pro Pro Val Val Arg Trp Leu Asn Glu Gln Arg Tyr Tyr Gly
        1250                1255                1260

Gly Gly Tyr Gly Ser Thr Gln Ala Thr Phe Met Val Phe Gln Ala
        1265                1270                1275

Leu Ala Gln Tyr Gln Lys Asp Ala Pro Asp His Gln Glu Leu Asn
        1280                1285                1290

Leu Asp Val Ser Leu Gln Leu Pro Ser Arg Ser Ser Lys Ile Thr
        1295                1300                1305

His Arg Ile His Trp Glu Ser Ala Ser Leu Leu Arg Ser Glu Glu
        1310                1315                1320

Thr Lys Glu Asn Glu Gly Phe Thr Val Thr Ala Glu Gly Lys Gly
        1325                1330                1335

Gln Gly Thr Leu Ser Val Val Thr Met Tyr His Ala Lys Ala Lys
        1340                1345                1350

```
Asp Gln Leu Thr Cys Asn Lys Phe Asp Leu Lys Val Thr Ile Lys
    1355                1360                1365

Pro Ala Pro Glu Thr Glu Lys Arg Pro Gln Asp Ala Lys Asn Thr
1370                1375                1380

Met Ile Leu Glu Ile Cys Thr Arg Tyr Arg Gly Asp Gln Asp Ala
    1385                1390                1395

Thr Met Ser Ile Leu Asp Ile Ser Met Met Thr Gly Phe Ala Pro
1400                1405                1410

Asp Thr Asp Asp Leu Lys Gln Leu Ala Asn Gly Val Asp Arg Tyr
    1415                1420                1425

Ile Ser Lys Tyr Glu Leu Asp Lys Ala Phe Ser Asp Arg Asn Thr
1430                1435                1440

Leu Ile Ile Tyr Leu Asp Lys Val Ser His Ser Glu Asp Asp Cys
    1445                1450                1455

Leu Ala Phe Lys Val His Gln Tyr Phe Asn Val Glu Leu Ile Gln
1460                1465                1470

Pro Gly Ala Val Lys Val Tyr Ala Tyr Tyr Asn Leu Glu Glu Ser
    1475                1480                1485

Cys Thr Arg Phe Tyr His Pro Glu Lys Glu Asp Gly Lys Leu Asn
1490                1495                1500

Lys Leu Cys Arg Asp Glu Leu Cys Arg Cys Ala Glu Glu Asn Cys
    1505                1510                1515

Phe Ile Gln Lys Ser Asp Asp Lys Val Thr Leu Glu Glu Arg Leu
1520                1525                1530

Asp Lys Ala Cys Glu Pro Gly Val Asp Tyr Val Tyr Lys Thr Arg
    1535                1540                1545

Leu Val Lys Val Gln Leu Ser Asn Asp Phe Asp Glu Tyr Ile Met
1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
1580                1585                1590

Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
1640                1645                1650

Glu Ser Met Val Val Phe Gly Cys Pro Asn
    1655                1660

<210> SEQ ID NO 10
<211> LENGTH: 5101
<212> TYPE: DNA
<213> ORGANISM: Homo sapiens

<400> SEQUENCE: 10
cactcctccc catcctctcc ctctgtccct ctgtccctct gaccctgcac tgtcccagca      60
ccatgggacc cacctcaggt cccagcctgc tgctcctgct actaacccac ctcccccctgg     120 ctctggggag tccatgtac tctatcatca ccccaacat cttgcggctg gagagcgagg       180
agaccatggt gctggaggcc cacgacgcgc aaggggatgt tccagtcact gttactgtcc     240
```

```
acgacttccc aggcaaaaaa ctagtgctgt ccagtgagaa gactgtgctg acccctgcca    300
ccaaccacat gggcaacgtc accttcacga tcccagccaa cagggagttc aagtcagaaa    360
aggggcgcaa caagttcgtg accgtgcagg ccaccttcgg gacccaagtg gtggagaagg    420
tggtgctggt cagcctgcag agcgggtacc tcttcatcca gacagacaag accatctaca    480
cccctggctc cacagttctc tatcggatct tcaccgtcaa ccacaagctg ctacccgtgg    540 gccgacggt catggtcaac attgagaacc cggaaggcat cccggtcaag caggactcct    600
tgtcttctca gaaccagctt ggcgtcttgc ccttgtcttg gacattccg gaactcgtca    660 acatgggcca gtggaagatc cgagcctact atgaaaactc accacagcag gtcttctcca    720
ctgagtttga ggtgaaggag tacgtgctgc ccagtttcga ggtcatagtg gagcctacag    780
agaaattcta ctacatctat aacgagaagg gcctggaggt caccatcacc gccaggttcc    840
tctacgggaa gaaagtggag ggaactgcct ttgtcatctt cgggatccag gatggcgaac    900
agaggatttc cctgcctgaa tccctcaagc gcattccgat tgaggatggc tcggggggagg    960 ttgtgctgag ccggaaggta ctgctggacg gggtgcagaa cccccgagca gaagacctgg   1020
tggggaagtc tttgtacgtg tctgccaccg tcatcttgca ctcaggcagt gacatggtgc   1080
aggcagagcg cagcgggatc cccatcgtga cctctcccta ccagatccac ttcaccaaga   1140
cacccaagta cttcaaacca ggaatgcct ttgacctcat ggtgttcgtg acgaaccctg   1200
atggctctcc agcctaccga gtccccgtgg cagtccaggg cgaggacact gtgcagtctc   1260
taacccaggg agatggcgtg gccaaactca gcatcaacac acaccccagc cagaagccct   1320
tgagcatcac ggtgcgcacg aagaagcagg agctctcgga ggcagagcag gctaccagga   1380
ccatgcaggc tctgccctac agcaccgtgg gcaactccaa caattacctg catctctcag   1440
tgctacgtac agagctcaga cccggggaga ccctcaacgt caacttcctc ctgcgaatgg   1500
accgcgccca cgaggccaag atccgctact acacctacct gatcatgaac aagggcaggc   1560
tgttgaaggc gggacgccag gtgcgagagc ccggccagga cctggtggtg ctgccctgt   1620 ccatcaccac cgacttcatc ccttccttcc gcctggtggc gtactacacg ctgatcggtg   1680
ccagcggcca gagggaggtg gtggccgact ccgtgtgggt ggacgtcaag gactcctgcg   1740
tgggctcgct ggtggtaaaa agcggccagt cagaagaccg gcagcctgta cctgggcagc   1800
agatgaccct gaagatagag ggtgaccacg ggccccgggt ggtactggtg gccgtggaca   1860
agggcgtgtt cgtgctgaat aagaagaaca aactgacgca gagtaagatc tgggacgtgg   1920
tggagaaggc agacatcggc tgcaccccgg gcagtgggaa ggattacgcc ggtgtcttct   1980
ccgacgcagg gctgaccttc acgagcagca gtggccagca gaccgcccag agggcagaac   2040
ttcagtgccc gcagccagcc gcccgccgac gccgttccgt gcagctcacg gagaagcgaa   2100
tggacaaagt cggcaagtac cccaaggagc tgcgcaagtg ctgcgaggac ggcatgcggg   2160
agaaccccat gaggttctcg tgccagcgcc ggacccgttt catctcccctg ggcgaggcgt   2220 gcaagaaggt cttcctggac tgctgcaact acatcacaga gctgcggcgg cagcacgcgc   2280
gggccagcca cctgggcctg gccaggagta acctggatga ggacatcatt gcagaagaga   2340
acatcgtttc ccgaagtgag ttcccagaga gctggctgtg gaacgttgag gacttgaaag   2400
agccaccgaa aaatggaatc tctacgaagc tcatgaatat attttttgaaa gactccatca   2460 ccacgtggga gattctggct gtgagcatgt cggacaagaa agggatctgt gtggcagacc   2520
ccttcgaggt cacagtaatg caggacttct tcatcgacct gcggctaccc tactctgttg   2580
ttcgaaacga gcaggtggaa atccgagccg ttctctacaa ttaccggcag aaccaagagc   2640
```

```
tcaaggtgag ggtggaacta ctccacaatc cagccttctg cagcctggcc accaccaaga    2700
ggcgtcacca gcagaccgta accatccccc ccaagtcctc gttgtccgtt ccatatgtca    2760
tcgtgccgct aaagaccggc ctgcaggaag tggaagtcaa ggctgctgtc taccatcatt    2820
tcatcagtga cggtgtcagg aagtccctga aggtcgtgcc ggaaggaatc agaatgaaca    2880
aaactgtggc tgttcgcacc ctggatccag aacgcctggg ccgtgaagga gtgcagaaag    2940
aggacatccc acctgcagac ctcagtgacc aagtcccgga caccgagtct gagaccagaa    3000
ttctcctgca agggacccca gtggcccaga tgacagagga tgccgtcgac gcggaacggc    3060
tgaagcacct cattgtgacc ccctcgggct gcggggaaca aacatgatc ggcatgacgc     3120 ccacggtcat cgctgtgcat tacctggatg aaacggagca gtgggagaag ttcggcctag    3180
agaagcggca gggggccttg gagctcatca agaaggggta cacccagcag ctggccttca    3240
gacaacccag ctctgccttt gcggccttcg tgaaacgggc acccagcacc tggctgaccg    3300
cctacgtggt caaggtcttc tctctggctg tcaacctcat cgccatcgac tcccaagtcc    3360 tctgcgggc tgttaaatgg ctgatcctgg agaagcagaa gcccgacggg gtcttccagg     3420
aggatgcgcc cgtgatacac caagaaatga ttggtggatt acggaacaac aacgagaaag    3480
acatggccct cacggccttt gttctcatct cgctgcagga ggctaaagat atttgcgagg    3540
agcaggtcaa cagcctgcca ggcagcatca ctaaagcagg agacttcctt gaagccaact    3600
acatgaacct acagagatcc tacactgtgg ccattgctgg ctatgctctg cccagatgg    3660 gcaggctgaa ggggcctctt cttaacaaat ttctgaccac agccaaagat aagaaccgct    3720
gggaggaccc tggtaagcag ctctacaacg tggaggccac atcctatgcc ctcttggccc    3780
tactgcagct aaaagacttt gactttgtgc ctcccgtcgt gcgttggctc aatgaacaga    3840
gatactacgg tggtggctat ggctctaccc aggccaccct catggtgttc caagccttgg    3900
ctcaatacca aaaggacgcc cctgaccacc aggaactgaa ccttgatgtg tccctccaac    3960
tgcccagccg cagctccaag atcacccacc gtatccactg gaatctgcc agcctcctgc     4020 gatcagaaga gaccaaggaa aatgagggtt tcacagtcac agctgaagga aaaggccaag    4080
gcaccttgtc ggtggtgaca atgtaccatg ctaaggccaa agatcaactc acctgtaata    4140
aattcgacct caaggtcacc ataaaaccag caccggaaac agaaaagagg cctcaggatg    4200
ccaagaacac tatgatcctt gagatctgta ccaggtaccg gggagaccag gatgccacta    4260
tgtctatatt ggacatatcc atgatgactg gctttgctcc agacacagat gacctgaagc    4320
agctggccaa tggtgttgac agatacatct ccaagtatga gctggacaaa gccttctccg    4380
ataggaacac cctcatcatc tacctggaca aggtctcaca ctctgaggat gactgtctag    4440 cttttcaaagt tcaccaatac tttaatgtag agcttatcca gcctggagca gtcaaggtct    4500
acgcctatta caacctggag gaaagctgta cccggttcta ccatccggaa aaggaggatg    4560
gaaagctgaa caagctctgc cgtgatgaac tgtgccgctg tgctgaggag aattgcttca    4620
tacaaaagtc ggatgacaag gtcaccctgg aagaacggct ggacaaggcc tgtgagccag    4680
gagtggacta tgtgtacaag acccgactgg tcaaggttca gctgtccaat gactttgacg    4740
agtacatcat ggccattgag cagaccatca agtcaggctc ggatgaggtg caggttggac    4800
agcagcgcac gttcatcagc cccatcaagt gcagagaagc cctgaagctg gaggagaaga    4860
aacactacct catgtggggt ctctcctccg atttctgggg agagaagccc aacctcagct    4920
acatcatcgg gaaggacact tgggtggagc actggcccga ggaggacgaa tgccaagacg    4980
```

```
aagagaacca gaaacaatgc caggacctcg gcgccttcac cgagagcatg gttgtctttg    5040
ggtgccccaa ctgaccacac ccccattccc ccactccaga taaagcttca gttatatctc    5100
a                                                                    5101
```

<210> SEQ ID NO 11
<211> LENGTH: 99
<212> TYPE: PRT
<213> ORGANISM: Homo sapiens

<400> SEQUENCE: 11

```
Met Lys Val Ser Ala Ala Leu Leu Cys Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

<210> SEQ ID NO 12
<211> LENGTH: 760
<212> TYPE: DNA
<213> ORGANISM: Homo sapiens

<400> SEQUENCE: 12

```
gaggaaccga gaggctgaga ctaacccaga acatccaat tctcaaactg aagctcgcac      60
tctcgcctcc agcatgaaag tctctgccgc ccttctgtgc ctgctgctca tagcagccac    120
cttcattccc caagggctcg ctcagccaga tgcaatcaat gccccagtca cctgctgtta    180
taacttcacc aataggaaga tctcagtgca gaggctcgcg agctatagaa gaatcaccag    240
cagcaagtgt cccaaagaag ctgtgatctt caagaccatt gtggccaagg agatctgtgc    300
tgaccccaag cagaagtggg ttcaggattc catggaccac ctggacaagc aaacccaaac    360
tccgaagact tgaacactca ctccacaacc caagaatctg cagctaactt attttcccct    420
agctttcccc agacaccctg ttttatttta ttataatgaa ttttgtttgt tgatgtgaaa    480
cattatgcct taagtaatgt taattcttat ttaagttatt gatgttttaa gtttatcttt    540
catggtacta gtgttttta gatacagaga cttggggaaa ttgcttttcc tcttgaacca    600
cagttctacc cctgggatgt tttgagggtc tttgcaagaa tcattaatac aaagaatttt    660
ttttaacatt ccaatgcatt gctaaaatat tattgtggaa atgaatattt tgtaactatt    720
acaccaaata aatatatttt tgtacaaaaa aaaaaaaaaa                          760
```

<210> SEQ ID NO 13
<211> LENGTH: 1065
<212> TYPE: PRT
<213> ORGANISM: Homo sapiens

<400> SEQUENCE: 13

```
Met Lys Ile Leu Ile Leu Gly Ile Phe Leu Phe Leu Cys Ser Thr Pro
1               5                   10                  15
```

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
        35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140

Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
            180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
            340                 345                 350

Gln Val Gln Glu Cys Asn Lys Ser Ser Lys Asp Asn Ile Arg Gly
        355                 360                 365

Lys His Val Arg His Tyr Tyr Ile Ala Ala Glu Ile Ile Trp Asn
    370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
            420                 425                 430

Phe Thr Asn Arg Lys Glu Arg Gly Pro Glu Glu Glu His Leu Gly Ile

```
                435                 440                 445
Leu Gly Pro Val Ile Trp Ala Glu Val Gly Asp Thr Ile Arg Val Thr
450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
                500                 505                 510

Glu Thr Phe Thr Tyr Glu Trp Thr Val Pro Lys Glu Val Gly Pro Thr
                515                 520                 525

Asn Ala Asp Pro Val Cys Leu Ala Lys Met Tyr Tyr Ser Ala Val Asp
530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
                565                 570                 575

Glu Phe Tyr Leu Phe Pro Thr Val Phe Asp Glu Asn Glu Ser Leu Leu
                580                 585                 590

Leu Glu Asp Asn Ile Arg Met Phe Thr Thr Ala Pro Asp Gln Val Asp
                595                 600                 605

Lys Glu Asp Glu Asp Phe Gln Glu Ser Asn Lys Met His Ser Met Asn
610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
                645                 650                 655

Gly Ile Tyr Phe Ser Gly Asn Thr Tyr Leu Trp Arg Gly Glu Arg Arg
                660                 665                 670

Asp Thr Ala Asn Leu Phe Pro Gln Thr Ser Leu Thr Leu His Met Trp
                675                 680                 685

Pro Asp Thr Glu Gly Thr Phe Asn Val Glu Cys Leu Thr Thr Asp His
690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
                725                 730                 735

Ala Ala Val Glu Val Glu Trp Asp Tyr Ser Pro Gln Arg Glu Trp Glu
                740                 745                 750

Lys Glu Leu His His Leu Gln Glu Gln Asn Val Ser Asn Ala Phe Leu
                755                 760                 765

Asp Lys Gly Glu Phe Tyr Ile Gly Ser Lys Tyr Lys Lys Val Val Tyr
                770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                805                 810                 815

Gly Asp Lys Val Lys Ile Ile Phe Lys Asn Met Ala Thr Arg Pro Tyr
                820                 825                 830

Ser Ile His Ala His Gly Val Gln Thr Glu Ser Ser Thr Val Thr Pro
                835                 840                 845

Thr Leu Pro Gly Glu Thr Leu Thr Tyr Val Trp Lys Ile Pro Glu Arg
850                 855                 860
```

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
            885                 890                 895

Leu Ile Val Cys Arg Arg Pro Tyr Leu Lys Val Phe Asn Pro Arg Arg
        900                 905                 910

Lys Leu Glu Phe Ala Leu Leu Phe Leu Val Phe Asp Glu Asn Glu Ser
            915                 920                 925

Trp Tyr Leu Asp Asp Asn Ile Lys Thr Tyr Ser Asp His Pro Glu Lys
        930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
            965                 970                 975

Gly Asp Glu Val Asn Trp Tyr Leu Met Gly Met Gly Asn Glu Ile Asp
        980                 985                 990

Leu His Thr Val His Phe His Gly His Ser Phe Gln Tyr Lys His Arg
            995                1000                1005

Gly Val Tyr Ser Ser Asp Val Phe Asp Ile Phe Pro Gly Thr Tyr
        1010                1015                1020

Gln Thr Leu Glu Met Phe Pro Arg Thr Pro Gly Ile Trp Leu Leu
        1025                1030                1035

His Cys His Val Thr Asp His Ile His Ala Gly Met Glu Thr Thr
        1040                1045                1050

Tyr Thr Val Leu Gln Asn Glu Asp Thr Lys Ser Gly
        1055                1060                1065

<210> SEQ ID NO 14
<211> LENGTH: 4674
<212> TYPE: DNA
<213> ORGANISM: Homo sapiens

<400> SEQUENCE: 14
acaccctaat gcctccaaca ataactgttg acttttatt ttcagtcaga gaagcctggc      60
aaccaagaac tgttttttg gtggtttacg agaacttaac tgaattggaa aatatttgct    120
ttaatgaaac aatttactct tgtgcaacac taaattgtgt caatcaagca ataaggaag    180 aaagtcttat ttataaaatt gcctgctcct gattttactt catttcttct caggctccaa   240 gaagggaaa aaaatgaaga ttttgatact tggtatttt ctgtttttat gtagtacccc     300
agcctgggcg aaagaaaagc attattacat tggaattatt gaaacgactt gggattatgc   360
ctctgaccat ggggaaaaga aacttatttc tgttgacacg aacattcca atatctatct    420 tcaaaatggc ccagatagaa ttgggagact atataagaag gccctttatc ttcagtacac    480
agatgaaacc tttaggacaa ctatagaaaa accggtctgg cttgggtttt taggccctat   540
tatcaaagct gaaactggag ataaagttta tgtacactta aaaaaccttg cctctaggcc   600
ctacaccttt cattcacatg gaataactta ctataaggaa catgaggggg ccatctaccc   660
tgataacacc acagattttc aaagagcaga tgacaaagta tatccaggag agcagtatac   720
atacatgttg cttgccactg aagaacaaag tcctggggaa ggagatggca attgtgtgac   780
taggatttac cattcccaca tgatgctcc aaagatatt gcctcaggac tcatcggacc    840
tttaataatc tgtaaaaaag attctctaga taaagaaaaa gaaaaacata ttgaccgaga   900
atttgtggtg atgttttctg tggtggatga aaatttcagc tggtacctag aagacaacat   960

```
taaaacctac tgctcagaac cagagaaagt tgacaaagac aacgaagact tccaggagag    1020
taacagaatg tattctgtga atggatacac ttttggaagt ctcccaggac tctccatgtg    1080
tgctgaagac agagtaaaat ggtacctttt tggtatgggt aatgaagttg atgtgcacgc    1140
agctttcttt cacgggcaag cactgactaa caagaactac cgtattgaca caatcaacct    1200
ctttcctgct accctgtttg atgcttatat ggtggcccag aaccctggag aatggatgct    1260
cagctgtcag aatctaaacc atctgaaagc cggtttgcaa gccttttttcc aggtccagga    1320 gtgtaacaag tcttcatcaa aggataatat ccgtgggaag catgttagac actactacat    1380
tgccgctgag gaaatcatct ggaactatgc tccctctggt atagacatct tcactaaaga    1440
aaacttaaca gcacctggaa gtgactcagc ggtgttttt gaacaaggta ccacaagaat    1500
tggaggctct tataaaaagc tggtttatcg tgagtacaca gatgcctcct tcacaaatcg    1560
aaaggagaga ggccctgaag aagagcatct tggcatcctg ggtcctgtca tttgggcaga    1620
ggtgggagac accatcagag taaccttcca taacaaagga gcatatcccc tcagtattga    1680
gccgattggg gtgagattca ataagaacaa cgagggcaca tactattccc caaattacaa    1740
cccccagagc agaagtgtgc ctccttcagc ctcccatgtg gcacccacag aaacattcac    1800
ctatgaatgg actgtcccca agaagtagg acccactaat gcagatcctg tgtgtctagc    1860
taagatgtat tattctgctg tggatcccac taaagatata ttcactgggc ttattgggcc    1920
aatgaaaata tgcaagaaag gaagtttaca tgcaaatggg agacagaaag atgtagacaa    1980
ggaattctat ttgtttccta cagtatttga tgagaatgag agtttactcc tggaagataa    2040
tattagaatg tttacaactg cacctgatca ggtggataag gaagatgaag actttcagga    2100
atctaataaa atgcactcca tgaatggatt catgtatggg aatcagccgg gtctcactat    2160
gtgcaaagga gattcggtcg tgtggtactt attcagcgcc ggaaatgagg ccgatgtaca    2220
tggaatatac ttttcaggaa acacatatct gtggagagga gaacgagag acacagcaaa    2280 cctcttccct caaacaagtc ttacgctcca catgtggcct gacacagagg ggacttttaa    2340
tgttgaatgc cttacaactg atcattacac aggcggcatg aagcaaaaat atactgtgaa    2400
ccaatgcagg cggcagtctg aggattccac cttctacctg ggagagagga catactatat    2460
cgcagcagtg gaggtggaat gggattattc cccacaaagg gagtgggaaa aggagctgca    2520
tcatttacaa gagcagaatg tttcaaatgc attttagat aagggagagt tttacatagg    2580
ctcaaagtac aagaaagttg tgtatcggca gtatactgat agcacattcc gtgttccagt    2640
ggagagaaaa gctgaagaag aacatctggg aattctaggt ccacaacttc atgcagatgt    2700
tggagacaaa gtcaaaatta tctttaaaaa catggccaca aggccctact caatacatgc    2760
ccatggggta caaacagaga gttctacagt tactccaaca ttaccaggtg aaactctcac    2820
ttacgtatgg aaaatcccag aaagatctgg agctggaaca gaggattctg cttgtattcc    2880
atgggcttat tattcaactg tggatcaagt taaggacctc tacagtggat taattggccc    2940
cctgattgtt tgtcgaagac cttacttgaa agtattcaat cccagaagga aactggaatt    3000
tgcccttctg tttctagttt ttgatgagaa tgaatcttgg tacttagatg acaacatcaa    3060
aacatactct gatcaccccg agaaagtaaa caaagatgat gaggaattca tagaaagcaa    3120
taaaatgcat gctattaatg aagaatgtt tggaaaccta caaggcctca caatgcacgt    3180
gggagatgaa gtcaactggt atctgatggg aatgggcaat gaaatagact acacactgt    3240 acattttcac ggccatagct tccaatacaa gcacaggga gtttatagtt ctgatgtctt    3300
```

-continued

```
tgacattttc cctggaacat accaaaccct agaaatgttt ccaagaacac ctggaatttg    3360
gttactccac tgccatgtga ccgaccacat tcatgctgga atggaaacca cttacaccgt    3420
tctacaaaat gaagacacca aatctggctg aatgaaataa attggtgata agtggaaaaa    3480
agagaaaaac caatgattca taacaatgta tgtgaaagtg taaaatagaa tgttactttg    3540
gaatgactat aaacattaaa agaagactgg aagcatacaa ctttgtacat ttgtggggga    3600
aaactattaa tttttttgcaa atggaaagat caacagacta taatgata catgactgac    3660 acttgtacac taggtaataa aactgattca tacagtctaa tgatatcacc gctgttaggg    3720
ttttataaaa ctgcatttaa aaaaagatct atgaccagat attctcctgg gtgctcctca    3780
aaggaacact attaaggttc attgaaatgt tttcaatcat tgccttccca ttgatccttc    3840
taacatgctg ttgacatcac acctaatatt cagagggaat gggcaaggta tgagggaagg    3900
aaataaaaaa taaaataaat aaaatagaat gacacaaatt tgagttttgt gaacccctga    3960
acagatggtc ttaaggacgt tatctggaac tggagaaaag cagagttgag agacaattct    4020
atagattaaa tcctggtaag gacaaacatt gccattagaa gaaaagcttc aaaatagacc    4080
tgtggcagat gtcacatgag tagaatttct gcccagcctt aactgcattc agaggataat    4140
atcaatgaac taaacttgaa ctaaaaattt tttaaacaaa aagttataaa tgaagacaca    4200
tggttgtgaa tacaatgatg tatttctta ttttcacata cactctagct aaaagagcaa    4260
gagtacacat caacaaaaat ggaaacaagg ctttggctga aaaaaacatg catttgacaa    4320
atcatgttaa tagctagaca agaagaaagt tagctttgta aacttctact tcatttgatt    4380
cagagaaaca gagcatgagt tttcttaaaa gtaacaagaa aaggaacaaa aaaaatgagg    4440
tttgaaatct tttaccatgg caaaacatta acatctttct caaaaacata gagaaatctg    4500
gaaaaatcaa gaagataaaa ttctggacca gttagtgaca ttctttcaag catacttgta    4560 aaatgttttcc ttaaagtgtt cttgggatga aaatgattgt catgtctcca acaacagtga    4620
actgatgttg ttccttggaa taaaagtcaa tccccacctt aaaaaaaaaa aaaa           4674
```

<210> SEQ ID NO 15
<211> LENGTH: 114
<212> TYPE: PRT
<213> ORGANISM: Homo sapiens

<400> SEQUENCE: 15

```
Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly
            20                  25                  30

Pro Ile Ala Ser Ala Gly Pro Ala Ala Ala Val Leu Arg Glu Leu Arg
        35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn
```

<210> SEQ ID NO 16

<211> LENGTH: 2475
<212> TYPE: DNA
<213> ORGANISM: Homo sapiens

<400> SEQUENCE: 16

```
gtgcagaagg cacgaggaag ccacagtgct ccggatcctc caatcttcgc tcctccaatc      60
tccgctcctc cacccagttc aggaacccgc daccgctcgc agcgctctct tgaccactat     120
gagcctcctg tccagccgcg cggcccgtgt ccccggtcct tcgagctcct tgtgcgcgct     180
gttggtgctg ctgctgctgc tgacgcagcc agggcccatc gccagcgctg tcctgccgc      240
tgctgtgttg agagagctgc gttgcgtttg tttacagacc acgcaaggag ttcatcccaa     300
aatgatcagt aatctgcaag tgttcgccat aggcccacag tgctccaagg tggaagtggt     360
agcctccctg aagaacggga aggaaatttg tcttgatcca gaagcccctt ttctaaagaa     420
agtcatccag aaaattttgg acggtggaaa caaggaaaac tgattaagag aaatgagcac     480
gcatggaaaa gtttcccagt cttcagcaga gaagttttct ggaggtctct gaacccaggg     540
aagacaagaa ggaaagattt tgttgttgtt tgtttatttg ttttttccagt agttagcttt     600
cttcctggat tcctcacttt gaagagtgtg aggaaaacct atgtttgccg cttaagcttt     660
cagctcagct aatgaagtgt ttagcatagt acctctgcta tttgctgtta ttttatctgc     720
tatgctattg aagttttggc aattgactat agtgtgagcc aggaatcact ggctgttaat     780
cttttcaaagt gtcttgaatt gtaggtgact attatattc caagaaatat tccttaagat     840
attaactgag aaggctgtgg atttaatgtg gaaatgatgt tcataagaa ttctgttgat      900
ggaaatacac tgttatcttc acttttataa gaaataggaa atattttaat gtttcttggg     960
gaatatgtta gagaatttcc ttactcttga ttgtgggata ctatttaatt atttcacttt    1020
agaaagctga gtgtttcaca ccttatctat gtagaatata tttccttatt cagaatttct    1080
aaaagtttaa gttctatgag ggctaatatc ttatcttcct ataattttag acattcttta    1140
tcttttttagt atggcaaact gccatcattt acttttaaac tttgatttta tatgctattt    1200
attaagtatt ttattaggag taccataatt ctggtagcta aatatatatt ttagatagat    1260
gaagaagcta gaaaacaggc aaattcctga ctgctagttt atatagaaat gtattctttt    1320
agttttttaaa gtaaaggcaa acttaacaat gacttgtact ctgaaagttt tggaaacgta    1380
ttcaaacaat ttgaatataa atttatcatt tagttataaa aatatatagc gacatcctcg    1440
aggccctagc atttctcctt ggatagggga ccagagagag cttggaatgt taaaaacaaa    1500
acaaaacaaa aaaaaacaag gagaagttgt ccaagggatg tcaatttttt atccctctgt    1560
atgggttaga ttttccaaaa tcataatttg aagaaggcca gcatttatgg tagaatatat    1620
aattatatat aaggtggcca cgctgggca agttccctcc ccactcacag ctttggcccc    1680
tttcacagag tagaacctgg gttagaggat tgcagaagac gagcggcagc ggggagggca    1740
gggaagatgc ctgtcgggtt tttagcacag ttcatttcac tgggattttg aagcatttct    1800
gtctgaatgt aaagcctgtt ctagtcctgg tgggacacac tggggttggg ggtgggggaa    1860
gatgcggtaa tgaaaccggt tagtcagtgt tgtcttaata tccttgataa tgctgtaaag    1920
tttatttta caaatatttc tgtttaagct atttcacctt tgtttggaaa tccttcccctt    1980
ttaaagagaa aatgtgacac ttgtgaaaag gcttgtagga aagctcctcc cttttttttct    2040
ttaaaccttt aaatgacaaa cctaggtaat taatggttgt gaattctat ttttgctttg     2100
tttttaatga acatttgtct ttcagaatag gattctgtga taatatttaa atggcaaaaa    2160
caaaacataa ttttgtgcaa ttaacaaagc tactgcaaga aaaataaaac atttcttggt    2220
```

-continued

```
aaaaacgtat gtatttatat attatatatt tatatataat atatattata tatttagcat    2280
tgctgagctt tttagatgcc tattgtgtat cttttaaagg ttttgaccat tttgttatga    2340
gtaattacat atatattaca ttcactatat taaaattgta ctttttttact atgtgtctca    2400 ttggttcata gtctttattt tgtcctttga ataaacatta aaagatttct aaacttcaaa    2460
aaaaaaaaaa aaaaa                                                     2475
```

<210> SEQ ID NO 17
<211> LENGTH: 266
<212> TYPE: PRT
<213> ORGANISM: Homo sapiens

<400> SEQUENCE: 17

```
Met Arg Val Thr Leu Ala Thr Ile Ala Trp Met Val Ser Phe Val Ser
1               5                   10                  15

Asn Tyr Ser His Thr Ala Asn Ile Leu Pro Asp Ile Glu Asn Glu Asp
            20                  25                  30

Phe Ile Lys Asp Cys Val Arg Ile His Asn Lys Phe Arg Ser Glu Val
        35                  40                  45

Lys Pro Thr Ala Ser Asp Met Leu Tyr Met Thr Trp Asp Pro Ala Leu
    50                  55                  60

Ala Gln Ile Ala Lys Ala Trp Ala Ser Asn Cys Gln Phe Ser His Asn
65                  70                  75                  80

Thr Arg Leu Lys Pro Pro His Lys Leu His Pro Asn Phe Thr Ser Leu
                85                  90                  95

Gly Glu Asn Ile Trp Thr Gly Ser Val Pro Ile Phe Ser Val Ser Ser
            100                 105                 110

Ala Ile Thr Asn Trp Tyr Asp Glu Ile Gln Asp Tyr Asp Phe Lys Thr
        115                 120                 125

Arg Ile Cys Lys Lys Val Cys Gly His Tyr Thr Gln Val Val Trp Ala
    130                 135                 140

Asp Ser Tyr Lys Val Gly Cys Ala Val Gln Phe Cys Pro Lys Val Ser
145                 150                 155                 160

Gly Phe Asp Ala Leu Ser Asn Gly Ala His Phe Ile Cys Asn Tyr Gly
                165                 170                 175

Pro Gly Gly Asn Tyr Pro Thr Trp Pro Tyr Lys Arg Gly Ala Thr Cys
            180                 185                 190

Ser Ala Cys Pro Asn Asn Asp Lys Cys Leu Asp Asn Leu Cys Val Asn
        195                 200                 205

Arg Gln Arg Asp Gln Val Lys Arg Tyr Tyr Ser Val Val Tyr Pro Gly
    210                 215                 220

Trp Pro Ile Tyr Pro Arg Asn Arg Tyr Thr Ser Leu Phe Leu Ile Val
225                 230                 235                 240

Asn Ser Val Ile Leu Ile Leu Ser Val Ile Ile Thr Ile Leu Val Gln
                245                 250                 255

His Lys Tyr Pro Asn Leu Val Leu Leu Asp
            260                 265
```

<210> SEQ ID NO 18
<211> LENGTH: 3924
<212> TYPE: DNA
<213> ORGANISM: Homo sapiens

<400> SEQUENCE: 18

```
agtgatgaac tcatgctctg ttctgttttc tcaaagctga agtcggctag gtttgcaaag    60
```

```
ctgtgggctg agcactcagg caatcacact ctcagaaact gcggcggctc tggactgcag    120
cctcccaagg ctccatgcca gacaaagcat gcgtgtcaca cttgctacaa tagcctggat    180
ggtttctttt gtctccaatt attcacacac agcaaatatt ttgccagata tcgaaaatga    240
agatttcatc aaagactgcg ttcgaatcca taacaagttc cgatcagagg tgaaaccaac    300
agccagtgat atgctataca tgacttggga cccagcacta gcccaaattg caaaagcatg    360
ggccagcaat tgccagtttt cacataatac acggctgaag ccaccccaca agctgcaccc    420
aaacttcact tcactgggag agaacatctg gactgggtct gtgcccattt tttctgtgtc    480
ttccgccatc acaaactggt atgacgaaat ccaggactat gacttcaaga ctcggatatg    540
caaaaaagtc tgtggccact acactcaggt tgtttgggca gatagttaca agttggctg     600 cgcagttcaa ttttgcccta agtttctgg ctttgacgct ctttccaatg gagcacattt      660
tatatgcaac tacgaccag gagggaatta cccaacttgg ccatataaga gaggagccac      720
ctgcagtgcc tgccccaata tgacaagtg tttggacaat ctctgtgtta accgacagcg      780
agaccaagtc aaacgttact actctgttgt atatccaggc tgcccatat atccacgtaa      840 cagatacact tctctctttc tcattgttaa ttcagtaatt ctaatactgt ctgttataat      900
taccattttg gtacagcaca agtaccctaa tttagttctt ttggactaat acaattcagg     960
aaagaaaaaa cccaaaaacc aacctcattc acatatggct ttttttttaa ccaataacaa    1020
ttaggtgtac ttctatttta aaacatttca gaaaaaaata tatgttatag caatactctt    1080
actcaaaaga gaaatttcc taactctatc agataaactc atctttagta taaataagca     1140
ttatttgcag gttgccacag gtggactttt agtaagtaac ctaacccatg tttcagcttc    1200
taaatctgca aaatgagcaa ggtacagtag cacatttta ggtgattctt agtaactcca     1260
gtagccttca ttagttaaaa acattattat tttttgcatg ctgcttcgac tctaaatatc    1320
tggttttccc tgtcttttg gtttactact tccccagatt cagaacagag gagtaactag     1380
gggatctgat tttagaggcc ttaattttct gttcatggac tgttaaaagt aaaaccaaac    1440
tttcaaaagg gataaaccta aatatttact tgttatcatt agagagggaa catcaaatgc    1500
tgggacatca ttactaacca atagcatcag acactggatt taatggataa tcacaatggt    1560
cgtaatgtat acaaagactt atataccact ttctcgtata aattttttcaa aaaatacaat   1620 aataatataa tttataaaga acactcttct atgaacaacc accaccacca aaaaaaaaaa   1680 aagcccctcag aaaatttctc acaaataagg caactaatgc ctgatatctc aaaatccttt   1740
acaaaaggag atagttctag tcaaggagtt ttgggtatgt tacttttttt tcttctttt     1800 cttttcatct gcctccatct taagtgcaat ttcttcagct gtaagagctc ccagtttctt    1860
attctttgct ttcttaacct tttccttgat gctggccaca tcaattttag tttcagtaga   1920
agctagacaa attaaaagca caacacatgt aatactttag attttaccaa gtaaaacaaa   1980
gaatatatgt ttaacaaaga atatatgttt aaggcagtta acttcagagt attcttataa   2040
ttgaataatt gaaaggtgat cacagtataa aatataaaaa cacttgccta aagcagttag    2100
aaatttcttc agattaagat aaaacaaatc ataaaatact ttatatatta gtacaagtat    2160
acataaaaat ggcataaatg gcataattga accaattact ggattcaact atattaagac    2220
tatttcctta aatcctactt cagactaaat tattttacct acattctttt ccatattttg    2280
gaacttctga gtcattattt tccatcttgc acattaaaat aatttaaaat tacatgtatc    2340
ccttctcaat aagtttaatc agctaaccct aagctagagg tcaaaatcta cttcctctaa    2400
```

```
tatcaaaacg aaaatttaaa gttttccaaa tattaattca atattaattg aatattcaat    2460
gaattaattc atttaatgtt agattaattc attgaatatt aattcaatga atgactaatt    2520
aatagtattt taacaagatt ttggtatatt taacaacatt ttggtaataa agacaataat    2580
ttgagagtgt gtggaagtcc ccctaataga agccaactat ctaatcaatg ccaaaagtgt    2640
gaacaaaata gagaaaggaa gcagtgaaaa agaatgcaac ttttcttac cattcaaagt     2700 acaggatcac agcataaaag aatcataaga taaacatca aactacccag caacctgaga     2760
agcacagagt gttaaagcct ccaccgtgtg gagaaactaa attagggtaa ctagctattg    2820
agtatattga gtaccttcaa agcactcaac tgacaggttt tacagactgg aaattataat    2880
acttatgaca tttctacctt ttatataacc aataatctac catagaatgt agtattttta    2940
aagctattaa caagcaatat attaaaataa taatgtatta tatctgtttc tgacccagtc    3000
tatgtacaat attgctggtg agccctctcc cttcagtgtg tcactgttca ctttggaggg    3060
ttactttagg aagaggataa gtgttaccac aggggaaaaa aatgcagaag aggatgcatc    3120
agaagaaatg gcatgacaat gttttctctt agtgtctttt aaatactagg ttagtgcgaa    3180
agtgatttct gccatttaaa aaccacaatc actttcgcac taatagctcc tgaataagac    3240
ctgtcagcat cctttagtct aaggtgatga gaaatccatg ttaccgatat agaagccaaa    3300
ctctaagcca agatcacata aagagaagaa aaagtacaac ttctgataat tcctctttga    3360
gaggcatgac agcagagctc agggatcttc ttgcatttct acagaagatg cactggctgc    3420
cctgggtttg tatctttcac aacaaagagt cttttccaag cacagaccag aggtcaggag    3480
aggactgtca atccagtttg cactgaaata ggcattagct gcctctaaat tataaattat    3540
ctcagccatc ccttgtcctt aggattagta attaatgaaa tgctaagaga actgatgaaa    3600
agatacaact gtttcttaaa aagattcaga caaatttatt atgggtttac ttttcctaat    3660
taataaagac ttttacatca tagaaagcat taccttcctt aggtttcaca attggttttt    3720
ccttaggtgg aataaatgct ttgtttcttt cctcttgtct cttactgatg gcttctgctt    3780
gtttagccta cattaataaa taaaaaatat atcagttaaa tgtatttata gttaaataat    3840
tcaagtatct atgaactttg ctattcatgt gagccagaca taaagtgccg tacctttatt    3900
gcttccaaaa aaaaaaaaaa aaaa                                           3924
```

<210> SEQ ID NO 19
<211> LENGTH: 297
<212> TYPE: PRT
<213> ORGANISM: Homo sapiens

<400> SEQUENCE: 19

```
Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
```

```
            100                 105                 110
Leu Cys Val Asn Ala Ser Ala Val Ser Arg Leu Arg Ala Tyr Leu Leu
            115                 120                 125
Pro Ala Pro Ala Pro Gly Glu Pro Ala Pro Gly Asn Ala Ser
        130                 135                 140
Glu Ser Glu Glu Asp Arg Ser Ala Gly Ser Val Glu Ser Pro Ser Val
145                 150                 155                 160
Ser Ser Thr His Arg Val Ser Asp Pro Lys Phe His Pro Leu His Ser
                165                 170                 175
Lys Ile Ile Ile Ile Lys Lys Gly His Ala Lys Asp Ser Gln Arg Tyr
                180                 185                 190
Lys Val Asp Tyr Glu Ser Gln Ser Thr Asp Thr Gln Asn Phe Ser Ser
                195                 200                 205
Glu Ser Lys Arg Glu Thr Glu Tyr Gly Pro Cys Arg Arg Glu Met Glu
            210                 215                 220
Asp Thr Leu Asn His Leu Lys Phe Leu Asn Val Leu Ser Pro Arg Gly
225                 230                 235                 240
Val His Ile Pro Asn Cys Asp Lys Lys Gly Phe Tyr Lys Lys Lys Gln
                245                 250                 255
Cys Arg Pro Ser Lys Gly Arg Lys Arg Gly Phe Cys Trp Cys Val Asp
                260                 265                 270
Lys Tyr Gly Gln Pro Leu Pro Gly Tyr Thr Thr Lys Gly Lys Glu Asp
                275                 280                 285
Val His Cys Tyr Ser Met Gln Ser Lys
            290                 295

<210> SEQ ID NO 20
<211> LENGTH: 264
<212> TYPE: PRT
<213> ORGANISM: Homo sapiens

<400> SEQUENCE: 20

Gly Ala Ser Ser Ala Gly Leu Gly Pro Val Val Arg Cys Glu Pro Cys
1               5                   10                  15
Asp Ala Arg Ala Leu Ala Gln Cys Ala Pro Pro Ala Val Cys Ala
                20                  25                  30
Glu Leu Val Arg Glu Pro Gly Cys Gly Cys Cys Leu Thr Cys Ala Leu
            35                  40                  45
Ser Glu Gly Gln Pro Cys Gly Ile Tyr Thr Glu Arg Cys Gly Ser Gly
        50                  55                  60
Leu Arg Cys Gln Pro Ser Pro Asp Glu Ala Arg Pro Leu Gln Ala Leu
65                  70                  75                  80
Leu Asp Gly Arg Gly Leu Cys Val Asn Ala Ser Ala Val Ser Arg Leu
                85                  90                  95
Arg Ala Tyr Leu Leu Pro Ala Pro Pro Ala Pro Gly Asn Ala Ser Glu
                100                 105                 110
Ser Glu Glu Asp Arg Ser Ala Gly Glu Val Glu Ser Pro Ser Val Ser
            115                 120                 125
Ser Thr His Arg Val Ser Asp Pro Lys Phe His Pro Leu His Ser Lys
        130                 135                 140
Ile Ile Ile Ile Lys Lys Gly His Ala Lys Asp Ser Gln Arg Tyr Lys
145                 150                 155                 160
Val Asp Tyr Glu Ser Gln Ser Thr Asp Thr Gln Asn Phe Ser Ser Glu
                165                 170                 175
```

```
Ser Lys Arg Glu Thr Glu Tyr Gly Pro Cys Arg Arg Glu Met Glu Asp
            180                 185                 190

Thr Leu Asn His Leu Lys Phe Leu Asn Val Leu Ser Pro Arg Gly Val
        195                 200                 205

His Ile Pro Asn Cys Asp Lys Lys Gly Phe Tyr Lys Lys Lys Gln Cys
        210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
            260

<210> SEQ ID NO 21
<211> LENGTH: 2638
<212> TYPE: DNA
<213> ORGANISM: Homo sapiens

<400> SEQUENCE: 21
```

| | | | | | |
|---|---|---|---|---|---|
| agatgcgagc | actgcggctg | ggcgctgagg | atcagccgct | tcctgcctgg | attccacagc | 60 |
| ttcgcgccgt | gtactgtcgc | cccatccctg | cgcgcccagc | ctgccaagca | gcgtgccccg | 120 |
| gttgcaggcg | tcatgcagcg | ggcgcgaccc | acgctctggg | ccgctgcgct | gactctgctg | 180 |
| gtgctgctcc | gcgggccgcc | ggtggcgcgg | gctggcgcga | gctcggcggg | cttgggtccc | 240 |
| gtggtgcgct | gcgagccgtg | cgacgcgcgt | gcactggccc | agtgcgcgcc | tccgcccgcc | 300 |
| gtgtgcgcg | agctggtgcg | cgagccgggc | tgcggctgct | gcctgacgtg | cgcactgagc | 360 |
| gagggccagc | cgtgcggcat | ctacaccgag | cgctgtggct | ccggccttcg | ctgccagccg | 420 |
| tcgcccgacg | aggcgcgacc | gctgcaggcg | ctgctggacg | gccgcgggct | ctgcgtcaac | 480 |
| gctagtgccg | tcagccgcct | gcgcgcctac | ctgctgccag | cgccgccagc | tccaggtgag | 540 |
| ccgcccgcgc | aggaaatgc | tagtgagtcg | gaggaagacc | gcagcgccgg | cagtgtggag | 600 |
| agcccgtccg | tctccagcac | gcaccgggtg | tctgatccca | gttccacccc | ctccattca | 660 |
| aagataatca | tcatcaagaa | agggcatgct | aaagacagcc | agcgctacaa | agttgactac | 720 |
| gagtctcaga | gcacagatac | ccagaacttc | tcctccgagt | ccaagcggga | gacagaatat | 780 |
| ggtccctgcc | gtagagaaat | ggaagacaca | ctgaatcacc | tgaagttcct | caatgtgctg | 840 |
| agtcccaggg | gtgtacacat | tcccaactgt | gacaagaagg | gatttatata | aaaagcag | 900 |
| tgtcgccctt | ccaaaggcag | gaagcgggc | ttctgctggt | gtgtggataa | gtatgggcag | 960 |
| cctctcccag | gctacaccac | caaggggaag | gaggacgtgc | actgctacag | catgcagagc | 1020 |
| aagtagacgc | ctgccgcaag | gttaatgtgg | agctcaaata | tgccttattt | tgcacaaaag | 1080 |
| actgccaagg | acatgaccag | cagctggcta | cagcctcgat | ttatatttct | gtttgtggtg | 1140 |
| aactgatttt | ttttaaacca | aagtttagaa | agaggttttt | gaaatgccta | tggtttcttt | 1200 |
| gaatggtaaa | cttgagcatc | ttttcacttt | ccagtagtca | gcaaagagca | gtttgaattt | 1260 |
| tcttgtcgct | tccatcaaa | atattcagag | actcgagcac | agcacccaga | cttcatgcgc | 1320 |
| ccgtggaatg | ctcaccacat | gttggtcgaa | gcggccgacc | actgactttg | tgacttaggc | 1380 |
| ggctgtgttg | cctatgtaga | aacacgctt | caccccact | ccccgtacag | tgcgcacagg | 1440 |
| ctttatcgag | aataggaaaa | cctttaaacc | ccggtcatcc | ggacatccca | acgcatgctc | 1500 |
| ctggagctca | cagccttctg | tggtgtcatt | tctgaaacaa | gggcgtggat | ccctcaacca | 1560 |
| agaagaatgt | ttatgtcttc | aagtgacctg | tactgcttgg | ggactattgg | agaaaataag | 1620 |

-continued

```
gtggagtcct acttgtttaa aaaatatgta tctaagaatg ttctagggca ctctgggaac    1680
ctataaaggc aggtatttcg ggccctcctc ttcaggaatc ttcctgaaga catggcccag    1740
tcgaaggccc aggatggctt ttgctgcggc cccgtggggt aggagggaca gagagacagg    1800
gagagtcagc ctccacattc agaggcatca caagtaatgg cacaattctt cggatgactg    1860
cagaaaatag tgttttgtag ttcaacaact caagacgaag cttatttctg aggataagct    1920 cttaaaggc aaagctttat tttcatctct catcttttgt cctccttagc acaatgtaaa     1980
aaagaatagt aatatcagaa caggaaggag gaatggcttg ctggggagcc catccaggac    2040
actgggagca catagagatt cacccatgtt tgttgaactt agagtcattc tcatgctttt    2100
ctttataatt cacacatata tgcagagaag atatgttctt gttaacattg tatacaacat    2160
agccccaaat atagtaagat ctatactaga taatcctaga tgaaatgtta gagatgctat    2220
atgatacaac tgtggccatg actgaggaaa ggagctcacg cccagagact gggctgctct    2280
cccggaggcc aaacccaaga aggtctggca aagtcaggct cagggagact ctgccctgct    2340
gcagacctcg gtgtggacac acgctgcata gagctctcct tgaaaacaga ggggtctcaa    2400
gacattctgc ctacctatta gcttttcttt attttttaa cttttggggg ggaaaagtat     2460
ttttgagaag tttgtcttgc aatgtattta taaatagtaa ataaagtttt taccattaaa    2520
aaaatatctt tcccttttgtt attgaccatc tctgggcttt gtatcactaa ttatttatt    2580 ttattatata ataattattt tattataata aaatcctgaa aggggaaaat aaaaaaaa     2638
```

<210> SEQ ID NO 22
<211> LENGTH: 240
<212> TYPE: PRT
<213> ORGANISM: Homo sapiens

<400> SEQUENCE: 22

```
Met Thr Pro His Arg Leu Leu Pro Pro Leu Leu Leu Leu Ala Leu
1               5                   10                  15

Leu Leu Ala Ala Ser Pro Gly Gly Ala Leu Ala Arg Cys Pro Gly Cys
            20                  25                  30

Gly Gln Gly Val Gln Ala Gly Cys Pro Gly Gly Cys Val Glu Glu
        35                  40                  45

Asp Gly Gly Ser Pro Ala Glu Gly Cys Ala Glu Ala Glu Gly Cys Leu
    50                  55                  60

Arg Arg Glu Gly Gln Glu Cys Gly Val Tyr Thr Pro Asn Cys Ala Pro
65                  70                  75                  80

Gly Leu Gln Cys His Pro Pro Lys Asp Asp Glu Ala Pro Leu Arg Ala
                85                  90                  95

Leu Leu Leu Gly Arg Gly Arg Cys Leu Pro Ala Arg Ala Pro Ala Val
            100                 105                 110

Ala Glu Glu Asn Pro Lys Glu Ser Lys Pro Gln Ala Gly Thr Ala Arg
        115                 120                 125

Pro Gln Asp Val Asn Arg Arg Asp Gln Gln Arg Asn Pro Gly Thr Ser
    130                 135                 140

Thr Thr Pro Ser Gln Pro Asn Ser Ala Gly Val Gln Asp Thr Glu Met
145                 150                 155                 160

Gly Pro Cys Arg Arg His Leu Asp Ser Val Leu Gln Leu Gln Thr
                165                 170                 175

Glu Val Tyr Arg Gly Ala Gln Thr Leu Tyr Val Pro Asn Cys Asp His
            180                 185                 190
```

```
Arg Gly Phe Tyr Arg Lys Arg Gln Cys Arg Ser Ser Gln Gly Gln Arg
            195                 200                 205

Arg Gly Pro Cys Trp Cys Val Asp Arg Met Gly Lys Ser Leu Pro Gly
            210                 215                 220

Ser Pro Asp Gly Asn Gly Ser Ser Ser Cys Pro Thr Gly Ser Ser Gly
225                 230                 235                 240

<210> SEQ ID NO 23
<211> LENGTH: 980
<212> TYPE: DNA
<213> ORGANISM: Homo sapiens

<400> SEQUENCE: 23
gcggcggcgg gcagcagctg cgctgcgact gctctggaag gagaggacgg ggcacaaacc      60
ctgaccatga ccccccacag gctgctgcca ccgctgctgc tgctgctagc tctgctgctc     120
gctgccagcc caggaggcgc cttggcgcgg tgcccaggct gcgggcaagg ggtgcaggcg     180
ggttgtccag ggggctgcgt ggaggaggag gatgggggt cgccagccga gggctgcgcg      240
gaagctgagg gctgtctcag gagggagggg caggagtgcg gggtctacac ccctaactgc     300
gccccaggac tgcagtgcca tccgcccaag gacgacgagg cgcctttgcg ggcgctgctg     360
ctcggccgag gccgctgcct tccggcccgc gcgcctgctg ttgcagagga gaatcctaag     420
gagagtaaac cccaagcagg cactgccgc ccacaggatg tgaaccgcag agaccaacag      480
aggaatccag gcacctctac cacgccctcc cagcccaatt ctgcgggtgt ccaagacact     540
gagatgggcc catgccgtag acatctggac tcagtgctgc agcaactcca gactgaggtc     600
taccgagggg ctcaaacact ctacgtgccc aattgtgacc atcgaggctt ctaccggaag     660
cggcagtgcc gctcctccca ggggcagcgc cgaggtccct gctggtgtgt ggatcggatg     720
ggcaagtccc tgccagggtc tccagatggc aatggaagct cctcctgccc cactgggagt     780
agcggctaaa gctgggggat agaggggctg caggccact ggaaggaaca tggagctgtc      840
atcactcaac aaaaaaccga ggccctcaat ccaccttcag gccccgcccc atgggcccct     900
caccgctggt tggaaagagt gttggtgttg gctgggtgt caataaagct gtgcttgggg      960
tcgctgaaaa aaaaaaaaaa                                                 980

<210> SEQ ID NO 24
<211> LENGTH: 271
<212> TYPE: PRT
<213> ORGANISM: Homo sapiens

<400> SEQUENCE: 24

Met Ala Lys Val Pro Asp Met Phe Glu Asp Leu Lys Asn Cys Tyr Ser
1               5                   10                  15

Glu Asn Glu Glu Asp Ser Ser Ile Asp His Leu Ser Leu Asn Gln
            20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
        50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110
```

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
        130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
                180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
        210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 25
<211> LENGTH: 159
<212> TYPE: PRT
<213> ORGANISM: Homo sapiens

<400> SEQUENCE: 25

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Leu His Asn Leu
        35                  40                  45

Asp Glu Ala Val Lys Phe Asp Met Gly Ala Tyr Lys Ser Ser Lys Asp
50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

<210> SEQ ID NO 26
<211> LENGTH: 2943
<212> TYPE: DNA
<213> ORGANISM: Homo sapiens

<400> SEQUENCE: 26
accaggcaac accattgaag gctcatatgt aaaaatccat gccttccttt ctcccaatct    60

-continued

```
ccattcccaa acttagccac tggcttctgg ctgaggcctt acgcatacct cccgggcttt    120
gcacacacct tcttctacag aagacacacc ttgggcatat cctacagaag accaggcttc    180
tctctggtcc ttggtagagg gctactttac tgtaacaggg ccagggtgga gagttctctc    240
ctgaagctcc atcccctcta taggaaatgt gttgacaata ttcagaagag taagaggatc    300
aagacttctt tgtgctcaaa taccactgtt ctcttctcta ccctgcccta accaggagct    360
tgtcacccca aactctgagg tgatttatgc cttaatcaag caaacttccc tcttcagaaa    420
agatggctca ttttccctca aaagttgcca ggagctgcca agtattctgc caattcaccc    480
tggagcacaa tcaacaaatt cagccagaac acaactacag ctactattag aactattatt    540
attaataaat tcctctccaa atctagcccc ttgacttcgg atttcacgat ttctcccttc    600
ctcctagaaa cttgataagt ttcccgcgct tccctttttc taagactaca tgtttgtcat    660
cttataaagc aaagggtgaa ataaatgaac caaatcaata acttctggaa tatctgcaaa    720
caacaataat atcagctatg ccatctttca ctattttagc cagtatcgag ttgaatgaac    780
atagaaaaat acaaaactga attcttccct gtaaattccc cgttttgacg acgcacttgt    840
agccacgtag ccacgcctac ttaagacaat tacaaaaggc gaagaagact gactcaggct    900
taagctgcca gccagagagg gagtcatttc attggcgttt gagtcagcaa agaagtcaag    960
atggccaaag ttccagacat gtttgaagac ctgaagaact gttacagtga aaatgaagaa   1020
gacagttcct ccattgatca tctgtctctg aatcagaaat ccttctatca tgtaagctat   1080
ggcccactcc atgaaggctg catggatcaa tctgtgtctc tgagtatctc tgaaacctct   1140
aaaacatcca agcttacctt caaggagagc atggtggtag tagcaaccaa cgggaaggtt   1200
ctgaagaaga gacggttgag tttaagccaa tccatcactg atgatgacct ggaggccatc   1260
gccaatgact cagaggaaga aatcatcaag cctaggtcag caccttttag cttcctgagc   1320
aatgtgaaat acaactttat gaggatcatc aaatacgaat tcatcctgaa tgacgccctc   1380
aatcaaagta taattcgagc caatgatcag tacctcacgg ctgctgcatt acataatctg   1440
gatgaagcag tgaaatttga catgggtgct tataagtcat caaaggatga tgctaaaatt   1500
accgtgattc taagaatctc aaaaactcaa ttgtatgtga ctgcccaaga tgaagaccaa   1560
ccagtgctgc tgaaggagat gcctgagata cccaaaacca tcacaggtag tgagaccaac   1620
ctcctcttct tctgggaaac tcacggcact aagaactatt tcacatcagt tgcccatcca   1680
aacttgttta ttgccacaaa gcaagactac tgggtgtgct tggcaggggg gccaccctct   1740
atcactgact ttcagatact ggaaaaccag gcgtaggtct ggagtctcac ttgtctcact   1800
tgtgcagtgt tgacagttca tatgtaccat gtacatgaag aagctaaatc ctttactgtt   1860
agtcatttgc tgagcatgta ctgagccttg taattctaaa tgaatgttta cactcttttgt   1920
aagagtggaa ccaacactaa catataatgt tgttatttaa agaacaccct atattttgca   1980
tagtaccaat cattttaatt attattcttc ataacaattt taggaggacc agagctactg   2040
actatggcta ccaaaaagac tctacccata ttacagatgg gcaaattaag gcataagaaa   2100
actaagaaat atgcacaata gcagttgaaa caagaagcca cagacctagg atttcatgat   2160
ttcatttcaa ctgtttgcct tctacttttta agttgctgat gaactcttaa tcaaatagca   2220
taagtttctg ggacctcagt tttatcattt tcaaaatgga gggaataata cctaagcctt   2280
cctgccgcaa cagttttttta tgctaatcag ggaggtcatt ttggtaaaat acttcttgaa   2340
gccgagcctc aagatgaagg caaagcacga aatgttattt tttaattatt atttatatat   2400
gtatttataa atatatttaa gataattata atatactata tttatgggaa cccttcatc   2460
```

| | |
|---|---|
| ctctgagtgt gaccaggcat cctccacaat agcagacagt gttttctggg ataagtaagt | 2520 |
| ttgatttcat taatacaggg cattttggtc caagttgtgc ttatcccata gccaggaaac | 2580 |
| tctgcattct agtacttggg agacctgtaa tcatataata aatgtacatt aattaccttg | 2640 |
| agccagtaat tggtccgatc tttgactctt ttgccattaa acttacctgg cattcttgt | 2700 |
| ttcaattcca cctgcaatca agtcctacaa gctaaaatta gatgaactca actttgacaa | 2760 |
| ccatgagacc actgttatca aactttctt ttctggaatg taatcaatgt ttcttctagg | 2820 |
| ttctaaaaat tgtgatcaga ccataatgtt acattattat caacaatagt gattgataga | 2880 |
| gtgttatcag tcataactaa ataaagcttg caacaaaatt ctctgacaaa aaaaaaaaa | 2940 |
| aaa | 2943 |

<210> SEQ ID NO 27
<211> LENGTH: 135
<212> TYPE: PRT
<213> ORGANISM: Homo sapiens

<400> SEQUENCE: 27

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135
```

<210> SEQ ID NO 28
<211> LENGTH: 586
<212> TYPE: DNA
<213> ORGANISM: Homo sapiens

<400> SEQUENCE: 28

| | |
|---|---|
| agttaaaagg gtgggagcgt ccgggggccc atctctctcg ggtggagtct tctgacagct | 60 |
| ggtgcgcctg cccgggaaca tcctcctgga ctcaatcatg gcttgtggtc tggtcgccag | 120 |
| caacctgaat ctcaaacctg gagagtgcct tcgagtgcga ggcgaggtgg ctcctgacgc | 180 |
| taagagcttc gtgctgaacc tgggcaaaga cagcaacaac ctgtgcctgc acttcaaccc | 240 |
| tcgcttcaac gcccacggcg acgccaacac catcgtgtgc aacagcaagg acggcggggc | 300 |
| ctgggggacc gagcagcggg aggctgtctt tcccttccag cctggaagtg ttgcagaggt | 360 |
| gtgcatcacc ttcgaccagg ccaacctgac cgtcaagctg ccagatggat acgaattcaa | 420 |
| gttccccaac cgcctcaacc tggaggccat caactacatg gcagctgacg gtgacttcaa | 480 |
| gatcaaatgt gtggcctttg actgaaatca gccagcccat ggcccccaat aaaggcagct | 540 |

-continued gcctctgctc cctctgaaaa aaaaaaaaaa aaaaaaaaaa aaaaaa                586

<210> SEQ ID NO 29
<211> LENGTH: 1721
<212> TYPE: PRT
<213> ORGANISM: Homo sapiens

<400> SEQUENCE: 29

```
Met Ala Gly Ala Trp Leu Arg Trp Gly Leu Leu Leu Trp Ala Gly Leu
1               5                   10                  15

Leu Ala Ser Ser Ala His Gly Arg Leu Arg Arg Ile Thr Tyr Val Val
            20                  25                  30

His Pro Gly Pro Gly Leu Ala Ala Gly Ala Leu Pro Leu Ser Gly Pro
        35                  40                  45

Pro Arg Ser Arg Thr Phe Asn Val Ala Leu Asn Ala Arg Tyr Ser Arg
    50                  55                  60

Ser Ser Ala Ala Gly Ala Pro Ser Arg Ala Ser Pro Gly Val Pro
65                  70                  75                  80

Ser Glu Arg Thr Arg Arg Thr Ser Lys Pro Gly Gly Ala Ala Leu Gln
                85                  90                  95

Gly Leu Arg Pro Pro Pro Pro Pro Glu Pro Ala Arg Pro Ala
            100                 105                 110

Val Pro Gly Gly Gln Leu His Pro Asn Pro Gly His Pro Ala Ala
            115                 120                 125

Ala Pro Phe Thr Lys Gln Gly Arg Gln Val Val Arg Ser Lys Val Pro
        130                 135                 140

Gln Glu Thr Gln Ser Gly Gly Ser Arg Leu Gln Val His Gln Lys
145                 150                 155                 160

Gln Gln Leu Gln Gly Val Asn Val Cys Gly Arg Cys Cys His Gly
                165                 170                 175

Trp Ser Lys Ala Pro Gly Ser Gln Arg Cys Thr Lys Pro Ser Cys Val
            180                 185                 190

Pro Pro Cys Gln Asn Gly Gly Met Cys Leu Arg Pro Gln Leu Cys Val
        195                 200                 205

Cys Lys Pro Gly Thr Lys Gly Lys Ala Cys Glu Thr Ile Ala Ala Gln
    210                 215                 220

Asp Thr Ser Ser Pro Val Phe Gly Gly Gln Ser Pro Gly Ala Ala Ser
225                 230                 235                 240

Ser Trp Gly Pro Pro Glu Gln Ala Ala Lys His Thr Ser Ser Lys Lys
                245                 250                 255

Ala Asp Thr Leu Pro Arg Val Ser Pro Val Ala Gln Met Thr Leu Thr
            260                 265                 270

Leu Lys Pro Lys Pro Ser Val Gly Leu Pro Gln Gln Ile His Ser Gln
        275                 280                 285

Val Thr Pro Leu Ser Ser Gln Ser Val Val Ile His His Gly Gln Thr
    290                 295                 300

Gln Glu Tyr Val Leu Lys Pro Lys Tyr Phe Pro Ala Gln Lys Gly Ile
305                 310                 315                 320

Ser Gly Glu Gln Ser Thr Glu Gly Ser Phe Pro Leu Arg Tyr Val Gln
                325                 330                 335

Asp Gln Val Ala Ala Pro Phe Gln Leu Ser Asn His Thr Gly Arg Ile
            340                 345                 350

Lys Val Val Phe Thr Pro Ser Ile Cys Lys Val Thr Cys Thr Lys Gly
        355                 360                 365
```

```
Ser Cys Gln Asn Ser Cys Glu Lys Gly Asn Thr Thr Thr Leu Ile Ser
    370                 375                 380

Glu Asn Gly His Ala Ala Asp Thr Leu Thr Ala Thr Asn Phe Arg Val
385                 390                 395                 400

Val Ile Cys His Leu Pro Cys Met Asn Gly Gln Cys Ser Ser Arg
                405                 410                 415

Asp Lys Cys Gln Cys Pro Pro Asn Phe Thr Gly Lys Leu Cys Gln Ile
            420                 425                 430

Pro Val His Gly Ala Ser Val Pro Lys Leu Tyr Gln His Ser Gln Gln
                435                 440                 445

Pro Gly Lys Ala Leu Gly Thr His Val Ile His Ser Thr His Thr Leu
    450                 455                 460

Pro Leu Thr Val Thr Ser Gln Gln Gly Val Lys Val Lys Phe Pro Pro
465                 470                 475                 480

Asn Ile Val Asn Ile His Val Lys His Pro Glu Ala Ser Val Gln
                485                 490                 495

Ile His Gln Val Ser Arg Ile Asp Gly Pro Thr Gly Gln Lys Thr Lys
                500                 505                 510

Glu Ala Gln Pro Gly Gln Ser Gln Val Ser Tyr Gln Gly Leu Pro Val
    515                 520                 525

Gln Lys Thr Gln Thr Ile His Ser Thr Tyr Ser His Gln Gln Val Ile
    530                 535                 540

Pro His Val Tyr Pro Val Ala Ala Lys Thr Gln Leu Gly Arg Cys Phe
545                 550                 555                 560

Gln Glu Thr Ile Gly Ser Gln Cys Gly Lys Ala Leu Pro Gly Leu Ser
                565                 570                 575

Lys Gln Glu Asp Cys Cys Gly Thr Val Gly Thr Ser Trp Gly Phe Asn
            580                 585                 590

Lys Cys Gln Lys Cys Pro Lys Lys Pro Ser Tyr His Gly Tyr Asn Gln
            595                 600                 605

Met Met Glu Cys Leu Pro Gly Tyr Lys Arg Val Asn Asn Thr Phe Cys
    610                 615                 620

Gln Asp Ile Asn Glu Cys Gln Leu Gln Gly Val Cys Pro Asn Gly Glu
625                 630                 635                 640

Cys Leu Asn Thr Met Gly Ser Tyr Arg Cys Thr Cys Lys Ile Gly Phe
                645                 650                 655

Gly Pro Asp Pro Thr Phe Ser Ser Cys Val Pro Asp Pro Val Ile
            660                 665                 670

Ser Glu Glu Lys Gly Pro Cys Tyr Arg Leu Val Ser Ser Gly Arg Gln
    675                 680                 685

Cys Met His Pro Leu Ser Val His Leu Thr Lys Gln Leu Cys Cys Cys
    690                 695                 700

Ser Val Gly Lys Ala Trp Gly Pro His Cys Glu Lys Cys Pro Leu Pro
705                 710                 715                 720

Gly Thr Ala Ala Phe Lys Glu Ile Cys Pro Gly Gly Met Gly Tyr Thr
                725                 730                 735

Val Ser Gly Val His Arg Arg Arg Pro Ile His His His Val Gly Lys
            740                 745                 750

Gly Pro Val Phe Val Lys Pro Lys Asn Thr Gln Pro Val Ala Lys Ser
    755                 760                 765

Thr His Pro Pro Pro Leu Pro Ala Lys Glu Glu Pro Val Glu Ala Leu
    770                 775                 780
```

```
Thr Phe Ser Arg Glu His Gly Pro Gly Val Ala Glu Pro Glu Val Ala
785                 790                 795                 800

Thr Ala Pro Pro Glu Lys Glu Ile Pro Ser Leu Asp Gln Glu Lys Thr
                805                 810                 815

Lys Leu Glu Pro Gly Gln Pro Gln Leu Ser Pro Gly Ile Ser Thr Ile
                820                 825                 830

His Leu His Pro Gln Phe Pro Val Val Ile Glu Lys Thr Ser Pro Pro
            835                 840                 845

Val Pro Val Glu Val Ala Pro Glu Ala Ser Thr Ser Ser Ala Ser Gln
850                 855                 860

Val Ile Ala Pro Thr Gln Val Thr Glu Ile Asn Glu Cys Thr Val Asn
865                 870                 875                 880

Pro Asp Ile Cys Gly Ala Gly His Cys Ile Asn Leu Pro Val Arg Tyr
                885                 890                 895

Thr Cys Ile Cys Tyr Glu Gly Tyr Arg Phe Ser Glu Gln Gln Arg Lys
                900                 905                 910

Cys Val Asp Ile Asp Glu Cys Thr Gln Val Gln His Leu Cys Ser Gln
                915                 920                 925

Gly Arg Cys Glu Asn Thr Glu Gly Ser Phe Leu Cys Ile Cys Pro Ala
            930                 935                 940

Gly Phe Met Ala Ser Glu Glu Gly Thr Asn Cys Ile Asp Val Asp Glu
945                 950                 955                 960

Cys Leu Arg Pro Asp Val Cys Gly Glu Gly His Cys Val Asn Thr Val
                965                 970                 975

Gly Ala Phe Arg Cys Glu Tyr Cys Asp Ser Gly Tyr Arg Met Thr Gln
            980                 985                 990

Arg Gly Arg Cys Glu Asp Ile Asp  Glu Cys Leu Asn Pro  Ser Thr Cys
        995                 1000                 1005

Pro Asp  Glu Gln Cys Val Asn  Ser Pro Gly Ser Tyr  Gln Cys Val
    1010                 1015                 1020

Pro Cys  Thr Glu Gly Phe Arg  Gly Trp Asn Gly Gln  Cys Leu Asp
    1025                 1030                 1035

Val Asp  Glu Cys Leu Glu Pro  Asn Val Cys Ala Asn  Gly Asp Cys
    1040                 1045                 1050

Ser Asn  Leu Glu Gly Ser Tyr  Met Cys Ser Cys His  Lys Gly Tyr
    1055                 1060                 1065

Thr Arg  Thr Pro Asp His  Lys  His Cys Arg Asp Ile  Asp Glu Cys
    1070                 1075                 1080

Gln Gln  Gly Asn Leu Cys Val  Asn Gly Gln Cys Lys  Asn Thr Glu
    1085                 1090                 1095

Gly Ser  Phe Arg Cys Thr Cys  Gly Gln Gly Tyr Gln  Leu Ser Ala
    1100                 1105                 1110

Ala Lys  Asp Gln Cys Glu Asp  Ile Asp Glu Cys Gln  His Arg His
    1115                 1120                 1125

Leu Cys  Ala His Gly Gln Cys  Arg Asn Thr Glu Gly  Ser Phe Gln
    1130                 1135                 1140

Cys Val  Cys Asp Gln Gly Tyr  Arg Ala Ser Gly Leu  Gly Asp His
    1145                 1150                 1155

Cys Glu  Asp Ile Asn Glu Cys  Leu Glu Asp Lys Ser  Val Cys Gln
    1160                 1165                 1170

Arg Gly  Asp Cys Ile Asn Thr  Ala Gly Ser Tyr Asp  Cys Thr Cys
    1175                 1180                 1185

Pro Asp  Gly Phe Gln Leu Asp  Asp Asn Lys Thr Cys  Gln Asp Ile
```

```
                1190                1195                1200
Asn Glu Cys Glu His Pro Gly Leu Cys Gly Pro Gln Gly Glu Cys
    1205                1210                1215
Leu Asn Thr Glu Gly Ser Phe His Cys Val Cys Gln Gln Gly Phe
    1220                1225                1230
Ser Ile Ser Ala Asp Gly Arg Thr Cys Glu Asp Ile Asp Glu Cys
    1235                1240                1245
Val Asn Asn Thr Val Cys Asp Ser His Gly Phe Cys Asp Asn Thr
    1250                1255                1260
Ala Gly Ser Phe Arg Cys Leu Cys Tyr Gln Gly Phe Gln Ala Pro
    1265                1270                1275
Gln Asp Gly Gln Gly Cys Val Asp Val Asn Glu Cys Glu Leu Leu
    1280                1285                1290
Ser Gly Val Cys Gly Glu Ala Phe Cys Glu Asn Val Glu Gly Ser
    1295                1300                1305
Phe Leu Cys Val Cys Ala Asp Glu Asn Gln Glu Tyr Ser Pro Met
    1310                1315                1320
Thr Gly Gln Cys Arg Ser Arg Thr Ser Thr Asp Leu Asp Val Asp
    1325                1330                1335
Val Asp Gln Pro Lys Glu Glu Lys Lys Glu Cys Tyr Tyr Asn Leu
    1340                1345                1350
Asn Asp Ala Ser Leu Cys Asp Asn Val Leu Ala Pro Asn Val Thr
    1355                1360                1365
Lys Gln Glu Cys Cys Cys Thr Ser Gly Ala Gly Trp Gly Asp Asn
    1370                1375                1380
Cys Glu Ile Phe Pro Cys Pro Val Leu Gly Thr Ala Glu Phe Thr
    1385                1390                1395
Glu Met Cys Pro Lys Gly Lys Gly Phe Val Pro Ala Gly Glu Ser
    1400                1405                1410
Ser Ser Glu Ala Gly Gly Glu Asn Tyr Lys Asp Ala Asp Glu Cys
    1415                1420                1425
Leu Leu Phe Gly Gln Glu Ile Cys Lys Asn Gly Phe Cys Leu Asn
    1430                1435                1440
Thr Arg Pro Gly Tyr Glu Cys Tyr Cys Lys Gln Gly Thr Tyr Tyr
    1445                1450                1455
Asp Pro Val Lys Leu Gln Cys Phe Asp Met Asp Glu Cys Gln Asp
    1460                1465                1470
Pro Ser Ser Cys Ile Asp Gly Gln Cys Val Asn Thr Glu Gly Ser
    1475                1480                1485
Tyr Asn Cys Phe Cys Thr His Pro Met Val Leu Asp Ala Ser Glu
    1490                1495                1500
Lys Arg Cys Ile Arg Pro Ala Glu Ser Asn Glu Gln Ile Glu Glu
    1505                1510                1515
Thr Asp Val Tyr Gln Asp Leu Cys Trp Glu His Leu Ser Asp Glu
    1520                1525                1530
Tyr Val Cys Ser Arg Pro Leu Val Gly Lys Gln Thr Thr Tyr Thr
    1535                1540                1545
Glu Cys Cys Cys Leu Tyr Gly Glu Ala Trp Gly Met Gln Cys Ala
    1550                1555                1560
Leu Cys Pro Leu Lys Asp Ser Asp Asp Tyr Ala Gln Leu Cys Asn
    1565                1570                1575
Ile Pro Val Thr Gly Arg Arg Gln Pro Tyr Gly Arg Asp Ala Leu
    1580                1585                1590
```

Val Asp Phe Ser Glu Gln Tyr Thr Pro Glu Ala Asp Pro Tyr Phe
    1595                1600                1605

Ile Gln Asp Arg Phe Leu Asn Ser Phe Glu Glu Leu Gln Ala Glu
    1610                1615                1620

Glu Cys Gly Ile Leu Asn Gly Cys Glu Asn Gly Arg Cys Val Arg
    1625                1630                1635

Val Gln Glu Gly Tyr Thr Cys Asp Cys Phe Asp Gly Tyr His Leu
    1640                1645                1650

Asp Thr Ala Lys Met Thr Cys Val Asp Val Asn Glu Cys Asp Glu
    1655                1660                1665

Leu Asn Asn Arg Met Ser Leu Cys Lys Asn Ala Lys Cys Ile Asn
    1670                1675                1680

Thr Asp Gly Ser Tyr Lys Cys Leu Cys Leu Pro Gly Tyr Val Pro
    1685                1690                1695

Ser Asp Lys Pro Asn Tyr Cys Thr Pro Leu Asn Thr Ala Leu Asn
    1700                1705                1710

Leu Glu Lys Asp Ser Asp Leu Glu
    1715                1720

<210> SEQ ID NO 30
<211> LENGTH: 6168
<212> TYPE: DNA
<213> ORGANISM: Homo sapiens

<400> SEQUENCE: 30

```
ggtcgcgccc gctggggccc gcgatggcgg gggcctggct caggtggggg ctcctgctct    60
gggcagggct cctcgcgtcc tcggcgcacg gccggctgcg gaggatcacc tacgtggtgc   120
acccgggccc cggcctggca gccggcgcct tgccccctga gcgggccccg cgttcgcgga   180
cattcaacgt cgcgctcaac gccaggtaca gccgcagctc ggcggctgcc ggcgccccca   240
gccgtgcctc ccccggggtc ccctcggaga ggacccggcg cacgagcaag ccgggcggcg   300
cggccctgca ggggctcaga ccgccgccgc cgccgccgcc ggagcctgcg cgtcccgcgg   360
tccccggcgg gcagctccac cccaatcccg cggccaccc ggcagccgcc ccgttcacca   420
aacaaggcag gcaagttgtg cgctccaagg tgccgcagga gacccagagc ggcggaggct   480
ctaggctgca ggttcaccag aagcagcagc tgcagggggt caatgtctgt ggagggcggt   540
gctgtcatgg ctggagtaag gcccctggct cccagaggtg caccaaacct agctgtgttc   600
cgccatgtca gaatggaggg atgtgtctcc ggccacaact ctgtgtgtgt aaaccaggga   660
ccaagggcaa agcctgtgaa acaatagctg cccaggacac ctcgtcacca gtctttggag   720
ggcagagtcc tgggctgct tcctcgtggg gccctcctga gcaagcagca aagcatactt   780
catctaagaa ggcagacact ctaccaagag tcagccctgt ggcccagatg accttaaccc   840
tcaagccgaa gccttcagtg ggactccccc agcagataca ttctcaagtg actcctcttt   900
cttcccagag tgtggtgatt caccatggcc agacccagga tacgtgctc aagcccaagt   960 actttccagc ccagaagggg atttcaggag agcagtccac tgaaggttct ttcccttaa  1020 gatatgtgca ggatcaagtt gcggcacctt tcagctgag taaccacact ggccgcatca  1080
aggtggtctt tactccgagc atctgtaaag tgacctgcac caagggcagc tgtcagaaca  1140
gctgtgagaa ggggaacacc accactctca ttagtgagaa tggtcatgct gccgacaccc  1200
tgacggccac gaacttccga gtggtaattt gccatcttcc atgtatgaat ggtggccagt  1260
gcagttcaag ggacaaatgt cagtgccctc caaatttcac aggaaaactt tgtcagatcc  1320
```

```
cagtccatgg tgccagcgtg cctaaacttt atcagcattc ccagcagcca ggcaaggcgt    1380
tggggacgca tgtcatccat tcaacacata ccttgcctct gaccgtgact agccagcaag    1440
gagtcaaagt gaaatttcct cctaacatag tcaatatcca tgtgaaacat cctcctgaag    1500
cttccgtcca gatacatcag gtttcaagaa ttgatggccc aacaggccag aagacaaaag    1560
aagctcaacc aggccaatcc caagtctcgt accaagggct tcctgtccag aagacccaga    1620
ccatacattc cacatactcc caccagcagg tcattcctca cgtctacccc gtggctgcta    1680
agacacagct tggccggtgc ttccaggaaa ccattgggtc acagtgtggc aaagcgctcc    1740
ctggcctttc aaagcaagag gactgctgtg gaactgtggg tacctcctgg gctttaaca    1800 aatgccagaa atgccccaag aaaccatctt atcatggata caaccaaatg atggaatgcc    1860
taccgggtta taagcgggtt aacaacacct tttgccaaga tattaatgaa tgtcagctac    1920
aaggtgtatg ccctaatggt gagtgtttga ataccatggg cagctatcga tgtacctgca    1980
aaataggatt tgggccggat cctacctttt caagttgtgt tcctgatccc cctgtgatct    2040
cggaagagaa agggccctgt taccgacttg tcagttctgg aagacagtgt atgcaccctc    2100
tgtctgttca cctcaccaag cagctctgct gttgtagtgt gggcaaggcc tggggcccac    2160
actgtgagaa atgtccccct ccaggcacag ctgcttttaa ggaaatctgt cctggtggaa    2220
tgggttatac ggtttctggc gttcatagac gcaggccaat ccatcaccat gtaggtaaag    2280
gacctgtatt tgtcaagcca agaacactc aacctgttgc taaaagtact catcctccac    2340
ctctcccagc caaggaagag ccagtggagg ccctgacctt ctcccgggaa cacgggccag    2400
gagtggcgga gccagaagtg gcaactgcac cccctgaaaa ggaaatacct tcattggatc    2460
aagagaaaac caaacttgag cctggtcaac cccagctgtc tccaggcatt tccactattc    2520
atctgcatcc acagtttcca gtagtgattg aaaaaacatc acctcctgtg cctgttgaag    2580
tagctcctga agcttctacg tctagtgcca gccaagtgat tgctcctact caagtgacag    2640
aaatcaatga atgtactgtg aaccctgata tctgtggagc aggacactgc attaacctac    2700
cagtgagata tacctgtata tgctacgagg gctacaggtt cagtgaacaa cagaggaaat    2760
gtgtggatat tgatgagtgt actcaggtcc aacacctctg ctcccaggc cgctgtgaaa    2820 acaccgaggg aagtttcttg tgcatttgcc cagcaggatt tatggccagt gaggagggta    2880
ctaactgcat agatgttgac gaatgcctga ggccggacgt ctgtgggag gggcactgtg    2940 tcaatactgt gggggccttc cggtgtgaat actgtgacag cgggtaccgc atgactcaga    3000
gaggccgttg tgaggatatt gatgaatgtt tgaatccaag cacttgtcca gatgagcagt    3060
gtgtgaattc tcctggatct taccagtgcg ttccctgcac agaaggattc cgaggctgga    3120
atggacagtg ccttgatgtg gacgagtgcc tggaaccaaa cgtctgcgca aatggtgatt    3180
gttccaacct tgaaggctcc tacatgtgtt catgccacaa aggctatacc cggactccgg    3240
accacaagca ctgtagagat attgatgaat gtcagcaagg gaatctatgt gtaaacgggc    3300
agtgcaaaaa taccgagggc tccttcaggt gcacctgtgg acaggggtac cagctgtcgg    3360
cagctaaaga ccagtgtgaa gacattgatg aatgccagca ccgtcatctc tgtgctcatg    3420
ggcagtgcag gaacactgag ggctctttc aatgtgtgtg tgaccagggt tacagagcat    3480
ctgggcttgg agaccactgt gaagatatca tgaatgctt ggaggacaag agtgtttgcc    3540
agagaggaga ctgcattaat actgcagggt cctatgattg tacttgtccg gatggatttc    3600
agctagatga caataaaaca tgtcaagata ttaatgaatg tgaacatcca gggctctgtg    3660
```

-continued

```
gtccgcaagg ggagtgccta aacacagagg gttctttcca ttgtgtctgc cagcagggtt    3720
tctcaatctc tgcagatggc cgtacgtgtg aagatattga tgaatgtgta acaacactg     3780
tttgtgacag tcacgggttt tgtgacaata cagctggctc cttccgctgc ctctgttatc    3840
agggctttca agccccacag gatgggcaag ggtgtgtgga tgtgaatgaa tgtgaactgc    3900
tcagtggggt gtgtggtgaa gccttctgtg aaaacgtgga agggtccttc ctgtgcgtgt    3960
gtgctgatga aaaccaagag tacagcccca tgactgggca gtgccgctcc cggacctcca    4020
cagatttaga tgtagatgta gatcaaccca agaagaaaa gaaagaatgc tactataatc     4080
tcaatgacgc cagtctctgt gataatgtgt tggcccccaa tgtcacgaaa caagaatgct    4140
gctgtacatc aggcgcggga tggggagata actgcgaaat cttcccctgc ccggtcttgg    4200
gaactgctga gttcactgaa atgtgtccca aagggaaagg ttttgtgcct gctggagaat    4260
catcttctga agctggtggt gagaactata agatgcaga tgaatgccta cttttggac     4320
aagaaatctg caaaaatggt ttctgtttga acactcggcc tgggtatgaa tgctactgta    4380
agcaagggac gtactatgat cctgtgaaac tgcagtgctt tgatatggat gaatgtcaag    4440
accccagtag ttgtattgat ggccagtgtg ttaatacaga gggctcttac aactgcttct    4500
gtactcaccc catggtcctg gatgcgtcag aaaaagatg tatacgaccg gctgagtcaa    4560
acgaacaaat agaagaaact gatgtctacc aagatttgtg ctgggaacat ctgagtgatg    4620
aatacgtgtg tagccggcct cttgtgggca agcagacaac gtacactgag tgctgctgtc    4680
tgtatggaga ggcctggggc atgcagtgtg ccctctgccc cctgaaggat tcagatgact    4740
atgctcagct gtgtaacatc cccgtgacgg gacgccggca gccatatgga cgggacgcct    4800
tggttgactt cagtgaacag tatactccag aagccgatcc ctacttcatc caagaccgtt    4860
ttctaaatag ctttgaggag ttacaggctg aggaatgcgg catcctcaat ggatgtgaaa    4920
atggtcgctg tgtgagggtc caggaaggtt acacctgcga ttgctttgat gggtatcact    4980
tggatacggc caagatgacc tgtgtcgatg taaatgaatg cgatgagttg aacaaccgga    5040
tgtctctctg caagaatgcc aagtgcatta acaccgatgg ttcctacaag tgtttgtgtc    5100
tgccaggcta cgtgccttct gacaagccaa actactgcac tccgttgaat accgccttga    5160
atttagagaa agacagtgac ctggagtgaa acagaatcta cataacctaa gcccatatac    5220
tctgcactgt gtaaaggaaa agggagaaat gtattatact tgagacattg cacctacccc    5280
ggaaggctgg aaatacagaa acagcatgga attgcaagtc ctctgaagac aatgagagga    5340
tttaggatga gcccgatagg tgtggcagac caaatggaca tttctctaaa aaaccagtat    5400
atatagtctg ttcatatgta aaattcaatg gaagagaggt ggaacagtgc tgttattta    5460
aacagaaggt tgtattatta tgttgttttg ttttttact attgcttgat taaatttggc    5520
atttaaatag tggtggaaat atttatata attttcattt tttggttgtg cagttccttg    5580
gctactgttt ttctttact tcagttttt aaaaatctca aatgaaaaag tcttcgatac     5640
aatattgtta agctgtatta taagtattgt tacacagggt tatgcaattc ccggcctgga    5700
gcattttga aattcaaatt gtctgtcctg tggagcaggc agtgattttg ttccaaaact    5760
ttgtatacac atttggagaa aagtacttta tatttcagt gttttgtctg attttaatgt     5820
ccgttcttag ccaagctgct agcaggtgtt aattggatcc ctttccttca ctgaaatgga    5880
agagtttata agcttacgtt agtattgtaa tatgtaaagt aagcccaaca aaatttttta    5940
aaaatttgat gatccccaat atatctacca ttgtatgtta aataaatcac cattttgta     6000
gaaaaaattc tacctgagag taattgtcaa tgagtacatg tgtataagtt gtatcccact    6060
```

```
ctccccactt ttatcttttc cagtggtctt ctgttaatgt agtgtcttt acaagttaat    6120
cattaaattt gttagatctt gttatgggct aaaaaaaaaa aaaaaaaa                6168
```

<210> SEQ ID NO 31
<211> LENGTH: 114
<212> TYPE: PRT
<213> ORGANISM: Homo sapiens

<400> SEQUENCE: 31

```
Met Asn Val Leu Leu Gly Ser Val Val Ile Phe Ala Thr Phe Val Thr
1               5                   10                  15

Leu Cys Asn Ala Ser Cys Tyr Phe Ile Pro Asn Glu Gly Val Pro Gly
                20                  25                  30

Asp Ser Thr Arg Lys Cys Met Asp Leu Lys Gly Asn Lys His Pro Ile
            35                  40                  45

Asn Ser Glu Trp Gln Thr Asp Asn Cys Glu Thr Cys Thr Cys Tyr Glu
        50                  55                  60

Thr Glu Ile Ser Cys Cys Thr Leu Val Ser Thr Pro Val Gly Tyr Asp
65                  70                  75                  80

Lys Asp Asn Cys Gln Arg Ile Phe Lys Lys Glu Asp Cys Lys Tyr Ile
                85                  90                  95

Val Val Glu Lys Lys Asp Pro Lys Lys Thr Cys Ser Val Ser Glu Trp
            100                 105                 110

Ile Ile
```

<210> SEQ ID NO 32
<211> LENGTH: 76
<212> TYPE: PRT
<213> ORGANISM: Homo sapiens

<400> SEQUENCE: 32

```
Met Asn Val Leu Leu Gly Ser Val Val Ile Phe Ala Thr Phe Val Thr
1               5                   10                  15

Leu Cys Asn Ala Ser Cys Tyr Phe Ile Pro Asn Glu Gly Val Pro Gly
                20                  25                  30

Asp Ser Thr Arg Met Phe Leu His Leu Trp Val Met Thr Lys Thr Thr
            35                  40                  45

Ala Lys Glu Ser Ser Arg Arg Arg Thr Ala Ser Ile Ser Trp Trp Arg
        50                  55                  60

Arg Arg Thr Gln Lys Arg Pro Val Leu Ser Val Asn
65                  70                  75
```

<210> SEQ ID NO 33
<211> LENGTH: 503
<212> TYPE: DNA
<213> ORGANISM: Homo sapiens

<400> SEQUENCE: 33

```
gtacctgtct ataaggagtc ctgcttatca caatgaatgt tctcctgggc agcgttgtga     60
tctttgccac cttcgtgact ttatgcaatg catcatgcta tttcatacct aatgagggag    120
ttccaggaga ttcaaccagg aaatgcatgg atctcaaagg aaacaaacac ccaataaact    180
cggagtggca gactgacaac tgtgagacat gcacttgcta cgaaacagaa atttcatgtt    240
gcacccttgt ttctacacct gtgggttatg acaaagacaa ctgccaaaga atcttcaaga    300
aggaggactg caagtatatc gtggtggaga agaaggaccc aaaaaagacc tgttctgtca    360
```

```
gtgaatggat aatctaatgt gcttctagta ggcacagggc tcccaggcca ggcctcattc    420
tcctctggcc tctaatagtc aatgattgtg tagccatgcc tatcagtaaa aagatttttg    480
agcaaacact tgaaaaaaaa aaa                                            503
```

<210> SEQ ID NO 34
<211> LENGTH: 397
<212> TYPE: DNA
<213> ORGANISM: Homo sapiens

<400> SEQUENCE: 34

```
gtacctgtct ataaggagtc ctgcttatca caatgaatgt tctcctgggc agcgttgtga     60
tctttgccac cttcgtgact ttatgcaatg catcatgcta tttcatacct aatgagggag    120
ttccaggaga ttcaaccagg atgtttctac acctgtgggt tatgacaaag acaactgcca    180
aagaatcttc aagaaggagg actgcaagta tatcgtggtg gagaagaagg acccaaaaaa    240
gacctgttct gtcagtgaat ggataatcta atgtgcttct agtaggcaca gggctcccag    300
gccaggcctc attctcctct ggcctctaat agtcaatgat tgtgtagcca tgcctatcag    360
taaaaagatt tttgagcaaa cacttgaaaa aaaaaaa                             397
```

<210> SEQ ID NO 35
<211> LENGTH: 510
<212> TYPE: PRT
<213> ORGANISM: Homo sapiens

<400> SEQUENCE: 35

Met Arg Pro Gly Leu Ser Phe Leu Leu Ala Leu Leu Phe Phe Leu Gly
1               5                   10                  15

Gln Ala Ala Gly Asp Leu Gly Asp Val Gly Pro Ile Pro Ser Pro
        20                  25                  30

Gly Phe Ser Ser Phe Pro Gly Val Asp Ser Ser Ser Phe Ser Ser
        35                  40                  45

Ser Ser Arg Ser Gly Ser Ser Ser Arg Ser Leu Gly Ser Gly Gly
        50                  55                  60

Ser Val Ser Gln Leu Phe Ser Asn Phe Thr Gly Ser Val Asp Asp Arg
65                  70                  75                  80

Gly Thr Cys Gln Cys Ser Val Ser Leu Pro Asp Thr Thr Phe Pro Val
                85                  90                  95

Asp Arg Val Glu Arg Leu Glu Phe Thr Ala His Val Leu Ser Gln Lys
                100                 105                 110

Phe Glu Lys Glu Leu Ser Lys Val Arg Glu Tyr Val Gln Leu Ile Ser
                115                 120                 125

Val Tyr Glu Lys Lys Leu Leu Asn Leu Thr Val Arg Ile Asp Ile Met
        130                 135                 140

Glu Lys Asp Thr Ile Ser Tyr Thr Glu Leu Asp Phe Glu Leu Ile Lys
145                 150                 155                 160

Val Glu Val Lys Glu Met Glu Lys Leu Val Ile Gln Leu Lys Glu Ser
                165                 170                 175

Phe Gly Gly Ser Ser Glu Ile Val Asp Gln Leu Glu Val Glu Ile Arg
                180                 185                 190

Asn Met Thr Leu Leu Val Glu Lys Leu Glu Thr Leu Asp Lys Asn Asn
        195                 200                 205

Val Leu Ala Ile Arg Arg Glu Ile Val Ala Leu Lys Thr Lys Leu Lys
    210                 215                 220

Glu Cys Glu Ala Ser Lys Asp Gln Asn Thr Pro Val Val His Pro Pro

|  |  |  |  |  |  |  |  |  |  |  |  |
|---|---|---|---|---|---|---|---|---|---|---|---|
| 225 | | | | | 230 | | | | | 235 | 240 |

Pro Thr Pro Gly Ser Cys Gly His Gly Gly Val Val Asn Ile Ser Lys
                245                 250                 255

Pro Ser Val Val Gln Leu Asn Trp Arg Gly Phe Ser Tyr Leu Tyr Gly
            260                 265                 270

Ala Trp Gly Arg Asp Tyr Ser Pro Gln His Pro Asn Lys Gly Leu Tyr
        275                 280                 285

Trp Val Ala Pro Leu Asn Thr Asp Gly Arg Leu Leu Glu Tyr Tyr Arg
    290                 295                 300

Leu Tyr Asn Thr Leu Asp Asp Leu Leu Leu Tyr Ile Asn Ala Arg Glu
305                 310                 315                 320

Leu Arg Ile Thr Tyr Gly Gln Gly Ser Gly Thr Ala Val Tyr Asn Asn
                325                 330                 335

Asn Met Tyr Val Asn Met Tyr Asn Thr Gly Asn Ile Ala Arg Val Asn
            340                 345                 350

Leu Thr Thr Asn Thr Ile Ala Val Thr Gln Thr Leu Pro Asn Ala Ala
        355                 360                 365

Tyr Asn Asn Arg Phe Ser Tyr Ala Asn Val Ala Trp Gln Asp Ile Asp
    370                 375                 380

Phe Ala Val Asp Glu Asn Gly Leu Trp Val Ile Tyr Ser Thr Glu Ala
385                 390                 395                 400

Ser Thr Gly Asn Met Val Ile Ser Lys Leu Asn Asp Thr Thr Leu Gln
                405                 410                 415

Val Leu Asn Thr Trp Tyr Thr Lys Gln Tyr Lys Pro Ser Ala Ser Asn
            420                 425                 430

Ala Phe Met Val Cys Gly Val Leu Tyr Ala Thr Arg Thr Met Asn Thr
        435                 440                 445

Arg Thr Glu Glu Ile Phe Tyr Tyr Asp Thr Asn Thr Gly Lys Glu
    450                 455                 460

Gly Lys Leu Asp Ile Val Met His Lys Met Gln Glu Lys Val Gln Ser
465                 470                 475                 480

Ile Asn Tyr Asn Pro Phe Asp Gln Lys Leu Tyr Val Tyr Asn Asp Gly
                485                 490                 495

Tyr Leu Leu Asn Tyr Asp Leu Ser Val Leu Gln Lys Pro Gln
            500                 505                 510

<210> SEQ ID NO 36
<211> LENGTH: 2935
<212> TYPE: DNA
<213> ORGANISM: Homo sapiens

<400> SEQUENCE: 36
ttttcctaca tgctggccat ggggaaatca ccactgggca ctataagaag cccctgggct       60
ctctgcagag ccagcggctc cagctaagag acaagatga ggcccggcct ctcatttctc      120
ctagcccttc tgttcttcct tggccaagct gcagggggatt tggggggatgt ggaccttcca      180 attcccagcc ccggcttcag ctctttccca ggtgttgact ccagctccag cttcagctcc      240
agctccaggt cgggctccag ctccagccgc agcttaggca gcggaggttc tgtgtcccag      300
ttgttttcca atttcaccgg ctccgtggat gaccgtggga cctgccagtg ctctgtttcc      360
ctgccagaca ccaccttcc cgtggacaga gtggaacgct ggaattcac agctcatgtt      420 ctttctcaga gtttgagaa agaactttcc aaagtgaggg aatatgtcca attaattagt      480
gtgtatgaaa agaaactgtt aaacctaact gtccgaattg acatcatgga gaaggatacc      540

```
atttcttaca ctgaactgga cttcgagctg atcaaggtag aagtgaagga gatggaaaaa      600
ctggtcatac agctgaagga gagttttggt ggaagctcag aaattgttga ccagctggag      660
gtggagataa gaaatatgac tctcttggta gagaagcttg agacactaga caaaaacaat      720
gtccttgcca ttcgccgaga aatcgtggct ctgaagacca agctgaaaga gtgtgaggcc      780
tctaaagatc aaaacacccc tgtcgtccac cctcctccca ctccagggag ctgtggtcat      840
ggtggtgtgg tgaacatcag caaaccgtct gtggttcagc tcaactggag agggttttct      900
tatctatatg gtgcttgggg tagggattac tctccccagc atccaaacaa aggactgtat      960
tgggtggcgc cattgaatac agatgggaga ctgttggagt attatagact gtacaacaca     1020
ctggatgatt tgctattgta tataaatgct cgagagttgc ggatcaccta tggccaaggt     1080
agtggtacag cagtttacaa caacaacatg tacgtcaaca tgtacaacac cgggaatatt     1140
gccagagtta acctgaccac caacacgatt gctgtgactc aaactctccc taatgctgcc     1200
tataataacc gcttttcata tgctaatgtt gcttggcaag atattgactt tgctgtggat     1260
gagaatggat tgtgggttat ttattcaact gaagccagcc tggtaacat ggtgattagt      1320
aaactcaatg acaccacact tcaggtgcta aacacttggt ataccaagca gtataaacca     1380
tctgcttcta acgccttcat ggtatgtggg gttctgtatg ccacccgtac tatgaacacc     1440
agaacagaag agatttttta ctattatgac acaaacacag ggaaagaggg caaactagac     1500
attgtaatgc ataagatgca ggaaaaagtg cagagcatta actataaccc ttttgaccag     1560
aaactttatg tctataacga tggttacctt ctgaattatg atctttctgt cttgcagaag     1620
ccccagtaag ctgtttagga gttagggtga agagaaaat gtttgttgaa aaatagtct       1680
tctccactta cttagatatc tgcaggggtg tctaaaagtg tgttcatttt gcagcaatgt     1740
ttaggtgcat agttctacca cactagagat ctaggacatt tgtcttgatt tggtgagttc     1800
tcttgggaat catctgcctc ttcaggcgca ttttgcaata aagtctgtct agggtgggat     1860
tgtcagaggt ctaggggcac tgtgggccta gtgaagccta ctgtgaggag gcttcactag     1920
aagccttaaa ttaggaatta aggaacttaa aactcagtat ggcgtctagg gattctttgt     1980
acaggaaata ttgcccaatg actagtcctc atccatgtag caccactaat tcttccatgc     2040
ctggaagaaa cctggggact tagttaggta gattaatatc tggagctcct cgagggacca     2100
aatctccaac tttttttttcc cctcactagc acctggaatg atgctttgta tgtggcagat     2160
aagtaaattt ggcatgctta tatattctac atctgtaaag tgctgagttt tatggagaga     2220
ggcctttta tgcattaaat tgtacatggc aaataaatcc cagaaggatc tgtagatgag     2280
gcacctgctt tttcttttct ctcattgtcc accttactaa aagtcagtag aatcttctac     2340
ctcataactt ccttccaaag gcagctcaga agattagaac cagacttact aaccaattcc     2400
accccccacc aaccccttc tactgcctac tttaaaaaaa ttaatagttt ctatggaac      2460
tgatctaaga ttagaaaaat taattttctt taatttcatt atgaactttt atttacatga     2520
ctctaagact ataagaaaat ctgatggcag tgacaaagtg ctagcattta ttgttatcta     2580
ataaagacct tggagcatat gtgcaactta tgagtgtatc agttgttgca tgtaattttt     2640
gcctttgttt aagcctggaa cttgtaagaa aatgaaaatt taatttttttt ttctaggacg     2700
agctatagaa aagctattga gagtatctag ttaatcagtg cagtagttgg aaaccttgct     2760
ggtgtatgtg atgtgcttct gtgctttttga atgactttat catctagtct ttgtctattt     2820
ttcctttgat gttcaagtcc tagtctatag gattggcagt ttaaatgctt tactccccct     2880
tttaaaataa atgattaaaa tgtgctttga aaaagtcaa aaaaaaaaa aaaaa           2935
```

<210> SEQ ID NO 37
<211> LENGTH: 256
<212> TYPE: PRT
<213> ORGANISM: Homo sapiens

<400> SEQUENCE: 37

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
    130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255

<210> SEQ ID NO 38
<211> LENGTH: 256
<212> TYPE: PRT
<213> ORGANISM: Homo sapiens

<400> SEQUENCE: 38

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

```
Gly Gly Thr Ser Gly Gly Leu Leu Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
            115                 120                 125

Leu Tyr Val Thr Ile Pro Leu Gly Ile Lys Leu Gln Val Asn Thr Pro
        130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255

<210> SEQ ID NO 39
<211> LENGTH: 256
<212> TYPE: PRT
<213> ORGANISM: Homo sapiens

<400> SEQUENCE: 39

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
            115                 120                 125

Leu Tyr Val Thr Ile Pro Leu Gly Ile Lys Leu Gln Val Asn Thr Pro
        130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
```

```
            195                 200                 205
Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255

<210> SEQ ID NO 40
<211> LENGTH: 1035
<212> TYPE: DNA
<213> ORGANISM: Homo sapiens

<400> SEQUENCE: 40
gagtggggga gagagaggag accaggacag ctgctgagac ctctaagaag tccagatact      60
aagagcaaag atgtttcaaa ctggggggcct cattgtcttc tacgggctgt tagcccagac    120
catggcccag tttggaggcc tgcccgtgcc cctggaccag accctgccct tgaatgtgaa     180
tccagccctg cccttgagtc ccacaggtct tgcaggaagc ttgacaaatg ccctcagcaa     240
tggcctgctg tctgggggcc tgttgggcat tctggaaaac cttccgctcc tggacatcct     300
gaagcctgga ggaggtactt ctggtggcct ccttggggga ctgcttggaa aagtgacgtc     360
agtgattcct ggcctgaaca acatcattga cataaaggtc actgacccccc agctgctgga   420 acttggcctt gtgcagagcc ctgatggcca ccgtctctat gtcaccatcc ctctcggcat    480
aaagctccaa gtgaatacgc ccctggtcgg tgcaagtctg ttgaggctgg ctgtgaagct    540
ggacatcact gcagaaatct tagctgtgag agataagcag gagaggatcc acctggtcct   600
tggtgactgc acccattccc ctggaagcct gcaaatttct ctgcttgatg gacttggccc    660 cctcccatt caaggtcttc tggacagcct cacagggatc ttgaataaag tcctgcctga    720
gttggttcag ggcaacgtgt gccctctggt caatgaggtt ctcagaggct ggacatcac    780 cctggtgcat gacattgtta acatgctgat ccacggacta cagtttgtca tcaaggtcta    840
agccttccag gaaggggctg gcctctgctg agctgcttcc cagtgctcac agatggctgg    900
cccatgtgct ggaagatgac acagttgcct tctctccgag gaacctgccc cctctccttt    960
cccaccaggc gtgtgtaaca tcccatgtgc ctcacctaat aaaatggctc ttcttctgca   1020
tcaaaaaaaa aaaaa                                                    1035

<210> SEQ ID NO 41
<211> LENGTH: 1090
<212> TYPE: DNA
<213> ORGANISM: Homo sapiens

<400> SEQUENCE: 41
gagtggggga gagagaggag accaggacag ctgctgagac ctctaagaag tccagatact      60
aagagcaaag atgtttcaaa ctggggggcct cattgtcttc tacgggctgt tagcccagac    120
catggcccag tttggaggcc tgcccgtgcc cctggaccag accctgccct tgaatgtgaa     180
tccagccctg cccttgagtc ccacaggtct tgcaggaagc ttgacaaatg ccctcagcaa     240
tggcctgctg tctgggggcc tgttgggcat tctggaaaac cttccgctcc tggacatcct     300
gaagcctgga ggaggtactt ctggtggcct ccttggggga ctgcttggaa aagtgacgtc     360
agtgattcct ggcctgaaca acatcattga cataaaggtc actgacccccc agctgctgga   420 acttggcctt gtgcagagcc ctgatggcca ccgtctctat gtcaccatcc ctctcggcat    480
```

```
aaagctccaa gtgaatacgc ccctggtcgg tgcaagtctg ttgaggctgg ctgtgaagct      540
ggacatcact gcagaaatct tagctgtgag agataagcag gagaggatcc acctggtcct      600
tggtgactgc acccattccc ctggaagcct gcaaatttct ctgcttgatg gacttggccc      660 cctcccatt caaggtcttc tggacagcct cacagggatc ttgaataaag tcctgcctga       720
gttggttcag ggcaacgtgt gccctctggt caatgaggtt ctcagaggct ggacatcac       780 cctggtgcat gacattgtta acatgctgat ccacggacta cagtttgtca tcaaggtcta     840
agccttccag gaaggggctg gcctctgctg agctgggtct cccccaaca gaactatttc      900 ttgctgctca atccatttcc tctgcccag cttcccagtg ctcacagatg gctggcccat      960
gtgctggaag atgacacagt tgccttctct ccgaggaacc tgcccctct cctttcccac     1020 caggcgtgtg taacatccca tgtgcctcac ctaataaaat ggctcttctt ctgcatcaaa    1080
aaaaaaaaa                                                            1090

<210> SEQ ID NO 42
<211> LENGTH: 1074
<212> TYPE: DNA
<213> ORGANISM: Homo sapiens

<400> SEQUENCE: 42
gagtggggga gagagaggag accaggacag ctgctgagac ctctaagaag tccagatact      60
aagagcaaag atgtttcaaa ctgggggcct cattgtcttc tacggctgt tagcccagac       120 catggcccag tttggaggcc tgcccgtgcc cctggaccag accctgccct tgaatgtgaa      180
tccagccctg cccttgagtc ccacaggtct tgcaggaagc ttgacaaatg ccctcagcaa      240
tggcctgctg tctgggggcc tgttgggcat tctggaaaac cttccgctcc tggacatcct      300
gaagcctgga ggaggtactt ctggtggcct ccttggggga ctgcttggaa aagtgacgtc      360
agtgattcct ggcctgaaca acatcattga cataaaggtc actgacccc agctgctgga      420 acttggcctt gtgcagagcc ctgatggcca ccgtctctat gtcaccatcc ctctcggcat     480
aaagctccaa gtgaatacgc ccctggtcgg tgcaagtctg ttgaggctgg ctgtgaagct     540
ggacatcact gcagaaatct tagctgtgag agataagcag gagaggatcc acctggtcct    600
tggtgactgc acccattccc ctggaagcct gcaaatttct ctgcttgatg gacttggccc    660 cctcccatt caaggtcttc tggacagcct cacagggatc ttgaataaag tcctgcctga     720
gttggttcag ggcaacgtgt gccctctggt caatgaggtt ctcagaggct ggacatcac     780 cctggtgcat gacattgtta acatgctgat ccacggacta cagtttgtca tcaaggtcta    840
agccttccag gaaggggctg gcctctgctg agctgaacta tttcttgctg ctcaatccat    900
ttcctctggc ccagcttccc agtgctcaca gatggctggc ccatgtgctg gaagatgaca    960
cagttgcctt ctctccgagg aacctgcccc ctctcctttc ccaccaggcg tgtgtaacat   1020
cccatgtgcc tcacctaata aaatggctct tcttctgcat caaaaaaaaa aaaa         1074

<210> SEQ ID NO 43
<211> LENGTH: 128
<212> TYPE: PRT
<213> ORGANISM: Homo sapiens

<400> SEQUENCE: 43

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
            20                  25                  30
```

Leu Ala Ser Ser Thr Lys Gly Gln Thr Lys Arg Asn Leu Ala Lys Gly
            35                  40                  45

Lys Glu Glu Ser Leu Asp Ser Asp Leu Tyr Ala Glu Leu Arg Cys Met
    50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
            115                 120                 125

<210> SEQ ID NO 44
<211> LENGTH: 1307
<212> TYPE: DNA
<213> ORGANISM: Homo sapiens

<400> SEQUENCE: 44
acttatctgc agacttgtag gcagcaactc accctcactc agaggtcttc tggttctgga        60
aacaactcta gctcagcctt ctccaccatg agcctcagac ttgataccac cccttcctgt       120
aacagtgcga gaccacttca tgccttgcag gtgctgctgc ttctgtcatt gctgctgact       180
gctctggctt cctccaccaa aggacaaact aagagaaact ggcgaaagg caaagaggaa        240 agtctagaca gtgacttgta tgctgaactc cgctgcatgt gtataaagac aacctctgga       300
attcatccca aaacatccca agtttggaa gtgatcggga aaggaaccca ttgcaaccaa        360
gtcgaagtga tagccacact gaaggatggg aggaaaatct gcctggaccc agatgctccc      420
agaatcaaga aaattgtaca gaaaaaattg gcaggtgatg aatctgctga ttaatttgtt      480
ctgtttctgc caaacttctt taactcccag gaagggtaga attttgaaac cttgattttc      540
tagagttctc atttattcag gataccatt cttactgtat taaaatttgg atatgtgttt      600
cattctgtct caaaaatcac atttattct gagaaggttg gttaaaagat ggcagaaaga      660
agatgaaaat aaataagcct ggtttcaacc ctctaattct tgcctaaaca ttggactgta      720 cttttgcattt ttttctttaa aaattctat tctaacacaa cttggttgat ttttcctggt      780
ctactttatg gttattagac atactcatgg gtattattag atttcataat ggtcaatgat      840
aataggaatt acatggagcc caacagagaa tatttgctca atacattttt gttaatatat      900
ttaggaactt aatggagtct ctcagtgtct tagtcctagg atgtcttatt taaaatactc      960
cctgaaagtt tattctgatg tttattttag ccatcaaaca ctaaaataat aaattggtga     1020
atatgaatct tataaactgt ggttagctgg tttaagtga atatatttgc cactagtaga     1080
acaaaaatag atgatgaaaa tgaattaaca tatctacata gttataattc tatcattaga     1140
atgagcctta taataagta caatatagga cttcaacctt actagactcc taattctaaa     1200
ttctactttt ttcatcaaca gaactttcat tcatttttta aaccctaaaa cttatacccta     1260 cactattctt acaaaaatat tcacatgaaa taaaaatttg ctattga                     1307

<210> SEQ ID NO 45
<211> LENGTH: 423
<212> TYPE: PRT
<213> ORGANISM: Homo sapiens

<400> SEQUENCE: 45

```
Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
            100                 105                 110

Ala Glu Ile His Gln Ser Phe Gln His Leu Leu Arg Thr Leu Asn Gln
        115                 120                 125

Ser Ser Asp Glu Leu Gln Leu Ser Met Gly Asn Ala Met Phe Val Lys
    130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Leu Asp Ser Gln Thr Met Met Val Leu Val
        195                 200                 205

Asn Tyr Ile Phe Phe Lys Ala Lys Trp Glu Met Pro Phe Asp Pro Gln
210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
    290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Ala Val Leu Asp Val Phe Glu Glu
        355                 360                 365

Gly Thr Glu Ala Ser Ala Ala Thr Ala Val Lys Ile Thr Leu Leu Ser
    370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
```

<210> SEQ ID NO 46
<211> LENGTH: 1629
<212> TYPE: DNA
<213> ORGANISM: Homo sapiens

<400> SEQUENCE: 46

| | | | | | |
|---|---|---|---|---|---|
| attcatgaaa | atccactact | ccagacagac | ggctttggaa | tccaccagct | acatccagct | 60 |
| ccctgaggca | gagttgagaa | tggagagaat | gttacctctc | ctggctctgg | ggctcttggc | 120 |
| ggctgggttc | tgccctgctg | tcctctgcca | ccctaacagc | ccacttgacg | aggagaatct | 180 |
| gacccaggag | aaccaagacc | gagggacaca | cgtggacctc | ggattagcct | ccgccaacgt | 240 |
| ggacttcgct | ttcagcctgt | acaagcagtt | agtcctgaag | gccctgata | agaatgtcat | 300 |
| cttctcccca | ctgagcatct | ccaccgcctt | ggccttcctg | tctctggggg | cccataatac | 360 |
| cacccctgaca | gagattctca | aaggcctcaa | gttcaacctc | acggagactt | ctgaggcaga | 420 |
| aattcaccag | agcttccagc | acctcctgcg | caccctcaat | cagtccagcg | atgagctgca | 480 |
| gctgagtatg | ggaaatgcca | tgtttgtcaa | agagcaactc | agtctgctgg | acaggttcac | 540 |
| ggaggatgcc | aagaggctgt | atggctccga | ggcctttgcc | actgactttc | aggactcagc | 600 |
| tgcagctaag | aagctcatca | acgactacgt | gaagaatgga | actaggggga | aaatcacaga | 660 |
| tctgatcaag | gaccttgact | cgcagacaat | gatggtcctg | gtgaattaca | tcttcttcaa | 720 |
| agccaaatgg | gagatgccct | ttgacccca | agatactcat | cagtcaaggt | tctacttgag | 780 |
| caagaaaaag | tgggtaatgg | tgcccatgat | gagtttgcat | cacctgacta | taccttactt | 840 |
| ccgggacgag | gagctgtcct | gcaccgtggt | ggagctgaag | tacacaggca | atgccagcgc | 900 |
| actcttcatc | ctccctgatc | aagacaagat | ggaggaagtg | gaagccatgc | tgctcccaga | 960 |
| gaccctgaag | cggtggagag | actctctgga | gttcagagag | ataggtgagc | tctacctgcc | 1020 |
| aaagtttttcc | atctcgaggg | actataacct | gaacgacata | cttctccagc | tgggcattga | 1080 |
| ggaagccttc | accagcaagg | ctgacctgtc | agggatcaca | ggggccagga | acctagcagt | 1140 |
| ctcccaggtg | gtccataagg | ctgtgcttga | tgtatttgag | gagggcacag | aagcatctgc | 1200 |
| tgccacagca | gtcaaaatca | ccctcctttc | tgcattagtg | gagacaagga | ccattgtgcg | 1260 |
| tttcaacagg | cccttcctga | tgatcattgt | ccctacagac | acccagaaca | tcttcttcat | 1320 |
| gagcaaagtc | accaatccca | agcaagccta | gagcttgcca | tcaagcagtg | gggctctcag | 1380 |
| taaggaactt | ggaatgcaag | ctggatgcct | gggtctctgg | gcacagcctg | gcccctgtgc | 1440 |
| accgagtggc | catggcatgt | gtggccctgt | ctgcttatcc | ttggaaggtg | acagcgattc | 1500 |
| cctgtgtagc | tctcacatgc | acaggggccc | atggactctt | cagtctggag | ggtcctgggc | 1560 |
| ctcctgacag | caataaataa | tttcgttgga | aaaaaaaaa | aaaaaaaaa | aaaaaaaaa | 1620 |
| aaaaaaaaa | | | | | | 1629 |

<210> SEQ ID NO 47
<211> LENGTH: 251
<212> TYPE: PRT
<213> ORGANISM: Homo sapiens

<400> SEQUENCE: 47

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
            35                  40                  45

Gly Leu Thr Thr Tyr Leu Leu Val Ser Gln Leu Arg Ala Gln Gly Glu
 50                  55                  60

Ala Cys Val Gln Phe Gln Ala Leu Lys Gly Gln Glu Phe Ala Pro Ser
 65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 48
<211> LENGTH: 192
<212> TYPE: PRT
<213> ORGANISM: Homo sapiens

<400> SEQUENCE: 48

Met Gln Leu Thr Lys Gly Arg Leu His Phe Ser His Pro Leu Ser His
 1               5                  10                  15

Thr Lys His Ile Ser Pro Phe Val Thr Asp Ala Pro Leu Arg Ala Asp
                20                  25                  30

Gly Asp Lys Pro Arg Ala His Leu Thr Val Val Arg Gln Thr Pro Thr
            35                  40                  45

Gln His Phe Lys Asn Gln Phe Pro Ala Leu His Trp Glu His Glu Leu
 50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110

Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
130                 135                 140

Val Gly Ser Asn Trp Phe Gln Pro Ile Tyr Leu Gly Ala Met Phe Ser

| 145 | | | 150 | | | | 155 | | | | 160 | |
|---|---|---|---|---|---|---|---|---|---|---|---|---|
| Leu | Gln | Glu | Gly | Asp | Lys | Leu | Met | Val | Asn | Val | Ser | Asp | Ile | Ser | Leu |

| | | | 165 | | | | | 170 | | | | 175 | |
|---|---|---|---|---|---|---|---|---|---|---|---|---|---|
| Val | Asp | Tyr | Thr | Lys | Glu | Asp | Lys | Thr | Phe | Phe | Gly | Ala | Phe | Leu | Leu |
| | | | 180 | | | | | 185 | | | | 190 | |

<210> SEQ ID NO 49
<211> LENGTH: 6705
<212> TYPE: DNA
<213> ORGANISM: Homo sapiens

<400> SEQUENCE: 49

| | |
|---|---|
| ggaaaaggga aggaggagac tgagtgatta agtcacccac tgtgagagct ggtcttctat | 60 |
| ttaatggggg ctctctctgc ccaggagtca gaggtgcctc caggagcagc aggagcatgg | 120 |
| ccgaggatct gggactgagc tttggggaaa cagccagtgt ggaaatgctg ccagagcacg | 180 |
| gcagctgcag gcccaaggcc aggagcagca gcgcacgctg gctctcacc tgctgcctgg | 240 |
| tgttgctccc cttccttgca ggactcacca catacctgct tgtcagccag ctccgggccc | 300 |
| agggagaggc ctgtgtgcag ttccaggctc taaaaggaca ggagtttgca ccttcacatc | 360 |
| agcaagttta tgcacctctt agagcagacg gagataagcc aagggcacac ctgacagttg | 420 |
| tgagacaaac tcccacacag cactttaaaa atcagttccc agctctgcac tgggaacatg | 480 |
| aactaggcct ggccttcacc aagaaccgaa tgaactatac caacaaattc ctgctgatcc | 540 |
| cagagtcggg agactacttc atttactccc aggtcacatt ccgtgggatg acctctgagt | 600 |
| gcagtgaaat cagacaagca ggccgaccaa acaagccaga ctccatcact gtggtcatca | 660 |
| ccaaggtaac agacagctac cctgagccaa cccagctcct catggggacc aagtctgtat | 720 |
| gcgaagtagg tagcaactgg ttccagccca tctacctcgg agccatgttc tccttgcaag | 780 |
| aaggggacaa gctaatggtg aacgtcagtg acatctcttt ggtggattac acaaaagaag | 840 |
| ataaaacctt ctttggagcc ttcttactat aggaggagag caaatatcat tatatgaaag | 900 |
| tcctctgcca ccgagttcct aatttttctt gttcaaatgt aattataacc aggggttttc | 960 |
| ttggggccgg gagtagggg cattccacag ggacaacgg ttagctatga aatttggggc | 1020 |
| ccaaaatttc acacttcatg tgccttactg atgagagtac taactggaaa aaggctgaag | 1080 |
| agagcaaata tattattaag atgggttgga ggattggcga gtttctaaat attaagacac | 1140 |
| tgatcactaa atgaatggat gatctactcg ggtcaggatt gaaagagaaa tatttcaaca | 1200 |
| ccttcctgct atacaatggt caccagtggt ccagttattg ttcaatttga tcataaattt | 1260 |
| gcttcaattc aggagctttg aaggaagtcc aaggaaagct ctagaaaaca gtataaactt | 1320 |
| tcagaggcaa atccttcac caattttcc acatactttc atgccttgcc taaaaaaaat | 1380 |
| gaaaagagag ttggtatgtc tcatgaatgt tcacacagaa ggagttggtt ttcatgtcat | 1440 |
| ctacagcata tgagaaaagc tacctttctt ttgattatgt acacagatat ctaaataagg | 1500 |
| aagtatgagt ttcacatgta tatcaaaaat acaacagttg cttgtattca gtagagtttt | 1560 |
| cttgcccacc tattttgtgc tgggttctac cttaacccag aagacactat gaaaaacaag | 1620 |
| acagactcca ctcaaaattt atatgaacac cactagatac ttcctgatca acatcagtc | 1680 |
| aacatactct aaagaataac tccaagtctt ggccaggcgc agtggctcac acctgtaatc | 1740 |
| ccaacacttt gggaggccaa ggtgggtgga tcatctaagg ccgggagttc aagaccagcc | 1800 |
| tgaccaacgt ggagaaaccc catctctact aaaaatacaa aattagccgg gcgtggtagc | 1860 |
| gcatggctgt aatcctggct actcaggagg ccgaggcaga agaattgctt gaactgggga | 1920 |

```
ggcagaggtt gcggtgagcc cagatcgcgc cattgcactc cagcctgggt aacaagagca    1980
aaactctgtc caaaaaaaaa aaataaaat aataactcca agcctttaaa aaatatcatc     2040
tgaaactgtt acatcagatt tctggcactc tactgactgt ggaagatagc cagctgactg    2100
gaagatagcc agctgattag ttccctgaag aaacctgaag acagatacct ggttaactag    2160
atcaactaca ctgccaactt gtttgatgct gagagacaat ggacttattc catgggggaa    2220
gggaaaaaag aagtcaatca ccaaatctga agaagttaac ctagatcttt gaggtttgat    2280
ttgcaacttt atatgcagag tattatgtgg gtattttccc ttaaaatatt caaagggatt    2340
tacatatggg attagctaat gagcctagcc aagaccttcc ctggaggaca ggctggtcat    2400
tgcggaggtc ccttctgtgc ttcagtgggt tcatatcctc tagtccgtat gattttccta    2460
cgctaatatg tcaagggcag gagaggcagc tctgttctcc tagcctttgt tgacttgtct    2520
gcaaagcagg aatctgccca tttgtttcca aggagcaaat gagctcatga gaatgaaaga    2580
tgttaacttc atgcattctg tgccatctga gcatttcggt attatatgac tggtgaccct    2640
tggcccgtat tataaatgct tcctatcctg ggagacctca tggatgagtc tgagaggaaa    2700
tttggcacca aaatcactct cactctggtt tccagtagac tatagaggca gagaggcatt    2760
tgagaggctc ctgagcaaag tgtccagtgt agcaggagca cttcattaat atttattgag    2820
ttataattaa ataaaaatta atttctgatt tctcagtttg gaggttaagg ctctaaatat    2880
attttctaac ctctgctagg ctaacttaag ccaggccttt ttcttgcctt ccctttctca    2940
aaacagtcag cacagactca gtgggagcac agaggagtgt ggtcacctcc acctggctca    3000
ccagagtctt catagaggaa gtgaagcctg gaagaaactg ggcgggcccc agatgaccac    3060
agggaaaggg catctcagat ggaggaatta cccttgactt aaagcagaaa agaaagattt    3120
ctcagtaact ccaaaacttg cttgatagga gaatattccc tcaaccaatt cctaggacaa    3180
tatttattgg tagatcaaga atgtttcctc aataactcta gtctagctcc atgatcagaa    3240
ctaacaccca ttaaaaacat aaaatgttct ttctgaaccg gtcttcatgg tgcgtgagag    3300
caccaagcag ctttggtatg caggaggagt tttgcacaga agagtggcct gctcaaacct    3360
gcccactgtt ctgtaggtga tctggtggat ctggaaattt atcccaagac aggaatttcc    3420
taatattcga agacatttga ggcttttggga aattctctgc tgtgcattta tttggctcct    3480
gtcataagct tgttttttaa agaatgtatc atagctcaag ttttttactgc tgattttgtt    3540 aaattctgta tagtatattt tttacggaaa ggcacagtca gacattccta atagggctca    3600
tgtcagaact tctgttccca aggcattatc tccatagcaa aaattagtgc actgttttca    3660
aaagtgaggt gggaaaatgc ttttaagatc atgtgatgtt cccctaaaag gggttaatgg    3720
ggtgtattca gggtttggga gggaggaaga agcatgcttt agaaaacagt aaatttaggg    3780
agaaaatgct ttgttggtta aatgtcactc aaaaggctga attcaaatca attccacaaa    3840
catttactga gtacctactg cccctgggga cacagagata aattatttag tctcagacac    3900
actcattcta acttcccagc acctctactg tctgcagatt cttaattta ttttggttgt     3960 attagctaat taattcgtaa actttaggca catggatcta ttctcattat gaaaatggat    4020
gccatttgat taaggctgat gactaacaaa atgatttgtg tttactcgaa gtgttttttt    4080
aaaaatagct actcaaggat agttttccat aaatcaagaa ggtaaaaaag ttcccatttt    4140
ttattgtaga atccattatt taaactacat gtagagacag gttattattt gctatattca    4200
agtttggtca tcaatacccct taaaaatatt agaatttat ggatgaccca gaaatgcttt    4260
```

```
gaaaatctgt gttcctcagc aaatacagag accatgatca aaatgcacag aatcactaac    4320
attttgatgc tagcatggtt tcagtctatt tggcagaaca gaattgatta tgctactaaa    4380
atttctttt ctttttttt ttttttttt ttgagacaga gtcttgcttt gtcacccagg       4440
ctgaagtgca gtggcaggat ctcagttcac tgcaacctct gcctcccagg ttcacgccat    4500
tctcctgctt cagcctcccg agtagctggg actacaggct cccaccacca tgcccggcta    4560
atttttgca tttttagtag agacggggt tcaccgtgtt agccaggatg gtctcgatct      4620
cctgacctcg tgatccgccc gcctcagcct tccaaagtgc tgggattaca ggcgtgagcc    4680
actgtgcccg gactctgatt ttttttttac taaggtacag taagaaaagg gaaagtgta     4740
cgttttcact tcctgaaata tgtcaggttg aatcaataat agagcacacc agaactcttg    4800
gctccatttc aacctaaact attcagttct catcacccca gaggaaattc cgcctctgtg    4860
ctggtcagta atccccctgg attataaaag tttaactaac tcactgtgca caaggcacgg    4920
ccattgccaa cattctcttg caaggtattt tcccaagccc ttacccaatt ctgtttccat    4980
gattgtgaca ttggggatta attctgcaag acagaactgt ttatattctg taccttaaaa    5040
acacatgcaa acatctcttg ccttaagatt tctggctttc ctatggccca gagtcctaga    5100
agtgttttga tatttgtagc agaatttcca agtgtacatc cttatcctgg atattaacat    5160
ttttgcatca tattggcagc tggacctaca gagaatttag tagactgtta acctaataag    5220
ccttgaatcc ttttgcacca gtggtgagag aatgtggatc agagccatca cctccatgcc    5280
ccgtcaccct ctaacaacca catttacaac ttccccagct ctgagacaca cttgcctcca    5340
ccccttccat caccccattt taagatgaaa ataccacacc agcctggaag gaagaagtta    5400
cttgcccagg gccacatagt gagttaaggg ctgatctaga gctaggaagc tgtcttcctg    5460
aaccataatc ctggactctt ctaacctctc tactcatcgc aaatagagtt cattttagtg    5520
atttgaagga agatgggaca agtattttca aacacctgta ggacaacatg gaagtgggag    5580
gagacttcta ctgtagctcc ccagagaaga gagctagggc tacagagttg cagttacaag    5640
gttgccctct ctggcttgat ccccaaagga attttctact ccaaaataga attttctag    5700
gatgctattt ctcagtccct ggagatactc aaacaaaggg cttgtcacaa gggttttgt     5760
agaagctatt cttcacagag gttgggggag agattaagcc aaaggatctc tgaggtcttt    5820
ttcaaatcta taattatgtg ccttttgtt cattgacttc catgtgttct agttgatcat     5880
tacaaacctg gcaggccttc tcaagggttc agtaattagc tgtcatttcc catttgtcca    5940
gagagtgtcc aacacaaaat acccctaaga tcttggccaa tagagaaatg tcatggaatt    6000
ttagaaatga cagtatctgc ggagtttatt ccaagttata tcatttcaaa gatgaagaaa    6060
cccaggctca gagggagcca tcacatccac accctgtcac ccttcgtggc cagtgccaga    6120
cagtagctag ttggatgcta aaagtagaat ttagatatct taacaataag cccagcagtc    6180
tttcaacttc attcgtaaat cattttgtt ttgagcatct gtcacgtggc agcacttgcc     6240
tggatactgg agagctgaga aggaatgcga caggcaagtc ctactctcac agtgtataca    6300
ttcaggagga acaagacaca cagtgccaag taaataaagt agctgaactt catcaaatga    6360
ttttattctt aaagtcatta aagcatgtaa tgttcccctt ttttttgttc aggggtgtac    6420
agattgaaga agtgtaggtg tttatgtggt tttagtgaca aaccccatgt gctttcattg    6480
attttatgtt ttatgttaaa acatcaaccg caaggtaaaa tgcatattgt atgttgttgg    6540
atacgtactt aactggtatg catcccatgt ctttgggtac tagtgtatga attctaatct    6600
ctgtaaatga aatgttgtat gtgttaatat atttaataga tgtaacttaa taaactggca    6660
```

<210> SEQ ID NO 50
<211> LENGTH: 6412
<212> TYPE: DNA
<213> ORGANISM: Homo sapiens

<400> SEQUENCE: 50

| | | | | | |
|---|---|---|---|---|---|
| ttgaagactg | aagaattttc | acactgtcaa | aaaaaaaaaa | aaaaa | 6705 |
| atgcaactca | caaagggccg | tcttcatttc | agtcaccctt | tgtctcatac | aaagcacatt | 60 |
| tctcctttg | ttacagatgc | acctcttaga | gcagacggag | ataagccaag | ggcacacctg | 120 |
| acagttgtga | gacaaactcc | cacacagcac | tttaaaaatc | agttcccagc | tctgcactgg | 180 |
| gaacatgaac | taggcctggc | cttcaccaag | aaccgaatga | actataccaa | caaattcctg | 240 |
| ctgatcccag | agtcgggaga | ctacttcatt | tactcccagg | tcacattccg | tgggatgacc | 300 |
| tctgagtgca | gtgaaatcag | acaagcaggc | cgaccaaaca | agccagactc | catcactgtg | 360 |
| gtcatcacca | aggtaacaga | cagctaccct | gagccaaccc | agctcctcat | ggggaccaag | 420 |
| tctgtatgcg | aagtaggtag | caactggttc | cagcccatct | acctcggagc | catgttctcc | 480 |
| ttgcaagaag | gggacaagct | aatggtgaac | gtcagtgaca | tctctttggt | ggattacaca | 540 |
| aaagaagata | aaaccttctt | tggagccttc | ttactatagg | aggagagcaa | atatcattat | 600 |
| atgaaagtcc | tctgccaccg | agttcctaat | tttctttgtt | caaatgtaat | tataaccagg | 660 |
| ggttttcttg | gggccgggag | taggggggcat | tccacaggga | caacggttta | gctatgaaat | 720 |
| ttggggccca | aaatttcaca | cttcatgtgc | cttactgatg | agagtactaa | ctggaaaaag | 780 |
| gctgaagaga | gcaaatatat | tattaagatg | ggttggagga | ttggcgagtt | tctaaatatt | 840 |
| aagcacactga | tcactaaatg | aatggatgat | ctactcgggt | caggattgaa | agagaaatat | 900 |
| ttcaacacct | tcctgctata | caatggtcac | cagtggtcca | gttattgttc | aatttgatca | 960 |
| taaatttgct | tcaattcagg | agctttgaag | gaagtccaag | gaaagctcta | gaaaacagta | 1020 |
| taaactttca | gaggcaaaat | ccttcaccaa | ttttttccaca | tactttcatg | ccttgcctaa | 1080 |
| aaaaaatgaa | aagagagttg | gtatgtctca | tgaatgttca | cacagaagga | gttggttttc | 1140 |
| atgtcatcta | cagcatatga | gaaaagctac | ctttcttttg | attatgtaca | cagatatcta | 1200 |
| aataaggaag | tatgagtttc | acatgtatat | caaaaataca | acagttgctt | gtattcagta | 1260 |
| gagttttctt | gcccacctat | tttgtgctgg | gttctacctt | aacccagaag | acactatgaa | 1320 |
| aaacaagaca | gactccactc | aaaatttata | tgaacaccac | tagatacttc | ctgatcaaac | 1380 |
| atcagtcaac | atactctaaa | gaataactcc | aagtcttggc | caggcgcagt | ggctcacacc | 1440 |
| tgtaatccca | acactttggg | aggccaaggt | gggtggatca | tctaaggccg | ggagttcaag | 1500 |
| accagcctga | ccaacgtgga | gaaacccat | ctctactaaa | aatacaaaat | tagccgggcg | 1560 |
| tggtagcgca | tggctgtaat | cctggctact | caggaggccg | aggcagaaga | attgcttgaa | 1620 |
| ctggggaggc | agaggttgcg | gtgagcccag | atcgcgccat | tgcactccag | cctgggtaac | 1680 |
| aagagcaaaa | ctctgtccaa | aaaaaaaaaa | ataaataat | aactccaagc | ctttaaaaaa | 1740 |
| tatcatctga | aactgttaca | tcagatttct | ggcactctac | tgactgtgga | agatagccag | 1800 |
| ctgactggaa | gatagccagc | tgattagttc | cctgaagaaa | cctgaagaca | gatacctggt | 1860 |
| taactagatc | aactacactg | ccaacttgtt | tgatgctgag | agacaatgga | cttattccat | 1920 |
| gggggaaggg | aaaaaagaag | tcaatcacca | aatctgaaga | agttaaccta | gatctttgag | 1980 |
| gtttgatttg | caactttata | tgcagagtat | tatgtgggta | ttttcccta | aaatattcaa | 2040 |

```
agggatttac atatgggatt agctaatgag cctagccaag accttccctg gaggacaggc    2100
tggtcattgc ggaggtccct tctgtgcttc agtgggttca tatcctctag tccgtatgat    2160
tttcctacgc taatatgtca agggcaggag aggcagctct gttctcctag cctttgttga    2220
cttgtctgca aagcaggaat ctgcccattt gtttccaagg agcaaatgag ctcatgagaa    2280
tgaaagatgt taacttcatg cattctgtgc catctgagca tttcggtatt atatgactgg    2340
tgacccttgg cccgtattat aaatgcttcc tatcctggga gacctcatgg atgagtctga    2400
gaggaaattt ggcaccaaaa tcactctcac tctggtttcc agtagactat agaggcagag    2460
aggcatttga gaggctcctg agcaaagtgt ccagtgtagc aggagcactt cattaatatt    2520
tattgagtta taattaaata aaaattaatt tctgatttct cagtttggag gttaaggctc    2580
taaatatatt ttctaacctc tgctaggcta acttaagcca ggccttttc ttgccttccc    2640 tttctcaaaa cagtcagcac agactcagtg ggagcacaga ggagtgtggt cacctccacc    2700
tggctcacca gagtcttcat agaggaagtg aagcctggaa gaaactgggc gggcccaga    2760 tgaccacagg gaaagggcat ctcagatgga ggaattaccc ttgacttaaa gcagaaaaga    2820
aagatttctc agtaactcca aaacttgctt gataggagaa tattccctca accaattcct    2880
aggacaatat ttattggtag atcaagaatg tttcctcaat aactctagtc tagctccatg    2940
atcagaacta acacccatta aaaacataaa atgttctttc tgaaccggtc ttcatggtgc    3000
gtgagagcac caagcagctt tggtatgcag gaggagtttt gcacagaaga gtggcctgct    3060
caaacctgcc cactgttctg taggtgatct ggtggatctg gaaatttatc ccaagacagg    3120
aatttcctaa tattcgaaga catttgaggc tttgggaaat tctctgctgt gcatttattt    3180
ggctcctgtc ataagcttgt tttttaaaga atgtatcata gctcaagttt ttactgctga    3240
ttttgttaaa ttctgtatag tatattttt acggaaaggc acagtcagac attcctaata    3300
gggctcatgt cagaacttct gttcccaagg cattatctcc atagcaaaaa ttagtgcact    3360
gttttcaaaa gtgaggtggg aaaatgcttt taagatcatg tgatgttccc ctaaaagggg    3420 ttaatgggt gtattcaggg tttgggaggg aggaagaagc atgctttaga aaacagtaaa    3480
tttagggaga aaatgctttg ttggttaaat gtcactcaaa aggctgaatt caaatcaatt    3540
ccacaaacat ttactgagta cctactgccc ctggggacac agagataaat tatttagtct    3600
cagacacact cattctaact tcccagcacc tctactgtct gcagattctt taatttattt    3660
tggttgtatt agctaattaa ttcgtaaact ttaggcacat ggatctattc tcattatgaa    3720
aatggatgcc atttgattaa ggctgatgac taacaaaatg atttgtgttt actcgaagtg    3780
tttttttaaa aatagctact caaggatagt tttccataaa tcaagaaggt aaaaaagttc    3840 ccattttta ttgtagaatc cattatttaa actacatgta gagacaggtt attatttgct    3900
atattcaagt ttggtcatca ataccttaa aaatattaga atttatgga tgacccagaa    3960 atgctttgaa aatctgtgtt cctcagcaaa tacagagacc atgatcaaaa tgcacagaat    4020
cactaacatt ttgatgctag catggtttca gtctatttgg cagaacagaa ttgattatgc    4080
tactaaaatt tctttttctt tttttttttt ttttttttg agacagagtc ttgctttgtc    4140
acccaggctg aagtgcagtg gcaggatctc agttcactgc aacctctgcc tcccaggttc    4200
acgccattct cctgcttcag cctcccgagt agctgggact acaggctccc accaccatgc    4260
ccggctaatt ttttgcattt ttagtagaga cggggtttca ccgtgttagc caggatggtc    4320
tcgatctcct gacctcgtga tccgcccgcc tcagccttcc aaagtgctgg gattacaggc    4380
gtgagccact gtgcccggac tctgattttt tttttactaa ggtacagtaa gaaaagggaa    4440
```

```
aagtgtacgt tttcacttcc tgaaatatgt caggttgaat caataataga gcacaccaga    4500
actcttggct ccatttcaac ctaaactatt cagttctcat caccccagag gaaattccgc    4560
ctctgtgctg gtcagtaatc cccctggatt ataaaagttt aactaactca ctgtgcacaa    4620
ggcacggcca ttgccaacat tctcttgcaa ggtattttcc caagcccttta cccaattctg    4680 tttccatgat tgtgacattg gggattaatt ctgcaagaca gaactgttta tattctgtac    4740
cttaaaaaca catgcaaaca tctcttgcct taagatttct ggctttccta tggcccagag    4800
tcctagaagt gttttgatat ttgtagcaga attttcaagt gtacatcctt atcctggata    4860
ttaacatttt tgcatcatat tggcagctgg acctacagag aatttagtag actgttaacc    4920
taataagcct tgaatccttt tgcaccagtg gtgagagaat gtggatcaga gccatcacct    4980
ccatgccccg tcaccctcta acaaccacat ttacaacttc cccagctctg agacacactt    5040
gcctccaccc cttccatcac cccattttaa gatgaaaata ccacaccagc ctggaaggaa    5100
gaagttactt gcccagggcc acatagtgag ttaagggctg atctagagct aggaagctgt    5160
cttcctgaac cataatcctg gactcttcta acctctctac tcatcgcaaa tagagttcat    5220
tttagtgatt tgaaggaaga tgggacaagt attttcaaac acctgtagga caacatggaa    5280
gtgggaggag acttctactg tagctcccca gagaagagag ctagggctac agagttgcag    5340
ttacaaggtt gccctctctg gcttgatccc caaaggaatt ttctactcca aaatagaatt    5400
tttctaggat gctatttctc agtccctgga gatactcaaa caaagggctt gtcacaaggg    5460
tttttgtaga agctattctt cacagaggtt gggggagaga ttaagccaaa ggatctctga    5520
ggtctttttc aaatctataa ttatgtggcc ttttgttcat tgacttccat gtgttctagt    5580
tgatcattac aaacctggca ggccttctca agggttcagt aattagctgt catttcccat    5640
ttgtccagag agtgtccaac acaaaatacc cctaagatct tggccaatag agaaatgtca    5700 tggaattttta gaaatgacag tatctgcgga gtttattcca agttatatca tttcaaagat    5760
gaagaaaccc aggctcagag ggagccatca catccacacc ctgtcaccct tcgtggccag    5820
tgccagacag tagctagttg gatgctaaaa gtagaattta gatatcttaa caataagccc    5880
agcagtcttt caacttcatt cgtaaatcat ttttgttttg agcatctgtc acgtggcagc    5940
acttgcctgg atactggaga gctgagaagg aatgcgacag gcaagtccta ctctcacagt    6000
gtatacattc aggaggaaca agacacacag tgccaagtaa ataaagtagc tgaacttcat    6060
caaatgattt tattcttaaa gtcattaaag catgtaatgt tcccctttt ttgtttcagg    6120 ggtgtacaga ttgaagaagt gtaggtgttt atgtggtttt agtgacaaac cccatgtgct    6180
ttcattgatt ttatgtttta tgttaaaaca tcaaccgcaa ggtaaaatgc atattgtatg    6240
ttgttggata cgtacttaac tggtatgcat cccatgtctt tgggtactag tgtatgaatt    6300
ctaatctctg taaatgaaat gttgtatgtg ttaatatatt taatagatgt aacttaataa    6360
actggcattg aagactgaag aattttcaca ctgtcaaaaa aaaaaaaaaa aa          6412
```

<210> SEQ ID NO 51
<211> LENGTH: 2176
<212> TYPE: PRT
<213> ORGANISM: Homo sapiens

<400> SEQUENCE: 51

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln

```
            20                  25                  30
Ala Gln Gln Met Val Gln Pro Gln Ser Pro Val Ala Val Ser Gln Ser
            35                  40                  45
Lys Pro Gly Cys Tyr Asp Asn Gly Lys His Tyr Gln Ile Asn Gln Gln
50                  55                  60
Trp Glu Arg Thr Tyr Leu Gly Asn Ala Leu Val Cys Thr Cys Tyr Gly
65                  70                  75                  80
Gly Ser Arg Gly Phe Asn Cys Glu Ser Lys Pro Glu Ala Glu Glu Thr
                    85                  90                  95
Cys Phe Asp Lys Tyr Thr Gly Asn Thr Tyr Arg Val Gly Asp Thr Tyr
                100                 105                 110
Glu Arg Pro Lys Asp Ser Met Ile Trp Asp Cys Thr Cys Ile Gly Ala
                115                 120                 125
Gly Arg Gly Arg Ile Ser Cys Thr Ile Ala Asn Arg Cys His Glu Gly
                130                 135                 140
Gly Gln Ser Tyr Lys Ile Gly Asp Thr Trp Arg Arg Pro His Glu Thr
145                 150                 155                 160
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
                180                 185                 190
Thr Ser Tyr Val Val Gly Glu Thr Trp Glu Lys Pro Tyr Gln Gly Trp
                195                 200                 205
Met Met Val Asp Cys Thr Cys Leu Gly Glu Gly Ser Gly Arg Ile Thr
                210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
                275                 280                 285
Val Arg Ala Ala Val Tyr Gln Pro Gln Pro His Pro Gln Pro Pro Pro
                290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
                340                 345                 350
Gly Asn Ser Asn Gly Glu Pro Cys Val Leu Pro Phe Thr Tyr Asn Gly
                355                 360                 365
Arg Thr Phe Tyr Ser Cys Thr Thr Glu Gly Arg Gln Asp Gly His Leu
                370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
                420                 425                 430
Asp Cys Thr Ser Glu Gly Arg Arg Asp Asn Met Lys Trp Cys Gly Thr
                435                 440                 445
```

```
Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860
```

```
Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Pro Thr Asp Leu Arg Phe Thr Asn Ile
```

```
            1265                1270                1275

Gly Pro Asp Thr Met Arg Val Thr Trp Ala Pro Pro Pro Ser Ile
            1280                1285                1290

Asp Leu Thr Asn Phe Leu Val Arg Tyr Ser Pro Val Lys Asn Glu
            1295                1300                1305

Glu Asp Val Ala Glu Leu Ser Ile Ser Pro Ser Asp Asn Ala Val
            1310                1315                1320

Val Leu Thr Asn Leu Leu Pro Gly Thr Glu Tyr Val Val Ser Val
            1325                1330                1335

Ser Ser Val Tyr Glu Gln His Glu Ser Thr Pro Leu Arg Gly Arg
            1340                1345                1350

Gln Lys Thr Gly Leu Asp Ser Pro Thr Gly Ile Asp Phe Ser Asp
            1355                1360                1365

Ile Thr Ala Asn Ser Phe Thr Val His Trp Ile Ala Pro Arg Ala
            1370                1375                1380

Thr Ile Thr Gly Tyr Arg Ile Arg His His Pro Glu His Phe Ser
            1385                1390                1395

Gly Arg Pro Arg Glu Asp Arg Val Pro His Ser Arg Asn Ser Ile
            1400                1405                1410

Thr Leu Thr Asn Leu Thr Pro Gly Thr Glu Tyr Val Val Ser Ile
            1415                1420                1425

Val Ala Leu Asn Gly Arg Glu Glu Ser Pro Leu Leu Ile Gly Gln
            1430                1435                1440

Gln Ser Thr Val Ser Asp Val Pro Arg Asp Leu Glu Val Val Ala
            1445                1450                1455

Ala Thr Pro Thr Ser Leu Leu Ile Ser Trp Asp Ala Pro Ala Val
            1460                1465                1470

Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala
            1490                1495                1500

Thr Ile Ser Gly Leu Lys Pro Gly Val Asp Tyr Thr Ile Thr Val
            1505                1510                1515

Tyr Ala Val Thr Gly Arg Gly Asp Ser Pro Ala Ser Ser Lys Pro
            1520                1525                1530

Ile Ser Ile Asn Tyr Arg Thr Glu Ile Asp Lys Pro Ser Gln Met
            1535                1540                1545

Gln Val Thr Asp Val Gln Asp Asn Ser Ile Ser Val Lys Trp Leu
            1550                1555                1560

Pro Ser Ser Ser Pro Val Thr Gly Tyr Arg Val Thr Thr Thr Pro
            1565                1570                1575

Lys Asn Gly Pro Gly Pro Thr Lys Thr Lys Thr Ala Gly Pro Asp
            1580                1585                1590

Gln Thr Glu Met Thr Ile Glu Gly Leu Gln Pro Thr Val Glu Tyr
            1595                1600                1605

Val Val Ser Val Tyr Ala Gln Asn Pro Ser Gly Glu Ser Gln Pro
            1610                1615                1620

Leu Val Gln Thr Ala Val Thr Thr Ile Pro Ala Pro Thr Asp Leu
            1625                1630                1635

Lys Phe Thr Gln Val Thr Pro Thr Ser Leu Ser Ala Gln Trp Thr
            1640                1645                1650

Pro Pro Asn Val Gln Leu Thr Gly Tyr Arg Val Arg Val Thr Pro
            1655                1660                1665
```

```
Lys Glu Lys Thr Gly Pro Met Lys Glu Ile Asn Leu Ala Pro Asp
    1670            1675                1680
Ser Ser Ser Val Val Val Ser Gly Leu Met Val Ala Thr Lys Tyr
    1685            1690                1695
Glu Val Ser Val Tyr Ala Leu Lys Asp Thr Leu Thr Ser Arg Pro
    1700            1705                1710
Ala Gln Gly Val Val Thr Thr Leu Glu Asn Val Ser Pro Pro Arg
    1715            1720                1725
Arg Ala Arg Val Thr Asp Ala Thr Glu Thr Thr Ile Thr Ile Ser
    1730            1735                1740
Trp Arg Thr Lys Thr Glu Thr Ile Thr Gly Phe Gln Val Asp Ala
    1745            1750                1755
Val Pro Ala Asn Gly Gln Thr Pro Ile Gln Arg Thr Ile Lys Pro
    1760            1765                1770
Asp Val Arg Ser Tyr Thr Ile Thr Gly Leu Gln Pro Gly Thr Asp
    1775            1780                1785
Tyr Lys Ile Tyr Leu Tyr Thr Leu Asn Asp Asn Ala Arg Ser Ser
    1790            1795                1800
Pro Val Val Ile Asp Ala Ser Thr Ala Ile Asp Ala Pro Ser Asn
    1805            1810                1815
Leu Arg Phe Leu Ala Thr Thr Pro Asn Ser Leu Leu Val Ser Trp
    1820            1825                1830
Gln Pro Pro Arg Ala Arg Ile Thr Gly Tyr Ile Ile Lys Tyr Glu
    1835            1840                1845
Lys Pro Gly Ser Pro Pro Arg Glu Val Val Pro Arg Pro Arg Pro
    1850            1855                1860
Gly Val Thr Glu Ala Thr Ile Thr Gly Leu Glu Pro Gly Thr Glu
    1865            1870                1875
Tyr Thr Ile Tyr Val Ile Ala Leu Lys Asn Asn Gln Lys Ser Glu
    1880            1885                1890
Pro Leu Ile Gly Arg Lys Lys Thr Gly Gln Glu Ala Leu Ser Gln
    1895            1900                1905
Thr Thr Ile Ser Trp Ala Pro Phe Gln Asp Thr Ser Glu Tyr Ile
    1910            1915                1920
Ile Ser Cys His Pro Val Gly Thr Asp Glu Glu Pro Leu Gln Phe
    1925            1930                1935
Arg Val Pro Gly Thr Ser Thr Ser Ala Thr Leu Thr Gly Leu Thr
    1940            1945                1950
Arg Gly Ala Thr Tyr Asn Ile Ile Val Glu Ala Leu Lys Asp Gln
    1955            1960                1965
Gln Arg His Lys Val Arg Glu Glu Val Val Thr Val Gly Asn Ser
    1970            1975                1980
Val Asn Glu Gly Leu Asn Gln Pro Thr Asp Asp Ser Cys Phe Asp
    1985            1990                1995
Pro Tyr Thr Val Ser His Tyr Ala Val Gly Asp Glu Trp Glu Arg
    2000            2005                2010
Met Ser Glu Ser Gly Phe Lys Leu Leu Cys Gln Cys Leu Gly Phe
    2015            2020                2025
Gly Ser Gly His Phe Arg Cys Asp Ser Ser Arg Trp Cys His Asp
    2030            2035                2040
Asn Gly Val Asn Tyr Lys Ile Gly Glu Lys Trp Asp Arg Gln Gly
    2045            2050                2055
```

| | | | | | | | | | | |
|---|---|---|---|---|---|---|---|---|---|---|
| Glu | Asn | Gly | Gln | Met | Met | Ser | Cys | Thr | Cys | Leu | Gly | Asn | Gly | Lys |
| 2060 | | | | | 2065 | | | | | 2070 |

Glu Asn Gly Gln Met Met Ser Cys Thr Cys Leu Gly Asn Gly Lys
2060                2065               2070

Gly Glu Phe Lys Cys Asp Pro His Glu Ala Thr Cys Tyr Asp Asp
    2075                2080               2085

Gly Lys Thr Tyr His Val Gly Glu Gln Trp Gln Lys Glu Tyr Leu
    2090                2095               2100

Gly Ala Ile Cys Ser Cys Thr Cys Phe Gly Gly Gln Arg Gly Trp
    2105                2110               2115

Arg Cys Asp Asn Cys Arg Arg Pro Gly Gly Glu Pro Ser Pro Glu
    2120                2125               2130

Gly Thr Thr Gly Gln Ser Tyr Asn Gln Tyr Ser Gln Arg Tyr His
    2135                2140               2145

Gln Arg Thr Asn Thr Asn Val Asn Cys Pro Ile Glu Cys Phe Met
    2150                2155               2160

Pro Leu Asp Val Gln Ala Asp Arg Glu Asp Ser Arg Glu
    2165                2170               2175

<210> SEQ ID NO 52
<211> LENGTH: 7912
<212> TYPE: DNA
<213> ORGANISM: Homo sapiens

<400> SEQUENCE: 52

```
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccgggaa ggcattagaa    180
gggatttttc ccgcaggttg cgaagggaag caaacttggt ggcaacttgc ctcccggtgc    240
gggcgtctct cccccaccgt ctcaacatgc ttagggtcc ggggcccggg ctgctgctgc     300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctggaacac ttaccgagtg ggtgacactt      600
atgagcgtcc taaagactcc atgatctggg actgtacctg catcgggct gggcgaggga      660
gaataagctg taccatcgca aaccgctgcc atgaaggggg tcagtcctac aagattggtg    720
acacctggag agaccacat gagactggtg gttacatgtt agagtgtgtg tgtcttggta     780
atggaaaagg agaatggacc tgcaagccca gctgagaa gtgttttgat catgctgctg       840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct caccccagc ctcctcccta tggccactgt gtcacagaca    1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatgagag ccatgtgtct taccattcac ctacaatggc aggacgttct    1380
actcctgcac cacagaaggg cgacaggacg gacatctttg gtgcagcaca acttcgaatt   1440
```

-continued

```
atgagcagga ccagaaatac tctttctgca cagaccacac tgttttggtt cagactcgag    1500
gaggaaattc caatggtgcc ttgtgccact tccccttcct atacaacaac cacaattaca    1560
ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg gtcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca agtggtcctg    2100
tcgaagtatt tatcactgag actccgagtc agcccaactc ccaccccatc cagtggaatg    2160
caccacagcc atctcacatt tccaagtaca ttctcaggtg gagacctaaa aattctgtag    2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccagggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
```

```
caccattgtc tccaccaaca aacttgcatc tggaggcaaa ccctgacact ggagtgctca    3840
cagtctcctg ggagaggagc accacccag acattactgg ttatagaatt accacaaccc     3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agctgttcct cctcccactg    4080
acctgcgatt caccaacatt ggtccagaca ccatgcgtgt cacctgggct ccaccccat     4140
ccattgattt aaccaacttc ctggtgcgtt actcacctgt gaaaaatgag gaagatgttg    4200
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380
actcttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg ccaacaatc aacagtttct gatgttccga     4620
gggacctgga agttgttgct gcgacccca ccagcctact gatcagctgg gatgctcctg     4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct gcagcccac agtggagtat gtggttagtg     5100
tctatgctca gaatccaagc ggagagagtc agcctctggt tcagactgca gtaaccacta    5160
ttcctgcacc aactgacctg aagttcactc aggtcacacc cacaagcctg agcgccagt     5220
ggacaccacc caatgttcag ctcactggat atcgagtgcg ggtgaccccc aaggagaaga    5280
ccggaccaat gaaagaaatc aaccttgctc ctgacagctc atccgtggtt gtatcaggac    5340
ttatggtggc caccaaatat gaagtgagtg tctatgctct taaggacact ttgacaagca    5400
gaccagctca gggagttgtc accactctgg agaatgtcag cccaccaaga agggctcgtg    5460
tgacagatgc tactgagacc accatcacca ttagctggag aaccaagact gagacgatca    5520
ctggcttcca agttgatgcc gttccagcca atggccagac tccaatccag agaaccatca    5580
agccagatgt cagaagctac accatcacag gtttacaacc aggcactgac tacaagatct    5640
acctgtacac cttgaatgac aatgctcgga gctcccctgt ggtcatcgac gcctccactg    5700
ccattgatgc accatccaac ctgcgtttcc tggccaccac acccaattcc ttgctggtat    5760
catggcagcc gccacgtgcc aggattaccg gctacatcat caagtatgag aagcctgggt    5820
ctcctcccag agaagtggtc cctcggcccc gccctggtgt cacagaggct actattactg    5880
gcctggaacc gggaaccgaa tatacaattt atgtcattgc cctgaagaat aatcagaaga    5940
gcgagcccct gattggaagg aaaaagacag acaagaagc tctctctcag acaaccatct    6000
catgggcccc attccaggac acttctgagt acatcatttc atgtcatcct gttggcactg    6060
atgaagaacc cttacagttc agggttcctg gaacttctac cagtgccact ctgacaggcc    6120
tcaccagagg tgccacctac aacatcatag tggaggcact gaaagaccag cagaggcata    6180
```

```
aggttcggga agaggttgtt accgtgggca actctgtcaa cgaaggcttg aaccaaccta    6240
cggatgactc gtgctttgac ccctacacag tttcccatta tgccgttgga gatgagtggg    6300
aacgaatgtc tgaatcaggc tttaaactgt tgtgccagtg cttaggcttt ggaagtggtc    6360
atttcagatg tgattcatct agatggtgcc atgacaatgg tgtgaactac agattggag    6420 agaagtggga ccgtcaggga gaaaatggcc agatgatgag ctgcacatgt cttgggaacg    6480
gaaaaggaga attcaagtgt gaccctcatg aggcaacgtg ttatgatgat gggaagacat    6540
accacgtagg agaacagtgg cagaaggaat atctcggtgc catttgctcc tgcacatgct    6600
ttggaggcca gcggggctgg cgctgtgaca actgccgcag acctgggggt gaacccagtc    6660
ccgaaggcac tactggccag tcctacaacc agtattctca gagataccat cagagaacaa    6720
acactaatgt taattgccca attgagtgct tcatgccttt agatgtacag gctgacagag    6780
aagattcccg agagtaaatc atctttccaa tccagaggaa caagcatgtc tctctgccaa    6840
gatccatcta aactggagtg atgttagcag acccagctta gagttcttct ttctttctta    6900
agccctttgc tctggaggaa gttctccagc ttcagctcaa ctcacagctt ctccaagcat    6960
caccctggga gtttcctgag ggttttctca taaatgaggg ctgcacattg cctgttctgc    7020
ttcgaagtat tcaataccgc tcagtatttt aaatgaagtg attctaagat ttggtttggg    7080
atcaatagga aagcatatgc agccaaccaa gatgcaaatg ttttgaaatg atatgaccaa    7140 aatttaagt aggaaagtca cccaaacact tctgctttca cttaagtgtc tggcccgcaa    7200
tactgtagga acaagcatga tcttgttact gtgatatttt aaatatccac agtactcact    7260
ttttccaaat gatcctagta attgcctaga aatatctttc tcttacctgt tatttatcaa    7320
tttttcccag tattttata cggaaaaaat tgtattgaaa acacttagta tgcagttgat    7380
aagaggaatt tggtataatt atggtgggtg attattttt atactgtatg tgccaaagct    7440
ttactactgt ggaaagacaa ctgtttaat aaaagattta cattccacaa cttgaagttc    7500
atctatttga tataagacac cttcggggga ataattcct gtgaatattc tttttcaatt    7560
cagcaaacat ttgaaaatct atgatgtgca agtctaattg ttgatttcag tacaagattt    7620
tctaaatcag ttgctacaaa aactgattgg ttttgtcac ttcatctctt cactaatgga    7680
gatagcttta cactttctgc tttaatagat ttaagtggac cccaatattt attaaaattg    7740
ctagtttacc gttcagaagt ataatagaaa taatctttag ttgctctttt ctaaccattg    7800
taattcttcc cttcttccct ccaccttttcc ttcattgaat aaacctctgt tcaaagagat    7860
tgcctgcaag ggaaataaaa atgactaaga tattaaaaaa aaaaaaaaa aa              7912
```

<210> SEQ ID NO 53
<211> LENGTH: 175
<212> TYPE: PRT
<213> ORGANISM: Homo sapiens

<400> SEQUENCE: 53

```
Met Glu Lys Ile Pro Val Ser Ala Phe Leu Leu Val Ala Leu Ser
1               5                   10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60
```

Ser Lys Thr Ser Asn Lys Pro Leu Met Ile Ile His His Leu Asp Glu
 65                  70                  75                  80

Cys Pro His Ser Gln Ala Leu Lys Lys Val Phe Ala Glu Asn Lys Glu
                 85                  90                  95

Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
        115                 120                 125

Met Phe Val Asp Pro Ser Leu Thr Val Arg Ala Asp Ile Thr Gly Arg
    130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175

<210> SEQ ID NO 54
<211> LENGTH: 996
<212> TYPE: DNA
<213> ORGANISM: Homo sapiens

<400> SEQUENCE: 54
aatcacttgg ggaaaggaag gttcgtttct gagttagcaa caagtaaatg cagcactagt    60
gggtgggatt gaggtatgcc ctggtgcata aatagagact cagctgtgct ggcacactca   120
gaagcttgga ccgcatccta gccgccgact cacacaaggc aggtgggtga ggaaatccag   180
agttgccatg gagaaaattc cagtgtcagc attcttgctc cttgtggccc tctcctacac   240
tctggccaga gataccacag tcaaacctgg agccaaaaag gacacaaagg actctcgacc   300
caaactgccc cagaccctct ccagaggttg gggtgaccaa ctcatctgga ctcagacata   360
tgaagaagct ctatataaat ccaagacaag caacaaaccc ttgatgatta ttcatcactt   420
ggatgagtgc ccacacagtc aagctttaaa gaaagtgttt gctgaaaata agaaatccaa   480
gaaattggca gagcagtttg tcctcctcaa tctggtttat gaaacaactg acaaacacct   540
ttctcctgat ggccagtatg tccccaggat tatgtttgtt gacccatctc tgacagttag   600
agccgatatc actggaagat attcaaatcg tctctatgct tacgaacctg cagatacagc   660
tctgttgctt gacaacatga gaaaagctct caagttgctg aagactgaat tgtaaagaaa   720
aaaaatctcc aagcccttct gtctgtcagg ccttgagact tgaaaccaga gaagtgtga   780 gaagactggc tagtgtggaa gcatagtgaa cacactgatt aggttatggt ttaatgttac   840
aacaactatt ttttaagaaa aacaagtttt agaaatttgg tttcaagtgt acatgtgtga   900
aaacaatatt gtatactacc atagtgagcc atgattttct aaaaaaaaaa ataaatgttt   960
tgggggtgtt ctgttttctc caaaaaaaaa aaaaaa                             996

<210> SEQ ID NO 55
<211> LENGTH: 313
<212> TYPE: PRT
<213> ORGANISM: Homo sapiens

<400> SEQUENCE: 55

Met Asn Gln Leu Ser Phe Leu Leu Phe Leu Ile Ala Thr Thr Arg Gly
 1               5                  10                  15

Trp Ser Thr Asp Glu Ala Asn Thr Tyr Phe Lys Glu Trp Thr Cys Ser
             20                  25                  30

Ser Ser Pro Ser Leu Pro Arg Ser Cys Lys Glu Ile Lys Asp Glu Cys
         35                  40                  45

```
Pro Ser Ala Phe Asp Gly Leu Tyr Phe Leu Arg Thr Glu Asn Gly Val
    50                  55                  60
Ile Tyr Gln Thr Phe Cys Asp Met Thr Ser Gly Gly Gly Trp Thr
 65              70                  75                  80
Leu Val Ala Ser Val His Glu Asn Asp Met Arg Gly Lys Cys Thr Val
                85                  90                  95
Gly Asp Arg Trp Ser Ser Gln Gln Gly Ser Lys Ala Val Tyr Pro Glu
                100                 105                 110
Gly Asp Gly Asn Trp Ala Asn Tyr Asn Thr Phe Gly Ser Ala Glu Ala
                115                 120                 125
Ala Thr Ser Asp Asp Tyr Lys Asn Pro Gly Tyr Tyr Asp Ile Gln Ala
            130                 135                 140
Lys Asp Leu Gly Ile Trp His Val Pro Asn Lys Ser Pro Met Gln His
145                 150                 155                 160
Trp Arg Asn Ser Ser Leu Leu Arg Tyr Arg Thr Asp Thr Gly Phe Leu
                165                 170                 175
Gln Thr Leu Gly His Asn Leu Phe Gly Ile Tyr Gln Lys Tyr Pro Val
            180                 185                 190
Lys Tyr Gly Glu Gly Lys Cys Trp Thr Asp Asn Gly Pro Val Ile Pro
            195                 200                 205
Val Val Tyr Asp Phe Gly Asp Ala Gln Lys Thr Ala Ser Tyr Tyr Ser
210                 215                 220
Pro Tyr Gly Gln Arg Glu Phe Thr Ala Gly Phe Val Gln Phe Arg Val
225                 230                 235                 240
Phe Asn Asn Glu Arg Ala Ala Asn Ala Leu Cys Ala Gly Met Arg Val
                245                 250                 255
Thr Gly Cys Asn Thr Glu His His Cys Ile Gly Gly Gly Tyr Phe
            260                 265                 270
Pro Glu Ala Ser Pro Gln Gln Cys Gly Asp Phe Ser Gly Phe Asp Trp
            275                 280                 285
Ser Gly Tyr Gly Thr His Val Gly Tyr Ser Ser Arg Glu Ile Thr
            290                 295                 300
Glu Ala Ala Val Leu Leu Phe Tyr Arg
305                 310

<210> SEQ ID NO 56
<211> LENGTH: 985
<212> TYPE: DNA
<213> ORGANISM: Homo sapiens

<400> SEQUENCE: 56
gtacaaaaaa gcaggctcca ccatgaacca actcagcttc ctgctgtttc tcatagcgac      60
caccagagga tggagtacag atgaggctaa tacttacttc aaggaatgga cctgttcttc     120
gtctccatct ctgcccagaa gctgcaagga aatcaaagac gaatgtccta gtgcatttga     180
tggcctgtat tttctccgca ctgagaatgg tgttatctac agaccttct gtgacatgac      240 ctctgggggt ggcggctgga ccctggtggc cagcgtgcac gagaatgaca tgcgtgggaa     300
gtgcacggtg ggcgatcgct ggtccagtca gcagggcagc aaagcagtct acccagaggg     360
ggacggcaac tgggccaact acaacacctt tggatctgca gaggcggcca cgagcgatga     420
ctacaagaac cctggctact acgacatcca ggccaaggac ctgggcatct ggcacgtgcc     480
caataagtcc cccatgcagc actggagaaa cagctccctg ctgaggtacc gcacggacac     540
tggcttcctc cagacactgg gacataatct gtttggcatc taccagaaat atccagtgaa     600
```

```
atatggagaa ggaaagtgtt ggactgacaa cggcccggtg atccctgtgg tctatgattt      660
tggcgacgcc cagaaaacag catcttatta ctcaccctat ggccagcggg aattcactgc      720
gggatttgtt cagttcaggg tatttaataa cgagagagca gccaacgcct tgtgtgctgg      780
aatgagggtc accggatgta acactgagca ccactgcatt ggtggaggag gatactttcc      840
agaggccagt ccccagcagt gtggagattt ttctggtttt gattggagtg gatatggaac      900
tcatgttggt tacagcagca gccgtgagat aactgaggca gctgtgcttc tattctatcg      960
ttgaatccac ccagctttct tgtac                                            985
```